United States Patent
Burgard et al.

(10) Patent No.: US 11,535,874 B2
(45) Date of Patent: Dec. 27, 2022

(54) MICROORGANISMS AND METHODS FOR ENHANCING THE AVAILABILITY OF REDUCING EQUIVALENTS IN THE PRESENCE OF METHANOL, AND FOR PRODUCING SUCCINATE RELATED THERETO

(71) Applicant: Genomatica, Inc., San Diego, CA (US)

(72) Inventors: Anthony P. Burgard, Bellefonte, PA (US); Robin E. Osterhout, San Diego, CA (US); Stephen J. Van Dien, Encinitas, CA (US); Cara Ann Tracewell, Solana Beach, CA (US); Priti Pharkya, San Diego, CA (US); Stefan Andrae, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 91 days.

(21) Appl. No.: 14/436,722

(22) PCT Filed: Oct. 21, 2013

(86) PCT No.: PCT/US2013/065887
§ 371 (c)(1),
(2) Date: Apr. 17, 2015

(87) PCT Pub. No.: WO2014/066235
PCT Pub. Date: May 1, 2014

(65) Prior Publication Data
US 2016/0083752 A1    Mar. 24, 2016

Related U.S. Application Data

(60) Provisional application No. 61/717,001, filed on Oct. 22, 2012, provisional application No. 61/766,642, filed on Feb. 19, 2013.

(51) Int. Cl.
| | | |
|---|---|---|
| *C12N 9/96* | (2006.01) |
| *C12P 7/46* | (2006.01) |
| *C12N 9/04* | (2006.01) |
| *C12N 9/06* | (2006.01) |
| *C12N 9/10* | (2006.01) |
| *C07C 55/10* | (2006.01) |
| *C08G 63/00* | (2006.01) |
| *C12N 15/70* | (2006.01) |
| *C12N 15/81* | (2006.01) |
| *C12P 7/24* | (2006.01) |
| *C07C 59/235* | (2006.01) |
| *C12N 15/74* | (2006.01) |
| *C12N 15/77* | (2006.01) |

(52) U.S. Cl.
CPC ............ *C12P 7/46* (2013.01); *C07C 55/10* (2013.01); *C07C 59/235* (2013.01); *C08G 63/00* (2013.01); *C12N 9/0006* (2013.01); *C12N 9/0028* (2013.01); *C12N 9/1007* (2013.01); *C12N 15/70* (2013.01); *C12N 15/74* (2013.01); *C12N 15/77* (2013.01); *C12N 15/81* (2013.01); *C12N 15/815* (2013.01); *C12P 7/24* (2013.01); *C12Y 101/01244* (2013.01); *C12Y 105/0102* (2013.01)

(58) Field of Classification Search
None
See application file for complete search history.

(56) References Cited

U.S. PATENT DOCUMENTS

| | | | |
|---|---|---|---|
| 6,686,194 B1 | 2/2004 | Mutzel et al. | |
| 7,127,379 B2 | 10/2006 | Palsson et al. | |
| 7,470,530 B2 | 12/2008 | Lee | |
| 7,973,222 B1* | 7/2011 | Izui ................... | C12N 15/8259 800/317.3 |
| 8,048,661 B2* | 11/2011 | Burgard ................. | C12P 7/42 435/183 |
| 8,377,666 B2* | 2/2013 | Haselbeck ............. | C12P 19/40 435/189 |
| 8,580,543 B2* | 11/2013 | Burk .................... | C08F 136/06 435/254.11 |
| 8,715,971 B2* | 5/2014 | Pharkya ................. | C12P 7/40 435/320.1 |
| 9,023,636 B2* | 5/2015 | Burk .................... | C12P 5/026 435/243 |
| 9,932,611 B2 | 4/2018 | Burgard et al. | |
| 2002/0012939 A1 | 1/2002 | Palsson | |
| 2002/0168654 A1 | 11/2002 | Maranas et al. | |
| 2003/0059792 A1 | 3/2003 | Palsson et al. | |

(Continued)

FOREIGN PATENT DOCUMENTS

| | | |
|---|---|---|
| EP | 0066994 A2 | 12/1982 |
| WO | WO 2002/055995 A2 | 7/2002 |

(Continued)

OTHER PUBLICATIONS

US 8,236,539 B2, 08/2012, Burgard et al. (withdrawn)
Li et al., (U.S. Pat. No. 8,236,539, 2012).*
Abdel-Hamid et al., "Pyruvate oxidase contributes to the aerobic growth efficiency of *Escherichia coli*,"*Microbiol.*, 147:1483-1498 (2001).

(Continued)

*Primary Examiner* — Hope A Robinson
(74) *Attorney, Agent, or Firm* — Greenberg Traurig

(57) ABSTRACT

Provided herein is a non-naturally occurring microbial organism (NNOMO) having a methanol metabolic pathway (MMP) that can enhance the availability of reducing equivalents in the presence of methanol. Such reducing equivalents can be used to increase the product yield of organic compounds produced by the microbial organism, such as succinate. Also provided herein are methods for using such an organism to produce succinate.

19 Claims, 4 Drawing Sheets

(56) References Cited

U.S. PATENT DOCUMENTS

| | | | |
|---|---|---|---|
| 2003/0119155 | A1 | 6/2003 | Yasueda et al. |
| 2003/0224363 | A1 | 12/2003 | Park et al. |
| 2003/0233218 | A1 | 12/2003 | Schilling |
| 2004/0009466 | A1 | 1/2004 | Maranas et al. |
| 2004/0029149 | A1 | 2/2004 | Palsson et al. |
| 2004/0072723 | A1 | 4/2004 | Palsson et al. |
| 2007/0042476 | A1 | 2/2007 | Lee et al. |
| 2007/0042477 | A1 | 2/2007 | Lee et al. |
| 2007/0054387 | A1 | 3/2007 | Lee |
| 2007/0184539 | A1 | 8/2007 | San et al. |
| 2008/0020436 | A1 | 1/2008 | Lee et al. |
| 2009/0047719 | A1 | 2/2009 | Burgard et al. |
| 2009/0075352 | A1 | 3/2009 | Lee et al. |
| 2009/0203095 | A1 | 8/2009 | Lee et al. |
| 2010/0159542 | A1 | 6/2010 | Scholten et al. |
| 2010/0330634 | A1 | 12/2010 | Park et al. |
| 2011/0129904 | A1 | 6/2011 | Burgard et al. |
| 2011/0201089 | A1 | 8/2011 | Burgard et al. |
| 2011/0207189 | A1 | 8/2011 | Burgard et al. |
| 2012/0003652 | A1 | 1/2012 | Reeves et al. |

FOREIGN PATENT DOCUMENTS

| | | | |
|---|---|---|---|
| WO | WO 2003/106998 | A1 | 12/2003 |
| WO | WO 2009/024294 | A1 | 2/2009 |
| WO | WO 2009/048202 | A1 | 4/2009 |
| WO | WO 2010/092155 | A1 | 8/2010 |
| WO | WO 2013/112939 | A2 | 8/2013 |

OTHER PUBLICATIONS

Andreesen et al., "Formate Dehydrogenase of Clostridium thermoaceticum: Incorporation of Selenium-75, and the Effects of Selenite, Molybdate, and Tungstate on the Enzyme," *J. Bacteriol.*, 116(2):867-873 (1973).

Angov, "Codon usage: nature's roadmap to expression and folding of proteins.," *Biotechnol. J.*, 6(6):650-659 (2011).

Ao et al., "Towards Kinetic Modeling of Global Metabolic Networks: Methylobacterium extorquens AM1 Growth as Validation," *Chin. J. Biotech.*, 24(6):980-994 (2008).

Araujo et al., "Before it gets started: Regulating Translation at the 5' UTR," *Comparative and Functional Genomics*, Article ID 475731, 8 pages (2012).

Arfman et al., "Purification and characterization of an activator protein for methanol dehydrogenase from thermotolerant *Bacillus* spp.," *J. Biol. Chem.*, 266:3955-3960 (1991).

Arikawa et al., "Soluble fumarate reductase isoenzymes from *Saccharomyces cerevisiae* are required for anaerobic growth," *FEMS Microbiol. Lett.*, 165:111-116 (1998).

Arps et al., "Genetics of Serine Pathway Enzymes in Methylobacterium extorquens AM1: Phosphoenolpyruvate Carboxylase and Malyl Coenzyme A Lyase," *J. Bacteriol.*, 175(12):3776-3783 (1993).

Arraiano et al., "The critical role of RNA processing and degradation in the control of gene expression," *FEMS Microbiol. Rev.*, 34(5):883-923 (2010).

Atteia et al., "Pyruvate Formate-lyase and a Novel Route of Eukaryotic ATP Synthesis in Chlamydomonas Mitochondria," *J. Biol. Chem.*, 281(15):9909-9918 (2006).

Bakker et al., "Stoichiometry and compartmentation of NADH metabolism in *Saccharomyces cerevisiae*" *FEMS Microbiol. Rev.*, 24:15-37 (2001).

Beopoulos et al., "Control of Lipid Accumulation in the Yeast *Yarrowia lipolytica*," *Appl. Environ. Microbiol.*, 74(24):7779-7789 (2008).

Bergquist et al., "Degenerate oligonucleotide gene shuffling (DOGS) and random drift mutagenesis (RNDM): Two complementary techniques for enzyme evolution," *Biomol. Eng.*, 22:63-72 (2005).

Bergquist et al., "Degenerate Oligonucleotide Gene Shuffling," *Methods Mol. Biol.*, 352:191-204 (2007).

Bernhard et al., "Functional and structural role of the cytochrome b subunit of the membrane-bound hydrogenase complex of Alcaligenes eutrophus H16," *Eur. J. Biochem.*, 248:179-186 (1997).

Bianchi et al., "*Escherichia coli* Ferredoxin NADP+ Reductase: Activation of *E. coli* Anaerobic Ribonucleotide Reduction, Cloning of the Gene (fpr), and Overexpression of the Protein," *J. Bacteriol.*, 175 (6):1590-1595 (1993).

Blaschkowski et al., "Routes of Flavodoxin and Ferredoxin Reduction in *Escherichia coli*. CoA-Acylating Pyruvate: Flavodoxin and NADPH: Flavodoxin Oxidoreductases Participating in the Activation of Pyruvate Formate-Lyase," *Eur. J. Biochem.*, 123:562-569 (1982).

Bleykasten-Grosshans et al., "Transposable elements in yeasts," *C.R. Biol.*, 334:679-686 (2011).

Boles et al., "Characterization of a Glucose-Repressed Pyruvate Kinase (Pyk2p) in *Saccharomyces cerevisiae* That is Catalytically Insensitive to Fructose-1,6-Bisphosphate," *J. Bacteriol.*, 179(9):2987-2993 (1997).

Bose et al., "Genetic Analysis of the Methanol- and Methylamine-Specific Methyltransferase 2 Genes of Methanosarcina acetivorans C2A," *J. Bacteriol.*, 190:4017-4026 (2008).

Bozzi et al., "Structural and biochemical studies of alcohol dehydrogenase isozymes from Kluyueromyces lactis," *Biochim. Biophys. Acta*, 1339:133-142 (1997).

Bricker et al., "A Mitochondrial Pyruvate Carrier Required for Pyruvate Uptake in Yeast, *Drosophila*, and Humans," *Science*, 337(6090):96-100 (2012).

Burgard et al., "Minimal reaction sets for *Escherichia coli* metabolism under different growth requirements and uptake environments," *Biotechnol. Prog.*, 17:791-797 (2001).

Burgard et al., "OptKnock: A Bilevel Programming Framework for Identifying Gene. Knockout Strategies for Microbial Strain Optimization," *Biotechnol. Bioeng.*, 84:647-657 (2003).

Burgdorf et al., "The Soluble $NAD^+$-Reducing [NiFe]-Hydrogenase from Ralstonia eutropha H16 Consists of Six Subunits and Can Be Specifically Activated by NADPH," *J. Bacteriol.*, 187(9):3122-3132 (2005).

Burke et al., "The isolation, characterization, and sequence of the pyruvate kinase gene of *Saccharomyces cerevisiae*," *J. Biol. Chem.*, 258(4):2193-2201 (1983).

Castel et al., "RNA interference in the nucleus: roles for small RNAs in transcription, epigenetics and beyond," *Nat. Rev. Genet.*, 14(2):100-112 (2013).

Chandra et al., "Pyruvate decarboxylase: a key enzyme for the oxidative metabolism of lactic acid by Acetobacter pasteurianus," *Arch. Microbiol.*, 176:443-451 (2001).

Chao et al., "The Effects of Wall Populations on Coexistence of Bacteria in the Liquid Phase of Chemostat Cultures," *J. Gen. Microbiol.*, 131:1229-1236 (1985).

Chen et al., "Phosphoenolpyruvate Carboxykinase Assayed at Physiological Concentrations of Metal Ions Has a High Affinity for $CO_2$," *Plant Physiol.*, 128:160-164 (2002).

Clark et al., "Purification and properties of 5,10-methylenetetrahydrofolate reductase, an iron-sulfur flavoprotein from Clostridium formicoaceticum," *J. Biol. Chem.*, 259(17):10845-10849 (1984).

Coco et al., "DNA shuffling method for generating highly recombined genes and evolved. enzymes," *Nat. Biotechnol.*, 19:354-359 (2001).

Colonna et al., "Synthesis and radiocarbon evidence of terephthalate polyesters completely prepared from renewable resources," *Green Chem.*, 13:2543-2548 (2011).

Coppi, "The hydrogenases of Geobacter sulfurreducens: a comparative genomic perspective," *Microbiology*, 151:1239-1254 (2005).

Cotelesage et al., "How does an enzyme recognize $CO_2$?," *Int. J. Biochem. Cell Biol.*, 39:1204-1210 (2007).

Cracknell et al., "A kinetic and thermodynamic understanding of O2 tolerance in [NiFe]-hydrogenases," *Proc. Natl. Acad. Sci. USA*, 106(49):20681-20686 (2009).

Currie et al., "Authentication and dating of biomass components of industial materials; links to sustainable technology," *Nuclear Instruments and Methods in Phyics Research B*, 172:281-287 (2000).

(56) References Cited

OTHER PUBLICATIONS

D'ari et al., "Purification, characterization, cloning, and amino acid sequence of the bifunctional. enzyme 5,10-methylenetetrahydrofolate dehydrogenase/5,10-methenyltetrahydrofolate cyclohydrolase from *Escherichia coli,*" *J. Biol. Chem.*, 266(35):23953-23958 (1991).
Daigaku et al., "Loss of heterozygosity in yeast can occur by ultraviolet irradiation during the S phase of the cell cycle," *Mut. Res.*, 600:177-183 (2006).
Daniel et al, "Biochemical and Molecular Characterization of the Oxidative Branch of Glycerol Utilization by Citrobacter freundii," *J. Bacteriol.*, 177(15):4392-4340 (1995).
Das et al., "Characterization of a Corrinoid Protein Involved in the C1 Metabolism of Strict Anaerobic Bacterium Moorella thermoacetica," *Proteins*, 67:167-176 (2007).
Datsenko et al., "One-step inactivation of chromosomal genes in *Escherichia coli* K-12 using PCR products," *Proc. Natl. Acad. Sci. USA*, 97(12):6640-6645 (2000).
De Bok et al., "Two W-containing formate dehydrogenases (CO2-reductases) involved in syntrophic propionate oxidation by Syntrophobacter fumaroxidans," *Eur. J. Biochem.*, 270:2476-2485 (2003).
De Crecy et al., "Development of a novel continuous culture device for experimental evolution of bacterial populations," *Appl. Microbiol. Biotechnol.*, 77:489-496 (2007).
De Graef et al., "The Steady-State Internal Redox State (NADH/NAD) Reflects the External Redox State and is Correlated With Catabolic Adaptation in *Escherichia coli,*" *J. Bacteriol.*, 181:2351-2357 (1999).
De Smidt et al., "The alcohol dehydrogenases of *Saccharomyces cerevisiae*: a comprehensive review," *FEMS Yeast Res.*, 8:967-978 (2008).
De Vries et al., "Physiology and genetics of methylotrophic bacteria," *FEMS Microbiol Rev.*, 6(1):57-101 (1990).
Diaz et al., Characterization of the hca Cluster Encoding the Dioxygenolytic Pathway for Initial Catabolism of 3-Phenylpropionic Acid in *Escherichia coli*K-12, *J. Bacteriol.*, 180(11):2915-2923 (1998).
Dietrich et al., "High-throughput metabolic engineering: advances in small-molecule screening and selection," *Annu. Rev. Biochem.*, 79:563-590 (2010).
Donovan et al., "Review: Optimizing inducer and culture conditions for expression of foreign proteins under the control of the lac promoter," *J. Ind. Microbiol.*, 16(3):145-154 (1996).
Drake, "Demonstration of hydrogenase in extracts of the homoacetate-fermenting bacterium Clostridium thermoaceticum," *J. Bacteriol.*, 150(2):702-709 (1982).
Drewke et al., "Ethanol Formation in adh0 Mutants Reveals the Existence of a Novel Acetaldehyde-Reducing Activity in *Saccharomyces cerevisiae,*" *J. Bacteriol.*, 172:3909-3917 (1990).
Dykhuizen, "Chemostats Used for Studying Natural Selection and Adaptive Evoluation," *Methods Enzymol.*, 613-631 (1993).
Eikmanns et al., "The phosphoenolpyruvate carboxylase gene of Corynebacterium glutamicum: Molecular cloning, nucleotide sequence, and expression," *Mol. Gen. Genet.*, 218:330-339 (1989).
Enomoto et al., "Cloning and Sequencing of the Gene Encoding the Soluble Fumarate Reductase from *Saccharomyces cerevisiae,*" *DNA Res.*, 3:263-267 (1996).
Eppler et al., "Glycerol-3-phosphate-mediated repression of malT in *Escherichia coli* does not require metabolism, depends on enzyme IIAG1c and is mediated by cAMP levels," *Mol. Microbiol.*, 33:1221-1231 (1999).
Fan et al., "Disruption of a gene encoding glycerol 3-phosphatase from Candida albicans impairs intracellular glycerol accumulation-mediated salt-tolerance," *FEMS Microbiol. Lett.*, 245:107-116 (2005).
Flores et al., "Growth recovery on glucose under aerobic conditions of an *Escherichia coli* strain carrying a phosphoenolpyruvate:carbohydrate phosphotransferase system deletion by inactivating arcA and overexpressing the genes coding for glucokinase and galactose permease," *J. Mol. Microbiol. Biotechnol.*, 13:105-116 (2007).

Fong et al., "Description and Interpretation of Adaptive Evolution of *Escherichia coli* K-12 MG1655 by Using a Genome-Scale In Silico Metabolic Model," *J. Bacteriol.*, 185(21):6400-6408 (2003).
Fong et al., "In Silico Design and Adaptive Evolution of *Escherichia coli* for Production of Lactic Acid," *Biotechnol. Bioeng.*, 91:643-648 (2005).
Fong et al., "Metabolic gene—deletion strains of *Escherichia coli* evolve to computationally predicted growth phenotypes," *Nat. Genet.*, 36(10):1056-1058 (2004).
Fox et al., "Characterization of the Region Encoding the CO-Induced Hydrogenase of Rhodospirillum rubrum," *J. Bacteriol.*, 178(21):6200-6208 (1996).
Fuchs, "Alternative Pathways of Carbon Dioxide Fixation: Insights into the Early Evolution of Life?," *Annu. Rev. Microbiol.*, 65:631-658 (2011).
Fujii et al., "Error-prone rolling circle amplification: the simplest random mutagenesis protocol," *Nat. Protocols*, 1(5):2493-2497 (2006).
Fujii et al., "One-step random mutagenesis by error-prone rolling circle amplification," *Nucleic Acids Res.*, 32(19):e145 (2004).
Fujinaga et al., "Cloning and Expression in *Escherichia coli* of the Gene Encoding the [2fe-2s] Ferredoxin from Clostridium Pasteurianum," *Biochem. Biophys. Res. Comm.*, 192(3):1115-1122 (1993).
Galagan et al., "The Genome of M. acetivorans Reveals Extensive Metabolic and Physiological Diversity," *Genome Res.*, 12:532-542 (2002).
Garcia-Alles et al., "Phosphoenolpyruvate- and ATP-Dependent Dihydroxyacetone Kinases: Covalent Substrate-Binding and Kinetic Mechanism," *Biochem.*, 43:13037-13045 (2004).
Germer et al., "Overexpression, Isolation, and Spectroscopic Characterization of the Bidirectional [NiFe] Hydrogenase from *Synechocystis* sp. PCC 6803," *J. Biol. Chem.*, 284(52):36462-36472 (2009).
Gibbs et al., "Degenerate oligonucleotide gene shuffling (DOGS): a method for enhancing the frequency of recombination with family shuffling," *Gene*, 271:13-20 (2001).
Gibson et al., "Physical and Genetic Interactions of Cytosolic Malate Dehydrogenase with Other Gluconeogenic Enzymes," *J. Biol. Chem.*, 278:25628-25636 (2003).
Goenrich et al., "A glutathione-dependent formaldehyde-activating enzyme (Gfa) from Paracoccus denitrificans detected and purified via two-dimensional proton exchange NMR spectroscopy," *J. Boil. Chem.*, 277(5):3069-3072 (2002).
Guest et al., "The Fumarase Genes of *Escherichia coli*: Location of the fumB Gene and Discovery of a new Gene (funC)," *J. gen. Microbiol.*, 131:2971-2984 (1985).
Gutknecht et al., "The dihydroxyacetone kinase of *Escherichia coli* utilizes a phosphoprotein instead of ATP as phosphoryl donor," *EMBO J.*, 20(10):2480-2486 (2001).
Guzman et al., "Tight Regulation, Modulation, and High-Level Expression by Vectors Containing the Arabinose PBAD Promoter," *J. Bacteriol.*, 177(14):4121-4130 (1995).
Hagemeier et al., "Insight into the mechanism of biological methanol activation based on the crystal structure of the methanol-cobalamin methyltransferase complex," *Proc. Natl. Acad. Sci. USA*, 103:18917-18922 (2006).
Hansen et al., "The Effect of the lacY Gene on the Induction of IPTG Inducible Promoters, Studied in *Escherichia coli* and Pseudomonas fiuorescens," *Curr, Microbiol.*, 36(6):341-347 (1998).
Harms et al., "Methanol:coenzyme M methyltransferase from Methanosarcina barkeri. Cloning, sequencing and differential transcription of the encoding genes, and functional overexpression of the mtaA gene in *Escherichia coli,*" *Eur. J. Biocehm.*, 235:653-659 (1996).
Hatrongjit et al., "A novel NADP+-dependent formate dehydrogenase from Burkholderia stabilis 15516: Screening, purification and characterization," *Enzyme Microbio. Tech.*, 46(7):557-561 (2010).
Hayes et al., "Combining computational and experimental screening for rapid optimization of protein properties," *Proc. Natl. Acad. Sci. USA*, 99(25):15926-15931 (2002).
Hayes, "Transposon-based strategies for microbial functional genomics and proteomics," *Annu. Rev. Genet.*, 37:3-29 (2003).
Heggeset et al., "Genome Sequence of Thermotolerant Bacillus methanolicus: Features and Regulation Related to Methylotrophy

(56) References Cited

OTHER PUBLICATIONS and Production of L-Lysine and L-Glutamate from Methanol," *Appl. Environ. Microbiol.*, 78(15):5170-5181 (2012).
Hektor et al., "Identification of a magnesium-dependent NAD(P)(H)-binding domain in the nicotinoprotein methanol dehydrogenase from Bacillus methanolicus," *J. Biol. Chem.*, 277:46966-46973 (2002).
Hemschemeier et al., "Biochemical and Physiological Characterization of the Pyruvate Formate-Lyase Pfl1 of Chlamydomonas reinhardtii, a Typically Bacterial Enzyme in a Eukaryotic Alga," *Eukaryot. Cell*, 7:518-526 (2008).
Hermann et al., "Biogenesis of cytochrome oxidase—Sophisticated assembly lines in the mitochondrial inner membrane," *Gene*, 354:43-52 (2005).
Hermann et al., "Energy conservation via electron-transferring flavoprotein in anaerobic bacteria," *J. Bacteriol.*, 190(3):784-791 (2008).
Herzig et al., "Identification and functional expression of the mitochondrial pyruvate carrier," *Science*, 337:93-96 (2012).
Hesslinger et al., "Novel keto acid formate-lyase and propionate kinase enzymes are components of an anaerobic pathway in *Escherichia coli* that degrades L-threonine to propionate," *Mol. Mcrobiol.*, 27:477-492 (1998).
Hibbert et al., "Directed evolution of biocatalytic processes," *Biomol. Eng.*, 22:11-19 (2005).
Hochstrasser, "Ubiquitin-Dependent Protein Degradation," *Annu. Rev. Genet.*, 30:405-439 (1996).
Hoffmeister et al., "Mitochondrial trans-2-Enoyl-CoA Reductase of Wax Ester Fermentation from Euglena gracilis Defines a New Family of Enzymes Involved in Lipid Synthesis," *J. Biol. Chem.*, 280:4329-4338 (2005).
Hohmann, "Characterisation of PDC2, a gene necessary for high level expression of pyruvate decarboxylase structural genes in *Saccharomyces cerevisiae*," *Mol. Gen. Genet.*, 241:657-666 (1993).
Houseley et al., "The Many Pathways of RNA Degradation," *Cell*, 136(4):763-776 (2009).
Huisman et al., "Enzyme evolution for chemical process applications," R.N. Patel (ed.), *Biocatalysis in the pharmaceutical and biotechnology industries*, CRC Press, p. 717-742 (2007).
Ibarra et al., "*Escherichia coli* K-12 undergoes adaptive evolution to achieve in silico predicted optimal growth," *Nature*, 420:186-189 (2002).
Ishida et al., "Efficient Production of L-Lactic Acid by Metabolically Engineered *Saccharomyces cerevisiae* with a Genome-Integrated L-Lactate Dehydrogenase Gene," *Appl. Environ. Microbiol.*, 71(4):1964-1970 (2005).
Ito et al., "Cloning and High-Level Expression of the Glutathione-Independent Formaldehyde Dehydrogenase Gene from Pseudomonas putida." *J. Bacteriol.*, 176:2483-2491 (1994).
Iverson et al., "Structure of the *Escherichia coli* Fumarate Reductase Respiratory Complex," *Science*, 284:1961-1966 (1999).
Iwakura et al., "Studies on Regulatory Functions of Malic Enzymes," *J. Biochem.*, 85(5):1355-1365 (1979).
Jacobi et al., "The hyp operon gene products are required for the maturation of catalytically active hydrogenase isoenzymes in *Escherichia coli*" *Arch. Microbiol.*, 158:444-451 (1992).
Jerome et al., "Development of a fed-batch process for the production of a dye-linked formaldehyde dehydrogenase in Hyphomicrobium zavarzinii ZV 580," *Appl. Microbiol. Biotechnol.*, 77:779-788 (2007).
Johnson et al., "Purification and properties of dihydroxyacetone kinase from Klebsiella pneumonia," *J. Bacteriol.*, 160(1):55-60 (1984).
Kai et al., "Phosphoenolpyruvate carboxylase: three-dimensional structure and molecular mechanisms," *Arch. Biochem. Biophys.*, 414:170-179 (2003).
Karlen et al, "Absolute determination of the activity of two $C^{14}$ dating standards," *Arkiv Geofysik*, 4:465-471 (1968).
Kato et al., "The Physiological Role of the Ribulose Monophosphate Pathway in Bacteria and Archaea," *Biosci. Biotechnol. Biochem.*, 70(1):10-21 (2006).

Kawasaki et al., "Transcriptional gene silencing by short interfering RNAs," *Curr. Opin. Mol. Ther.*, 7(2):125-131 (2005).
Kellum et al., "Effects of Cultivation Gas Phase on Hydrogenase of the Acetogen Clostridium thermoaceticum," *J. Bacteriol.*, 160(1):466-469 (1984).
Kerscher et al., "A single external enzyme confers alternative NADH:ubiquinone oxidoreductase activity in Yarrowia lipolytica," *J. Cell Science*, 112:2347-2354 (1999).
Killenberg-Jabs et al., "Active oligomeric states of pyruvate decarboxylase and their functional characterization," *Eur. J. Biochem.*, 268:1698-1704 (2001).
Kim et al., "Construction of an *Escherichia coli* K-12 Mutant for Homoethanologenic Fermentation of Glucose or Xylose without Foreign Genes," *Appl. Environ. Microbiol.*, 73(6):1766-1771 (2007).
Kim et al., "Dihydrolipoamide Dehydrogenase Mutation Alters the NADH Sensitivity of Pyruvate Dehydrogenase Complex of *Escherichia coli* K-12," *J. Bacteriol.*, 190:3851-3858 (2008).
Kim et al., "Effect of Overexpression of Actinobacillus succinogenes Phosphoenolpyruvate Carboxykinase on Succinate Production in *Escherichia coli*," *Appl. Environ. Microbiol.*, 70(2):1238-1241 (2004).
Kloosterman et al., "Molecular, Biochemical, and Functional Characterization of a Nudix Hydrolase Protein That Stimulates the Activity of a Nicotinoprotein Alcohol Dehydrogenase," *J. Biol. Chem.*, 277(38):34785-34792 (2002).
Knappe et al., "Post-translational activation introduces a free radical into pyruvate formate-lyase," *Proc. Natl. Acad. Sci. USA*, 81:1332-1335 (1984).
Kobayashi et al., "Physicochemical, Catalytic, and Immunochemical Properties of Fumarases Crystallized Separately from Mitochondrial and Cytosolic Fractions of Rat Liver," *J. Biochem.*, 89:1923-1931 (1981).
Koland et al., "Proximity of reactive cysteine residue and flavin in *Escherichia coli* pyruvate oxidase as estimated by fluorescence energy transfer," *Biochem.*, 21:4438-4442 (1982).
Kretz et al., "Gene Site Saturation Mutagenesis: A Comprehensive Mutagenesis Approach," *Methods Enzymol.*, 388:3-11 (2004).
Krieger et al., "Pyruvate decarboxylase from Kluyveromyces lactis: An enzyme with an extraordinary substrate activation behavior," *Eur. J. Biochem.*, 269:3256-3263 (2002).
Kurdistani et al., "Histone acetylation and deacetylation in yeast," *Nat. Rev. Mol. Cell Biol.*, 4(4):276-284 (2003).
Kwon et al., "Influence of Gluconeogenic Phosphoenolpyruvate Carboxykinase (PCK) Expression on Succinic Acid Fermentation in *Escherichia coli* Under High Bicarbonate Condition," *J. Microbiol. Biotechnol.*, 16(9):1448-1452 (2006).
Laivenieks et al., "Cloning, Sequencing, and Overexpression of the Anaerobiospirillum succiniciproducens Phosphoenolpyruvate Carboxykinase (pckA) Gene," *Appl. Environ. Microbiol.*, 63(6):2273-2280 (1997).
Lee et al., "A new approach to directed gene evolution by recombined extension on truncated templates (RETT)," *J. Molec. Catalysis*, 26:119-129 (2003).
Lee et al., "Antisense technology in molecular and cellular bioengineering," *Curr. Opin. Biotechnol.*, 14(5):505-511 (2003).
Lee et al., "Cloning and Characterization of Mannheimia succiniciproducens MBEL55E Phosphoenolpyruvate Carboxykinase (pckA) Gene," *Biotechnol. Bioprocess Eng.*, 7:95-99 (2002).
Lehtio et al., "Crystal Structure of a Glycyl Radical Enzyme from Archaeoglobus fulgidus," *J. Mol. Biol.*, 357:221-235 (2006).
Lehtio et al., "The pyruvate formate lyase family: sequences, structures and activation," *Protein Eng. Des. Sel.*, 17:545-552 (2004).
Lenski et al., "Dynamics of adaptation and diversification: a 10,000-generation experiment with bacterial populations," *Proc. Natl. Acad. Sci. USA*, 91:6808-6814 (1994).
Leppanen et al., "Pyruvate formate lyase is structurally homologous to type I ribonucleotide reductase," *Structure*, 7:733-744 (1999).
Li et al., "Integrated electromicrobial conversion of CO2 to higher alcohols,"*Science*, 335:1596 (2012).
Li et al., "Properties of Nicotinamide Adenine Dinucleotide Phosphate-Dependent Formate Dehydrogenase from Clostridium thermoaceticum," *J. Bacteriol.*, 92:405-412 (1966).

(56) References Cited

OTHER PUBLICATIONS

Lin et al., "Fed-Batch Culture of a Metabolically Engineered *Escherichia coli* Strain Designed for High-Level Succinate Production and Yield Under Aerobic Conditions," *Biotechnol. Bioeng.*, 90:775-779 (2005).
Lovell et al., "Cloning and expression in *Escherichia coli* of the Clostridium thermoaceticum gene encoding thermostable formyltetrahydrofolate synthetase," *Arch. Microbiol.*, 149:280-285 (1988).
Lovell et al., "Primary structure of the thermostable formyltetrahydrofolate synthetase from Clostridium thermoaceticum," *Biocehmistry*, 29:5687-5694 (1990).
Low et al., "Mimicking Somatic Hypermutation: Affinity Maturation of Antibodies Displayed on Bacteriophage Using a Bacterial Mutator Strain," *J. Mol. Biol.*, 260:359-368 (1996).
Lutz et al., "Dissecting the functional program of *Escherichia coli* promoters: the combined mode of action of Lac repressor and AraC activator," *Proc. Natl. Acad. Sci. USA*, 98:11248-11253 (2001).
Lutz et al., "Rapid generation of incremental truncation libraries for protein engineering using alpa-phosphothioate nucleotides," *Nucleic Acids Res.*, 29(4):e16 (2001).
Maeda et al., "Enhanced hydrogen production from glucose by metabolically engineered *Escherichia coli*," *Appl. Microbiol. Biotechnol.*, 77:879-890 (2007).
Maeder et al., "The Methanosarcina barkeri Genome: Comparative Analysis with Methanosarcina acetivorans and Methanosarcina mazei Reveals Extensive Rearrangement within Methanosarcinal Genomes," *J. Bacteriol.*, 188:7922-7931 (2006).
Maklashina et al., "Anaerobic Expression of *Escherichia coli* Succinate Dehydrogenase: Functional Replacement of Fumarate Reductase in the Respiratory Chain during Anaerobic Growth," *J. Bacteriol.*, 180(22):5989-5996 (1998).
Maklashina et al., "Fumarate Reductase and Succinate Oxidase Activity of *Escherichia coli* Complex II Homologs are Perturbed Differently by Mutation of the Flavin Binding Domain," *J. Biol. Chem.*, 281(16):11357-11365 (2006).
Makuc et al., "The putative monocarboxylate permeases of the yeast *Saccharomyces cerevisiae* do not transport monocarboxylic acids across the plasma membrane," *Yeast*, 18:1131-1143 (2001).
Mann et al., "Protemic analysis of post-translational modifications," *Nature Biotech.*, 21:255-261 (2003).
Mann, "An International Reference Material for Radiocarbon Dating," *Radiocarbon*, 25(2):519-527 (1983).
Mattevi et al., "Atomic structure of the cubic core of the pyruvate dehydrogenase multienzyme complex," *Science*, 255:1544-1550 (1992).
Mcalister-Henn et al., "Isolation and Expression of the Gene Encoding Yeast Mitochondrial Malate Dehydrogenase," *Bacteriol.*, 169(11):5157-5166 (1987).
Mccue et al., "Gene Expression and Stress Response Mediated by the Epigenetic Regulation of a Transposable Element Small RNA," *PLoS Genet.*, 8(2):e1002474 (2012).
Melchiorsen et al., "The level of pyruvate-formate lyase controls the shift from homolactic to mixed-acid product formation in Lactococcus lactis," *Appl. Microbiol. Biotechnol.*, 58:338-344 (2002).
Menzel et al., "Enzymatic evidence for an involvement of pyruvate dehydrogenase in the anaerobic glycerol metabolism of Klebsiella pneumonia," *J. Biotechnol.*, 56:135-142 (1997).
Miko, "Phenotype Variability: Penetrance and Expressivity," *Nature Education*, 1(1):137 (2008).
Minard et al., "Isolation, Nucleotide Sequence Analysis, and Disruption of the MDH2 Gene from *Saccharomyces cerevisiae*: Evidence for Three Isozymes of Yeast Malate Dehydrogenase," *Mol. Cell. Biol.*, 11:370-380 (1991).
Mitsui et al., "Formaldehyde Fixation Contributes to Detoxification for Growth of a Nonmethylotroph, Burkholderia cepacia TM1, on Vanillic Acid," *Appl. Environ. Microbiol.*, 69(10):6128-6132 (2003).
Mizobata et al., "Purification and Characterization of a Thermostable Class II Fumarase from Thermus thermophiles," *Arch. Biochem. Biophys.*, 355(1):49-55 (1998).

Molin et al., "Dihydroxyacetone Kinases in *Saccharomyces cerevisiae* are Involved in Detoxification of Dihydroxyacetone," *J. Biol. Chem.*, 278(3):1415-1423 (2003).
Mukhopadhyay et al., "Pyruvate carboxylase from *Mycobacterium smegmatis*: stabilization, rapid purication, molecular and biochemical characterization and regulation of the cellular level," *Biochim. Biophys. Acta*, 1475:191-206 (2000).
Muller et al., "Nucleotide exchange and excision technology (NExT) DNA shuffling: a robust method for DNA fragmentation and directed evolution," *Nucleic Acids Res.*, 33(13):e117 (2005).
Muratsubaki et al., "One of the Fumarate Reductase Isoenzymes from *Saccharomyces cerevisiae* is Encoded by the OSM1 Gene," *Arch. Biochem. Biophys.*, 352(2):175-181 (1998).
Myronova et al., "Three-Dimensional Structure Determination of a Protein Supercomplex That Oxidizes Methane to Formaldehyde in Methylococcus capsulatus (Bath)," *Biochem.*, 45:11905-11914 (2006).
Nagy et al., "Formyltetrahydrofolate Hydrolase, a Regulatory Enzyme That Functions to Balance Pools of Tetrahydrofolate and One-Carbon Tetrahydrofolate Adducts in *Escherichia coli*," *J. Bacteriol.*, 177(5):1292-1298 (1995).
Naidu et al., "Characterization of a Three-Component Vanillate O-Demethylase from Moorella thermoacetica," *J. Bacteriol.*, 183(11):3276-3281 (2001).
Nakai et al., "A Knowledge Base for Predicting Protein Localization Sites in Eukaryotic Cells," *Genomics*, 14(4):897-911 (1992).
Nakano et al., "Characterization of Anaerobic Fermentative Growth of Bacillus subtilis: Identification of Fermentation End Products and Genes Required for Growth," *J. Bacteriol.*, 179(21):6749-6755 (1997).
Ness et al., "Synthetic shuffling expands functional protein diversity by allowing amino acids to recombine independently," *Nat. Biotechnol.*, 20:1251-1255 (2002).
Nishizawa et al., "Regulation of inducible gene expression by natural antisense transcripts," *Front. Biosci.*, 17:938-958 (2012).
Nunn et al., "The nucleotide sequence and deduced amino acid sequence of the genes for cytochrome q, and a hypothetical second subunit of the methanol dehydrogenase of Methylobacterium Ami," *Nucl. Acids Res.*, 16(15):7722 (1988).
O'brien et al., "Chemical, physical and enzymatic comparisons of formyltetrahydrofolate synthetases from thermo- and mesophilic Clostridia," *Experientia Suppl.*, 26:249-262 (1976).
O'brien et al., "Regulation by lipids of cofactor binding to a peripheral membrane enzyme: binding of thiamin pyrophosphate to pyruvate oxidase," *Biochem.*, 16:3105-3109 (1977).
O'brien et al., "Studies of the thiamin pyrophosphate binding site of *Escherichia coli* pyruvate. oxidase. Evidence for an essential tryptophan residue" *J. Biol. Chem.*, 255:3302-3307 (1980).
O'sullivan, "Aptasensors—the future of biosensing?," *Anal. Bioanal. Chem.*, 372(1):44-48 (2002).
Orita et al., "Bifunctional enzyme fusion of 3-hexulose-6-phosphate synthase and 6-phospho-3-hexuloisomerase," *Appl. Microbiol. Biotechnol.*, 76:439-445 (2007).
Ostermeier et al., "A combinatorial approach to hybrid enzymes independent of DNA homology," *Nat. Biotechnol.*, 17:1205-1209 (1999).
Ostermeier et al., "Combinatorial protein engineering by incremental truncation," *Proc. Natl. Acad. Sci. USA*, 96:3562-3567 (1999).
Otten et al., "Directed evolution: selecting today's biocatalysts," *Biomol. Eng.*, 22:1-9 (2005).
Park et al., "Growth of Mycobacteria on Carbon Monoxide and Methanol," *J. Bact.*, 185(1):142-147 (2003).
Parkin et al., "Rapid and Efficient Electrocatalytic CO2/CO Interconversions by Carboxydothermus hydrogenoformans CO Dehydrogenase I on an Electrode," *J. Am. Chem. Soc.*, 129:10328-10329 (2007).
Pasquinelli, "MicroRNAs and their targets: recognition, regulation and an emerging reciprocal relationship," *Nat. Rev. Genet.*, 13(4):271-282 (2012).
Passoth et al., "Molecular cloning of alcohol dehydrogenase genes of the yeast *Pichia stipitis* and identification of the fermentative ADH," *Yeast*, 14:1311-1323 (1998).
Paxton et al., "Role of branched-chain 2-oxo acid dehydrogenase and pyruvate dehydrogenase in 2-oxobutyrate metabolism," *Biochem. J.*, 234:295-303 (1986).

(56) References Cited

OTHER PUBLICATIONS

Pierce et al., "The complete genome sequence of Moorella thermoacetica (f. Clostridium thermoaceticum)," Environ. Microbiol., 10(10):2550-2573 (2008).
Poehlein et al., "An Ancient Pathway Combining Carbon Dioxide Fixation with the Generation and Utilization of a Sodium Ion Gradient for ATP Synthesis," PLoS One, 7(3):e33439 (2012).
Popp et al., "Fermentative Production of L-Glycerol 3-Phosphate Utilizing a Saccharomyces cerevisiae Strain With an Engineered Glycerol Biosynthetic Pathway," Biotechnol. Bioeng., 100:497-505 (2008).
Portnoy et al., "Aerobic Fermentation of D-Glucose by an Evolved Cytochrome Oxidase-Deficient Escherichia coli Strain," Appl. Environ. Microbiol., 74(24):7561-7569 (2008).
Pritchard et al., "A general model of error-prone PCR," J. Theor. Biol., 234:497-509 (2005).
Pritchett et al., "Genetic, physiological and biochemical characterization of multiple methanol methyltransferase isozymes in Methanosarcina acetivorans C2A," Mol. Microbiol., 56(5):1183-1194 (2005).
Pronk et al., "Pyruvate metabolism in Saccharomyces cerevisiae," Yeast, 12:1607-1633 (1996).
Ragsdale, "Life with Carbon Monoside," Crit. Rev. Biochem. Mol. Biol., 39:165-195 (2004).
Ragsdale et al., "Acetogenesis and the Wood-Ljungdahl Pathway of CO2 Fixation." Biochim. Biophys. Acta, 1784(12):1873-1898 (2008).
Rajpal et al., "A general method for greatly improving the affinity of antibodies by using combinatorial libraries," Proc. Natl. Acad. Sci. USA, 102:8466-8471 (2005).
Rakhely et al., "Cyanobacterial-Type, Heteropentameric, $NAD^+$-Reducing NiFe Hydrogenase in the Purple Sulfur Photosynthetic Bacterium Thiocapsa roseopersicina," Appl. Environ. Microbiol., 70(2):722-728 (2004).
Rangarajan et al., "Structure of [NiFe] Hydrogenase Maturation Protein HypE from Escherichia coli and Its Interaction with HypF," J. Bacter., 190(4):1447-1458 (2008).
Reda et al., "Reversible interconversion of carbon dioxide and formate by an electroactive enzyme," Proc. Natl. Acad. Sci. USA, 105:10654-10658 (2008).
Reetz et al., "Directed Evolution of an Enantioselective Enzyme through Combinatorial Multiple-Cassette Mutagenesis," Angew. Chem. Int. Ed. Engl., 40:3589-3591 (2001).
Reetz et al., "Iterative saturation mutagenesis (ISM) for rapid directed evolution of functional enzymes," Nat. Protocols, 2:891-903 (2007).
Reetz et al., "Iterative Saturation Mutagenesis on the Basis of B Factors as a Strategy for Increasing Protein Thermostability," Angew. Chem. Int. Ed. Engl., 45:7745-7751 (2006).
Reidhaar-Olson et al., "Combinatorial Cassette Mutagenesis as a Probe of the Informational Content of Protein Sequences," Science, 241:53-57 (1988).
Reidhaar-Olson et al., "Random Mutagenesis of Protein Sequences Using Oligonucleotide Cassettes," Methods Enzymol., 208:564-586 (1991).
Ringnér et al., "Folding free energies of 5'-UTRs impact post-transcriptional regulation on a genomic scale in yeast," PLoS Comput Biol., 1(7):e72 (2005).
Ro et al., "Dihydroxyacetone Synthase from a Methanol-Utilizing Carboxydobacterium, Acinetobacter sp. Strain JC1 DSM 3803," J. Bact., 179(19):6041-6047 (1997).
Russel et al., "Peptide Signals Encode Protein Localization," J. Bact., 189(21):7581-7585 (2007).
Sanchez et al., "Efficient succinic acid production from glucose through overexpression of pyruvate carboxylase in an Escherichia coli alcohol dehydrogenase and lactate dehydrogenase mutant," Biotechnol. Prog., 21(2):358-365 (2005).
Sass et al., "Folding of Fumarase during Mitochondrial Import Determines its Dual Targeting in Yeast," J. Biol. Chem., 278:45109-45116 (2003).

Sauer et al., "Methanol:coenzyme M methyltransferase from Methanosarcina barkeri. Zinc dependence and thermodynamics of the methanol:cob(I)alamin methyltransferase reaction," Eur. J. Biocehm., 243:670-677 (1997).
Sawers et al., "Characterization and Physiological Roles of Membrane-Bound Hydrogenase Isoenzymes from Salmonella typhimurium," J. Bacteriol., 168:398-404 (1986).
Sawers et al., "Differential Expression of Hydrogenase Isoenzymes in Escherichia coli K-12: Evidence for a Third Isoenzyme," J. Bacteriol., 164(3):1324-1331 (1985).
Sawers et al., "Purification and properties of membrane-bound hydrogenase isoenzyme 1 from anaerobically grown Escherichia coli K12," Eur. J. Biochem., 156:265-275 (1986).
Sawers, "The hydrogenases and formate dehydrogenases of Escherichia coli," Antonie van Leeuwenhoek, 66:57-88 (1994).
Schink et al., "The Membrane-Bound Hydrogenase of Alcaligenes Eutrophus," Biochim. Biophys, Acta, 567:315-324 (1979).
Schneider et al., "Purification and properties of soluble hydrogenase from Alcaligenes eutrophus H 16," Biochim. Biophys. Acta, 452:66-80 (1976).
Schreiner et al., "Pyruvate:Quinone Oxidoreductase in Corynebacterium glutamicum: Molecular Analysis of the pqo Gene, Significance of the Enzyme, and Phylogenetic Aspects," J. Bacteriol., 188:1341-1350 (2006).
Seedorf et al., "The genome of Clostridium kluyveri, a strict anaerobe with unique metabolic features," Proc. Natl. Acad. Sci. USA, 105(6):2128-2133 (2008).
Selifonova et al., "Rapid Evolution of Novel Traits in Microorganisms," Appl. Environ. Microbiol., 67:3645-3649 (2001).
Sen et al., "Developments in Directed Evolution for Improving Enzyme Functions," Appl. Biochem. Biotechnol., 143:212-223 (2007).
Shao et al., "Random-priming in vitro recombination: an effective tool for directed evolution," Nucleic Acids Res., 26(2):681-683 (1998).
Sheppard et al., "Purification and Properties of NADH-Dependent 5,10-Methylenetetrahydrofolate Reductase (MetF) from Escherichia coli," J. Bacteriol., 181(3):718-725 (1999).
Shimoyama et al., "MmcBC inPelotomaculum thermopropionicum represents a novel group of prokaryotic fumarases," FEMS Microbiol. Lett., 270:207-213 (2007).
Sieber et al., "Libraries of hybrid proteins related sequenc efrsom distantly," Nat. Biotechnol., 19:456-460 (2001).
Siebold et al., "A mechanism of covalent substrate binding in the x-ray structure of subunit K of the Escherichia coli dihydroxyacetone kinase," Proc. Natl. Acad. Sci. USA, 100(14):8188-8192 (2003).
Siegert et al., "Exchanging the substrate specificities of pyruvate decarboxylase from Zymomonas mobilis and benzoylformate decarboxylase from Pseudomonas putida," Prot. Eng. Des. Sel., 18:345-357 (2005).
Simanshu et al., "Structure and function of enzymes involved in the anaerobic degradation of L-threonine to propionate," J. Biosci., 32:1195-1206 (2007).
Simicevic et al., "DNA-centered approaches to characterize regulatory protein-DNA interaction complexes," Mol. Biosyst., 6(3):462-468 (2010).
Skarstedt et al., "Escherichia coli acetate kinase mechanism studied by net initial rate, equilibrium, and independent isotopic exchange kinetics," J. Biol. Chem., 251:6775-6783 (1976).
Smith et al., "Fumarate metabolism and the microaerophily of Campylobacter species," Int. J. Biochem. Cell. Biol., 31:961-975 (1999).
Soini et al., "High cell density media for Escherichia coli are generally designed for aerobic cultivations—consequences for large-scale bioprocesses and shake flask cultures," Microb. Call Fact., 7:26 (2008).
Speer et al., "Sequence of the gene for a NAD(P)-dependent formaldehyde dehydrogenase (class III alcohol dehydrogenase) from a marine methanotroph Methylobacter marinus A45," FEMS Microbiol. Lett., 121(3):349-355 (1994).
St. Maurice et al., "Flavodoxin:Quinone Reductase (FqrB): a Redox Partner of Pyruvate:Ferredoxin Oxidoreductase That Reversibly

(56) References Cited

OTHER PUBLICATIONS

Couples Pyruvate Oxidation to NADPH Production in Helicobacter pylori and Campylobacter jejuni," *J. Bacteriol.*, 189:4764-4773 (2007).
Steffan et al., "Isolation and Characterization of the Yeast Gene Encoding the MDH3 Isozyme of Malate Dehydrogenase," *J. Biol. Chem.*, 267:24708-24715 (1992).
Steinbuchel et al., "NAD-linked L(+)-lactate dehydrogenase from the strict aerobe alcaligenes eutrophus. 2. Kinetic properties and inhibition by oxaloacetate," *Eur. J. Biochem.*, 130:329-334 (1983).
Stemmer, "DNA shuffling by random fragmentation and reassembly: in vitro recombination for molecular evolution," *PRoc. Natil. Acad. Sci. USA*, 91:10747-10751 (1994).
Stemmer, "Rapid evolution of a protein in vitro by DNA shuffling," *Nature*, 370:389-391 (1994).
Stols et al., "Expression of Ascaris suum Malic Enzyme in a Mutant *Escherichia coli* Allows Production of Succinic Acid from Glucose," *Appl. Biochem. Biotechnol.*, 63-65:153-158 (1997).
Stols et al., "Production of Succinic Acid through Overexpression of NAD+-Dependent Malic Enzyme in an *Escherichia coli* Mutant," *Appl. Environ. Microbiol.*, 63(7):2695-2701 (1997).
Sunga et al., "The Pichia pastoris formaldehyde dehydrogenase gene (FLD1) as a marker for selection of multicopy expression strains of P. pastoris,"*Gene*, 330:39-47 (2004).
Sunohara et al., "Nascent-peptide-mediated ribosome stalling at a stop codon induces mRNA cleavage resulting in nonstop mRNA that is recognized by tmRNA," *RNA*, 10(3):378-386 (2004).
Sunohara et al., "Ribosome stalling during translation elongation induces cleavage of mRNA being translated in *Escherichia coli*," *J. Biol. Chem.*, 279(15):15368-15375 (2004).
Suzuki et al., "*Corynebacterium* sp. U-96 contains a cluster of genes of enzymes for the catabolism of sarcosine to pyruvate," *Bioci. Biotechnol. Biochem.*, 69(5):952-956 (2005).
Suzuki, "Phosphotransacetylase of *Escherichia coli* B, activation by pyruvate and inhibition by NADH and certain nucleotides," *bIOCHIM. bIOPHYS. aCTA*, 191:559-569 (1969).
Takacs et al., "Formate hydrogenlyase in the hyperthermophilic archaeon, Thermococcus litoralis," *BMC Microbiol.*, 8:88 (2008).
Takahashi et al., "Functional assignment of the ORF2-iscS-iscU-iscA-hscB-hscA-fdx-ORF3 gene cluster involved in the assembly of Fe—S clusters in *Escherichia coli*," *J. Biochem.*, 126:917-926 (1999).
Takahashi-Abbe et al., "Biochemical and functional properties of a pyruvate formate-lyase (PFL)-activating system in *Streptococcus mutans*," *Oral Micronoil. Immunol.*, 18:293-297 (2003).
Takeo, "Existence and Properties of Two Malle Enzymes in *Escherichia coli*: Especially of NAD-linked Enzyme," *J. Biochem.*, 66(3):379-387 (1969).
Tallant et al., "Coenzyme M Methylase Activity of the 480-Kilodalton Corrinoid Protein from Methanosarcina barkeri," *J. Bacteriol.*, 178:1295-1301 (1996).
Tallant et al., "Methylthiol:Coenzyme M Methyltransferase from Methanosarcina barkeri, an Enzyme of Methanogenesis from Dimethylsulfide and Methylmercaptopropionate," *J. Bacteriol.*, 179(22):6902-6911 (1997).
Tallant et al., "The MtsA Subunit of the Methylthiol:Coenzyme M Methyltransferase of Methanosarcina barkeri Catalyses Both Half-reactions of Corrinoid-dependent Dimethylsulfide: Coenzyme M Methyl Transfer," *J. Biol. Chem.*, 276(6):4485-4493 (2001).
Ter Schure et al., "Pyruvate decarboxylase catalyzes decarboxylation of branched-chain 2-oxo acids but is not essential for fuse1 alcohol production by *Saccharomyces cerevisiae.,*"*Appl. Environ. Microbiol.*, 64(4):1303-1307 (1998).
Todisco et al., "Identification of the Mitochondrial NAD+ Transporter in *Saccharomyces cerevisiae*,"*J. Biol. Chem.*, 281(3):1524-1531 (2006).
Tseng et al., "Oxygen- and Growth Rate-Dependent Regulation of *Escherichia coli* Fumarase (FumA, FumB, and FumC) Activity," *J. Bacteriol.*, 183:461-467 (2001).
Valdez-Hevia et al., "Isolation and characterization of the gene encoding phosphoenolpyruvate carboxykinase from *Saccharomyces cerevisiae*," *FEBS Lett.*, 258(2):313-316 (1989).
Van Maris et al., "Overproduction of Threonine Aldolase Circumvents the Biosynthetic Role of Pyruvate Decarboxylase in Glucose-Limited Chemostat Cultures of *Saccharomyces cerevisiae*," *Appl. Environ. Microbiol.*, 69(4):2094-2099 (2003).
Van Vliet et al., "The iron-induced ferredoxin FdxA of Campylobacter jejuni is involved in aerotolerance," *FEMS Microbiol. Letters*, 196:189-193 (2001).
Vardar-Schara et al., "Metabolically engineered bacteria for producing hydrogen via fermentation," *Microbial Biotechnology*, 1(2):107-125 (2008).
Volkov et al., "Random chimeragenesis by heteroduplex recombination," *Methods Enzymol.*, 328:456-463 (2000).
Volkov et al., "Recombination and chimeragenesis by in vitro heteroduplex formation and in vivo repair," *Nucleic Acids Res.*, 27(18):e18 (1999).
Vonck et al., "Electron microscopic analysis and biochemical characterization of a novel methanol dehydrogenase from the thermotolerant *Bacillus* sp. C1," *J. Biol. Chem.*, 266(6):3949-3954 (1991).
Vorholt et al., "Novel Formaldehyde-Activating Enzyme in Methylobacterium extorquens AM1 Required for Growth on Methanol," *J. Bacteriol.*, 182(23):6645-6650 (2000).
Walker et al., "Yeast pyruvate carboxylase: Identification of two genes encoding isoenzymes," *Biochem. Biophys. Res. Commun., Biochem. Biophys. Res. Comm.*, 176(3):1210-1217 (1991).
Wang et al., "Activation of Silent Genes by Transposons Tn5 and Tn10," *Genetics*, 120:875-885 (1988).
Wang et al., "NADP+ Reduction with Reduced Ferredoxin and NADP+ Reduction with NADH are Coupled via an Electron-Bifurcating Enzyme Complex in Clostridium kluyveri," *J. Bacteriol.*, 192(19):5115-5123 (2010).
Wang et al., "Overview of regulatory strategies and molecular elements in metabolic engineering of bacteria," *Mol. Biotechnol.*, 52(3):300-308 (2012).
Weidner et al., "Molecular Characterization of the Genes Encoding Pyruvate Formate-Lyase and Its Activating Enzyme of Clostridium pasteurianum," *J. Bacteriol.*, 178:2440-2444 (1996).
Whitehead et al., "Cloning and Expression in *Escherichia coli* of the Gene for 10-formyltetrahydrofolate synthetase from Clostridium acidiurici ("Clostridium acidi-urici")," *J. Bacteriol.*, 167(1):205-209 (1986).
Whitehead et al., "Nucleotide sequence of the Clostridium acidiurici ("Clostridium acidi-urici") gene for 10-formyltetrahydrofolate synthetase shows extensive amino acid homology with the trifunctional enzyme C1-tetrahydrofolate synthase from *Saccharomyces cerevisiae*," *J. Bacteriol.*, 170(7):3255-3261 (1988).
Wieland et al., "Engineering of ribozyme-based riboswitches for mammalian cells," *Methods*, 56(3):351-357 (2012).
Wong et al., "Molecular Properties of Pyruvate Formate-Lyase Activating Enzyme,"*Biochem.*, 32:14102-14110 (1993).
Wong et al., "Sequence saturation mutagenesis (SeSaM): a novel method for directed evolution," *Nucelic Acids Res.*, 32(3):e26 (2004).
Wong et al., "Sequence saturation mutagenesis with tunable mutation frequencies," *Anal. Biocehm.*, 341:187-189 (2005).
Wong et al., "Transversion-enriched sequence saturation mutagenesis (SeSaM-Tv+): A random mutagenesis method with consecutive nucleotide exchanges that complements the bias of error-prone PCR," *Biotechnol. J.*, 3:74-82 (2008).
Woods et al., "Two biochemically distinct classes of fumarase in *Escherichia coli*," *Biochium. Biophys. Acta*, 954:14-26 (1988).
Wu et al., "Life in Hot Carbon Monoxide: The Complete Genome Sequence of Carboxydothermus hydrogenoformans Z-2901," *PLoS Genet.*, 1(5):e65 (2005).
Yamamoto et al., "Carboxylation reaction catalyzed by 2-oxoglutarate:ferredoxin oxidoreductases from Hydrogenobacter thermophiles," *Extremophiles*, 14:79-85 (2010).
Yamamoto et al., "Purification and Properties of NADP-dependent Formate Dehydrogenase from Clostridium thermoaceticum, a TungstenSelenium-Iron Protein," *J. Biol. Chem.*, 258(3):1826-1832 (1983).

(56) References Cited

OTHER PUBLICATIONS

Yang et al., "Collaborative spirit of histone deacetylases in regulating chromatin structure and gene expression," *Curr. Opin. Genet. Dev.*, 13(2):143-453 (2003).

Yasueda et al., "Bacillus subtilis yckG and yckF Encode Two Key Enzymes of the Ribulose Monophosphate Pathway Used by Methylotrophs, and yckH is Required for Their Expression," *J. Bacteriol.*, 181(23):7154-7160 (1999).

Yim et al., "Metabolic engineering of *Escherichia coli* for direct production of 1,4-butanediol," *Nat. Chem. Biol.*, 7:445-452 (2011).

Yoon et al., "NADH:ferredoxin reductase and NAD-reducing hydrogenase activities in *Hydrogenobacter thermophilus* strain TK-6," *FEMS Microbiol. Letters*, 139:139-142 (1996).

Yuan et al., "Prokaryotic ubiquitin-like ThiS fusion enhances the heterologous protein overexpression and aggregation in *Escherichia coli*," *PLoS One*, 8(4):e62529 (2013).

Zhang et al., "Metabolic evolution of energy-conserving pathways for succinate production in *Escherichia coli*," *Proc. Natl. Acad. Sci. USA*, 106(48):20180-20185 (2009).

Zhao et al., "Molecular evolution by staggered extension process (StEP) in vitro recombination," *Nat. Biotechnol.*, 16(3):258-261 (1998).

Zhou et al., "Engineering a native homoethanol pathway in *Escherichia coli* B for ethanol production," *Biotechnol. Lett.*, 30:335-342 (2008).

Zhou et al., "Isolation, crystallization and preliminary X-ray analysis of a methanol-induced corrinoid protein from Moorella thermoacetica," *Acta Crystallogr.*, F61:537-540 (2005).

Zhou et al., "The remarkable structural and functional organization of the eukaryotic pyruvate dehydrogenase complexes," *Proc. Natl. Acad. Sci. USA*, 98(26):14802-14807 (2001).

Zhu et al., "A Mutant crp Allele That Differentially Activates the Operons of the fuc Regulon in *Escherichia coli*," *J. Bacteriol.*, 170:2352-2358 (1988).

Drake et al., "Physiology of the thermophilic acetogen Moorella thermoacetica," *Res. Microbiol.*, 155:869-883 (2004).

Vorholt, "Co-factor-dependent pathways of formaldehyde oxidation in methylotrophic bacteria," *Arch. Microbiol.*, 178(4):239-249 (2002).

\* cited by examiner

US 11,535,874 B2

MICROORGANISMS AND METHODS FOR ENHANCING THE AVAILABILITY OF REDUCING EQUIVALENTS IN THE PRESENCE OF METHANOL, AND FOR PRODUCING SUCCINATE RELATED THERETO

CROSS-REFERENCE TO RELATED APPLICATIONS

This application is a 371 national stage application of international application Serial No. PCT/US2013/065887 filed Oct. 21, 2013, which claims the benefit of U.S. Ser. No. 61/766,642 filed Feb. 19, 2013, and U.S. Ser. No. 61/717,001 filed Oct. 22, 2012, each of which is incorporated herein by reference in its entirety.

1. SUMMARY

Provided herein are methods generally relating to metabolic and biosynthetic processes and microbial organisms capable of producing organic compounds. Specifically, provided herein is a non-naturally occurring microbial organism (NNOMO) having a methanol metabolic pathway (MMP) that can enhance the availability of reducing equivalents in the presence of methanol and/or convert methanol to formaldehyde. Such NNOMOs and reducing equivalents can be used to increase the product yield of organic compounds produced by the microbial organism, such as succinate. Also provided herein are NNOMOs and methods thereof to produce optimal yields of succinate.

In a first aspect, provided herein is a NNOMO having a methanol metabolic pathway (MMP), wherein said organism comprises at least one exogenous nucleic acid encoding a MMP enzyme (MMPE) expressed in a sufficient amount to enhance the availability of reducing equivalents in the presence of methanol and/or convert methanol to formaldehyde. In certain embodiments, the MMP comprises one or more enzymes selected from the group consisting of a methanol methyltransferase (EM1); a methylenetetrahydrofolate reductase (EM2); a methylenetetrahydrofolate dehydrogenase (EM3); a methenyltetrahydrofolate cyclohydrolase (EM4); a formyltetrahydrofolate deformylase (EM5); a formyltetrahydrofolate synthetase (EM6); a formate hydrogen lyase (EM15); a hydrogenase (EM16); a formate dehydrogenase (EM8); a methanol dehydrogenase (EM9); a formaldehyde activating enzyme (EM10); a formaldehyde dehydrogenase (EM11); a S-(hydroxymethyl)glutathione synthase (EM12); a glutathione-dependent formaldehyde dehydrogenase (EM13); and an S-formylglutathione hydrolase (EM14). Such organisms advantageously allow for the production of reducing equivalents, which can then be used by the organism for the production of succinate using any one of the succinate pathways provided herein.

In one embodiment, the MMP comprises an EM9. In another embodiment, the MMP comprises an EM9 and an EM10. In other embodiments, the MMP comprises an EM1 and an EM2. In one embodiment, the MMP comprises an EM9, an EM3, an EM4 and an EM5. In another embodiment, the MMP comprises an EM9, an EM3, an EM4 and an EM6. In other embodiments, the MMP comprises an EM9 and an EM11. In another embodiment, the MMP comprises an EM9, an EM12, and EM13 and an EM14. In other embodiments, the MMP comprises an EM9, an EM13 and an EM14. In an embodiment, the MMP comprises an EM9, an EM10, an EM3, an EM4 and an EM5. In another embodiment, the MMP comprises an EM9, an EM10, an EM3, an EM4 and an EM6. In other embodiments, the MMP comprises an EM1, an EM2, an EM3, and EM4, and EM5. In one embodiment, the MMP comprises an EM1, an EM2, an EM3, an EM4 and EM6. In certain of the above embodiments, the MMP further comprises an EM8. In other of the above embodiments, the MMP further comprises and EM15. In yet other of the above embodiments, the MMP further comprises an EM16. In certain embodiments, the organism comprises two, three, four, five, six or seven exogenous nucleic acids, each encoding a MMPE.

In a second aspect, provided herein is a NNOMO having (1) a MMP, wherein said organism comprises at least one exogenous nucleic acid encoding a MMPE expressed in a sufficient amount to enhance the availability of reducing equivalents in the presence of methanol; and (2) a succinate pathway (SucP). In some embodiments, the organism further comprises at least one nucleic acid encoding a SucP enzyme (SucPE) expressed in a sufficient amount to produce succinate. In some embodiments, the nucleic acid is an exogenous nucleic acid. In other embodiments, the nucleic acid is an endogenous nucleic acid. In certain embodiments, the SucPE is selected from the group consisting of a phosphoenolpyruvate (PEP) carboxylase (ES1A) or a PEP carboxykinase (ES1B); a pyruvate carboxylase (ES2); a malate dehydrogenase (ES3); a malic enzyme (ES4); a fumarase (ES5); and a fumarate reductase (ES6).

In one embodiment, the SucP comprises an ES1A, an ES3, and ES5 and an ES6. In another embodiment, the SucP comprises an ES1B, an ES3, and ES5 and an ES6. In other embodiments, the SucP comprises an ES2, an ES3, and ES5 and an ES6. In another embodiment, the SucP comprises and ES4, ES5 and ES6.

In other embodiments, the organism having a MMP, either alone or in combination with a SucP, as provided herein, further comprises a formaldehyde assimilation pathway (FAP) that utilizes formaldehyde, e.g., obtained from the oxidation of methanol, in the formation of intermediates of certain central metabolic pathways that can be used, for example, in the formation of biomass. In certain embodiments, the organism further comprises a FAP, wherein said organism comprises at least one exogenous nucleic acid encoding a formaldehyde assimilation pathway enzyme (FAPE) expressed in a sufficient amount to produce an intermediate of glycolysis and/or a metabolic pathway that can be used in the formation of biomass. In one embodiment, the FAPE is expressed in a sufficient amount to produce an intermediate of glycolysis. In another embodiment, the FAPE is expressed in a sufficient amount to produce an intermediate of a metabolic pathway that can be used in the formation of biomass. In some of the embodiments, the FAP comprises a hexulose-6-phosphate (H6P) synthase (EF1), a 6-phospho-3-hexuloisomerase (EF2), a dihydroxyacetone (DHA) synthase (EF3) or a DHA kinase (EF4). In one embodiment, the FAP comprises an EF1 and an EF2. In one embodiment, the FAP comprises an EF1 and an EF2. In one embodiment, the intermediate is a H6P, a fructose-6-phosphate (F6P), or a combination thereof. In other embodiments, the FAP comprises an EF3 or an EF4. In one embodiment, the intermediate is a DHA, a DHA phosphate (DHAP), or a combination thereof. In certain embodiments, the organism comprises two exogenous nucleic acids, each encoding a FAPE.

In certain embodiments, provided herein is a NNOMO having a MMP, wherein said organism comprises at least one exogenous nucleic acid encoding an EM9 expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP. In certain embodiments, the organism further comprises at least one exogenous nucleic acid encoding a FAPE expressed in a sufficient amount to produce an intermediate of glycolysis. In certain embodiments, the FAPE is selected from the group consisting of an EF1, an EF2, an EF3 and an EF4.

In certain embodiments, at least one exogenous nucleic acid is a heterologous nucleic acid. In some embodiments, the organism is in a substantially anaerobic culture medium. In some embodiments, the microbial organism is a species of bacteria, yeast, or fungus.

In some embodiments, the organism further comprises one or more gene disruptions, occurring in one or more endogenous genes encoding protein(s) or enzyme(s) involved in native production of ethanol, glycerol, acetate, lactate, formate, $CO_2$, and/or amino acids by said microbial organism, wherein said one or more gene disruptions confer increased production of succinate in said microbial organism. In some embodiments, one or more endogenous enzymes involved in native production of ethanol, glycerol, acetate, lactate, formate, $CO_2$ and/or amino acids by the microbial organism, has attenuated enzyme activity or expression levels. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In another aspect, provided herein is a method of producing formaldehyde, comprising culturing a NNOMO provided herein under conditions and for a sufficient period of time to produce formaldehyde. In certain embodiment, the NNOMO comprises an exogenous nucleic acid encoding an EM9. In certain embodiments, the formaldehyde is consumed to provide a reducing equivalent. In other embodiments, the formaldehyde is consumed to incorporate into succinate or another target product.

In another aspect, provided herein is a method of producing an intermediate of glycolysis and/or a metabolic pathway that can be used in the formation of biomass, comprising culturing a NNOMO provided herein under conditions and for a sufficient period of time to produce the intermediate In certain embodiment, the NNOMO comprises an exogenous nucleic acid encoding an EM9. In certain embodiments, the formaldehyde is consumed to provide a reducing equivalent. In other embodiments, the formaldehyde is consumed to incorporate into succinate or another target product.

In other aspects, provided herein are methods for producing succinate, comprising culturing any one of the NNOMOs comprising a MMP and a SucP provided herein under conditions and for a sufficient period of time to produce succinate. In certain embodiments, the organism is cultured in a substantially anaerobic culture medium.

2. BRIEF DESCRIPTION OF THE DRAWINGS

FIG. 1 shows exemplary metabolic pathways enabling the extraction of reducing equivalents from methanol. The enzymatic transformations shown are carried out by the following enzymes: 1A) a methanol methyltransferase (EM1), 1B) a methylenetetrahydrofolate reductase (EM2), 1C) a methylenetetrahydrofolate dehydrogenase (EM3), 1D) a methenyltetrahydrofolate cyclohydrolase (EM4), 1E) a formyltetrahydrofolate deformylase (EM5), 1F) a formyltetrahydrofolate synthetase (EM6), 1G) a formate hydrogen lyase (EM15), 1H) a hydrogenase (EM16), 1I) a formate dehydrogenase (EM8), 1J) a methanol dehydrogenase (EM9), 1K) a formaldehyde activating enzyme (EM10), 1L) a formaldehyde dehydrogenase (EM11), 1M) a S-(hydroxymethyl)glutathione synthase (EM12), 1N) a glutathione-dependent formaldehyde dehydrogenase (EM13), and 1O) a S-formylglutathione hydrolase (EM14). In certain embodiments, steps K and/or M are spontaneous.

FIG. 2 shows exemplary SucPs, which can be used to increase succinate yields from carbohydrates when reducing equivalents produced by a MMP provided herein are available. For example, pathways for the production of succinate from glucose, $CO_2$, and reducing equivalents (e.g., MeOH) at a theoretical yield of 2.0 mol succinate/mol glucose are provided. The enzymatic transformations shown are carried out by the following enzymes: 2A) a PEP carboxylase (ES1A) or a PEP carboxykinase (ES1B); 2B) a pyruvate carboxylase (ES2); 2C) a malate dehydrogenase (ES3); 2D) a malic enzyme (ES4); 2E) a fumarase (ES5); and 2F) a fumarate reductase (ES6). Succinate production can be carried out by 2A, 2C, 2E and 2F; 2B, 2C, 2E and 2F; or 2D, 2E and 2F.

3. DETAILED DESCRIPTION

3.1 Definitions

Figure 1:
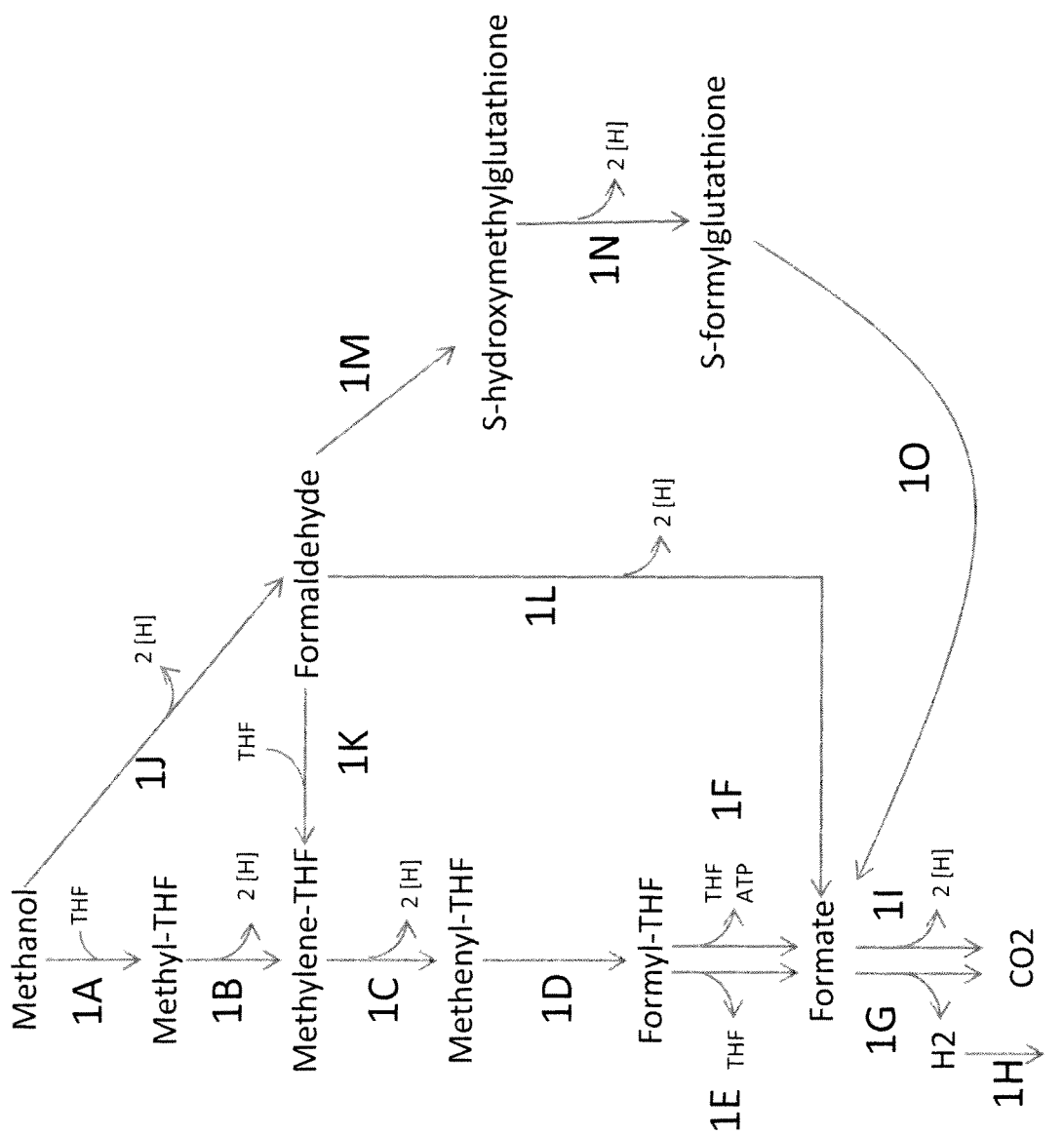

As used herein, the term "non-naturally occurring" when used in reference to a microbial organism or microorganism provided herein is intended to mean that the microbial organism has at least one genetic alteration not normally found in a naturally occurring strain of the referenced species, including wild-type strains of the referenced species. Genetic alterations include, for example, modifications introducing expressible nucleic acids encoding metabolic polypeptides, other nucleic acid additions, nucleic acid deletions and/or other functional disruption of the microbial organism's genetic material. Such modifications include, for example, coding regions and functional fragments thereof, for heterologous, homologous or both heterologous and homologous polypeptides for the referenced species. Additional modifications include, for example, non-coding regulatory regions in which the modifications alter expression of a gene or operon. Exemplary metabolic polypeptides include enzymes or proteins within a succinate biosynthetic pathway.

As used herein, "succinate" is the ionized form of succinic acid (IUPAC name butanedioic acid), and it is understood that succinate and succinic acid can be used interchangeably throughout to refer to the compound in any of its neutral or ionized forms, including any salt forms thereof. It is understood by those skilled understand that the specific form will depend on the pH. The chemical structure of succinic acid is shown below:

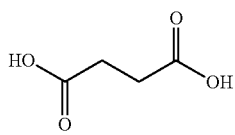

A metabolic modification refers to a biochemical reaction that is altered from its naturally occurring state. Therefore, NNOMOs can have genetic modifications to nucleic acids encoding metabolic polypeptides, or functional fragments thereof. Exemplary metabolic modifications are disclosed herein.

As used herein, the term "isolated" when used in reference to a microbial organism is intended to mean an organism that is substantially free of at least one component as the referenced microbial organism is found in nature. The term includes a microbial organism that is removed from some or all components as it is found in its natural environment. The term also includes a microbial organism that is removed from some or all components as the microbial organism is found in non-naturally occurring environments. Therefore, an isolated microbial organism is partly or completely separated from other substances as it is found in nature or as it is grown, stored or subsisted in non-naturally occurring environments. Specific examples of isolated microbial organisms include partially pure microbes, substantially pure microbes and microbes cultured in a medium that is non-naturally occurring.

As used herein, the terms "microbial," "microbial organism" or "microorganism" are intended to mean any organism that exists as a microscopic cell that is included within the domains of archaea, bacteria or eukarya. Therefore, the term is intended to encompass prokaryotic or eukaryotic cells or organisms having a microscopic size and includes bacteria, archaea and eubacteria of all species as well as eukaryotic microorganisms such as yeast and fungi. The term also includes cell cultures of any species that can be cultured for the production of a biochemical.

As used herein, the term "CoA" or "coenzyme A" is intended to mean an organic cofactor or prosthetic group (nonprotein portion of an enzyme) whose presence is required for the activity of many enzymes (the apoenzyme) to form an active enzyme system. Coenzyme A functions in certain condensing enzymes, acts in acetyl or other acyl group transfer and in fatty acid synthesis and oxidation, pyruvate oxidation and in other acetylation.

As used herein, the term "substantially anaerobic" when used in reference to a culture or growth condition is intended to mean that the amount of oxygen is less than about 10% of saturation for dissolved oxygen in liquid media. The term also is intended to include sealed chambers of liquid or solid medium maintained with an atmosphere of less than about 1% oxygen.

As used herein, the term "gene disruption," or grammatical equivalents thereof, is intended to mean a genetic alteration that renders the encoded gene product inactive or attenuated. The genetic alteration can be, for example, deletion of the entire gene, deletion of a regulatory sequence required for transcription or translation, deletion of a portion of the gene which results in a truncated gene product, or by any of various mutation strategies that inactivate or attenuate the encoded gene product. One particularly useful method of gene disruption is complete gene deletion because it reduces or eliminates the occurrence of genetic reversions in the NNOMOs provided herein. A gene disruption also includes a null mutation, which refers to a mutation within a gene or a region containing a gene that results in the gene not being transcribed into RNA and/or translated into a functional gene product. Such a null mutation can arise from many types of mutations including, for example, inactivating point mutations, deletion of a portion of a gene, entire gene deletions, or deletion of chromosomal segments. The phenotypic effect of a gene disruption can be a null mutation, which can arise from many types of mutations including inactivating point mutations, entire gene deletions, and deletions of chromosomal segments or entire chromosomes. Specific antisense nucleic acid compounds and enzyme inhibitors, such as antibiotics, can also produce null mutant phenotype, therefore being equivalent to gene disruption.

As used herein, the term "growth-coupled" when used in reference to the production of a biochemical product is intended to mean that the biosynthesis of the referenced biochemical product is produced during the growth phase of a microorganism. In a particular embodiment, the growth-coupled production can be obligatory, meaning that the biosynthesis of the referenced biochemical is an obligatory product produced during the growth phase of a microorganism. The term "growth-coupled" when used in reference to the consumption of a biochemical is intended to mean that the referenced biochemical is consumed during the growth phase of a microorganism.

As used herein, the term "attenuate," or grammatical equivalents thereof, is intended to mean to weaken, reduce or diminish the activity or amount of an enzyme or protein. Attenuation of the activity or amount of an enzyme or protein can mimic complete disruption if the attenuation causes the activity or amount to fall below a critical level required for a given pathway to function. However, the attenuation of the activity or amount of an enzyme or protein that mimics complete disruption for one pathway, can still be sufficient for a separate pathway to continue to function. For example, attenuation of an endogenous enzyme or protein can be sufficient to mimic the complete disruption of the same enzyme or protein for production of a fatty alcohol, fatty aldehyde or fatty acid product provided herein, but the remaining activity or amount of enzyme or protein can still be sufficient to maintain other pathways, such as a pathway that is critical for the microbial organism to survive, reproduce or grow. Attenuation of an enzyme or protein can also be weakening, reducing or diminishing the activity or amount of the enzyme or protein in an amount that is sufficient to increase yield of a fatty alcohol, fatty aldehyde or fatty acid product provided herein, but does not necessarily mimic complete disruption of the enzyme or protein.

"Exogenous" as it is used herein is intended to mean that the referenced molecule or the referenced activity is introduced into the host microbial organism. The molecule can be introduced, for example, by introduction of an encoding nucleic acid into the host genetic material such as by integration into a host chromosome or as non-chromosomal genetic material such as a plasmid. Therefore, the term as it is used in reference to expression of an encoding nucleic acid refers to introduction of the encoding nucleic acid in an expressible form into the microbial organism. When used in reference to a biosynthetic activity, the term refers to an activity that is introduced into the host reference organism. The source can be, for example, a homologous or heterologous encoding nucleic acid that expresses the referenced activity following introduction into the host microbial organism. Therefore, the term "endogenous" refers to a referenced molecule or activity that is present in the host. Similarly, the term when used in reference to expression of an encoding nucleic acid refers to expression of an encoding nucleic acid contained within the microbial organism. The term "heterologous" refers to a molecule or activity derived from a source other than the referenced species whereas "homologous" refers to a molecule or activity derived from the host microbial organism. Accordingly, exogenous expression of an encoding nucleic acid provided herein can utilize either or both a heterologous or homologous encoding nucleic acid.

It is understood that when more than one nucleic acid is included in a microbial organism that the more than one nucleic acids refers to the referenced encoding nucleic acid or biosynthetic activity, as discussed above. In some embodiments, the nucleic acid is an exogenous nucleic acid. In other embodiments, the nucleic acid is an endogenous nucleic acid. It is further understood, as disclosed herein, that such more than one exogenous nucleic acids can be introduced into the host microbial organism on separate nucleic acid molecules, on polycistronic nucleic acid molecules, or a combination thereof, and still be considered as more than one exogenous nucleic acid. For example, as disclosed herein a microbial organism can be engineered to express two or more exogenous nucleic acids encoding a desired pathway enzyme or protein. In the case where two exogenous nucleic acids encoding a desired activity are introduced into a host microbial organism, it is understood that the two exogenous nucleic acids can be introduced as a single nucleic acid, for example, on a single plasmid, on separate plasmids, can be integrated into the host chromosome at a single site or multiple sites, and still be considered as two exogenous nucleic acids. Similarly, it is understood that more than two exogenous nucleic acids can be introduced into a host organism in any desired combination, for example, on a single plasmid, on separate plasmids, can be integrated into the host chromosome at a single site or multiple sites, and still be considered as two or more exogenous nucleic acids, for example three exogenous nucleic acids. Thus, the number of referenced exogenous nucleic acids or biosynthetic activities refers to the number of encoding nucleic acids or the number of biosynthetic activities, not the number of separate nucleic acids introduced into the host organism.

The NNOMOs provided herein can contain stable genetic alterations, which refers to microorganisms that can be cultured for greater than five generations without loss of the alteration. Generally, stable genetic alterations include modifications that persist greater than 10 generations, particularly stable modifications will persist more than about 25 generations, and more particularly, stable genetic modifications will be greater than 50 generations, including indefinitely.

Those skilled in the art will understand that the genetic alterations, including metabolic modifications exemplified herein, are described with reference to a suitable host organism such as *E. coli* and their corresponding metabolic reactions or a suitable source organism for desired genetic material such as genes for a desired metabolic pathway. However, given the complete genome sequencing of a wide variety of organisms and the high level of skill in the area of genomics, those skilled in the art will readily be able to apply the teachings and guidance provided herein to essentially all other organisms. For example, the *E. coli* metabolic alterations exemplified herein can readily be applied to other species by incorporating the same or analogous encoding nucleic acid from species other than the referenced species. Such genetic alterations include, for example, genetic alterations of species homologs, in general, and in particular, orthologs, paralogs or nonorthologous gene displacements.

An ortholog is a gene or genes that are related by vertical descent and are responsible for substantially the same or identical functions in different organisms. For example, mouse epoxide hydrolase and human epoxide hydrolase can be considered orthologs for the biological function of hydrolysis of epoxides. Genes are related by vertical descent when, for example, they share sequence similarity of sufficient amount to indicate they are homologous, or related by evolution from a common ancestor. Genes can also be considered orthologs if they share three-dimensional structure but not necessarily sequence similarity, of a sufficient amount to indicate that they have evolved from a common ancestor to the extent that the primary sequence similarity is not identifiable. Genes that are orthologous can encode proteins with sequence similarity of about 25% to 100% amino acid sequence identity. Genes encoding proteins sharing an amino acid similarity less that 25% can also be considered to have arisen by vertical descent if their three-dimensional structure also shows similarities. Members of the serine protease family of enzymes, including tissue plasminogen activator and elastase, are considered to have arisen by vertical descent from a common ancestor.

Orthologs include genes or their encoded gene products that through, for example, evolution, have diverged in structure or overall activity. For example, where one species encodes a gene product exhibiting two functions and where such functions have been separated into distinct genes in a second species, the three genes and their corresponding products are considered to be orthologs. For the production of a biochemical product, those skilled in the art will understand that the orthologous gene harboring the metabolic activity to be introduced or disrupted is to be chosen for construction of the NNOMO. An example of orthologs exhibiting separable activities is where distinct activities have been separated into distinct gene products between two or more species or within a single species. A specific example is the separation of elastase proteolysis and plasminogen proteolysis, two types of serine protease activity, into distinct molecules as plasminogen activator and elastase. A second example is the separation of *mycoplasma* 5'-3' exonuclease and *Drosophila* DNA polymerase III activity. The DNA polymerase from the first species can be considered an ortholog to either or both of the exonuclease or the polymerase from the second species and vice versa.

In contrast, paralogs are homologs related by, for example, duplication followed by evolutionary divergence and have similar or common, but not identical functions. Paralogs can originate or derive from, for example, the same species or from a different species. For example, microsomal epoxide hydrolase (epoxide hydrolase I) and soluble epoxide hydrolase (epoxide hydrolase II) can be considered paralogs because they represent two distinct enzymes, co-evolved from a common ancestor, that catalyze distinct reactions and have distinct functions in the same species. Paralogs are proteins from the same species with significant sequence similarity to each other suggesting that they are homologous, or related through co-evolution from a common ancestor. Groups of paralogous protein families include HipA homologs, luciferase genes, peptidases, and others.

A nonorthologous gene displacement is a nonorthologous gene from one species that can substitute for a referenced gene function in a different species. Substitution includes, for example, being able to perform substantially the same or a similar function in the species of origin compared to the referenced function in the different species. Although generally, a nonorthologous gene displacement will be identifiable as structurally related to a known gene encoding the referenced function, less structurally related but functionally similar genes and their corresponding gene products nevertheless will still fall within the meaning of the term as it is used herein. Functional similarity requires, for example, at least some structural similarity in the active site or binding region of a nonorthologous gene product compared to a gene encoding the function sought to be substituted. Therefore, a nonorthologous gene includes, for example, a paralog or an unrelated gene.

Therefore, in identifying and constructing the NNOMOs provided herein having succinate biosynthetic capability, those skilled in the art will understand with applying the teaching and guidance provided herein to a particular species that the identification of metabolic modifications can include identification and inclusion or inactivation of orthologs. To the extent that paralogs and/or nonorthologous gene displacements are present in the referenced microorganism that encode an enzyme catalyzing a similar or substantially similar metabolic reaction, those skilled in the art also can utilize these evolutionarily related genes.

Orthologs, paralogs and nonorthologous gene displacements can be determined by methods well known to those skilled in the art. For example, inspection of nucleic acid or amino acid sequences for two polypeptides will reveal sequence identity and similarities between the compared sequences. Based on such similarities, one skilled in the art can determine if the similarity is sufficiently high to indicate the proteins are related through evolution from a common ancestor. Algorithms well known to those skilled in the art, such as Align, BLAST, Clustal W and others compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 25% to 100% sequence identity. Proteins that are unrelated can have an identity which is essentially the same as would be expected to occur by chance, if a database of sufficient size is scanned (about 5%). Sequences between 5% and 24% may or may not represent sufficient homology to conclude that the compared sequences are related. Additional statistical analysis to determine the significance of such matches given the size of the data set can be carried out to determine the relevance of these sequences.

Exemplary parameters for determining relatedness of two or more sequences using the BLAST algorithm, for example, can be as set forth below. Briefly, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

3.2 Microbial Organisms that Utilize Reducing Equivalents Produced by the Metabolism of Methanol Provided herein are MMPs engineered to improve the availability of reducing equivalents, which can be used for the production of product molecules. Exemplary product molecules include, without limitation, succinate, although given the teachings and guidance provided herein, it will be recognized by one skilled in the art that any product molecule that utilizes reducing equivalents in its production can exhibit enhanced production through the biosynthetic pathways provided herein.

Methanol is a relatively inexpensive organic feedstock that can be derived from synthesis gas components, CO and $H_2$, via catalysis. Methanol can be used as a source of reducing equivalents to increase the molar yield of product molecules from carbohydrates.

Succinate is a compound of commercial interest due to its use as a precursor to commodity chemicals in the food, pharmaceutical, detergent and polymer industries. Biological succinate production is also a green process where the greenhouse gas $CO_2$ must be fixed into succinate during sugar fermentation.

Despite efforts to develop bacterial strains producing increased succinate yields, many approaches previously employed have several drawbacks which hinder applicability in commercial settings. For example, many such strains generally are unstable in commercial fermentation processes due to selective pressures favoring the unaltered or wild-type parental counterparts.

Thus, there exists a need for microorganisms having commercially beneficial characteristics of increased production of succinate. The present invention satisfies this need and provides related advantages as well.

Accordingly, provided herein is bioderived succinate produced according to the methods described herein and biobased products comprising or obtained using the bioderived succinate. The biobased product can comprise at least 5%, at least 10%, at least 20%, at least 30%, at least 40% or at least 50% bioderived succinate. The biobased product can comprises a portion of said bioderived succinate as a repeating unit. The biobased product can be a molded product obtained by molding the biobased product.

Figure 2:
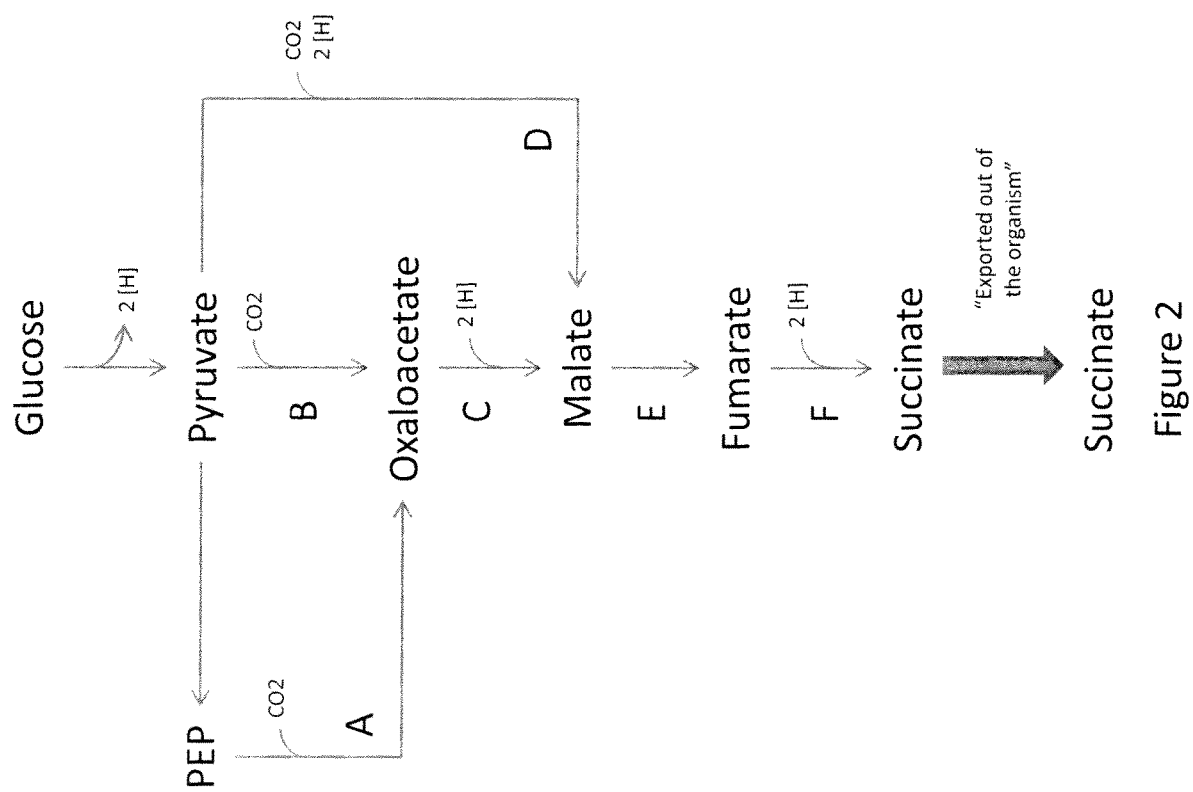

In numerous engineered pathways, realization of maximum product yields based on carbohydrate feedstock is hampered by insufficient reducing equivalents or by loss of reducing equivalents to byproducts. Methanol is a relatively inexpensive organic feedstock that can be used to generate reducing equivalents by employing one or more methanol metabolic enzymes as shown in FIG. 1. The reducing equivalents produced by the metabolism of methanol by one or more of the MMPs can then be used to power the glucose to succinate production pathways, for example, as shown in FIG. 2.

The product yields per C-mol of substrate of microbial cells synthesizing reduced fermentation products such as succinate are limited by insufficient reducing equivalents in the carbohydrate feedstock. Reducing equivalents, or electrons, can be extracted from methanol using one or more of the enzymes described in FIG. 1. The reducing equivalents are then passed to acceptors such as oxidized ferredoxins, oxidized quinones, oxidized cytochromes, NAD(P)+, water, or hydrogen peroxide to form reduced ferredoxin, reduced quinones, reduced cytochromes, NAD(P)H, $H_2$, or water, respectively. Reduced ferredoxin, reduced quinones and NAD(P)H are particularly useful as they can serve as redox carriers for various Wood-Ljungdahl pathway, reductive TCA cycle, or product pathway enzymes.

Specific examples of how additional redox availability from methanol can improve the yield of reduced products such as succinate are shown.

Succinate can be produced solely from sugars such as glucose and $CO_2$ with a maximum theoretical yield of 1.71 mol succinate/mol glucose or 1.12 g/g.

$$7C_6H_{12}O_6+6CO_2=12C_4H_6O_4+6H_2O$$

Identical or similar g/g yields are achievable on other carbohydrates (for example, xylose and arabinose).

$$8.4C_5H_{10}O_5+6CO_2=12C_4H_6O_4+6H_2O$$

Alternatively, assuming that an ample source of reducing equivalents (for example, CO or $H_2$) is present, succinate can be produced completely from CO or $CO_2$ via the reductive TCA (rTCA) cycle, associated anapleurotic reactions, and enzymes for the extraction of reducing equivalents from CO and/or $H_2$.

$$7CO+3H_2O=C_4H_6O_4+3CO_2$$

$$7H_2+4CO_2=C_4H_6O_4+4H_2O$$

When both feedstocks of sugar and methanol are available, the methanol can be utilized to generate reducing equivalents by employing one or more of the enzymes shown in FIG. 1. The reducing equivalents generated from methanol can be utilized to power the glucose to succinate production pathways, e.g., as shown in FIG. 2. Theoretically, all carbons in glucose will be conserved, thus resulting in a maximal theoretical yield to produce succinate from glucose at 2 mol succinate per mol of glucose under either aerobic or anaerobic conditions as shown in FIG. 2:

$$C_6H_{12}O_6+0.667CH_3OH+1.333CO_2 \rightarrow 2C_4H_6O_4+1.333H_2O$$

Supplementing carbohydrate feeds with external reducing equivalents is an attractive option for production of succinate through the reductive TCA cycle. A reductive TCA SucP is particularly useful for the engineering of a eukaryotic organism (e.g., *Saccharomyces cerevisiae*) for the production of succinate, as reactions associated with the conversion of oxaloacetate to alpha-ketoglutarate or pyruvate to acetyl-CoA are not required. Eukaryotic organisms are advantaged over some bacterial species (e.g., *Escherichia coli*) in that they can tolerate lower pH conditions. Production of succinate at a pH lower than the pKa's of the acid groups ($pK_{a1}$=4.2, $pK_{a2}$=5.6) is desirable since a higher percentage of final product will be in the acid form (i.e., succinic acid) and not the salt form.

A major challenge associated with engineering a eukaryotic organism to achieve a high yield of succinate from carbohydrates alone is that several requisite enzymes are not exclusively localized to the cytosol. In fact, enzymes such as pyruvate dehydrogenase and citrate synthase are predominantly mitochondrial or peroxisomal. Thus, engineering a eukaryotic organism to achieve a high yield of succinate would require shuttling of metabolic precursors across cellular compartments or extensive strain engineering to localize several of the requisite enzymes to one compartment, preferably the cytosol. This embodiment provides a means of simplifying the pathway engineering by limiting the number of TCA cycle enzymes that are required to carry high flux. One can thus envision the development of a succinate producing microorganism in which most, if not all, of the enzymes in FIG. 1 are cytosolic.

In a first aspect, provided herein is a NNOMO having a MMP, wherein said organism comprises at least one exogenous nucleic acid encoding a MMPE expressed in a sufficient amount to enhance the availability of reducing equivalents in the presence of methanol. In other embodiments, the MMPE is expressed in a sufficient amount to convert methanol to formaldehyde. In certain embodiments, the MMP comprises one or more enzymes selected from the group consisting of an EM1; an EM2; an EM3; an EM4; an EM5; an EM6; an EM15; an EM16; an EM8; an EM9; an EM10; an EM11; an EM12; an EM13; and an EM14. Such organisms, in certain embodiments, advantageously allow for the production of reducing equivalents, which can then be used by the organism for the production of succinate using any one of the SucPs provided herein.

In certain embodiments, the MMP comprises 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, and 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is an EM10; 1L is an EM11; 1M is an EM12; 1N is EM13; and 1O is EM14. In some embodiments, 1K is spontaneous. In other embodiments, 1K is an EM10. In some embodiments, 1M is spontaneous. In other embodiments, 1M is an EM12.

In one embodiment, the MMP comprises 1A. In another embodiment, the MMP comprises 1B. In another embodiment, the MMP comprises 1C. In yet another embodiment, the MMP comprises 1D. In one embodiment, the MMP comprises 1E. In another embodiment, the MMP comprises 1F. In another embodiment, the MMP comprises 1G. In yet another embodiment, the MMP comprises 1H. In one embodiment, the MMP comprises 1I. In another embodiment, the MMP comprises 1J. In another embodiment, the MMP comprises 1K. In yet another embodiment, the MMP comprises 1L. In yet another embodiment, the MMP comprises 1M. In another embodiment, the MMP comprises 1N. In yet another embodiment, the MMP comprises 1O. Any combination of two, three, four, five, six, seven, eight, nine, ten, eleven, twelve, thirteen, fourteen or fifteen MMPEs 1A, 1B, 1C, 1D, 1E, 1F, 1G, 1H, 1I, 1J, 1K, 1L, 1M, 1N, and 1O is also contemplated.

In some embodiments, the MMP is a MMP depicted in FIG. 1.

In one aspect, provided herein is a NNOMO having a MMP, wherein said organism comprises at least one exogenous nucleic acid encoding a MMPE expressed in a sufficient amount to enhance the availability of reducing equivalents in the presence of methanol, wherein said MMP comprises: (i) 1A and 1B, (ii) 1J; or (iii) 1J and 1K. In one embodiment, the MMP comprises 1A and 1B. In another embodiment, the MMP comprises 1J. In one embodiment, the MMP comprises 1J and 1K. In certain embodiments, the MMP comprises 1A, 1B, 1C, 1D, and 1E. In some embodiments, the MMP comprises 1A, 1B, 1C, 1D and 1F. In some embodiments, the MMP comprises 1J, 1C, 1D and 1E. In one embodiment, the MMP comprises 1J, 1C, 1D and 1F. In another embodiment, the MMP comprises 1J and 1L. In yet another embodiment, the MMP comprises 1J, 1M, 1N and 1O. In certain embodiments, the MMP comprises 1J, 1N and 1O. In some embodiments, the MMP comprises 1J, 1K, 1C, 1D and 1E. In one embodiment, the MMP comprises 1J, 1K, 1C, 1D and 1F. In some embodiments, 1K is spontaneous. In other embodiments, 1K is an EM10. In some embodiments, 1M is spontaneous. In other embodiments, 1M is an EM12.

In certain embodiments, the MMP comprises 1I. In certain embodiments, the MMP comprises 1A, 1B, 1C, 1D, 1E and 1I. In some embodiments, the MMP comprises 1A, 1B, 1C, 1D, 1F and 1I. In some embodiments, the MMP comprises 1J, 1C, 1D, 1E and 1I. In one embodiment, the MMP comprises 1J, 1C, 1D, 1F and 1I. In another embodiment, the MMP comprises 1J, 1L and 1I. In yet another embodiment, the MMP comprises 1J, 1M, 1N, 1O and 1I. In certain embodiments, the MMP comprises 1J, 1N, 1O and 1I. In some embodiments, the MMP comprises 1J, 1K, 1C, 1D, 1E and 1I. In one embodiment, the MMP comprises 1J, 1K, 1C, 1D, 1F and 1I. In some embodiments, 1K is spontaneous. In other embodiments, 1K is an EM10. In some embodiments, 1M is spontaneous. In other embodiments, 1M is an EM12.

In certain embodiments, the MMP comprises 1G. In certain embodiments, the MMP comprises 1A, 1B, 1C, 1D, 1E and 1G. In some embodiments, the MMP comprises 1A, 1B, 1C, 1D, 1F and 1G. In some embodiments, the MMP comprises 1J, 1C, 1D, 1E and 1G. In one embodiment, the MMP comprises 1J, 1C, 1D, 1F and 1G. In another embodiment, the MMP comprises 1J, 1L and 1G. In yet another embodiment, the MMP comprises 1J, 1M, 1N, 1O and 1G. In certain embodiments, the MMP comprises 1J, 1N, 1O and 1G. In some embodiments, the MMP comprises 1J, 1K, 1C, 1D, 1E and 1G. In one embodiment, the MMP comprises 1J, 1K, 1C, 1D, 1F and 1G. In some embodiments, 1K is spontaneous. In other embodiments, 1K is an EM10. In some embodiments, 1M is spontaneous. In other embodiments, 1M is an EM12.

In certain embodiments, the MMP comprises 1G and 1H. In certain embodiments, the MMP comprises 1A, 1B, 1C, 1D, 1E, 1G and 1H. In some embodiments, the MMP comprises 1A, 1B, 1C, 1D, 1F, 1G and 1H. In some embodiments, the MMP comprises 1J, 1C, 1D, 1E, 1G and 1H. In one embodiment, the MMP comprises 1J, 1C, 1D, 1F, 1G and 1H. In another embodiment, the MMP comprises 1J, 1L, 1G and 1H. In yet another embodiment, the MMP comprises 1J, 1M, 1N, 1O, 1G and 1H. In certain embodiments, the MMP comprises 1J, 1N, 1O, 1G and 1H. In some embodiments, the MMP comprises 1J, 1K, 1C, 1D, 1E, 1G and 1H. In one embodiment, the MMP comprises 1J, 1K, 1C, 1D, 1F, 1G and 1H. In some embodiments, 1K is spontaneous. In other embodiments, 1K is an EM10. In some embodiments, 1M is spontaneous. In other embodiments, 1M is an EM12.

In certain embodiments, the formation of 5-hydroxymethylglutathione from formaldehyde is spontaneous (see, e.g., FIG. 1, step M). In some embodiments, the formation of 5-hydroxymethylglutathione from formaldehyde is catalyzed by an EM12 (see, e.g., FIG. 1, step M). In certain embodiments, the formation of methylene-THF from formaldehyde is spontaneous (see, e.g., FIG. 1, step K). In certain embodiments, the formation of methylene-THF from formaldehyde is catalyzed by an EM10 (see, e.g., FIG. 1, step K).

In certain embodiments, the organism comprises two, three, four, five, six or seven exogenous nucleic acids, each encoding a MMPE. In certain embodiments, the organism comprises two exogenous nucleic acids, each encoding a MMPE. In certain embodiments, the organism comprises three exogenous nucleic acids, each encoding a MMPE. In certain embodiments, the organism comprises four exogenous nucleic acids, each encoding a MMPE. In certain embodiments, the organism comprises five exogenous nucleic acids, each encoding a MMPE. In certain embodiments, the organism comprises six exogenous nucleic acids, each encoding a MMPE. In certain embodiments, the organism comprises seven exogenous nucleic acids, each encoding a MMPE.

Any non-naturally occurring eukaryotic organism comprising a MMP and engineered to comprise a MMPE, such as those provided herein, can be engineered to further comprise one or more SucPEs.

In one embodiment, the NNOMO further comprises a SucP. In some embodiments, the organism further comprises at least one nucleic acid encoding a SucPE expressed in a sufficient amount to produce succinate. In some embodiments, the nucleic acid is an exogenous nucleic acid. In other embodiments, the nucleic acid is an endogenous nucleic acid. In certain embodiments, the SucPE is selected from the group consisting of a ES1A or a ES1B; a ES2; a ES3; a ES4; a ES5; and a ES6.

In some embodiments, the NNOMOs having a SucP includes a set of SucPEs.

Enzymes, genes and methods for engineering pathways from glucose to various products, such as succinate, into a microorganism, are now known in the art (see, e.g., U.S. Publ. No. 2011/0201089, which is herein incorporated by reference in its entirety). A set of SucPEs represents a group of enzymes that can convert pyruvate or phosphoenolpyruvate to succinate, for example, as shown in FIG. 2. The additional reducing equivalents obtained from the MMPs, as disclosed herein, improve the yields of all these products when utilizing carbohydrate-based feedstock.

Exemplary enzymes for the conversion glucose to succinate (e.g., via pyruvate) include a ES1A or a ES1B (FIG. 2, step A); a ES2 (FIG. 2, step B); a ES3 (FIG. 2, step C); a ES4 (FIG. 2, step D); a ES5 (FIG. 2, step E); and a ES6 (FIG. 2, step F).

In one aspect, provided herein is a NNOMO, comprising (1) a MMP, wherein said organism comprises at least one exogenous nucleic acid encoding a MMPE in a sufficient amount to enhance the availability of reducing equivalents in the presence of methanol; and (2) a SucP. In some embodiments, the organism further comprises at least one nucleic acid (e.g., an endogenous and/or exogenous nucleic acid) encoding a SucPE expressed in a sufficient amount to produce succinate. In one embodiment, the at least one exogenous nucleic acid encoding the MMPE enhances the availability of reducing equivalents in the presence of methanol in a sufficient amount to increase the amount of succinate produced by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the SucP comprises 2A, 2B, 2C, 2D, 2E or 2F, or any combination thereof, wherein 2A is a ES1A or a ES1B; 2B is a ES2; 2C is a ES3; 2D is a ES4; 2E is a ES5; and 2F is a ES6. In some embodiments, 1K is spontaneous. In other embodiments, 1K is an EM10. In some embodiments, 1M is spontaneous. In other embodiments, 1M is an EM12. In some embodiments, 2A is a ES1A. In other embodiments, 2A is a ES1B.

In one embodiment, the SucP comprises 2A. In another embodiment, the SucP comprises 2B. In an embodiment, the SucP comprises 2C. In another embodiment, the SucP comprises 2D. In another embodiment, the SucP comprises 2E. In an embodiment, the SucP comprises 2F. Any combination of two, three, four, five or six SucPEs 2A, 2B, 2C, 2D, 2E and 2F is also contemplated. In some embodiments, 2A is a ES1A. In other embodiments, 2A is a ES1B.

In some embodiments, the MMP is a MMP depicted in FIG. 1, and the SucP is a SucP depicted in FIG. 2.

Exemplary sets of SucPEs to convert glucose to succinate (e.g., via pyruvate or phosphoenolpyruvate) according to FIG. 2 include (i) 2A, 2C, 2E and 2F; (ii) 2B, 2C, 2E and 2F; and (iii) 2D, 2E and 2F. In some embodiments, 2A is a ES1A. In other embodiments, 2A is a ES1B.

In one embodiment, (1) the MMP comprises 1A and 1B; and (2) the SucP comprises 2A, 2C, 2E and 2F. In another embodiment, (1) the MMP comprises 1J; and (2) the SucP comprises 2A, 2C, 2E and 2F. In one embodiment, (1) the MMP comprises 1J and 1K; and (2) the SucP comprises 2A, 2C, 2E and 2F. In certain embodiments, (1) the MMP comprises 1A, 1B, 1C, 1D, and 1E; and (2) the SucP comprises 2A, 2C, 2E and 2F. In some embodiments, (1) the MMP comprises 1A, 1B, 1C, 1D and 1F; and (2) the SucP comprises 2A, 2C, 2E and 2F. In some embodiments, (1) the MMP comprises 1J, 1C, 1D and 1E; and (2) the SucP comprises 2A, 2C, 2E and 2F. In one embodiment, (1) the MMP comprises 1J, 1C, 1D and 1F; and (2) the SucP comprises 2A, 2C, 2E and 2F. In another embodiment, (1) the MMP comprises 1J and 1L; and (2) the SucP comprises 2A, 2C, 2E and 2F. In yet another embodiment, (1) the MMP comprises 1J, 1M, 1N and 1O; and (2) the SucP comprises 2A, 2C, 2E and 2F. In certain embodiments, (1) the MMP comprises 1J, 1N and 1O; and (2) the SucP comprises 2A, 2C, 2E and 2F. In some embodiments, (1) the MMP comprises 1J, 1K, 1C, 1D and 1E; and (2) the SucP comprises 2A, 2C, 2E and 2F. In one embodiment, (1) the MMP comprises 1J, 1K, 1C, 1D and 1F; and (2) the SucP comprises 2A, 2C, 2E and 2F. In certain embodiments, (1) the MMP comprises 1I; and (2) the SucP comprises 2A, 2C, 2E and 2F. In certain embodiments, (1) the MMP comprises 1A, 1B, 1C, 1D, 1E and 1I; and (2) the SucP comprises 2A, 2C, 2E and 2F. In some embodiments, (1) the MMP comprises 1A, 1B, 1C, 1D, 1F and 1I; and (2) the SucP comprises 2A, 2C, 2E and 2F. In some embodiments, (1) the MMP comprises 1J, 1C, 1D, 1E and 1I; and (2) the SucP comprises 2A, 2C, 2E and 2F. In one embodiment, (1) the MMP comprises 1J, 1C, 1D, 1F and 1I; and (2) the SucP comprises 2A, 2C, 2E and 2F. In another embodiment, (1) the MMP comprises 1J, 1L and 1I; and (2) the SucP comprises 2A, 2C, 2E and 2F. In yet another embodiment, (1) the MMP comprises 1J, 1M, 1N, 1O and 1I; and (2) the SucP comprises 2A, 2C, 2E and 2F. In certain embodiments, (1) the MMP comprises 1J, 1N, 1O and 1I; and (2) the SucP comprises 2A, 2C, 2E and 2F. In some embodiments, (1) the MMP comprises 1J, 1K, 1C, 1D, 1E and 1I; and (2) the SucP comprises 2A, 2C, 2E and 2F. In one embodiment, (1) the MMP comprises 1J, 1K, 1C, 1D, 1F and 1I; and (2) the SucP comprises 2A, 2C, 2E and 2F. In certain embodiments, (1) the MMP comprises 1G; and (2) the SucP comprises 2A, 2C, 2E and 2F. In certain embodiments, (1) the MMP comprises 1A, 1B, 1C, 1D, 1E and 1G; and (2) the SucP comprises 2A, 2C, 2E and 2F. In some embodiments, (1) the MMP comprises 1A, 1B, 1C, 1D, 1F and 1G; and (2) the SucP comprises 2A, 2C, 2E and 2F. In some embodiments, (1) the MMP comprises 1J, 1C, 1D, 1E and 1G; and (2) the SucP comprises 2A, 2C, 2E and 2F. In one embodiment, (1) the MMP comprises 1J, 1C, 1D, 1F and 1G; and (2) the SucP comprises 2A, 2C, 2E and 2F. In another embodiment, (1) the MMP comprises 1J, 1L and 1G; and (2) the SucP comprises 2A, 2C, 2E and 2F. In yet another embodiment, (1) the MMP comprises 1J, 1M, 1N, 1O and 1G; and (2) the SucP comprises 2A, 2C, 2E and 2F. In certain embodiments, (1) the MMP comprises 1J, 1N, 1O and 1G; and (2) the SucP comprises 2A, 2C, 2E and 2F. In some embodiments, (1) the MMP comprises 1J, 1K, 1C, 1D, 1E and 1G; and (2) the SucP comprises 2A, 2C, 2E and 2F. In one embodiment, (1) the MMP comprises 1J, 1K, 1C, 1D, 1F and 1G; and (2) the SucP comprises 2A, 2C, 2E and 2F. In certain embodiments, (1) the MMP comprises 1G and 1H; and (2) the SucP comprises 2A, 2C, 2E and 2F. In certain embodiments, (1) the MMP comprises 1A, 1B, 1C, 1D, 1E, 1G and 1H; and (2) the SucP comprises 2A, 2C, 2E and 2F. In some embodiments, (1) the MMP comprises 1A, 1B, 1C, 1D, 1F, 1G and 1H; and (2) the SucP comprises 2A, 2C, 2E and 2F. In some embodiments, (1) the MMP comprises 1J, 1C, 1D, 1E, 1G and 1H; and (2) the SucP comprises 2A, 2C, 2E and 2F. In one embodiment, (1) the MMP comprises 1J, 1C, 1D, 1F, 1G and 1H; and (2) the SucP comprises 2A, 2C, 2E and 2F. In another embodiment, (1) the MMP comprises 1J, 1L, 1G and 1H; and (2) the SucP comprises 2A, 2C, 2E and 2F. In yet another embodiment, (1) the MMP comprises 1J, 1M, 1N, 1O, 1G and 1H; and (2) the SucP comprises 2A, 2C, 2E and 2F. In certain embodiments, (1) the MMP comprises 1J, 1N, 1O, 1G and 1H; and (2) the SucP comprises 2A, 2C, 2E and 2F. In some embodiments, (1) the MMP comprises 1J, 1K, 1C, 1D, 1E, 1G and 1H; and (2) the SucP comprises 2A, 2C, 2E and 2F. In one embodiment, (1) the MMP comprises 1J, 1K, 1C, 1D, 1F, 1G and 1H; and (2) the SucP comprises 2A, 2C, 2E and 2F. In some embodiments, 1K is spontaneous. In other embodiments, 1K is an EM10. In some embodiments, 1M is spontaneous. In other embodiments, 1M is an EM12. In some embodiments, 2A is a ES1A. In other embodiments, 2A is a ES1B.

In one embodiment, (1) the MMP comprises 1A and 1B; and (2) the SucP comprises 2B, 2C, 2E and 2F. In another embodiment, (1) the MMP comprises 1J; and (2) the SucP comprises 2B, 2C, 2E and 2F. In one embodiment, (1) the MMP comprises 1J and 1K; and (2) the SucP comprises 2B, 2C, 2E and 2F. In certain embodiments, (1) the MMP comprises 1A, 1B, 1C, 1D, and 1E; and (2) the SucP comprises 2B, 2C, 2E and 2F. In some embodiments, (1) the MMP comprises 1A, 1B, 1C, 1D and 1F; and (2) the SucP comprises 2B, 2C, 2E and 2F. In some embodiments, (1) the MMP comprises 1J, 1C, 1D and 1E; and (2) the SucP comprises 2B, 2C, 2E and 2F. In one embodiment, (1) the MMP comprises 1J, 1C, 1D and 1F; and (2) the SucP comprises 2B, 2C, 2E and 2F. In another embodiment, (1) the MMP comprises 1J and 1L; and (2) the SucP comprises 2B, 2C, 2E and 2F. In yet another embodiment, (1) the MMP comprises 1J, 1M, 1N and 1O; and (2) the SucP comprises 2B, 2C, 2E and 2F. In certain embodiments, (1) the MMP comprises 1J, 1N and 1O; and (2) the SucP comprises 2B, 2C, 2E and 2F. In some embodiments, (1) the MMP comprises 1J, 1K, 1C, 1D and 1E; and (2) the SucP comprises 2B, 2C, 2E and 2F. In one embodiment, (1) the MMP comprises 1J, 1K, 1C, 1D and 1F; and (2) the SucP comprises 2B, 2C, 2E and 2F. In certain embodiments, (1) the MMP comprises 1I; and (2) the SucP comprises 2B, 2C, 2E and 2F. In certain embodiments, (1) the MMP comprises 1A, 1B, 1C, 1D, 1E and 1I; and (2) the SucP comprises 2B, 2C, 2E and 2F. In some embodiments, (1) the MMP comprises 1A, 1B, 1C, 1D, 1F and 1I; and (2) the SucP comprises 2B, 2C, 2E and 2F. In some embodiments, (1) the MMP comprises 1J, 1C, 1D, 1E and 1I; and (2) the SucP comprises 2B, 2C, 2E and 2F. In one embodiment, (1) the MMP comprises 1J, 1C, 1D, 1F and 1I; and (2) the SucP comprises 2B, 2C, 2E and 2F. In another embodiment, (1) the MMP comprises 1J, 1L and 1I; and (2) the SucP comprises 2B, 2C, 2E and 2F. In yet another embodiment, (1) the MMP comprises 1J, 1M, 1N, 1O and 1I; and (2) the SucP comprises 2B, 2C, 2E and 2F. In certain embodiments, (1) the MMP comprises 1J, 1N, 1O and 1I; and (2) the SucP comprises 2B, 2C, 2E and 2F. In some embodiments, (1) the MMP comprises 1J, 1K, 1C, 1D, 1E and 1I; and (2) the SucP comprises 2B, 2C, 2E and 2F. In one embodiment, (1) the MMP comprises 1J, 1K, 1C, 1D, 1F and 1I; and (2) the SucP comprises 2B, 2C, 2E and 2F. In certain embodiments, (1) the MMP comprises 1G; and (2) the SucP comprises 2B, 2C, 2E and 2F. In certain embodiments, (1) the MMP comprises 1A, 1B, 1C, 1D, 1E and 1G; and (2) the SucP comprises 2B, 2C, 2E and 2F. In some embodiments, (1) the MMP comprises 1A, 1B, 1C, 1D, 1F and 1G; and (2) the SucP comprises 2B, 2C, 2E and 2F. In some embodiments, (1) the MMP comprises 1J, 1C, 1D, 1E and 1G; and (2) the SucP comprises 2B, 2C, 2E and 2F. In one embodiment, (1) the MMP comprises 1J, 1C, 1D, 1F and 1G; and (2) the SucP comprises 2B, 2C, 2E and 2F. In another embodiment, (1) the MMP comprises 1J, 1L and 1G; and (2) the SucP comprises 2B, 2C, 2E and 2F. In yet another embodiment, (1) the MMP comprises 1J, 1M, 1N, 1O and 1G; and (2) the SucP comprises 2B, 2C, 2E and 2F. In certain embodiments, (1) the MMP comprises 1J, 1N, 1O and 1G; and (2) the SucP comprises 2B, 2C, 2E and 2F. In some embodiments, (1) the MMP comprises 1J, 1K, 1C, 1D, 1E and 1G; and (2) the SucP comprises 2B, 2C, 2E and 2F. In one embodiment, (1) the MMP comprises 1J, 1K, 1C, 1D, 1F and 1G; and (2) the SucP comprises 2B, 2C, 2E and 2F. In certain embodiments, (1) the MMP comprises 1G and 1H; and (2) the SucP comprises 2B, 2C, 2E and 2F. In certain embodiments, (1) the MMP comprises 1A, 1B, 1C, 1D, 1E, 1G and 1H; and (2) the SucP comprises 2B, 2C, 2E and 2F. In some embodiments, (1) the MMP comprises 1A, 1B, 1C, 1D, 1F, 1G and 1H; and (2) the SucP comprises 2B, 2C, 2E and 2F. In some embodiments, (1) the MMP comprises 1J, 1C, 1D, 1E, 1G and 1H; and (2) the SucP comprises 2B, 2C, 2E and 2F. In one embodiment, (1) the MMP comprises 1J, 1C, 1D, 1F, 1G and 1H; and (2) the SucP comprises 2B, 2C, 2E and 2F. In another embodiment, (1) the MMP comprises 1J, 1L, 1G and 1H; and (2) the SucP comprises 2B, 2C, 2E and 2F. In yet another embodiment, (1) the MMP comprises 1J, 1M, 1N, 1O, 1G and 1H; and (2) the SucP comprises 2B, 2C, 2E and 2F. In certain embodiments, (1) the MMP comprises 1J, 1N, 1O, 1G and 1H; and (2) the SucP comprises 2B, 2C, 2E and 2F. In some embodiments, (1) the MMP comprises 1J, 1K, 1C, 1D, 1E, 1G and 1H; and (2) the SucP comprises 2B, 2C, 2E and 2F. In one embodiment, (1) the MMP comprises 1J, 1K, 1C, 1D, 1F, 1G and 1H; and (2) the SucP comprises 2B, 2C, 2E and 2F. In some embodiments, 1K is spontaneous. In other embodiments, 1K is an EM10. In some embodiments, 1M is spontaneous. In other embodiments, 1M is an EM12.

In one embodiment, (1) the MMP comprises 1A and 1B; and (2) the SucP comprises 2D, 2E and 2F. In another embodiment, (1) the MMP comprises 1J; and (2) the SucP comprises 2D, 2E and 2F. In one embodiment, (1) the MMP comprises 1J and 1K; and (2) the SucP comprises 2D, 2E and 2F. In certain embodiments, (1) the MMP comprises 1A, 1B, 1C, 1D, and 1E; and (2) the SucP comprises 2D, 2E and 2F. In some embodiments, (1) the MMP comprises 1A, 1B, 1C, 1D and 1F; and (2) the SucP comprises 2D, 2E and 2F. In some embodiments, (1) the MMP comprises 1J, 1C, 1D and 1E; and (2) the SucP comprises 2D, 2E and 2F. In one embodiment, (1) the MMP comprises 1J, 1C, 1D and 1F; and (2) the SucP comprises 2D, 2E and 2F. In another embodiment, (1) the MMP comprises 1J and 1L; and (2) the SucP comprises 2D, 2E and 2F. In yet another embodiment, (1) the MMP comprises 1J, 1M, 1N and 1O; and (2) the SucP comprises 2D, 2E and 2F. In certain embodiments, (1) the MMP comprises 1J, 1N and 1O; and (2) the SucP comprises 2D, 2E and 2F. In some embodiments, (1) the MMP comprises 1J, 1K, 1C, 1D and 1E; and (2) the SucP comprises 2D, 2E and 2F. In one embodiment, (1) the MMP comprises 1J, 1K, 1C, 1D and 1F; and (2) the SucP comprises 2D, 2E and 2F. In certain embodiments, (1) the MMP comprises 1I; and (2) the SucP comprises 2D, 2E and 2F. In certain embodiments, (1) the MMP comprises 1A, 1B, 1C, 1D, 1E and 1I; and (2) the SucP comprises 2D, 2E and 2F. In some embodiments, (1) the MMP comprises 1A, 1B, 1C, 1D, 1F and 1I; and (2) the SucP comprises 2D, 2E and 2F. In some embodiments, (1) the MMP comprises 1J, 1C, 1D, 1E and 1I; and (2) the SucP comprises 2D, 2E and 2F. In one embodiment, (1) the MMP comprises 1J, 1C, 1D, 1F and 1I; and (2) the SucP comprises 2D, 2E and 2F. In another embodiment, (1) the MMP comprises 1J, 1L and 1I; and (2) the SucP comprises 2D, 2E and 2F. In yet another embodiment, (1) the MMP comprises 1J, 1M, 1N, 1O and 1I; and (2) the SucP comprises 2D, 2E and 2F. In certain embodiments, (1) the MMP comprises 1J, 1N, 1O and 1I; and (2) the SucP comprises 2D, 2E and 2F. In some embodiments, (1) the MMP comprises 1J, 1K, 1C, 1D, 1E and 1I; and (2) the SucP comprises 2D, 2E and 2F. In one embodiment, (1) the MMP comprises 1J, 1K, 1C, 1D, 1F and 1I; and (2) the SucP comprises 2D, 2E and 2F. In certain embodiments, (1) the MMP comprises 1G; and (2) the SucP comprises 2D, 2E and 2F. In certain embodiments, (1) the MMP comprises 1A, 1B, 1C, 1D, 1E and 1G; and (2) the SucP comprises 2D, 2E and 2F. In some embodiments, (1) the MMP comprises 1A, 1B, 1C, 1D, 1F and 1G; and (2) the SucP comprises 2D, 2E and 2F. In some embodiments, (1) the MMP comprises 1J, 1C, 1D, 1E and 1G; and (2) the SucP comprises 2D, 2E and 2F. In one embodiment, (1) the MMP comprises 1J, 1C, 1D, 1F and 1G; and (2) the SucP comprises 2D, 2E and 2F. In another embodiment, (1) the MMP comprises 1J, 1L and 1G; and (2) the SucP comprises 2D, 2E and 2F. In yet another embodiment, (1) the MMP comprises 1J, 1M, 1N, 1O and 1G; and (2) the SucP comprises 2D, 2E and 2F. In certain embodiments, (1) the MMP comprises 1J, 1N, 1O and 1G; and (2) the SucP comprises 2D, 2E and 2F. In some embodiments, (1) the MMP comprises 1J, 1K, 1C, 1D, 1E and 1G; and (2) the SucP comprises 2D, 2E and 2F. In one embodiment, (1) the MMP comprises 1J, 1K, 1C, 1D, 1F and 1G; and (2) the SucP comprises 2D, 2E and 2F. In certain embodiments, (1) the MMP comprises 1G and 1H; and (2) the SucP comprises 2D, 2E and 2F. In certain embodiments, (1) the MMP comprises 1A, 1B, 1C, 1D, 1E, 1G and 1H; and (2) the SucP comprises 2D, 2E and 2F. In some embodiments, (1) the MMP comprises 1A, 1B, 1C, 1D, 1F, 1G and 1H; and (2) the SucP comprises 2D, 2E and 2F. In some embodiments, (1) the MMP comprises 1J, 1C, 1D, 1E, 1G and 1H; and (2) the SucP comprises 2D, 2E and 2F. In one embodiment, (1) the MMP comprises 1J, 1C, 1D, 1F, 1G and 1H; and (2) the SucP comprises 2D, 2E and 2F. In another embodiment, (1) the MMP comprises 1J, 1L, 1G and 1H;

and (2) the SucP comprises 2D, 2E and 2F. In yet another embodiment, (1) the MMP comprises 1J, 1M, 1N, 1O, 1G and 1H; and (2) the SucP comprises 2D, 2E and 2F. In certain embodiments, (1) the MMP comprises 1J, 1N, 1O, 1G and 1H; and (2) the SucP comprises 2D, 2E and 2F. In some embodiments, (1) the MMP comprises 1J, 1K, 1C, 1D, 1E, 1G and 1H; and (2) the SucP comprises 2D, 2E and 2F. In one embodiment, (1) the MMP comprises 1J, 1K, 1C, 1D, 1F, 1G and 1H; and (2) the SucP comprises 2D, 2E and 2F. In some embodiments, 1K is spontaneous. In other embodiments, 1K is an EM10. In some embodiments, 1M is spontaneous. In other embodiments, 1M is an EM12.

In one embodiment, the NNOMO comprises (1) a MMP comprising 1A and 1B; 1J; 1J and 1K; 1A, 1B, 1C, 1D, and 1E; 1A, 1B, 1C, 1D and 1F; 1J, 1C, 1D and 1E; 1J, 1C, 1D and 1F; 1J and 1L; 1J, 1M, 1N and 1O; 1J, 1N and 1O; 1J, 1K, 1C, 1D and 1E; 1J, 1K, 1C, 1D and 1F; 1I; 1A, 1B, 1C, 1D, 1E and 1I; 1A, 1B, 1C, 1D, 1F and 1I; 1J, 1C, 1D, 1E and 1I; 1J, 1C, 1D, 1F and 1I; 1J, 1L and 1I; 1J, 1M, 1N, 1O and 1I; 1J, 1N, 1O and 1I; 1J, 1K, 1C, 1D, 1E and 1I; 1J, 1K, 1C, 1D, 1F and 1I; 1G; 1A, 1B, 1C, 1D, 1E and 1G; 1A, 1B, 1C, 1D, 1F and 1G; 1J, 1C, 1D, 1E and 1G; 1J, 1C, 1D, 1F and 1G; 1J, 1L and 1G; 1J, 1M, 1N, 1O and 1G; 1J, 1N, 1O and 1G; 1J, 1K, 1C, 1D, 1E and 1G; 1J, 1K, 1C, 1D, 1F and 1G; 1G and 1H; 1A, 1B, 1C, 1D, 1E, 1G and 1H; 1A, 1B, 1C, 1D, 1F, 1G and 1H; 1J, 1C, 1D, 1E, 1G and 1H; 1J, 1C, 1D, 1F, 1G and 1H; 1J, 1L, 1G and 1H; 1J, 1M, 1N, 1O, 1G and 1H; 1J, 1N, 1O, 1G and 1H; 1J, 1K, 1C, 1D, 1E, 1G and 1H; or 1J, 1K, 1C, 1D, 1F, 1G and 1H; and (2) a SucP. In some embodiments, 1K is spontaneous. In other embodiments, 1K is an EM10. In some embodiments, 1M is spontaneous. In other embodiments, 1M is an EM12.

Any MMP provided herein can be combined with any SucP provided herein.

Figure 3:
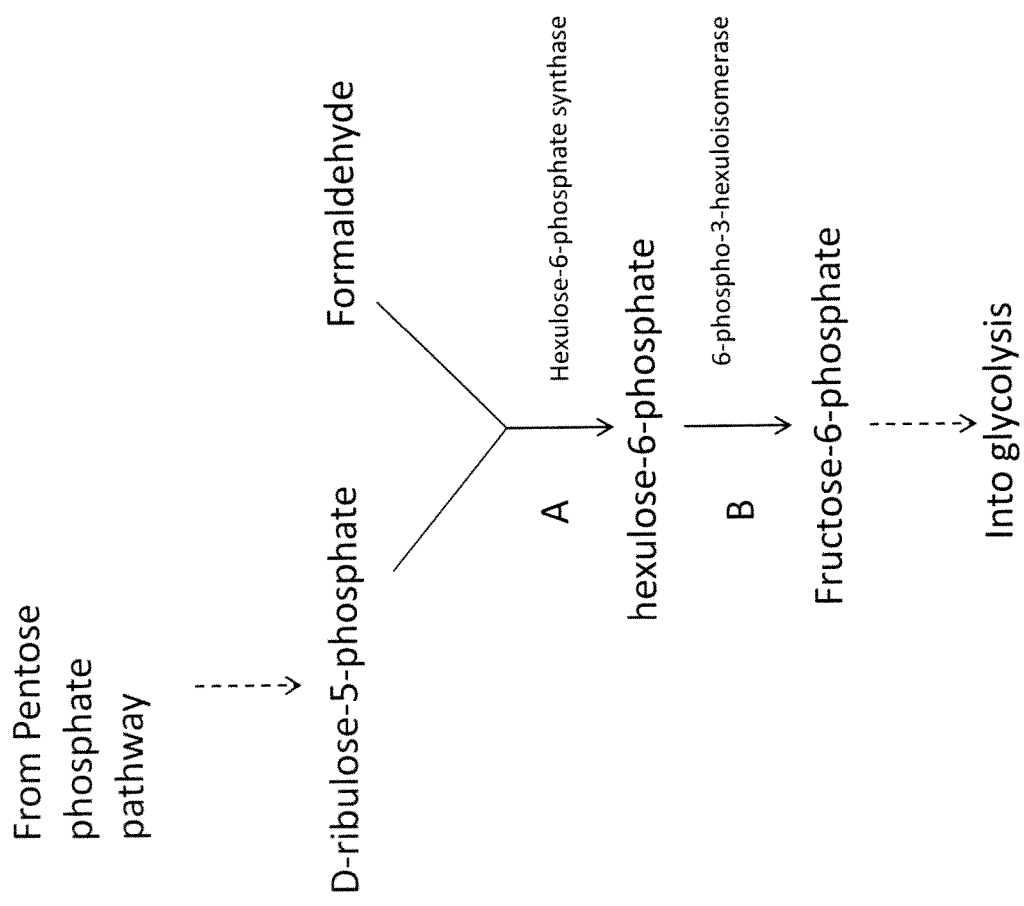
FIG. 3 shows an exemplary FAP. The enzymatic transformations are carried out by the following enzymes: 3A) a H6P synthase (EF1), and 3B) a 6-phospho-3-hexuloisomerase (EF2).
Figure 4:
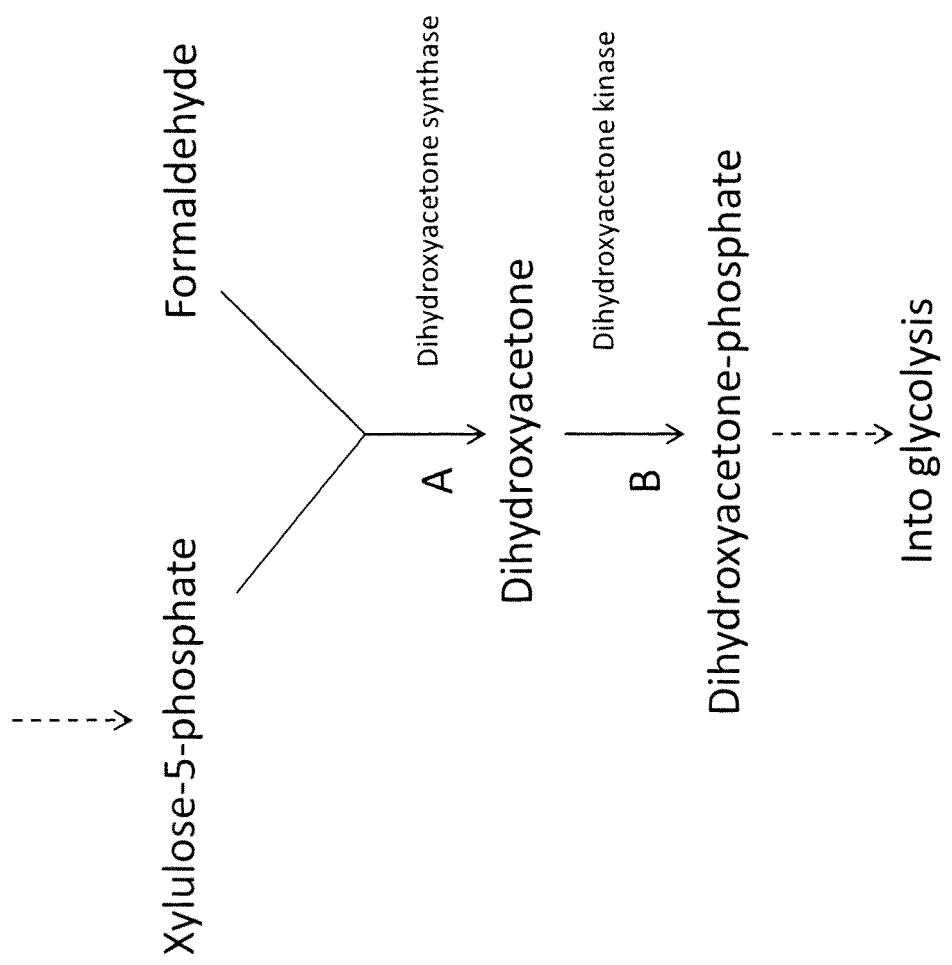
FIG. 4 shows an exemplary FAP. The enzymatic transformations are carried out by the following enzymes: 4A) a DHA synthase (EF3), and 4B) a DHA kinase (EF4).

Also provided herein are exemplary pathways, which utilize formaldehyde produced from the oxidation of methanol (e.g., as provided in FIG. 1, step J) in the formation of intermediates of certain central metabolic pathways that can be used for the formation of biomass. One exemplary FAP that can utilize formaldehyde produced from the oxidation of methanol (e.g., as provided in FIG. 1) is shown in FIG. 3, which involves condensation of formaldehyde and D-ribulose-5-phosphate to form H6P by EF1 (FIG. 3, step A). The enzyme can use $Mg^{2+}$ or $Mn^{2+}$ for maximal activity, although other metal ions are useful, and even non-metal-ion-dependent mechanisms are contemplated. H6P is converted into F6P by EF2 (FIG. 3, step B). Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and glyceraldehyde-3-phosphate (G3P), which is an intermediate in glycolysis (FIG. 4, step A). The DHA obtained from DHA synthase is then further phosphorylated to form DHAP by an EF4 (FIG. 4, step B). DHAP can be assimilated into glycolysis and several other pathways. Rather than converting formaldehyde to formate and on to $CO_2$ off-gassed, the pathways provided in FIGS. 3 and 4 show that carbon is assimilated, going into the final product.

Thus, in one embodiment, an organism having a MMP, either alone or in combination with a SucP, as provided herein, further comprises a FAP that utilizes formaldehyde, e.g., obtained from the oxidation of methanol, in the formation of intermediates of certain central metabolic pathways that can be used, for example, in the formation of biomass.

In some of embodiments, the FAP comprises 3A or 3B, wherein 3A is an EF1 and 3B is an EF2 In other embodiments, the FAP comprises 4A or 4B, wherein 4A is an EF3 and 4B is a EF4.

In certain embodiments, provided herein is a NNOMO having a MMP, wherein said organism comprises at least one exogenous nucleic acid encoding an EM9 (1J) expressed in a sufficient amount to enhance the availability of reducing equivalents in the presence of methanol and/or expressed in a sufficient amount to convert methanol to formaldehyde. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In some embodiments, the microbial organism further comprises a FAP. In certain embodiments, the organism further comprises at least one exogenous nucleic acid encoding a FAPE expressed in a sufficient amount to produce an intermediate of glycolysis and/or a metabolic pathway that can be used, for example, in the formation of biomass. In certain embodiments, the FAPE is selected from the group consisting of an EF1 (3A), EF2 (3B), EF3 (4A) and EF4 (4B). In certain embodiments, the NNOMO further comprises a SucP.

In some embodiments, the exogenous nucleic acid encoding an EM9 is expressed in a sufficient amount to produce an amount of formaldehyde greater than or equal to 1 µM, 10 µM, 20 µM, or 50 µM, or a range thereof, in culture medium or intracellularly. In other embodiments, the exogenous nucleic acid encoding an EM9 is capable of producing an amount of formaldehyde greater than or equal to 1 µM, 10 µM, 20 µM, or 50 µM, or a range thereof, in culture medium or intracellularly. In some embodiments, the range is from 1 µM to 50 µM or greater. In other embodiments, the range is from 10 µM to 50 µM or greater. In other embodiments, the range is from 20 µM to 50 µM or greater. In other embodiments, the amount of formaldehyde production is 50 µM or greater, for example, 55 mM, 60 µM, 65 mM, 70 µM, 75 µM, 80 µM, 85 µM, 90 µM, 95 µM or 100 µM. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the EM9 is selected from those provided herein, e.g., as exemplified in Example I (see FIG. 1, step J). In certain embodiments, the amount of formaldehyde production is determined by a whole cell assay, such as that provided in Example I (see FIG. 1, step J), or by another assay provided herein or otherwise known in the art. In certain embodiments, formaldehyde utilization activity is absent in the whole cell.

In certain embodiments, the exogenous nucleic acid encoding an EM9 is expressed in a sufficient amount to produce at least 1×, 2×, 3×, 4×, 5×, 6×, 7×, 8×, 9×, 10×, 15×, 20×, 30×, 40×, 50×, 100× or more formaldehyde in culture medium or intracellularly. In other embodiments, the exogenous nucleic acid encoding an EM9 is capable of producing an amount of formaldehyde at least 1×, 2×, 3×, 4×, 5×, 6×, 7×, 8×, 9×, 10×, 15×, 20×, 30×, 40×, 50×, 100×, or a range thereof, in culture medium or intracellularly. In some embodiments, the range is from 1× to 100×. In other embodiments, the range is from 2× to 100×. In other embodiments, the range is from 5× to 100×. In other embodiments, the range is from 10× to 100×. In other embodiments, the range is from 50× to 100×. In some embodiments, the amount of formaldehyde production is at least 20×. In other embodiments, the amount of formaldehyde production is at least 50×. In specific embodiments, the amount of formaldehyde production is in excess of, or as compared to, that of a negative control, e.g., the same species of organism that does not comprise the exogenous nucleic acid, such as a wild-type microbial organism or a control microbial organism thereof. In certain embodiments, the EM9 is selected from those provided herein, e.g., as exemplified in Example I (see FIG. 1, step J). In certain embodiments, the amount of formaldehyde production is determined by a whole cell assay, such as that provided in Example I (see FIG. 1, step J), or by another assay provided herein or otherwise known in the art. In certain embodiments, formaldehyde utilization activity is absent in the whole cell.

In one aspect, provided herein is a NNOMO, comprising (1) a MMP, wherein said organism comprises at least one exogenous nucleic acid encoding a MMPE in a sufficient amount to enhance the availability of reducing equivalents in the presence of methanol and/or expressed in a sufficient amount to convert methanol to formaldehyde; and (2) a FAP, wherein said organism comprises at least one exogenous nucleic acid encoding a FAPE expressed in a sufficient amount to produce an intermediate of glycolysis and/or a metabolic pathway that can be used, for example, in the formation of biomass. In some embodiments, the organism comprises at least one exogenous nucleic acid encoding an EM9 expressed in a sufficient amount to enhance the availability of reducing equivalents in the presence of methanol. In other embodiments, the organism comprises at least one exogenous nucleic acid encoding an EM9 expressed in a sufficient amount to convert methanol to formaldehyde. In specific embodiments, the MMP comprises an EM9 (1J). In certain embodiments, the FAPE is 3A, and the intermediate is a H6P, a F6P, or a combination thereof. In other embodiments, the FAPE is 3B, and the intermediate is a H6P, a F6P, or a combination thereof. In yet other embodiments, the FAPE is 3A and 3B, and the intermediate is a H6P, a F6P, or a combination thereof. In some embodiments, the FAPE is 4A, and the intermediate is a DHA, a DHAP, or a combination thereof. In other embodiments, the FAPE is 4B, and the intermediate is a DHA, a DHAP, or a combination thereof. In yet other embodiments, the FAPE is 4A and 4B, and the intermediate is a DHA, a DHAP, or a combination thereof. In one embodiment, the at least one exogenous nucleic acid encoding the MMPE, in the presence of methanol, sufficiently enhances the availability of reducing equivalents and sufficiently increases formaldehyde assimilation to increase the production of succinate or other products described herein by the non-naturally microbial organism. In some embodiments, the MMP comprises any of the various combinations of MMPEs described above or elsewhere herein.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM5; 1J is an EM9; 1K is spontaneous or EM10; 1L is an EM11; 1M is spontaneous or an EM12; 1N is EM13 and 1O is EM14; and (2) the FAP comprises 3A, 3B or a combination thereof, wherein 3A is an EF1, and 3B is an EF2. In some embodiments, 1K is spontaneous. In other embodiments, 1K is an EM10. In some embodiments, 1M is spontaneous. In other embodiments, 1M is an EM12. In some embodiments, the intermediate is a H6P. In other embodiments, the intermediate is a F6P. In yet other embodiments, the intermediate is a H6P and a F6P.

In one embodiment, the FAP comprises 3A. In another embodiment, the FAP comprises 3B. In one embodiment, the FAP comprises 3A and 3B.

In some embodiments, the MMP is a MMP depicted in FIG. 1, and a FAP depicted in FIG. 3. An exemplary set of FAPEs to convert D-ribulose-5-phosphate and formaldehyde to F6P (via H6P) according to FIG. 3 include 3A and 3B.

In a specific embodiment, (1) the MMP comprises 1J; and (2) the FAP comprises 3A and 3B. In other embodiments, (1) the MMP comprises 1J and 1K; and (2) the FAP comprises 3A and 3B. In some embodiments, (1) the MMP comprises 1J, 1C, 1D and 1E; and (2) the FAP comprises 3A and 3B. In one embodiment, (1) the MMP comprises 1J, 1C, 1D and 1F; and (2) the FAP comprises 3A and 3B. In another embodiment, (1) the MMP comprises 1J and 1L; and (2) the FAP comprises 3A and 3B. In yet another embodiment, (1) the MMP comprises 1J, 1M, 1N and 1O; and (2) the FAP comprises 3A and 3B. In certain embodiments, (1) the MMP comprises 1J, 1N and 1O; and (2) the FAP comprises 3A and 3B. In some embodiments, (1) the MMP comprises 1J, 1K, 1C, 1D and 1E; and (2) the FAP comprises 3A and 3B. In one embodiment, (1) the MMP comprises 1J, 1K, 1C, 1D and 1F; and (2) the FAP comprises 3A and 3B. In some embodiments, (1) the MMP comprises 1J, 1C, 1D, 1E and 1I; and (2) the FAP comprises 3A and 3B. In one embodiment, (1) the MMP comprises 1J, 1C, 1D, 1F and 1I; and (2) the FAP comprises 3A and 3B. In another embodiment, (1) the MMP comprises 1J, 1L and 1I; and (2) the FAP comprises 3A and 3B. In yet another embodiment, (1) the MMP comprises 1J, 1M, 1N, 1O and 1I; and (2) the FAP comprises 3A and 3B. In certain embodiments, (1) the MMP comprises 1J, 1N, 1O and 1I; and (2) the FAP comprises 3A and 3B. In some embodiments, (1) the MMP comprises 1J, 1K, 1C, 1D, 1E and 1I; and (2) the FAP comprises 3A and 3B. In one embodiment, (1) the MMP comprises 1J, 1K, 1C, 1D, 1F and 1I; and (2) the FAP comprises 3A and 3B. In some embodiments, (1) the MMP comprises 1J, 1C, 1D, 1E and 1G; and (2) the FAP comprises 3A and 3B. In one embodiment, (1) the MMP comprises 1J, 1C, 1D, 1F and 1G; and (2) the FAP comprises 3A and 3B. In another embodiment, (1) the MMP comprises 1J, 1L and 1G; and (2) the FAP comprises 3A and 3B. In yet another embodiment, (1) the MMP comprises 1J, 1M, 1N, 1O and 1G; and (2) the FAP comprises 3A and 3B. In certain embodiments, (1) the MMP comprises 1J, 1N, 1O and 1G; and (2) the FAP comprises 3A and 3B. In some embodiments, (1) the MMP comprises 1J, 1K, 1C, 1D, 1E and 1G; and (2) the FAP comprises 3A and 3B. In one embodiment, (1) the MMP comprises 1J, 1K, 1C, 1D, 1F and 1G; and (2) the FAP comprises 3A and 3B. In some embodiments, (1) the MMP comprises 1J, 1C, 1D, 1E, 1G and 1H; and (2) the FAP comprises 3A and 3B. In one embodiment, (1) the MMP comprises 1J, 1C, 1D, 1F, 1G and 1H; and (2) the FAP comprises 3A and 3B. In another embodiment, (1) the MMP comprises 1J, 1L, 1G and 1H; and (2) the FAP comprises 3A and 3B. In yet another embodiment, (1) the MMP comprises 1J, 1M, 1N, 1O, 1G and 1H; and (2) the FAP comprises 3A and 3B. In certain embodiments, (1) the MMP comprises 1J, 1N, 1O, 1G and 1H; and (2) the FAP comprises 3A and 3B. In some embodiments, (1) the MMP comprises 1J, 1K, 1C, 1D, 1E, 1G and 1H; and (2) the FAP comprises 3A and 3B. In one embodiment, (1) the MMP comprises 1J, 1K, 1C, 1D, 1F, 1G and 1H; and (2) the FAP comprises 3A and 3B. In some embodiments, 1K is spontaneous. In other embodiments, 1K is an EM10. In some embodiments, 1M is spontaneous. In some embodiments, the intermediate is a H6P. In other embodiments, the intermediate is a F6P. In yet other embodiments, the intermediate is a H6P and a F6P.

In certain embodiments, (1) the MMP comprises: 1A, 1B, 1C, 1D, 1E, 1F, 1G, 1H, 1I, 1J, 1K, 1L, 1M, 1N, or 1O or any combination of 1A, 1B, 1C, 1D, 1E, 1F, 1G, 1H, 1I, 1J, 1K, 1L, 1M, 1N, or 1O, thereof, wherein 1A is an EM1; 1B is an EM2; 1C is an EM3; 1D is an EM4; 1E is an EM5; 1F is an EM6; 1G is an EM15; 1H is an EM16, 1I is an EM8; 1J is an EM9; 1K is spontaneous or EM10; 1L is an EM11; 1M is spontaneous or an EM12; 1N is EM13 and 1O is EM14; and (2) the FAP comprises 4A, 4B or a combination thereof, wherein 4A is an EF3 and 4B is an EF4. In some embodiments, 1K is spontaneous. In other embodiments, 1K is an EM10. In some embodiments, 1M is spontaneous. In other embodiments, 1M is an EM12. In some embodiments, the intermediate is a DHA. In other embodiments, the intermediate is a DHAP. In yet other embodiments, the intermediate is a DHA and a DHAP.

In one embodiment, the FAP comprises 4A. In another embodiment, the FAP comprises 4B. In one embodiment, the FAP comprises 4A and 4B.

In some embodiments, the MMP is a MMP depicted in FIG. 1, and a FAP depicted in FIG. 4. An exemplary set of FAPEs to convert xyulose-5-phosphate and formaldehyde to DHAP (via DHA) according to FIG. 4 include 4A and 4B.

In a specific embodiment, (1) the MMP comprises 1J; and (2) the FAP comprises 4A and 4B. In other embodiments, (1) the MMP comprises 1J and 1K; and (2) the FAP comprises 4A and 4B. In some embodiments, (1) the MMP comprises 1J, 1C, 1D and 1E; and (2) the FAP comprises 4A and 4B. In one embodiment, (1) the MMP comprises 1J, 1C, 1D and 1F; and (2) the FAP comprises 4A and 4B. In another embodiment, (1) the MMP comprises 1J and 1L; and (2) the FAP comprises 4A and 4B. In yet another embodiment, (1) the MMP comprises 1J, 1M, 1N and 1O; and (2) the FAP comprises 4A and 4B. In certain embodiments, (1) the MMP comprises 1J, 1N and 1O; and (2) the FAP comprises 4A and 4B. In some embodiments, (1) the MMP comprises 1J, 1K, 1C, 1D and 1E; and (2) the FAP comprises 4A and 4B. In one embodiment, (1) the MMP comprises 1J, 1K, 1C, 1D and 1F; and (2) the FAP comprises 4A and 4B. In some embodiments, (1) the MMP comprises 1J, 1C, 1D, 1E and 1I; and (2) the FAP comprises 4A and 4B. In one embodiment, (1) the MMP comprises 1J, 1C, 1D, 1F and 1I; and (2) the FAP comprises 4A and 4B. In another embodiment, (1) the MMP comprises 1J, 1L and 1I; and (2) the FAP comprises 4A and 4B. In yet another embodiment, (1) the MMP comprises 1J, 1M, 1N, 1O and 1I; and (2) the FAP comprises 4A and 4B. In certain embodiments, (1) the MMP comprises 1J, 1N, 1O and 1I; and (2) the FAP comprises 4A and 4B. In some embodiments, (1) the MMP comprises 1J, 1K, 1C, 1D, 1E and 1I; and (2) the FAP comprises 4A and 4B. In one embodiment, (1) the MMP comprises 1J, 1K, 1C, 1D, 1F and 1I; and (2) the FAP comprises 4A and 4B. In some embodiments, (1) the MMP comprises 1J, 1C, 1D, 1E and 1G; and (2) the FAP comprises 4A and 4B. In one embodiment, (1) the MMP comprises 1J, 1C, 1D, 1F and 1G; and (2) the FAP comprises 4A and 4B. In another embodiment, (1) the MMP comprises 1J, 1L and 1G; and (2) the FAP comprises 4A and 4B. In yet another embodiment, (1) the MMP comprises 1J, 1M, 1N, 1O and 1G; and (2) the FAP comprises 4A and 4B. In certain embodiments, (1) the MMP comprises 1J, 1N, 1O and 1G; and (2) the FAP comprises 4A and 4B. In some embodiments, (1) the MMP comprises 1J, 1K, 1C, 1D, 1E and 1G; and (2) the FAP comprises 4A and 4B. In one embodiment, (1) the MMP comprises 1J, 1K, 1C, 1D, 1F and 1G; and (2) the FAP comprises 4A and 4B. In some embodiments, (1) the MMP comprises 1J, 1C, 1D, 1E, 1G and 1H; and (2) the FAP comprises 4A and 4B. In one embodiment, (1) the MMP comprises 1J, 1C, 1D, 1F, 1G and 1H; and (2) the FAP comprises 4A and 4B. In some embodiments, (1) the MMP comprises 1J, 1C, 1D, 1E, 1G and 1H; and (2) the FAP comprises 4A and 4B. In one embodiment, (1) the MMP comprises 1J, 1C, 1D, 1F, 1G and 1H; and (2) the FAP comprises 4A and 4B. In another embodiment, (1) the MMP comprises 1J, 1L, 1G and 1H; and (2) the FAP comprises 4A and 4B. In yet another embodiment, (1) the MMP comprises 1J, 1M, 1N, 1O, 1G and 1H; and (2) the FAP comprises 4A and 4B. In certain embodiments, (1) the MMP comprises 1J, 1N, 1O, 1G and 1H; and (2) the FAP comprises 4A and 4B. In some embodiments, (1) the MMP comprises J, 1K, 1C, 1D, 1E, 1G and 1H; and (2) the FAP comprises 4A and 4B. In one embodiment, (1) the MMP comprises 1J, 1K, 1C, 1D, 1F, 1 G and 1H; and (2) the FAP comprises 4A and 4B. In some embodiments, 1K is spontaneous. In other embodiments, 1K is an EM10. In some embodiments, 1M is spontaneous. In some embodiments, the intermediate is a DHA. In other embodiments, the intermediate is a DHAP. In yet other embodiments, the intermediate is a DHA and a DHAP.

Any MMP provided herein can be combined with any FAP provided herein. In addition, any MMP provided herein can be combined with any SucP and any formaldehyde pathway provided herein.

Also provided herein are methods of producing formaldehyde comprising culturing a NNOMO having a MMP provided herein. In some embodiments, the MMP comprises 1J. In certain embodiments, the organism is cultured in a substantially anaerobic culture medium. In specific embodiments, the formaldehyde is an intermediate that is consumed (assimilated) in the production of succinate and other products described herein.

Also provided herein are methods of producing an intermediate of glycolysis and/or a metabolic pathway that can be used, for example, in the formation of biomass, comprising culturing a NNOMO having a MMP and a FAP, as provided herein, under conditions and for a sufficient period of time to produce the intermediate. In some embodiments, the intermediate is a H6P. In other embodiments, the intermediate is a F6P. In yet other embodiments, the intermediate is a H6P and a F6P. In some embodiments, the intermediate is a DHA. In other embodiments, the intermediate is a DHAP. In yet other embodiments, the intermediate is a DHA and a DHAP. In some embodiments, the MMP comprises 1J. In certain embodiments, the organism is cultured in a substantially anaerobic culture medium. Such biomass can also be used in methods of producing any of the products, such as the biobased products, provided elsewhere herein.

In certain embodiments, the organism comprises two, three, four or five nucleic acids, each encoding a SucPE. In some embodiments, the organism comprises two nucleic acids, each encoding a SucPE. In some embodiments, the organism comprises three nucleic acids, each encoding a SucPE. In some embodiments, the organism comprises four nucleic acids, each encoding a SucPE. In other embodiments, the organism comprises five nucleic acids, each encoding a SucPE. In some embodiments, the nucleic acid encoding a SucPE is an exogenous nucleic acid. In other embodiments, the nucleic acid encoding an SucPE is an endogenous nucleic acid. In certain embodiments, the organism comprises two, three, four, five, six or seven nucleic acids, each encoding a SucPE; and the organism further comprises two, three, four, five, six or seven exogenous nucleic acids, each encoding a MMPE. In certain embodiments, the organism further comprises two exogenous nucleic acids, each encoding a MMPE. In certain embodiments, the organism further comprises three exogenous nucleic acids, each encoding a MMPE. In certain embodiments, the organism comprises further four exogenous nucleic acids, each encoding a MMPE. In certain embodiments, the organism further comprises five exogenous nucleic acids, each encoding a MMPE. In certain embodiments, the organism further comprises six exogenous nucleic acids, each encoding a MMPE. In certain embodiments, the organism further comprises seven exogenous nucleic acids, each encoding a MMPE.

In some embodiments, the organism comprises two or more exogenous nucleic acids, each encoding a FAPE. In some embodiments, the organism comprises two exogenous nucleic acids, each encoding a FAPE. In certain embodiments, the organism comprises two exogenous nucleic acids, each encoding a FAPE; and the organism further comprises two, three, four, five, six or seven exogenous nucleic acids, each encoding a MMPE. In certain embodiments, the organism further comprises two exogenous nucleic acids, each encoding a MMPE. In certain embodiments, the organism further comprises three exogenous nucleic acids, each encoding a MMPE. In certain embodiments, the organism comprises further four exogenous nucleic acids, each encoding a MMPE. In certain embodiments, the organism further comprises five exogenous nucleic acids, each encoding a MMPE. In certain embodiments, the organism further comprises six exogenous nucleic acids, each encoding a MMPE. In certain embodiments, the organism further comprises seven exogenous nucleic acids, each encoding a MMPE.

In some embodiments, the at least one exogenous nucleic acid encoding a MMPE is a heterologous nucleic acid. In other embodiments, the at least one exogenous nucleic acid encoding a FAPE is a heterologous nucleic acid. In other embodiments, the at least one nucleic acid encoding a SucPE is a heterologous nucleic acid. In certain embodiments, the at least one exogenous nucleic acid encoding a MMPE is a heterologous nucleic acid, and the at least one nucleic acid encoding a SucPE is a heterologous nucleic acid. In other embodiments, the at least one exogenous nucleic acid encoding a MMPE is a heterologous nucleic acid, and the at least one exogenous nucleic acid encoding a FAPE is a heterologous nucleic acid.

In certain embodiments, the organism is in a substantially anaerobic culture medium.

In some embodiments, formaldehyde produced from EM9 (FIG. 1, step J) in certain of the NNOMO provided herein is used for generating energy, redox and/or formation of biomass. Two such pathways are shown in FIG. 3. Additionally, several organisms use an alternative pathway called the "serine cycle" for formaldehyde assimilation. These organisms include the methylotroph, *Methylobacterium extorquens* AM1, and another, *Methylobacterium organophilum*. The net balance of this cycle is the fixation of two mols of formaldehyde and 1 mol of $CO_2$ into 1 mol of 3-phosphoglycerate, which is used for biosynthesis, at the expense of 2 mols ATP and the oxidation of 2 mols of NAD(P)H.

In the first reaction of the serine pathway, formaldehyde reacts with glycine to form serine. The reaction is catalyzed by serine hydroxymethyltransferase (SHMT), an enzyme that uses tetrahydrofolate (THF) as a cofactor. This leads to the formation of 5,10-methylenetetrahydrofolate. During the reaction, formaldehyde is transferred from 5,10-methylenetetrahydrofolate to the glycine, forming L-serine. In the next step, serine is transaminated with glyoxylate as the amino group acceptor by the enzyme serine-glyoxylate aminotransferase, to produce hydroxypyruvate and glycine. Hydroxypyruvate is reduced to glycerate by hydroxypyruvate reductase. Glycerate 2-kinase catalyzes the addition of a phosphate group from ATP to produce 2-phosphoglycerate.

Some of the 2-phosphoglycerate is converted by phosphoglycerate mutase to 3-phosphoglycerate, which is an intermediate of the central metabolic pathways and used for biosynthesis. The rest of the 2-phosphoglycerate is converted by an enolase to PEP. PEP carboxylase then catalyzes the fixation of carbon dioxide coupled to the conversion of PEP to oxaloacetate, which is reduced to malate by malate dehydrogenase, an NAD-linked enzyme. In some embodiments, the exogenous malate dehydrogenase genes are *Rhizopus delemar* malate dehydrogenase genes encoding the amino acid sequence disclosed in WO2013112939 as SEQ ID NO: 167 or its variants. Malate is activated to malyl coenzyme A by malate thiokinase and is cleaved by malyl coenzyme A lyase into acetyl CoA and glyoxylate. These two enzymes (malate thiokinase and malyl coenzyme A lyase), as well as hydroxypyruvate reductase and glycerate-2-kinase, are uniquely present in methylotrophs that contain the serine pathway.

In organisms that possess isocitrate lyase, a key enzyme of the glyoxylate cycle, acetyl CoA is converted to glyoxylate by the glyoxylate cycle. However, if the enzyme is missing, it is converted by another unknown pathway (deVries et al, *FEMS Microbiol Rev*, 6 (1): 57-101 (1990)). The resulting glyoxylate can serve as substrate for serine-glyoxylate aminotransferase, regenerating glycine and closing the circle.

It is understood that any of the pathways disclosed herein, as described in the Examples and exemplified in the figures, including the pathways of FIGS. 1, 2, 3 and 4, can be utilized to generate a NNOMO that produces any pathway intermediate or product, as desired. A non-limiting example of such an intermediate or product is succinate. As disclosed herein, such a microbial organism that produces an intermediate can be used in combination with another microbial organism expressing downstream pathway enzymes to produce a desired product. However, it is understood that a non-naturally occurring eukaryotic organism that produces a SucP intermediate can be utilized to produce the intermediate as a desired product.

In certain embodiments, a NNOMO comprising a MMP and a SucP provided herein, further comprises one or more gene disruptions. In certain embodiments, the one or more gene disruptions confer increased production of succinate in the organism. In other embodiments, a NNOMO comprising a MMP and a FAP provided herein, further comprises one or more gene disruptions. In some embodiments, the gene disruption is in an endogenous gene encoding a protein and/or enzyme involved in native production of ethanol, glycerol, acetate, lactate, formate, $CO_2$, amino acids, or any combination thereof, by said microbial organism. In one embodiment, the gene disruption is in an endogenous gene encoding a protein and/or enzyme involved in native production of ethanol. In another embodiment, the gene disruption is in an endogenous gene encoding a protein and/or enzyme involved in native production of glycerol. In other embodiments, the gene disruption is in an endogenous gene encoding a protein and/or enzyme involved in native production of acetate. In another embodiment, the gene disruption is in an endogenous gene encoding a protein and/or enzyme involved in native production of lactate. In one embodiment, the gene disruption is in an endogenous gene encoding a protein and/or enzyme involved in native production of formate. In another embodiment, the gene disruption is in an endogenous gene encoding a protein and/or enzyme involved in native production of $CO_2$. In other embodiments, the gene disruption is in an endogenous gene encoding a protein and/or enzyme involved in native production of amino acids by said microbial organism. The protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. Non-limiting exemplary genes encoding these proteins or enzymes are provided in Example V below. In certain embodiments, the one or more gene disruptions confer increased production of formaldehyde in the organism. In another embodiment, the gene disruption is in an endogenous gene encoding a protein and/or enzyme involved in a native formaldehyde utilization pathway. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In other embodiments, a NNOMO comprising a MMP and a SucP provided herein, further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In some embodiments, a NNOMO comprising a MMP and a FAP provided herein, further comprises one or more endogenous proteins or enzymes involved in native production of ethanol, glycerol, acetate, lactate, formate, CO2 and/or amino acids by said microbial organism, wherein said one or more endogenous proteins or enzymes has attenuated protein or enzyme activity and/or expression levels. In one embodiment the endogenous protein or enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. Non-limiting exemplary genes encoding these proteins or enzymes are provided in Example V below.

Each of the non-naturally occurring alterations provided herein (see, e.g., Example V) result in increased production and an enhanced level of succinate, for example, during the exponential growth phase of the microbial organism, compared to a strain that does not contain such metabolic alterations, under appropriate culture conditions. Appropriate conditions include, for example, those disclosed herein, including conditions such as particular carbon sources or reactant availabilities and/or adaptive evolution.

In certain embodiments, provided herein are NNOMO having genetic alterations such as gene disruptions that increase production of, for example, succinate, for example, growth-coupled production of succinate. Product production can be, for example, obligatorily linked to the exponential growth phase of the microorganism by genetically altering the metabolic pathways of the cell, as disclosed herein. The genetic alterations can increase the production of the desired product or even make the desired product an obligatory product during the growth phase. Appropriate conditions include, for example, those disclosed herein, including conditions such as particular carbon sources or reactant availabilities and/or adaptive evolution.

Given the teachings and guidance provided herein (see, e.g., Example V), those skilled in the art will understand that to introduce a metabolic alteration, such as attenuation of an enzyme, it can be necessary to disrupt the catalytic activity of the one or more enzymes involved in the reaction. Alternatively, a metabolic alteration can include disrupting expression of a regulatory protein or cofactor necessary for enzyme activity or maximal activity. Furthermore, genetic loss of a cofactor necessary for an enzymatic reaction can also have the same effect as a disruption of the gene encoding the enzyme. Disruption can occur by a variety of methods including, for example, deletion of an encoding gene or incorporation of a genetic alteration in one or more of the encoding gene sequences. The encoding genes targeted for disruption can be one, some, or all of the genes encoding enzymes involved in the catalytic activity. For example, where a single enzyme is involved in a targeted catalytic activity, disruption can occur by a genetic alteration that reduces or eliminates the catalytic activity of the encoded gene product. Similarly, where the single enzyme is multimeric, including heteromeric, disruption can occur by a genetic alteration that reduces or destroys the function of one or all subunits of the encoded gene products. Destruction of activity can be accomplished by loss of the binding activity of one or more subunits required to form an active complex, by destruction of the catalytic subunit of the multimeric complex or by both. Other functions of multimeric protein association and activity also can be targeted in order to disrupt a metabolic reaction provided herein. Such other functions are well known to those skilled in the art. Similarly, a target enzyme activity can be reduced or eliminated by disrupting expression of a protein or enzyme that modifies and/or activates the target enzyme, for example, a molecule required to convert an apoenzyme to a holoenzyme. Further, some or all of the functions of a single polypeptide or multimeric complex can be disrupted according to the invention in order to reduce or abolish the catalytic activity of one or more enzymes involved in a reaction or metabolic modification provided herein. Similarly, some or all of enzymes involved in a reaction or metabolic modification provided herein can be disrupted so long as the targeted reaction is reduced or eliminated.

Given the teachings and guidance provided herein (see, e.g., Example V), those skilled in the art also will understand that an enzymatic reaction can be disrupted by reducing or eliminating reactions encoded by a common gene and/or by one or more orthologs of that gene exhibiting similar or substantially the same activity. Reduction of both the common gene and all orthologs can lead to complete abolishment of any catalytic activity of a targeted reaction. However, disruption of either the common gene or one or more orthologs can lead to a reduction in the catalytic activity of the targeted reaction sufficient to promote coupling of growth to product biosynthesis. Exemplified herein are both the common genes encoding catalytic activities for a variety of metabolic modifications as well as their orthologs. Those skilled in the art will understand that disruption of some or all of the genes encoding a enzyme of a targeted metabolic reaction can be practiced in the methods provided herein and incorporated into the NNOMOs provided herein in order to achieve the increased production of succinate or growth-coupled product production.

Given the teachings and guidance provided herein (see, e.g., Example V), those skilled in the art also will understand that enzymatic activity or expression can be attenuated using well known methods. Reduction of the activity or amount of an enzyme can mimic complete disruption of a gene if the reduction causes activity of the enzyme to fall below a critical level that is normally required for a pathway to function. Reduction of enzymatic activity by various techniques rather than use of a gene disruption can be important for an organism's viability. Methods of reducing enzymatic activity that result in similar or identical effects of a gene disruption include, but are not limited to: reducing gene transcription or translation; destabilizing mRNA, protein or catalytic RNA; and mutating a gene that affects enzyme activity or kinetics (See, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999). Natural or imposed regulatory controls can also accomplish enzyme attenuation including: promoter replacement (See, Wang et al., *Mol. Biotechnol.* 52(2):300-308 (2012)); loss or alteration of transcription factors (Dietrick et al., *Annu. Rev. Biochem.* 79:563-590 (2010); and Simicevic et al., *Mol. Biosyst.* 6(3):462-468 (2010)); introduction of inhibitory RNAs or peptides such as siRNA, antisense RNA, RNA or peptide/small-molecule binding aptamers, ribozymes, aptazymes and riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); and addition of drugs or other chemicals that reduce or disrupt enzymatic activity such as an enzyme inhibitor, an antibiotic or a target-specific drug.

One skilled in the art will also understand and recognize that attenuation of an enzyme (see, e.g., Example V) can be done at various levels. For example, at the gene level, a mutation causing a partial or complete null phenotype, such as a gene disruption, or a mutation causing epistatic genetic effects that mask the activity of a gene product (Miko, *Nature Education* 1(1) (2008)), can be used to attenuate an enzyme. At the gene expression level, methods for attenuation include: coupling transcription to an endogenous or exogenous inducer, such as isopropylthio-β-galactoside (IPTG), then adding low amounts of inducer or no inducer during the production phase (Donovan et al., *J. Ind. Microbiol.* 16(3):145-154 (1996); and Hansen et al., *Curr. Microbiol.* 36(6):341-347 (1998)); introducing or modifying a positive or a negative regulator of a gene; modify histone acetylation/deacetylation in a eukaryotic chromosomal region where a gene is integrated (Yang et al., *Curr. Opin. Genet. Dev.* 13(2):143-153 (2003) and Kurdistani et al., *Nat. Rev. Mol. Cell Biol.* 4(4):276-284 (2003)); introducing a transposition to disrupt a promoter or a regulatory gene (Bleykasten-Brosshans et al., *C. R. Biol.* 33(8-9):679-686 (2011); and McCue et al., *PLoS Genet.* 8(2):e1002474 (2012)); flipping the orientation of a transposable element or promoter region so as to modulate gene expression of an adjacent gene (Wang et al., *Genetics* 120(4):875-885 (1988); Hayes, *Annu. Rev. Genet.* 37:3-29 (2003); in a diploid organism, deleting one allele resulting in loss of heterozygosity (Daigaku et al., *Mutation Research/Fundamental and Molecular Mechanisms of Mutagenesis* 600(1-2)177-183 (2006)); introducing nucleic acids that increase RNA degradation (Houseley et al., *Cell,* 136(4):763-776 (2009); or in bacteria, for example, introduction of a transfer-messenger RNA (tmRNA) tag, which can lead to RNA degradation and ribosomal stalling (Sunohara et al., *RNA* 10(3):378-386 (2004); and Sunohara et al., *J. Biol. Chem.* 279:15368-15375 (2004)). At the translational level, attenuation can include: introducing rare codons to limit translation (Angov, *Biotechnol. J.* 6(6):650-659 (2011)); introducing RNA interference molecules that block translation (Castel et al., *Nat. Rev. Genet.* 14(2):100-112 (2013); and Kawasaki et al., *Curr. Opin. Mol. Ther.* 7(2):125-131 (2005); modifying regions outside the coding sequence, such as introducing secondary structure into an untranslated region (UTR) to block translation or reduce efficiency of translation (Ringnér et al., *PLoS Comput. Biol.* 1(7):e72 (2005)); adding RNAase sites for rapid transcript degradation (Pasquinelli, *Nat. Rev. Genet.* 13(4):271-282 (2012); and Arraiano et al., *FEMS Microbiol. Rev.* 34(5):883-932 (2010); introducing antisense RNA oligomers or antisense transcripts (Nashizawa et al., *Front. Biosci.* 17:938-958 (2012)); introducing RNA or peptide aptamers, ribozymes, aptazymes, riboswitches (Wieland et al., *Methods* 56(3):351-357 (2012); O'Sullivan, *Anal. Bioanal. Chem.* 372(1):44-48 (2002); and Lee et al., *Curr. Opin. Biotechnol.* 14(5):505-511 (2003)); or introducing translational regulatory elements involving RNA structure that can prevent or reduce translation that can be controlled by the presence or absence of small molecules (Araujo et al., *Comparative and Functional Genomics,* Article ID 475731, 8 pages (2012)). At the level of enzyme localization and/or longevity, enzyme attenuation can include: adding a degradation tag for faster protein turnover (Hochstrasser, *Annual Rev. Genet.* 30:405-439 (1996); and Yuan et al., *PLoS One* 8(4):e62529 (2013)); or adding a localization tag that results in the enzyme being secreted or localized to a subcellular compartment in a eukaryotic cell, where the enzyme would not be able to react with its normal substrate (Nakai et al. *Genomics* 14(4):897-911 (1992); and Russell et al., *J. Bact.* 189(21)7581-7585 (2007)). At the level of post-translational regulation, enzyme attenuation can include: increasing intracellular concentration of known inhibitors; or modifying post-translational modified sites (Mann et al., *Nature Biotech.* 21:255-261 (2003)). At the level of enzyme activity, enzyme attenuation can include: adding an endogenous or an exogenous inhibitor, such as an enzyme inhibitor, an antibiotic or a target-specific drug, to reduce enzyme activity; limiting availability of essential cofactors, such as vitamin B12, for an enzyme that requires the cofactor; chelating a metal ion that is required for enzyme activity; or introducing a dominant negative mutation. The applicability of a technique for attenuation described above can depend upon whether a given host microbial organism is prokaryotic or eukaryotic, and it is understand that a determination of what is the appropriate technique for a given host can be readily made by one skilled in the art.

In some embodiments, microaerobic designs can be used based on the growth-coupled formation of the desired product. To examine this, production cones can be constructed for each strategy by first maximizing and, subsequently minimizing the product yields at different rates of biomass formation feasible in the network. If the rightmost boundary of all possible phenotypes of the mutant network is a single point, it implies that there is a unique optimum yield of the product at the maximum biomass formation rate possible in the network. In other cases, the rightmost boundary of the feasible phenotypes is a vertical line, indicating that at the point of maximum biomass the network can make any amount of the product in the calculated range, including the lowest amount at the bottommost point of the vertical line. Such designs are given a low priority.

The succinate-production strategies identified by the methods disclosed herein such as the OptKnock framework are generally ranked on the basis of their (i) theoretical yields, and (ii) growth-coupled succinate formation characteristics.

The succinate-production strategies identified in the various tables disclosed herein (e.g., Example V) can be disrupted to increase production of succinate. Accordingly, also provided herein is a NNOMO having metabolic modifications coupling succinate production to growth of the organism, where the metabolic modifications includes disruption of one or more genes selected from the genes encoding proteins and/or enzymes shown in the various tables disclosed herein.

Each of the strains can be supplemented with additional deletions if it is determined that the strain designs do not sufficiently increase the production of succinate and/or couple the formation of the product with biomass formation. Alternatively, some other enzymes not known to possess significant activity under the growth conditions can become active due to adaptive evolution or random mutagenesis. Such activities can also be knocked out. However, the list of gene deletion disclosed herein allows the construction of strains exhibiting high-yield production of succinate, including growth-coupled production of succinate.

In another aspect, provided herein is a method for producing succinate, comprising culturing any one of the NNOMOs comprising a MMP and a SucP provided herein under conditions and for a sufficient period of time to produce succinate. In certain embodiments, the organism is cultured in a substantially anaerobic culture medium.

In one embodiment, provided herein are methods for producing succinate, comprising culturing an organism provided herein (e.g., a NNOMOs comprising a MMP and a SucP) under conditions and for a sufficient period of time to produce succinate. In some embodiments, the method comprises culturing, for a sufficient period of time to produce succinate, a NNOMO, comprising (1) a MMP, wherein said organism comprises at least one exogenous nucleic acid encoding a MMPE in a sufficient amount to enhance the availability of reducing equivalents in the presence of methanol; and (2) a SucP.

In certain embodiments of the methods provided herein, the organism further comprises at least one nucleic acid encoding a SucPE expressed in a sufficient amount to produce succinate. In some embodiments, the nucleic acid encoding a SucPE is an exogenous nucleic acid. In other embodiments, the nucleic acid encoding an SucPE is an endogenous nucleic acid. In some embodiments, the organism further comprises one or more gene disruptions provided herein that confer increased production of succinate in the organism. In certain embodiments, the one or more gene disruptions occurs in an endogenous gene encoding a protein or enzyme involved in native production of ethanol, glycerol, acetate, lactate, formate, $CO_2$ and/or amino acids by said microbial organism. In other embodiments, the organism further comprises one or more endogenous proteins or enzymes involved in native production of ethanol, glycerol, acetate, lactate, formate, $CO_2$ and/or amino acids by said microbial organism, wherein said one or more endogenous proteins or enzymes has attenuated protein or enzyme activity and/or expression levels. In certain embodiments, the organism is a Crabtree positive, eukaryotic organism, and the organism is cultured in a culture medium comprising glucose. In certain embodiments, the organism comprises from one to twenty-five gene disruptions. In other embodiments, the organism comprises from one to twenty gene disruptions. In some embodiments, the organism comprises from one to fifteen gene disruptions. In other embodiments, the organism comprises from one to ten gene disruptions. In some embodiments, the organism comprises from one to five gene disruptions. In certain embodiments, the organism comprises 1, 2, 3, 4, 5, 6, 7, 8, 9, 10, 11, 12, 13, 14, 15, 16, 17, 18, 19, 20, 21, 22, 23, 24 or 25 gene disruptions or more.

In an additional embodiment, provided is a NNOMO having a SucP, FAP and/or MMP, wherein the NNOMO comprises at least one exogenous nucleic acid encoding an enzyme or protein that converts a substrate to a product. By way of example, in FIG. 1, the substrate of 1J is methanol, and the product is formaldehyde; the substrate of 1L is formaldehyde, and the product is formate; and so forth. One skilled in the art will understand that these are merely exemplary and that any of the substrate-product pairs disclosed herein suitable to produce a desired product and for which an appropriate activity is available for the conversion of the substrate to the product can be readily determined by one skilled in the art based on the teachings herein. Thus, provided herein are NNOMOs containing at least one exogenous nucleic acid encoding an enzyme or protein, where the enzyme or protein converts the substrates and products of a MMP, such as that shown in FIG. 1; a SucP, such as that shown in FIG. 2; and/or a FAP, such as that shown in FIG. 3 or 4.

While generally described herein as a microbial organism that contains a SucP, FAP, and/or a MMP, it is understood that provided herein are also NNOMO comprising at least one nucleic acid encoding a SucP, FAP, and/or a MMPE expressed in a sufficient amount to produce an intermediate of a SucP, FAP, and/or a MMP intermediate. For example, as disclosed herein, a SucP is exemplified in FIG. 2. Therefore, in addition to a microbial organism containing a SucP that produces succinate, also provided herein is a NNOMO comprising at least one nucleic acid encoding a SucPE, where the microbial organism produces a SucP intermediate. In some embodiments, the nucleic acid encoding a SucPE is an exogenous nucleic acid. In other embodiments, the nucleic acid encoding an SucPE is an endogenous nucleic acid.

In some embodiments, the carbon feedstock and other cellular uptake sources such as phosphate, ammonia, sulfate, chloride and other halogens can be chosen to alter the isotopic distribution of the atoms present in succinate or any SucP intermediate. The various carbon feedstock and other uptake sources enumerated above will be referred to herein, collectively, as "uptake sources." Uptake sources can provide isotopic enrichment for any atom present in the product succinate, and/or SucP intermediate, or for side products generated in reactions diverging away from a SucP. Isotopic enrichment can be achieved for any target atom including, for example, carbon, hydrogen, oxygen, nitrogen, sulfur, phosphorus, chloride or other halogens. The same holds true for the MMPs and FAPs, as well as intermediates thereof, provided herein.

In some embodiments, the uptake sources can be selected to alter the carbon-12, carbon-13, and carbon-14 ratios. In some embodiments, the uptake sources can be selected to alter the oxygen-16, oxygen-17, and oxygen-18 ratios. In some embodiments, the uptake sources can be selected to alter the hydrogen, deuterium, and tritium ratios. In some embodiments, the uptake sources can selected to alter the nitrogen-14 and nitrogen-15 ratios. In some embodiments, the uptake sources can be selected to alter the sulfur-32, sulfur-33, sulfur-34, and sulfur-35 ratios. In some embodiments, the uptake sources can be selected to alter the phosphorus-31, phosphorus-32, and phosphorus-33 ratios. In some embodiments, the uptake sources can be selected to alter the chlorine-35, chlorine-36, and chlorine-37 ratios.

In some embodiments, the isotopic ratio of a target atom can be varied to a desired ratio by selecting one or more uptake sources. An uptake source can be derived from a natural source, as found in nature, or from a man-made source, and one skilled in the art can select a natural source, a man-made source, or a combination thereof, to achieve a desired isotopic ratio of a target atom. An example of a man-made uptake source includes, for example, an uptake source that is at least partially derived from a chemical synthetic reaction. Such isotopically enriched uptake sources can be purchased commercially or prepared in the laboratory and/or optionally mixed with a natural source of the uptake source to achieve a desired isotopic ratio. In some embodiments, a target isotopic ratio of an uptake source can be obtained by selecting a desired origin of the uptake source as found in nature For example, as discussed herein, a natural source can be a biobased derived from or synthesized by a biological organism or a source such as petroleum-based products or the atmosphere. In some such embodiments, a source of carbon, for example, can be selected from a fossil fuel-derived carbon source, which can be relatively depleted of carbon-14, or an environmental or atmospheric carbon source, such as $CO_2$, which can possess a larger amount of carbon-14 than its petroleum-derived counterpart.

Isotopic enrichment is readily assessed by mass spectrometry using techniques known in the art such as Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC) and/or high performance liquid chromatography (HPLC).

The unstable carbon isotope carbon-14 or radiocarbon makes up for roughly 1 in $10^{12}$ carbon atoms in the earth's atmosphere and has a half-life of about 5700 years. The stock of carbon is replenished in the upper atmosphere by a nuclear reaction involving cosmic rays and ordinary nitrogen ($^{14}N$). Fossil fuels contain no carbon-14, as it decayed long ago. Burning of fossil fuels lowers the atmospheric carbon-14 fraction, the so-called "Suess effect".

Methods of determining the isotopic ratios of atoms in a compound are well known to those skilled in the art. Isotopic enrichment is readily assessed by mass spectrometry using techniques known in the art such as accelerated mass spectrometry (AMS), Stable Isotope Ratio Mass Spectrometry (SIRMS) and Site-Specific Natural Isotopic Fractionation by Nuclear Magnetic Resonance (SNIF-NMR). Such mass spectral techniques can be integrated with separation techniques such as liquid chromatography (LC), high performance liquid chromatography (HPLC) and/or gas chromatography, and the like.

In the case of carbon, ASTM D6866 was developed in the United States as a standardized analytical method for determining the biobased content of solid, liquid, and gaseous samples using radiocarbon dating by the American Society for Testing and Materials (ASTM) International. The standard is based on the use of radiocarbon dating for the determination of a product's biobased content. ASTM D6866 was first published in 2004, and the current active version of the standard is ASTM D6866-11 (effective Apr. 1, 2011). Radiocarbon dating techniques are well known to those skilled in the art, including those described herein.

The biobased content of a compound is estimated by the ratio of carbon-14 ($^{14}C$) to carbon-12 ($^{12}C$). Specifically, the Fraction Modern (Fm) is computed from the expression: Fm=(S−B)/(M−B), where B, S and M represent the $^{14}C/^{12}C$ ratios of the blank, the sample and the modern reference, respectively. Fraction Modern is a measurement of the deviation of the $^{14}C/^{12}C$ ratio of a sample from "Modern." Modern is defined as 95% of the radiocarbon concentration (in AD 1950) of National Bureau of Standards (NBS) Oxalic Acid I (i.e., standard reference materials (SRM) 4990b) normalized to $\delta^{13}C_{VPDB}$=−19 per mil (Olsson, *The use of Oxalic acid as a Standard*. in, *Radiocarbon Variations and Absolute Chronology*, Nobel Symposium, 12th Proc., John Wiley & Sons, New York (1970)). Mass spectrometry results, for example, measured by ASM, are calculated using the internationally agreed upon definition of 0.95 times the specific activity of NBS Oxalic Acid I (SRM 4990b) normalized to $\delta^{13}C_{VPDB}$=−19 per mil. This is equivalent to an absolute (AD 1950) $^{14}C/^{12}C$ ratio of 1.176±0.010×10$^{-12}$ (Karlen et al., *Arkiv Geofysik*, 4:465-471 (1968)). The standard calculations take into account the differential uptake of one isotope with respect to another, for example, the preferential uptake in biological systems of $C^{12}$ over $C^{13}$ over $C^{14}$, and these corrections are reflected as a Fm corrected for $\delta^{13}$.

An oxalic acid standard (SRM 4990b or HOx 1) was made from a crop of 1955 sugar beet. Although there were 1000 lbs made, this oxalic acid standard is no longer commercially available. The Oxalic Acid 11 standard (HOx 2; N.I.S.T designation SRM 4990 C) was made from a crop of 1977 French beet molasses. In the early 1980's, a group of 12 laboratories measured the ratios of the two standards. The ratio of the activity of Oxalic acid II to 1 is 1.2933±0.001 (the weighted mean). The isotopic ratio of HOx II is −17.8 per mille. ASTM D6866-11 suggests use of the available Oxalic Acid II standard SRM 4990 C (Hox2) for the modern standard (see discussion of original vs. currently available oxalic acid standards in Mann, *Radiocarbon*, 25(2):519-527 (1983)). A Fm=0% represents the entire lack of carbon-14 atoms in a material, thus indicating a fossil (for example, petroleum based) carbon source. A Fm=100%, after correction for the post-1950 injection of carbon-14 into the atmosphere from nuclear bomb testing, indicates an entirely modern carbon source. As described herein, such a "modern" source includes biobased sources.

As described in ASTM D6866, the percent modern carbon (pMC) can be greater than 100% because of the continuing but diminishing effects of the 1950s nuclear testing programs, which resulted in a considerable enrichment of carbon-14 in the atmosphere as described in ASTM D6866-11. Because all sample carbon-14 activities are referenced to a "pre-bomb" standard, and because nearly all new biobased products are produced in a post-bomb environment, all pMC values (after correction for isotopic fraction) must be multiplied by 0.95 (as of 2010) to better reflect the true biobased content of the sample. A biobased content that is greater than 103% suggests that either an analytical error has occurred, or that the source of biobased carbon is more than several years old.

ASTM D6866 quantifies the biobased content relative to the material's total organic content and does not consider the inorganic carbon and other non-carbon containing substances present. For example, a product that is 50% starch-based material and 50% water would be considered to have a Biobased Content=100% (50% organic content that is 100% biobased) based on ASTM D6866. In another example, a product that is 50% starch-based material, 25% petroleum-based, and 25% water would have a Biobased Content=66.7% (75% organic content but only 50% of the product is biobased). In another example, a product that is 50% organic carbon and is a petroleum-based product would be considered to have a Biobased Content=0% (50% organic carbon but from fossil sources). Thus, based on the well known methods and known standards for determining the biobased content of a compound or material, one skilled in the art can readily determine the biobased content and/or prepared downstream products having a desired biobased content.

Applications of carbon-14 dating techniques to quantify bio-based content of materials are known in the art (Currie et al., *Nuclear Instruments and Methods in Physics Research B*, 172:281-287 (2000)). For example, carbon-14 dating has been used to quantify bio-based content in terephthalate-containing materials (Colonna et al., *Green Chemistry*, 13:2543-2548 (2011)). Notably, polypropylene terephthalate (PPT) polymers derived from renewable 1,3-propanediol and petroleum-derived terephthalic acid resulted in Fm values near 30% (i.e., since 3/11 of the polymeric carbon derives from renewable 1,3-propanediol and 8/11 from the fossil end member terephthalic acid) (Currie et al., supra, 2000). In contrast, polybutylene terephthalate polymer derived from both renewable BDO and renewable terephthalic acid resulted in bio-based content exceeding 90% (Colonna et al., supra, 2011).

Accordingly, in some embodiments, the present invention provides succinate, or a SucP intermediate thereof, that has a carbon-12, carbon-13, and carbon-14 ratio that reflects an atmospheric carbon, also referred to as environmental carbon, uptake source. For example, in some aspects, the succinate, or a succinate intermediate thereof can have an Fm value of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98% or as much as 100%. In some such embodiments, the uptake source is $CO_2$. In some embodiments, the present invention provides succinate, or a succinate intermediate thereof, that has a carbon-12, carbon-13, and carbon-14 ratio that reflects petroleum-based carbon uptake source. In this aspect, the a succinate, or a succinate intermediate can have an Fm value of less than 95%, less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 2% or less than 1%. In some embodiments, the present invention provides a succinate, or a succinate intermediate thereof, that has a carbon-12, carbon-13, and carbon-14 ratio that is obtained by a combination of an atmospheric carbon uptake source with a petroleum-based uptake source. Using such a combination of uptake sources is one way by which the carbon-12, carbon-13, and carbon-14 ratio can be varied, and the respective ratios would reflect the proportions of the uptake sources.

Further, the present invention relates, in part, to biologically produced succinate, or a succinate intermediate thereof, as disclosed herein, and to the products derived therefrom, wherein the a succinate, or an intermediate thereof, has a carbon-12, carbon-13, and carbon-14 isotope ratio of about the same value as the $CO_2$ that occurs in the environment. For example, in some aspects provided is bioderived succinate, or an intermediate thereof, having a carbon-12 versus carbon-13 versus carbon-14 isotope ratio of about the same value as the $CO_2$ that occurs in the environment, or any of the other ratios disclosed herein. It is understood, as disclosed herein, that a product can have a carbon-12 versus carbon-13 versus carbon-14 isotope ratio of about the same value as the $CO_2$ that occurs in the environment, or any of the ratios disclosed herein, wherein the product is generated from bioderived succinate, or an intermediate thereof, as disclosed herein, wherein the bioderived product is chemically modified to generate a final product. Methods of chemically modifying a bioderived product of succinate, or an intermediate thereof, to generate a desired product are well known to those skilled in the art, as described herein. Also provided are products made or derived from succinate, including but not limited to butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as polypropylene (PP), polystyrene (PS) and polycarbonate (PC), and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, having a carbon-12 versus carbon-13 versus carbon-14 isotope ratio of about the same value as the $CO_2$ that occurs in the environment, wherein Also provided are products made or derived from succinate, including but not limited to butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, are generated directly from or in combination with bioderived succinate or a bioderived intermediate thereof, as disclosed herein.

Succinate, as well as intermediates thereof, are chemicals used in commercial and industrial applications. Non-limiting examples of such applications include production of butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. Moreover, succinate are also used as a raw material in the production of a wide range of products including butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. Accordingly, in some embodiments, provided is biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, comprising one or more of bioderived succinate, or a bioderived intermediate thereof, produced by a NNOMO provided herein or produced using a method disclosed herein.

As used herein, the term "bioderived" means derived from or synthesized by a biological organism and can be considered a renewable resource since it can be generated by a biological organism. Such a biological organism, in particular the microbial organisms disclosed herein, can utilize feedstock or biomass, such as, sugars or carbohydrates obtained from an agricultural, plant, bacterial, or animal source. Alternatively, the biological organism can utilize atmospheric carbon. As used herein, the term "biobased" means a product as described above that is composed, in whole or in part, of a bioderived compound provided herein. A biobased or bioderived product is in contrast to a petroleum derived product, wherein such a product is derived from or synthesized from petroleum or a petrochemical feedstock.

In some embodiments, provided is butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, comprising bioderived succinate, or a bioderived intermediate thereof, wherein the bioderived succinate, or bioderived intermediate thereof, includes all or part of the a succinate, or an intermediate thereof, used in the production of butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. Thus, in some aspects, provided is a biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, comprising at least 2%, at least 3%, at least 5%, at least 10%, at least 15%, at least 20%, at least 25%, at least 30%, at least 35%, at least 40%, at least 50%, at least 60%, at least 70%, at least 80%, at least 90%, at least 95%, at least 98% or 100% bioderived succinate, or a bioderived succinate intermediate, as disclosed herein. Additionally, in some aspects, provided is biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, wherein the a succinate, or a succinate intermediate, used in its production is a combination of bioderived and petroleum derived succinate, or a succinate intermediate thereof. For example, biobased butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, can be produced using 50% bioderived succinate and 50% petroleum derived succinate or other desired ratios such as 60%/40%, 70%/30%, 80%/20%, 90%/10%, 95%/5%, 100%/0%, 40%/60%, 30%/70%, 20%/80%, 10%/90% of bioderived/petroleum derived precursors, so long as at least a portion of the product comprises a bioderived product produced by the microbial organisms disclosed herein. It is understood that methods for producing butanediol, tetrahydrofuran, pyrrolidone, solvents, paints, deicers, plastics, fuel additives, fabrics, carpets, pigments, detergents, metal plating; polymers such as polybutylene succinate polymers, which can be used as a biodegradable plastic to replace conventional plastics in applications such as flexible packaging, agricultural films and compostable bags; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like, using the bioderived succinate, or a bioderived succinate intermediate thereof, provided herein are well known in the art.

In one embodiment, the product is a butanediol. In one embodiment, the product is a tetrahydrofuran. In one embodiment, the product is a pyrrolidone. In one embodiment, the product is a solvent. In one embodiment, the product is a paint. In one embodiment, the product is a deicer. In one embodiment, the product is a plastic. In one embodiment, the product is a fuel additive. In one embodiment, the product is a fabric. In one embodiment, the product is a carpet. In one embodiment, the product is a pigment. In one embodiment, the product is a detergent. In one embodiment, the product is a metal plating. In one embodiment, the product is a polymer. In one embodiment, the product is a polybutylene succinate polymer. In one embodiment, the product is a biodegradable plastic. In one embodiment, the product is a flexible packaging. In one embodiment, the product is an agricultural film. In one embodiment, the product is a compostable bag. In one embodiment, the product is a combination of polybutylene succinate with polymers such as PP, PS and PC, and with plastics such as polylactic acid, polyhydroxyalkanoate, and poly-3-hydroxy butyrateco-valerate. In one embodiment, the product is a combination of polybutylene succinate with fibers or fillers for applications such as automotive interiors, nonwovens, construction materials and consumer goods In some embodiments, provided herein is a culture medium comprising bioderived succinate. In some embodiments, the bioderived succinate is produced by culturing a NNOMO having a MMP and SucP, as provided herein. In certain embodiments, the bioderived succinate has a carbon-12, carbon-13 and carbon-14 isotope ratio that reflects an atmospheric carbon dioxide uptake source. In one embodiment, the culture medium is separated from a NNOMO having a MMP and SucP.

In other embodiments, provided herein is a bioderived succinate. In some embodiments, the bioderived succinate is produced by culturing a NNOMO having a MMP and SucP, as provided herein. In certain embodiments, the bioderived succinate has a carbon-12, carbon-13 and carbon-14 isotope ratio that reflects an atmospheric carbon dioxide uptake source. In some embodiments, the bioderived succinate has an Fm value of at least 80%, at least 85%, at least 90%, at least 95% or at least 98%. In certain embodiments, the bioderived succinate is a component of culture medium.

In certain embodiments, provided herein is a composition comprising a bioderived succinate provided herein, for example, a bioderived succinate produced by culturing a NNOMO having a MMP and SucP, as provided herein. In some embodiments, the composition further comprises a compound other than said bioderived succinate. In certain embodiments, the compound other than said bioderived succinate is a trace amount of a cellular portion of a NNOMO having a MMP and a SucP, as provided herein.

In some embodiments, provided herein is a biobased product comprising a bioderived succinate provided herein. In certain embodiments, the biobased product is a butanediol, tetrahydrofuran, pyrrolidone, solvent, paint, deicer, plastic, fuel additive, fabric, carpet, pigment, detergent, metal plating, polymer, polybutylene succinate polymer, biodegradable plastic, flexible packaging, agricultural film, compostable bag; a combination of polybutylene succinate with polymers such as PP, PS and PC, and with plastics such as polylactic acid, polyhydroxyalkanoate, and poly-3-hydroxy butyrateco-valerate; and a combination of polybutylene succinate with fibers or fillers for applications such as automotive interiors, nonwovens, construction materials and consumer goods, and the like. In certain embodiments, the biobased product comprises at least 5% bioderived succinate. In certain embodiments, the biobased product comprises at least 10% bioderived succinate. In some embodiments, the biobased product comprises at least 20% bioderived succinate. In other embodiments, the biobased product comprises at least 30% bioderived succinate. In some embodiments, the biobased product comprises at least 40% bioderived succinate. In other embodiments, the biobased product comprises at least 50% bioderived succinate. In one embodiment, the biobased product comprises a portion of said bioderived succinate as a repeating unit. In another embodiment, provided herein is a molded product obtained by molding the biobased product provided herein. In other embodiments, provided herein is a process for producing a biobased product provided herein, comprising chemically reacting said bioderived succinate with itself or another compound in a reaction that produces said biobased product.

In certain embodiments, provided herein is a polymer comprising or obtained by converting the bioderived succinate. In other embodiments, provided herein is a method for producing a polymer, comprising chemically of enzymatically converting the bioderived succinate to the polymer. In yet other embodiments, provided herein is a composition comprising the bioderived succinate, or a cell lysate or culture supernatant thereof.

Also provided herein is a method of producing formaldehyde, comprising culturing a NNOMO provided herein (e.g., comprising an exogenous nucleic acid encoding an EM9 (1J)) under conditions and for a sufficient period of time to produce formaldehyde. In certain embodiments, the formaldehyde is consumed to provide a reducing equivalent. In other embodiments, the formaldehyde is consumed to incorporate into succinate. In yet other embodiments, the formaldehyde is consumed to incorporate into another target product.

Also provided herein is a method of producing an intermediate of glycolysis and/or an intermediate of a metabolic pathway that can be used in the formation of biomass, comprising culturing a NNOMO provided herein (e.g., comprising an exogenous nucleic acid encoding an EM9 (1J)) under conditions and for a sufficient period of time to produce the intermediate. In one embodiment, the method is a method of producing an intermediate of glycolysis. In other embodiments, the method is a method of producing an intermediate of a metabolic pathway that can be used in the formation of biomass. In certain embodiments, the intermediate is consumed to provide a reducing equivalent. In other embodiment, the intermediate is consumed to incorporate into succinate. In yet other embodiments, the formaldehyde is consumed to incorporate into another target product.

The invention is described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction and that reference to any of these metabolic constituents also references the gene or genes encoding the enzymes that catalyze, or proteins involved in, the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes, or a protein associated with the reaction, as well as the reactants and products of the reaction.

Microbial organisms generally lack the capacity to synthesize succinate, and therefore any of the compounds disclosed herein to be within the succinate family of compounds, or otherwise known by those in the art to be within the succinate family of compounds. Moreover, organisms having all of the requisite metabolic enzymatic capabilities are not known to produce succinate from the enzymes described and biochemical pathways exemplified herein. In contrast, the NNOMOs provided herein can generate succinate as a product, as well as intermediates thereof. The biosynthesis of succinate, as well as intermediates thereof, is particularly useful in chemical synthesis of succinate family of compounds, it also allows for the further biosynthesis of succinate family compounds and avoids altogether chemical synthesis procedures.

The NNOMOs provided herein that can produce succinate are produced by ensuring that a host microbial organism includes functional capabilities for the complete biochemical synthesis of at least one succinate biosynthetic pathway provided herein. Ensuring at least one requisite succinate biosynthetic pathway confers succinate biosynthesis capability onto the host microbial organism.

The organisms and methods are described herein with general reference to the metabolic reaction, reactant or product thereof, or with specific reference to one or more nucleic acids or genes encoding an enzyme associated with or catalyzing, or a protein associated with, the referenced metabolic reaction, reactant or product. Unless otherwise expressly stated herein, those skilled in the art will understand that reference to a reaction also constitutes reference to the reactants and products of the reaction. Similarly, unless otherwise expressly stated herein, reference to a reactant or product also references the reaction, and reference to any of these metabolic constituents also references the gene or genes encoding the enzymes that catalyze or proteins involved in the referenced reaction, reactant or product. Likewise, given the well known fields of metabolic biochemistry, enzymology and genomics, reference herein to a gene or encoding nucleic acid also constitutes a reference to the corresponding encoded enzyme and the reaction it catalyzes or a protein associated with the reaction as well as the reactants and products of the reaction.

The NNOMOs described herein can be produced by introducing expressible nucleic acids encoding one or more of the enzymes or proteins participating in one or more methanol metabolic, formaldehyde assimilation, and/or succinate biosynthetic pathways. Depending on the host microbial organism chosen for biosynthesis, nucleic acids for some or all of a particular methanol metabolic, formaldehyde assimilation, and/or succinate biosynthetic pathway can be expressed. For example, if a chosen host is deficient in one or more enzymes or proteins for a desired metabolic, assimilation, or biosynthetic pathway, then expressible nucleic acids for the deficient enzyme(s) or protein(s) are introduced into the host for subsequent exogenous expression. Alternatively, if the chosen host exhibits endogenous expression of some pathway genes, but is deficient in others, then an encoding nucleic acid is needed for the deficient enzyme(s) or protein(s) to achieve succinate biosynthesis and/or methanol metabolism. Thus, a NNOMO described herein can be produced by introducing exogenous enzyme or protein activities to obtain a desired metabolic pathway and/or a desired biosynthetic pathway can be obtained by introducing one or more exogenous enzyme or protein activities that, together with one or more endogenous enzymes or proteins, produces a desired product such as succinate.

Host microbial organisms can be selected from, and the NNOMOs generated in, for example, bacteria, yeast, fungus or any of a variety of other microorganisms applicable or suitable to fermentation processes. Exemplary bacteria include any species selected from the order Enterobacteriales, family Enterobacteriaceae, including the genera *Escherichia* and *Klebsiella*; the order Aeromonadales, family Succinivibrionaceae, including the genus *Anaerobiospirillum*; the order Pasteurellales, family Pasteurellaceae, including the genera *Actinobacillus* and *Mannheimia*; the order Rhizobiales, family Bradyrhizobiaceae, including the genus *Rhizobium*; the order Bacillales, family Bacillaceae, including the genus *Bacillus*; the order Actinomycetales, families Corynebacteriaceae and Streptomycetaceae, including the genus *Corynebacterium* and the genus *Streptomyces*, respectively; order Rhodospirillales, family Acetobacteraceae, including the genus *Gluconobacter*, the order Sphingomonadales, family Sphingomonadaceae, including the genus *Zymomonas*; the order Lactobacillales, families Lactobacillaceae and Streptococcaceae, including the genus *Lactobacillus* and the genus *Lactococcus*, respectively; the order Clostridiales, family Clostridiaceae, genus *Clostridium*; and the order Pseudomonadales, family Pseudomonadaceae, including the genus *Pseudomonas*. Non-limiting species of host bacteria include *Escherichia coli, Klebsiella oxytoca, Anaerobiospirillum succiniciproducens, Actinobacillus succinogenes, Mannheimia succiniciproducens, Rhizobium etli, Bacillus subtilis, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens,* and *Pseudomonas putida*.

Similarly, exemplary species of yeast or fungi species include any species selected from the order Saccharomycetales, family Saccaromycetaceae, including the genera *Saccharomyces, Kluyveromyces* and *Pichia*; the order Saccharomycetales, family Dipodascaceae, including the genus *Yarrowia*; the order Schizosaccharomycetales, family Schizosaccaromycetaceae, including the genus *Schizosaccharomyces*; the order Eurotiales, family Trichocomaceae, including the genus *Aspergillus*; and the order Mucorales, family Mucoraceae, including the genus *Rhizopus*. Non-limiting species of host yeast or fungi include *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica,* and the like. *E. coli* is a particularly useful host organism since it is a well characterized microbial organism suitable for genetic engineering. Other particularly useful host organisms include yeast such as *Saccharomyces cerevisiae*. It is understood that any suitable microbial host organism can be used to introduce metabolic and/or genetic modifications to produce a desired product.

In some embodiments, the host microbial organism can be a recombinant microbial organism having increased succinate (succinic acid) production as compared to the wild-type microbial organism. Increased succinate production can be generated by introduction of one or more gene disruptions of a host microbial organism gene and/or an exogenous nucleic acid. Methods of increasing succinate production in a microbial organism are well known in the art. For example, the host microbial organism can be a recombinant bacteria, such as a rumen bacteria, that includes a gene disruption in one or more genes selected from a lactate dehydrogenase gene (IdhA), a pyruvate formate-lyase gene (pfl), a phosphotransacetylase gene (pta), and an acetate kinase gene (ackA) as described in U.S. Publication 2007-0054387, published Mar. 8, 2007, now U.S. Pat. No. 7,470,530, and U.S. Publication 2009-0203095, published Aug. 13, 2009. For example, in one aspect, the host microbial organism can include a gene disruption in a gene encoding IdhA, pta, and ackA, without disrupting a gene encoding pfl. Accordingly, in some aspects, the bacteria that can be used as a host microbial organism include, but are not limited to, a *Mannheimia* species (e.g., *Mannheimia* sp. LPK, *Mannheimia* sp. LPK4, *Mannheimia* sp. LPK7, *Mannheimia* sp. LPK (KCTC 10558BP), *Mannheimia succiniciproducens* MBEL55E (KCTC 0769BP), *Mannheimia succiniciproducens* PALK (KCTC10973BP), *Mannheimia succiniciproducens* ALK, or *Mannheimia succiniciproducens* ALKt), an *Actinobacillus* species (e.g., *Actinobacillus succinogenes*), a *Bacteroides* species, a *Succinimonas* species, a *Succinivibrio* species, or an *Anaerobiospirillum* species (e.g., *Anaerobiospirillum succiniciproducens*).

Additional methods for producing a host microbial organism having increased succinate production are also well known in the art. For example, the host microbial organism can have genes disruptions in genes encoding IdhA, pfl and a phosphopyruvate carboxylase (ppc), or alternatively/additionally gene disruptions in genes encoding a glucose phosphotransferase (ptsG) and a pyruvate kinase (pykA and pykF), or alternatively/additionally gene disruptions in a gene encoding a succinic semialdehyde dehydrogenase (GabD, sad), or alternatively/additionally introduction or amplification of a nucleic acid encoding a C4-dicarboxylate transport protein (DctA), which is associated with transport of succinate, as described in U.S. Publication 2010-0330634, published Dec. 30, 2010. Accordingly, a host microbial organism can include a Lumen bacteria, a *Corynebacterium* species, a *Brevibacterium* species or an *Escherichia* species (e.g., *Escherichia coli*, in particular strain W3110GFA, as disclosed in U.S. Publication 2009-0075352, published Mar. 19, 2009). As yet another example, a host microbial organism having increased succinate production can be generated by introducing an exogenous nucleic acid encoding an enzyme or protein that increases production of succinate are described in U.S. Publication 2007-0042476, published Feb. 22, 2007, U.S. Publication 2007-0042477, published Feb. 22, 2007, and U.S. Publication 2008-0020436, published Jan. 24, 2008, which disclose introduction of a nucleic acid encoding a malic enzyme B (maeB), a fumarate hydratase C (fumC), a formate dehydrogenase D (fdhD), PEP carboxykinase, pyruvate carboxylase, or a formate dehydrogenase E (fdhE). Additional useful host microbial organisms include, but are not limited to, a microbial organism that can produce succinate using glycerol as a carbon source, as disclosed in WO 2009/048202, or an organism that simultaneously use sucrose and glycerol as carbon sources to produce succinate by weakening a catabolic inhibition mechanism of the glycerol by sucrose as described in EP 2612905.

Additional microbes having high succinate production suitable for use as a host microbial organism for the pathways and methods described herein include those bacterial strains described in International Publications WO 2010/092155 and WO 2009/024294, and U.S. Publication 2010-0159542, published Jun. 24, 2010 and those yeast strains described in International Publication WO 2013/112939, published Aug. 1, 2013. For example, bacterial strains of the genus *Pasteurella*, which are gram negative, facultative anaerobes, motile, pleimorphic and often catalase- and oxidase-positive, specifically *Pasteurella* strain DD1 and its variants, are suitable host microbial organisms. *Pasteurella* strain DD1 is the bacterial strain deposited under the Budapest Treaty with DSMZ (Deutsche Sammlungvon Mikroorganismen und Zellkulturen, GmbH), Germany, having deposit number DSM18541, and was originally isolated from the rumen of a cow of German origin. Improved variants of DD1, are described in WO 2010/092155, are also suitable host microbial organisms, and include, but are not limited to, LU15348 (DD1 with deletion of pfl gene); LU15050 (DD1 deletion of ldh gene); and LU15224 (DD1 with deletion of both pfl and ldh genes). Additional host bacteria include succinate-producers isolated from bovine rumen belonging to the genus *Mannheimia*, specifically the species *Mannheimia succiniciproducens*, and strain *Mannheimia succiniciproducens* MBEL55E and its variants.

Exemplary host yeast strains, as described in WO 2013/112939, can be genetically modified yeast cells that include modifications to enhance succinate production and/or export, and, in some aspects, selected for succinate tolerance. Accordingly, in some embodiments, the high succinate producing host cell can be a yeast cell comprising a genetic modification to enhance succinate production and/or export, and in some aspects be tolerant of increased intracellular and/or extracellular succinate concentrations. In some embodiments, the genetically modified yeast cell belongs to a genus selected from the group consisting of *Issatchenkia, Candida, Pichia, Zygosaccharomyces, Kluyveromyces, Saccharomyces, Debaryomyces*, and *Saccharomycopsis*. Thus, in some embodiments, the genetically modified yeast cell is a species selected from the group consisting of *Issatchenkia orientalis, Candida lambica, Candida sorboxylosa, Candida zemplinina, Candida geochares, Pichia membranifaciens, Zygosaccharomyces kombuchaensis, Candida sorbosivorans, Kluyveromyces marxianus, Candida vanderwaltii, Candida sorbophila, Zygosaccharomyces bisporus, Zygosaccharomyces lentus, Saccharomyces bayanus, Saccharomyces bulderi, Debaryomyces castellii, Candida boidinii, Candida etchellsii, Kluyveromyces lactis, Pichiajadinii, Pichia anomala, Saccharomycopsis cralaegensis*, and *Pichia jadinii*. In some embodiments, the genetically modified yeast cell is from the *Pichia fermentans/Issatchenkia orientalis* clade.

Depending on the succinate biosynthetic, methanol metabolic and/or FAP constituents of a selected host microbial organism, the NNOMOs provided herein will, in some embodiments, include at least one exogenously expressed succinate, formaldehyde assimilation and/or MMP-encoding nucleic acid and up to all encoding nucleic acids for one or more succinate biosynthetic pathways, FAPs and/or MMPs. For example, succinate biosynthesis can be established in a host deficient in a pathway enzyme or protein through exogenous expression of the corresponding encoding nucleic acid. In a host deficient in all enzymes or proteins of a SucP, exogenous expression of all enzyme or proteins in the pathway can be included, although it is understood that all enzymes or proteins of a pathway can be expressed even if the host contains at least one of the pathway enzymes or proteins. For example, exogenous expression of all enzymes or proteins in a pathway for production of succinate can be included. The same holds true for the MMPs and FAPs provided herein. In some embodiments, the nucleic acid encoding a SucPE is an exogenous nucleic acid. In other embodiments, the nucleic acid encoding an SucPE is an endogenous nucleic acid.

In certain embodiments, the NNOMO comprises (1) a MMP, wherein said organism comprises one or more exogenous nucleic acids encoding a MMPE provided herein, and (2) a SucP, but the microbial organism does not further comprise one or more exogenous nucleic acids encoding a SucPE provided herein. In some embodiments, SucPE(s) provided herein are endogenous to the microbial organism and the nucleic acid encoding an SucPE is an endogenous nucleic acid. In other embodiments, only a single SucPE is encoded by an exogenous nucleic acid, e.g., a ES4 (FIG. 2, step G), whereas the remaining SucPEs are encoded by one or more endogenous nucleic acids.

Given the teachings and guidance provided herein, those skilled in the art will understand that the number of encoding nucleic acids to introduce in an expressible form will, at least, parallel the SucP, FAP, and MMP deficiencies of the selected host microbial organism. Therefore, a NNOMO provided herein can have one, two, three, four, five, six, seven, eight, nine, or up to all nucleic acids encoding the enzymes or proteins constituting a MMP, FAP, and/or succinate biosynthetic pathway disclosed herein. In some embodiments, the NNOMOs also can include other genetic modifications that facilitate or optimize succinate biosynthesis, formaldehyde assimilation, and/or methanol metabolism or that confer other useful functions onto the host microbial organism. One such other functionality can include, for example, augmentation of the synthesis of one or more of the SucP precursors.

Generally, a host microbial organism is selected such that it produces the precursor of a SucP, either as a naturally produced molecule or as an engineered product that either provides de novo production of a desired precursor or increased production of a precursor naturally produced by the host microbial organism. A host organism can be engineered to increase production of a precursor, as disclosed herein. In addition, a microbial organism that has been engineered to produce a desired precursor can be used as a host organism and further engineered to express enzymes or proteins of a SucP.

In some embodiments, a NNOMO provided herein is generated from a host that contains the enzymatic capability to synthesize succinate, assimilate formaldehyde and/or metabolize methanol. In this specific embodiment it can be useful to increase the synthesis or accumulation of a SucP product, FAP product and/or MMP product (e.g., reducing equivalents and/or formaldehyde) to, for example, drive SucP reactions toward succinate production. Increased synthesis or accumulation can be accomplished by, for example, overexpression of nucleic acids encoding one or more of the above-described succinate, formaldehyde assimilation and/or MMPEs or proteins. Over expression the enzyme(s) and/or protein(s) of the SucP, formaldehyde assimilation, and/or MMP can occur, for example, through exogenous expression of the endogenous gene(s), or through exogenous expression of the heterologous gene(s). Therefore, naturally occurring organisms can be readily generated to be NNOMOs, for example, producing succinate through overexpression of one, two, three, four, five, six, seven, eight, up to all nucleic acids encoding succinate biosynthetic pathway, and/or MMPEs or proteins. Naturally occurring organisms can also be readily generated to be NNOMOs, for example, assimilating formaldehyde, through overexpression of one, two, three, four, five, six, seven, eight, up to all nucleic acids encoding FAP, and/or MMPEs or proteins. In addition, a non-naturally occurring organism can be generated by mutagenesis of an endogenous gene that results in an increase in activity of an enzyme in the succinate, formaldehyde assimilation and/or MMP biosynthetic pathway.

In particularly useful embodiments, exogenous expression of the encoding nucleic acids is employed. Exogenous expression confers the ability to custom tailor the expression and/or regulatory elements to the host and application to achieve a desired expression level that is controlled by the user. However, endogenous expression also can be utilized in other embodiments such as by removing a negative regulatory effector or induction of the gene's promoter when linked to an inducible promoter or other regulatory element. Thus, an endogenous gene having a naturally occurring inducible promoter can be up-regulated by providing the appropriate inducing agent, or the regulatory region of an endogenous gene can be engineered to incorporate an inducible regulatory element, thereby allowing the regulation of increased expression of an endogenous gene at a desired time. Similarly, an inducible promoter can be included as a regulatory element for an exogenous gene introduced into a NNOMO.

It is understood that, in methods provided herein, any of the one or more exogenous nucleic acids can be introduced into a microbial organism to produce a NNOMO provided herein. The nucleic acids can be introduced so as to confer, for example, a succinate biosynthetic, formaldehyde assimilation and/or MMP onto the microbial organism. Alternatively, encoding nucleic acids can be introduced to produce an intermediate microbial organism having the biosynthetic capability to catalyze some of the required reactions to confer succinate biosynthetic, formaldehyde assimilation and/or methanol metabolic capability. For example, a NNOMO having a succinate biosynthetic pathway, FAP and/or MMP can comprise at least two exogenous nucleic acids encoding desired enzymes or proteins. Thus, it is understood that any combination of two or more enzymes or proteins of a biosynthetic pathway, FAP and/or metabolic pathway can be included in a NNOMO provided herein. Similarly, it is understood that any combination of three or more enzymes or proteins of a biosynthetic pathway, FAP and/or metabolic pathway can be included in a NNOMO provided herein, as desired, so long as the combination of enzymes and/or proteins of the desired biosynthetic pathway, FAP and/or metabolic pathway results in production of the corresponding desired product. Similarly, any combination of four or more enzymes or proteins of a biosynthetic pathway, FAP and/or MMP as disclosed herein can be included in a NNOMO provided herein, as desired, so long as the combination of enzymes and/or proteins of the desired biosynthetic, assimilation and/or metabolic pathway results in production of the corresponding desired product. In specific embodiments, the biosynthetic pathway is a succinate biosynthetic pathway.

In addition to the metabolism of methanol, assimilation of formaldehyde, and biosynthesis of succinate, as described herein, the NNOMOs and methods provided also can be utilized in various combinations with each other and with other microbial organisms and methods well known in the art to achieve product biosynthesis by other routes. For example, one alternative to produce succinate, other than use of the succinate producers is through addition of another microbial organism capable of converting a SucP intermediate to succinate. One such procedure includes, for example, the fermentation of a microbial organism that produces a SucP intermediate. The SucP intermediate can then be used as a substrate for a second microbial organism that converts the SucP intermediate to succinate. The SucP intermediate can be added directly to another culture of the second organism or the original culture of the SucP intermediate producers can be depleted of these microbial organisms by, for example, cell separation, and then subsequent addition of the second organism to the fermentation broth can be utilized to produce the final product without intermediate purification steps. The same holds true for the MMPs and FAPs provided herein.

In other embodiments, the NNOMOs and methods provided herein can be assembled in a wide variety of subpathways to achieve biosynthesis of, for example, succinate. In these embodiments, biosynthetic pathways for a desired product can be segregated into different microbial organisms, and the different microbial organisms can be co-cultured to produce the final product. In such a biosynthetic scheme, the product of one microbial organism is the substrate for a second microbial organism until the final product is synthesized. For example, the biosynthesis of succinate can be accomplished by constructing a microbial organism that contains biosynthetic pathways for conversion of one pathway intermediate to another pathway intermediate or the product. Alternatively, succinate also can be biosynthetically produced from microbial organisms through co-culture or co-fermentation using two organisms in the same vessel, where the first microbial organism produces a succinate intermediate and the second microbial organism converts the intermediate to succinate. The same holds true for the MMPs and FAPs provided herein.

Given the teachings and guidance provided herein, those skilled in the art will understand that a wide variety of combinations and permutations exist for the NNOMOs and methods together with other microbial organisms, with the co-culture of other NNOMOs having subpathways and with combinations of other chemical and/or biochemical procedures well known in the art to produce succinate and/or metabolize methanol.

Sources of encoding nucleic acids for a succinate, formaldehyde assimilation, or MMPE or protein can include, for example, any species where the encoded gene product is capable of catalyzing the referenced reaction. Such species include both prokaryotic and eukaryotic organisms including, but not limited to, bacteria, including archaea and eubacteria, and eukaryotes, including yeast, plant, insect, animal, and mammal, including human. Exemplary species for such sources include, for example, *Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium dificile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas* species, including *Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter* species, including *Acinetobacter calcoaceticus* and *Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilus, Acetobacter pasteurians, Kluyveromyces lactis, Eubacterium barkeri, Bacteroides capillosus, Anaerotruncus colihominis, Natranaerobius thermophilusm, Campylobacterjejuni, Haemophilus influenzae, Serratia marcescens, Citrobacter amalonaticus, Myxococcus xanthus. Fusobacterium nuleatum, Penicillium chrysogenum,* marine gamma proteobacterium, butyrate-producing bacterium, *Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis* MC2 155, *Mycobacterium avium* subsp. *paratuberculosis* K-10, *Mycobacterium marinum* M, *Tsukamurella paurometabola* DSM 20162, *Cyanobium* PCC7001, *Dictyostelium discoideum* AX4, as well as other exemplary species disclosed herein or available as source organisms for corresponding genes.

In certain embodiments, sources of encoding nucleic acids for a SucPE include *Actinobacillus succinogenes, Anaerobiospirillum succiniciproducens, Ascaris suum, Campylobacter jejuni, Candida albicans, Candida tropicalis* MYA-3404. *Corynebacterium glutamicum, Escherichia coli, Haemophilus influenza, Kluyveromyces lactis* NRRL Y-1140, *Mannheimia succiniciproducens, Megathyrsus maximus, Methylobacterium extorquens, Mycobacterium smegmatis, Pelotomaculum thermopropionicum, Rattus norvegicus, Saccharomyces cerevisiae, Thermus thermophilus,* and *Yarrowia lipolytica*

In certain embodiments, sources of encoding nucleic acids for a MMPE include, *Acinetobacter baumannii* Naval-82, *Actinobacillus succinogenes* 130Z, *Allochromatium vinosum* DSM 180, *Azotobacter vinelandii* DJ, *Bacillus alcalophilus* ATCC 27647, *Bacillus azotoformans* LMG 9581, *Bacillus coagulans* 36D1, *Bacillus methanolicus* MGA3, *Bacillus methanolicus* PB1, *Bacillus methanolicus* PB-1, *Bacillus smithii, Bacillus subtilis, Burkholderia ceno-* cepacia, Burkholderia cepacia, Burkholderia multivorans, Burkholderia pyrrocinia, Burkholderia stabilis, Burkholderia thailandensis E264, Burkholderiales bacterium Joshi_001, Campylobacter jejuni, Candida boidinii, Candida methylica, Carboxydothermus hydrogenoformans, Carboxydothermus hydrogenoformans Z-2901, Caulobacter sp. AP07, Clostridium acetobutylicum ATCC 824, Clostridium acidurici, Clostridium carboxidivorans P7, Clostridium cellulovorans 743B, Clostridium kluyveri, Clostridium kluyveri DSM 555, Clostridium ljungdahlii, Clostridium ljungdahlii DSM 13528, Clostridium pasteurianum, Clostridium pasteurianum DSM 525, Clostridium perfringens, Clostridium perfringens ATCC 13124, Clostridium perfringens str. 13, Clostridium phytofermentans ISDg, Corynebacterium glutamicum ATCC 14067, Corynebacterium glutamicum R, Corynebacterium sp. U-96, Corynebacterium variabile, Cupriavidus necator N-1, Desulfitobacterium hafniense, Desulfitobacterium metallireducens DSM 15288, Desulfotomaculum reducens MI-1, Desulfovibrio africanus str. Walvis Bay, Desulfovibrio fructosovorans JJ, Desulfovibrio vulgaris str. Hildenborough, Desulfovibrio vulgaris str. 'Miyazaki F', Escherichia coli, Escherichia coli K-12, Escherichia coli K-12 MG1655, Flavobacterium frigoris, Geobacillus sp. Y4. IMC1, Geobacillus themodenitrificans NG80-2, Geobacter bemidjiensis Bem, Geobacter sulfurreducens, Geobacter sulfurreducens PCA, Helicobacter pylori, Homo sapiens, human gut metagenome, Hydrogenobacter thermophilus, Hyphomicrobium denitrificans ATCC 51888. Hyphomicrobium zavarzinii, Klebsiella pneumoniae subsp. pneumoniae MGH 78578, Lysinibacillus fusiformis, Lysinibacillus sphaericus, Mesorhizobium loti MAFF303099, Methanosarcina acetivorans, Methanosarcina acetivorans C2A, Methanosarcina barkeri, Methanosarcina mazei Tuc01, Methylobacter marinus, Methylobacterium extorquens, Methylobacterium extorquens AM1, Methylococcus capsulatis, Moorella thermoacetica, Mycobacterium smegmatis, Nitrosopumilus salaria BD31, Nitrososphaera gargensis Ga9.2, Nostoc sp. PCC 7120, Paenibacillus peoriae KCTC 3763, Paracoccus denitrificans, Photobacterium profundum 3TCK, Pichia pastoris, Picrophilus torridus DSM9790, Pseudomonas aeruginosa PA01, Pseudomonas putida, Pseudomonas syringae pv. syringae B728a, Ralstonia eutropha, Ralstonia eutropha H16, Rhodobacter capsulatus, Rhodobacter sphaeroides, Rhodobacter sphaeroides ATCC 17025, Rhodopseudomonas palustris, Rhodopseudomonas palustris CGA009, Rhodopseudomonas palustris DX-1, Rhodospirillum rubrum, Saccharomyces cerevisiae, Saccharomyces cerevisiae S288c, Salmonella enterica subsp. enterica serovar Typhimurium str. LT2, Sebaldella termitidis ATCC 33386, Shewanella oneidensis MR-1, Sinorhizobium meliloti 1021, Sulfolobus acidocalarius, Sulfolobus solfataricus P-2, Synechocystis str. PCC 6803, Syntrophobacter fumaroxidans, Thauera aromatica, Thermoanaerobacter sp. X514, Thermococcus litoralis, Thermoplasma acidophilum, Thiocapsa roseopersicina, Vibrio harveyi ATCC BAA-1116, Xanthobacter autotrophicus Py2, and Zea mays.

In certain embodiments, sources of encoding nucleic acids for a FAPE include Aminomonas aminovorus, Bacillus methanolicus MGA3. Bacillus methanolicus PB1, Bacillus subtilis, Candida boidinii, Citrobacter freundii, Escherichia coli, Geobacillus sp. GHH01, Geobacillus sp. M10EXG Geobacillus sp. Y4.1MC1, Klebsiella pneumonia. Methylobacillus flagellates, Methylobacillus flagellatus KT, Methylococcus capsulatas, Methylomicrobium album BG8, Methylomonas aminofaciens, Methylovorus glucosetrophus SIP3-4, Methylovorus sp. MP688, Mycobacter sp. strain JC1 DSM 3803, Mycobacterium gastri, Ogataea angusta, Ogataea parapolymorpha DL-1 (Hansenula polymorpha DL-1), Pyrococcus abyssi, Pyrococcus furiosus, Pyrococcus horikoshii OT3, Saccharomyces cerevisiae S288c, and Thermococcus kodakaraensis.

However, with the complete genome sequence available for now more than 550 species (with more than half of these available on public databases such as the NCBI), including 395 microorganism genomes and a variety of yeast, fungi, plant, and mammalian genomes, the identification of genes encoding the requisite succinate biosynthetic pathway, methanol metabolic and/or formaldehyde assimilation activity for one or more genes in related or distant species, including for example, homologues, orthologs, paralogs and nonorthologous gene displacements of known genes, and the interchange of genetic alterations between organisms is routine and well known in the art. Accordingly, the metabolic alterations allowing biosynthesis of succinate, metabolism of methanol and/or assimilation of formaldehyde described herein with reference to a particular organism such as E. coli can be readily applied to other microorganisms, including prokaryotic and eukaryotic organisms alike. Given the teachings and guidance provided herein, those skilled in the art will know that a metabolic alteration exemplified in one organism can be applied equally to other organisms.

In some instances, such as when an alternative succinate biosynthetic, formaldehyde assimilation and/or MMP exists in an unrelated species, succinate biosynthesis, formaldehyde assimilation and/or methanol metabolism can be conferred onto the host species by, for example, exogenous expression of a paralog or paralogs from the unrelated species that catalyzes a similar, yet non-identical metabolic reaction to replace the referenced reaction. Because certain differences among metabolic networks exist between different organisms, those skilled in the art will understand that the actual gene usage between different organisms may differ. However, given the teachings and guidance provided herein, those skilled in the art also will understand that the teachings and methods provided herein can be applied to all microbial organisms using the cognate metabolic alterations to those exemplified herein to construct a microbial organism in a species of interest that will synthesize succinate, assimilate formaldehyde, and/or metabolize methanol.

A nucleic acid molecule encoding a SucPE or protein can also include a nucleic acid molecule that hybridizes to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. Hybridization conditions can include highly stringent, moderately stringent, or low stringency hybridization conditions that are well known to one of skill in the art such as those described herein. Similarly, a nucleic acid molecule that can be used in the invention can be described as having a certain percent sequence identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number. For example, the nucleic acid molecule can have at least 65%, 70%, 75%, 80%, 85%, 90%, 91%, 92%, 93%, 94%, 95%, 96%, 97%, 98% or 99% sequence identity to a nucleic acid described herein.

Stringent hybridization refers to conditions under which hybridized polynucleotides are stable. As known to those of skill in the art, the stability of hybridized polynucleotides is reflected in the melting temperature (Tm) of the hybrids. In general, the stability of hybridized polynucleotides is a function of the salt concentration, for example, the sodium ion concentration and temperature. A hybridization reaction can be performed under conditions of lower stringency, followed by washes of varying, but higher, stringency. Reference to hybridization stringency relates to such washing conditions. Highly stringent hybridization includes conditions that permit hybridization of only those nucleic acid sequences that form stable hybridized polynucleotides in 0.018M NaCl at 65° C., for example, if a hybrid is not stable in 0.018M NaCl at 65° C., it will not be stable under high stringency conditions, as contemplated herein. High stringency conditions can be provided, for example, by hybridization in 50% formamide, 5× Denhart's solution, 5×SSPE, 0.2% SDS at 42° C., followed by washing in 0.1×SSPE, and 0.1% SDS at 65° C. Hybridization conditions other than highly stringent hybridization conditions can also be used to describe the nucleic acid sequences disclosed herein. For example, the phrase moderately stringent hybridization refers to conditions equivalent to hybridization in 50% formamide, 5× Denhart's solution, 5×SSPE, 0.2% SDS at 42° C., followed by washing in 0.2×SSPE, 0.2% SDS, at 42° C. The phrase low stringency hybridization refers to conditions equivalent to hybridization in 10% formamide, 5× Denhart's solution, 6×SSPE, 0.2% SDS at 22° C., followed by washing in 1×SSPE, 0.2% SDS, at 37° C. Denhart's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M (EDTA). Other suitable low, moderate and high stringency hybridization buffers and conditions are well known to those of skill in the art and are described, for example, in Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

A nucleic acid molecule encoding a SucPE or protein of the invention can have at least a certain sequence identity to a nucleotide sequence disclosed herein. According, in some aspects of the invention, a nucleic acid molecule encoding a SucPE or protein has a nucleotide sequence of at least 65% identity, at least 70% identity, at least 75% identity, at least 80% identity, at least 85% identity, at least 90% identity, at least 91% identity, at least 92% identity, at least 93% identity, at least 94% identity, at least 95% identity, at least 96% identity, at least 97% identity, at least 98% identity, or at least 99% identity to a nucleic acid disclosed herein by SEQ ID NO, GenBank and/or GI number or a nucleic acid molecule that hybridizes to a nucleic acid molecule that encodes an amino acid sequence disclosed herein by SEQ ID NO, GenBank and/or GI number.

Sequence identity (also known as homology or similarity) refers to sequence similarity between two nucleic acid molecules or between two polypeptides. Identity can be determined by comparing a position in each sequence, which may be aligned for purposes of comparison. When a position in the compared sequence is occupied by the same base or amino acid, then the molecules are identical at that position. A degree of identity between sequences is a function of the number of matching or homologous positions shared by the sequences. The alignment of two sequences to determine their percent sequence identity can be done using software programs known in the art, such as, for example, those described in Ausubel et al., *Current Protocols in Molecular Biology*, John Wiley and Sons, Baltimore, Md. (1999). Preferably, default parameters are used for the alignment. One alignment program well known in the art that can be used is BLAST set to default parameters. In particular, programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the National Center for Biotechnology Information.

Methods for constructing and testing the expression levels of a non-naturally occurring succinate-producing host can be performed, for example, by recombinant and detection methods well known in the art. Such methods can be found described in, for example, Sambrook et al., *Molecular Cloning: A Laboratory Manual*, Third Ed., Cold Spring Harbor Laboratory, New York (2001); and Ausubel et al., *Current Protocols in Molecular Biology*, John Wiley and Sons, Baltimore, Md. (1999).

Exogenous nucleic acid sequences involved in a pathway for metabolism of methanol, assimilation of formaldehyde and/or production of succinate can be introduced stably or transiently into a host cell using techniques well known in the art including, but not limited to, conjugation, electroporation, chemical transformation, transduction, transfection, and ultrasound transformation. For exogenous expression in *E. coli* or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. For example, removal of a mitochondrial leader sequence led to increased expression in *E. coli* (Hoffmeister et al., *J. Biol. Chem.* 280:4329-4338 (2005)). For exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. Thus, it is understood that appropriate modifications to a nucleic acid sequence to remove or include a targeting sequence can be incorporated into an exogenous nucleic acid sequence to impart desirable properties. Furthermore, genes can be subjected to codon optimization with techniques well known in the art to achieve optimized expression of the proteins.

An expression vector or vectors can be constructed to include one or more succinate biosynthetic, formaldehyde assimilation and/or MMP encoding nucleic acids as exemplified herein operably linked to expression control sequences functional in the host organism. Expression vectors applicable for use in the microbial host organisms provided include, for example, plasmids, phage vectors, viral vectors, episomes and artificial chromosomes, including vectors and selection sequences or markers operable for stable integration into a host chromosome. Additionally, the expression vectors can include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The transformation of exogenous nucleic acid sequences involved in a metabolic or synthetic pathway can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

Suitable purification and/or assays to test, e.g., for the production of succinate can be performed using well known methods. Suitable replicates such as triplicate cultures can be grown for each engineered strain to be tested. For example, product and byproduct formation in the engineered production host can be monitored. The final product and intermediates, and other organic compounds, can be analyzed by methods such as HPLC (High Performance Liquid Chromatography), GC-MS (Gas Chromatography-Mass Spectroscopy) and LC-MS (Liquid Chromatography-Mass Spectroscopy) or other suitable analytical methods using routine procedures well known in the art. The release of product in the fermentation broth can also be tested with the culture supernatant. Byproducts and residual glucose can be quantified by HPLC using, for example, a refractive index detector for glucose and alcohols, and a UV detector for organic acids (Lin et al., *Biotechnol. Bioeng.* 90:775-779 (2005)), or other suitable assay and detection methods well known in the art. The individual enzyme or protein activities from the exogenous DNA sequences can also be assayed using methods well known in the art. Exemplary assays for the activity of methanol dehydrogenase (FIG. 1, step J) are provided in the Example I.

The succinate can be separated from other components in the culture using a variety of methods well known in the art. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, and ultrafiltration. All of the above methods are well known in the art.

Any of the NNOMOs described herein can be cultured to produce and/or secrete the biosynthetic products, or intermediates thereof. For example, the succinate producers can be cultured for the biosynthetic production of succinate. Accordingly, in some embodiments, provided is culture medium having a succinate, formaldehyde assimilation and/or MMP intermediate described herein. In some aspects, the culture medium can also be separated from the NNOMOs provided herein that produced the succinate, formaldehyde assimilation and/or MMP intermediate. Methods for separating a microbial organism from culture medium are well known in the art. Exemplary methods include filtration, flocculation, precipitation, centrifugation, sedimentation, and the like.

In certain embodiments, for example, for the production of the production of succinate, the recombinant strains are cultured in a medium with carbon source and other essential nutrients. It is sometimes desirable and can be highly desirable to maintain anaerobic conditions in the fermenter to reduce the cost of the overall process. Such conditions can be obtained, for example, by first sparging the medium with nitrogen and then sealing the flasks with a septum and crimp-cap. For strains where growth is not observed anaerobically, microaerobic or substantially anaerobic conditions can be applied by perforating the septum with a small hole for limited aeration. Exemplary anaerobic conditions have been described previously and are well-known in the art. Exemplary aerobic and anaerobic conditions are described, for example, in U.S. Publ. No. 2009/0047719. Fermentations can be performed in a batch, fed-batch or continuous manner, as disclosed herein. Fermentations can be performed in a batch, fed-batch or continuous manner, as disclosed herein. Fermentations can also be conducted in two phases, if desired. The first phase can be aerobic to allow for high growth and therefore high productivity, followed by an anaerobic phase of high succinate yields.

If desired, the pH of the medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium, can include, for example, any carbohydrate source which can supply a source of carbon to the NNOMO. Such sources include, for example, sugars such as glucose, xylose, arabinose, galactose, mannose, fructose, sucrose and starch; or glycerol, alone as the sole source of carbon or in combination with other carbon sources described herein or known in the art. In one embodiment, the carbon source is a sugar. In one embodiment, the carbon source is a sugar-containing biomass. In some embodiments, the sugar is glucose. In one embodiment, the sugar is xylose. In another embodiment, the sugar is arabinose. In one embodiment, the sugar is galactose. In another embodiment, the sugar is fructose. In other embodiments, the sugar is sucrose. In one embodiment, the sugar is starch. In certain embodiments, the carbon source is glycerol. In some embodiments, the carbon source is crude glycerol. In one embodiment, the carbon source is crude glycerol without treatment. In other embodiments, the carbon source is glycerol and glucose. In another embodiment, the carbon source is methanol and glycerol. In one embodiment, the carbon source is carbon dioxide. In one embodiment, the carbon source is formate. In one embodiment, the carbon source is methane. In one embodiment, the carbon source is methanol In certain embodiments, methanol is used alone as the sole source of carbon or in combination with other carbon sources described herein or known in the art. In a specific embodiment, the methanol is the only (sole) carbon source. In one embodiment, the carbon source is chemoelectro-generated carbon (see, e.g., Liao et al. (2012) Science 335:1596). In one embodiment, the chemoelectro-generated carbon is methanol. In one embodiment, the chemoelectro-generated carbon is formate. In one embodiment, the chemoelectro-generated carbon is formate and methanol. In one embodiment, the carbon source is a carbohydrate and methanol. In one embodiment, the carbon source is a sugar and methanol. In another embodiment, the carbon source is a sugar and glycerol. In other embodiments, the carbon source is a sugar and crude glycerol. In yet other embodiments, the carbon source is a sugar and crude glycerol without treatment. In one embodiment, the carbon source is a sugar-containing biomass and methanol. In another embodiment, the carbon source is a sugar-containing biomass and glycerol. In other embodiments, the carbon source is a sugar-containing biomass and crude glycerol. In yet other embodiments, the carbon source is a sugar-containing biomass and crude glycerol without treatment. In some embodiments, the carbon source is a sugar-containing biomass, methanol and a carbohydrate. Other sources of carbohydrate include, for example, renewable feedstocks and biomass. Exemplary types of biomasses that can be used as feedstocks in the methods provided herein include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein for the production of succinate and other pathway intermediates.

In one embodiment, the carbon source is glycerol. In certain embodiments, the glycerol carbon source is crude glycerol or crude glycerol without further treatment. In a further embodiment, the carbon source comprises glycerol or crude glycerol, and also sugar or a sugar-containing biomass, such as glucose. In a specific embodiment, the concentration of glycerol in the fermentation broth is maintained by feeding crude glycerol, or a mixture of crude glycerol and sugar (e.g., glucose). In certain embodiments, sugar is provided for sufficient strain growth. In some embodiments, the sugar (e.g., glucose) is provided at a molar concentration ratio of glycerol to sugar of from 200:1 to 1:200. In some embodiments, the sugar (e.g., glucose) is provided at a molar concentration ratio of glycerol to sugar of from 100:1 to 1:100. In some embodiments, the sugar (e.g., glucose) is provided at a molar concentration ratio of glycerol to sugar of from 100:1 to 5:1. In some embodiments, the sugar (e.g., glucose) is provided at a molar concentration ratio of glycerol to sugar of from 50:1 to 5:1. In certain embodiments, the sugar (e.g., glucose) is provided at a molar concentration ratio of glycerol to sugar of 100:1. In one embodiment, the sugar (e.g., glucose) is provided at a molar concentration ratio of glycerol to sugar of 90:1. In one embodiment, the sugar (e.g., glucose) is provided at a molar concentration ratio of glycerol to sugar of 80:1. In one embodiment, the sugar (e.g., glucose) is provided at a molar concentration ratio of glycerol to sugar of 70:1. In one embodiment, the sugar (e.g., glucose) is provided at a molar concentration ratio of glycerol to sugar of 60:1. In one embodiment, the sugar (e.g., glucose) is provided at a molar concentration ratio of glycerol to sugar of 50:1. In one embodiment, the sugar (e.g., glucose) is provided at a molar concentration ratio of glycerol to sugar of 40:1. In one embodiment, the sugar (e.g., glucose) is provided at a molar concentration ratio of glycerol to sugar of 30:1. In one embodiment, the sugar (e.g., glucose) is provided at a molar concentration ratio of glycerol to sugar of 20:1. In one embodiment, the sugar (e.g., glucose) is provided at a molar concentration ratio of glycerol to sugar of 10:1. In one embodiment, the sugar (e.g., glucose) is provided at a molar concentration ratio of glycerol to sugar of 5:1. In one embodiment, the sugar (e.g., glucose) is provided at a molar concentration ratio of glycerol to sugar of 2:1. In one embodiment, the sugar (e.g., glucose) is provided at a molar concentration ratio of glycerol to sugar of 1:1. In certain embodiments, the sugar (e.g., glucose) is provided at a molar concentration ratio of glycerol to sugar of 1:100. In one embodiment, the sugar (e.g., glucose) is provided at a molar concentration ratio of glycerol to sugar of 1:90. In one embodiment, the sugar (e.g., glucose) is provided at a molar concentration ratio of glycerol to sugar of 1:80. In one embodiment, the sugar (e.g., glucose) is provided at a molar concentration ratio of glycerol to sugar of 1:70. In one embodiment, the sugar (e.g., glucose) is provided at a molar concentration ratio of glycerol to sugar of 1:60. In one embodiment, the sugar (e.g., glucose) is provided at a molar concentration ratio of glycerol to sugar of 1:50. In one embodiment, the sugar (e.g., glucose) is provided at a molar concentration ratio of glycerol to sugar of 1:40. In one embodiment, the sugar (e.g., glucose) is provided at a molar concentration ratio of glycerol to sugar of 1:30. In one embodiment, the sugar (e.g., glucose) is provided at a molar concentration ratio of glycerol to sugar of 1:20. In one embodiment, the sugar (e.g., glucose) is provided at a molar concentration ratio of glycerol to sugar of 1:10. In one embodiment, the sugar (e.g., glucose) is provided at a molar concentration ratio of glycerol to sugar of 1:5. In one embodiment, the sugar (e.g., glucose) is provided at a molar concentration ratio of glycerol to sugar of 1:2. In certain embodiments of the ratios provided above, the sugar is a sugar-containing biomass. In certain other embodiments of the ratios provided above, the glycerol is a crude glycerol or a crude glycerol without further treatment. In other embodiments of the ratios provided above, the sugar is a sugar-containing biomass, and the glycerol is a crude glycerol or a crude glycerol without further treatment.

Crude glycerol can be a by-product produced in the production of biodiesel, and can be used for fermentation without any further treatment. Biodiesel production methods include (1) a chemical method wherein the glycerol-group of vegetable oils or animal oils is substituted by low-carbon alcohols such as methanol or ethanol to produce a corresponding fatty acid methyl esters or fatty acid ethyl esters by transesterification in the presence of acidic or basic catalysts; (2) a biological method where biological enzymes or cells are used to catalyze transesterification reaction and the corresponding fatty acid methyl esters or fatty acid ethyl esters are produced; and (3) a supercritical method, wherein transesterification reaction is carried out in a supercritical solvent system without any catalysts. The chemical composition of crude glycerol can vary with the process used to produce biodiesel, the transesterification efficiency, recovery efficiency of the biodiesel, other impurities in the feedstock, and whether methanol and catalysts were recovered. For example, the chemical compositions of eleven crude glycerol collected from seven Australian biodiesel producers reported that glycerol content ranged between 38% and 96%, with some samples including more than 14% methanol and 29% ash. In certain embodiments, the crude glycerol comprises from 5% to 99% glycerol. In some embodiments, the crude glycerol comprises from 10% to 90% glycerol. In some embodiments, the crude glycerol comprises from 10% to 80% glycerol. In some embodiments, the crude glycerol comprises from 10% to 70% glycerol. In some embodiments, the crude glycerol comprises from 10% to 60% glycerol. In some embodiments, the crude glycerol comprises from 10% to 50% glycerol. In some embodiments, the crude glycerol comprises from 10% to 40% glycerol. In some embodiments, the crude glycerol comprises from 10% to 30% glycerol. In some embodiments, the crude glycerol comprises from 10% to 20% glycerol. In some embodiments, the crude glycerol comprises from 80% to 90% glycerol. In some embodiments, the crude glycerol comprises from 70% to 90% glycerol. In some embodiments, the crude glycerol comprises from 60% to 90% glycerol. In some embodiments, the crude glycerol comprises from 50% to 90% glycerol. In some embodiments, the crude glycerol comprises from 40% to 90% glycerol. In some embodiments, the crude glycerol comprises from 30% to 90% glycerol. In some embodiments, the crude glycerol comprises from 20% to 90% glycerol. In some embodiments, the crude glycerol comprises from 20% to 40% glycerol. In some embodiments, the crude glycerol comprises from 40% to 60% glycerol. In some embodiments, the crude glycerol comprises from 60% to 80% glycerol. In some embodiments, the crude glycerol comprises from 50% to 70% glycerol. In one embodiment, the glycerol comprises 5% glycerol. In one embodiment, the glycerol comprises 10% glycerol. In one embodiment, the glycerol comprises 15% glycerol. In one embodiment, the glycerol comprises 20% glycerol. In one embodiment, the glycerol comprises 25% glycerol. In one embodiment, the glycerol comprises 30% glycerol. In one embodiment, the glycerol comprises 35% glycerol. In one embodiment, the glycerol comprises 40% glycerol. In one embodiment, the glycerol comprises 45% glycerol. In one embodiment, the glycerol comprises 50% glycerol. In one embodiment, the glycerol comprises 55% glycerol. In one embodiment, the glycerol comprises 60% glycerol. In one embodiment, the glycerol comprises 65% glycerol. In one embodiment, the glycerol comprises 70% glycerol. In one embodiment, the glycerol comprises 75% glycerol. In one embodiment, the glycerol comprises 80% glycerol. In one embodiment, the glycerol comprises 85% glycerol. In one embodiment, the glycerol comprises 90% glycerol. In one embodiment, the glycerol comprises 95% glycerol. In one embodiment, the glycerol comprises 99% glycerol.

In one embodiment, the carbon source is methanol or formate. In certain embodiments, methanol is used as a carbon source in the FAPs provided herein. In one embodiment, the carbon source is methanol or formate. In other embodiments, formate is used as a carbon source in the FAPs provided herein. In specific embodiments, methanol is used as a carbon source in the MMPs provided herein, either alone or in combination with the product pathways provided herein. In one embodiment, the carbon source is methanol. In another embodiment, the carbon source is formate.

In one embodiment, the carbon source comprises methanol, and sugar (e.g., glucose) or a sugar-containing biomass. In another embodiment, the carbon source comprises formate, and sugar (e.g., glucose) or a sugar-containing biomass. In one embodiment, the carbon source comprises methanol, formate, and sugar (e.g., glucose) or a sugar-containing biomass. In specific embodiments, the methanol or formate, or both, in the fermentation feed is provided as a mixture with sugar (e.g., glucose) or sugar-comprising biomass. In certain embodiments, sugar is provided for sufficient strain growth.

In certain embodiments, the carbon source comprises methanol and a sugar (e.g., glucose). In some embodiments, the sugar (e.g., glucose) is provided at a molar concentration ratio of methanol to sugar of from 200:1 to 1:200. In some embodiments, the sugar (e.g., glucose) is provided at a molar concentration ratio of methanol to sugar of from 100:1 to 1:100. In some embodiments, the sugar (e.g., glucose) is provided at a molar concentration ratio of methanol to sugar of from 100:1 to 5:1. In some embodiments, the sugar (e.g., glucose) is provided at a molar concentration ratio of methanol to sugar of from 50:1 to 5:1. In certain embodiments, the sugar (e.g., glucose) is provided at a molar concentration ratio of methanol to sugar of 100:1. In one embodiment, the sugar (e.g., glucose) is provided at a molar concentration ratio of methanol to sugar of 90:1. In one embodiment, the sugar (e.g., glucose) is provided at a molar concentration ratio of methanol to sugar of 80:1. In one embodiment, the sugar (e.g., glucose) is provided at a molar concentration ratio of methanol to sugar of 70:1. In one embodiment, the sugar (e.g., glucose) is provided at a molar concentration ratio of methanol to sugar of 60:1. In one embodiment, the sugar (e.g., glucose) is provided at a molar concentration ratio of methanol to sugar of 50:1. In one embodiment, the sugar (e.g., glucose) is provided at a molar concentration ratio of methanol to sugar of 40:1. In one embodiment, the sugar (e.g., glucose) is provided at a molar concentration ratio of methanol to sugar of 30:1. In one embodiment, the sugar (e.g., glucose) is provided at a molar concentration ratio of methanol to sugar of 20:1. In one embodiment, the sugar (e.g., glucose) is provided at a molar concentration ratio of methanol to sugar of 10:1. In one embodiment, the sugar (e.g., glucose) is provided at a molar concentration ratio of methanol to sugar of 5:1. In one embodiment, the sugar (e.g., glucose) is provided at a molar concentration ratio of methanol to sugar of 2:1. In one embodiment, the sugar (e.g., glucose) is provided at a molar concentration ratio of methanol to sugar of 1:1. In certain embodiments, the sugar (e.g., glucose) is provided at a molar concentration ratio of methanol to sugar of 1:100. In one embodiment, the sugar (e.g., glucose) is provided at a molar concentration ratio of methanol to sugar of 1:90. In one embodiment, the sugar (e.g., glucose) is provided at a molar concentration ratio of methanol to sugar of 1:80. In one embodiment, the sugar (e.g., glucose) is provided at a molar concentration ratio of methanol to sugar of 1:70. In one embodiment, the sugar (e.g., glucose) is provided at a molar concentration ratio of methanol to sugar of 1:60. In one embodiment, the sugar (e.g., glucose) is provided at a molar concentration ratio of methanol to sugar of 1:50. In one embodiment, the sugar (e.g., glucose) is provided at a molar concentration ratio of methanol to sugar of 1:40. In one embodiment, the sugar (e.g., glucose) is provided at a molar concentration ratio of methanol to sugar of 1:30. In one embodiment, the sugar (e.g., glucose) is provided at a molar concentration ratio of methanol to sugar of 1:20. In one embodiment, the sugar (e.g., glucose) is provided at a molar concentration ratio of methanol to sugar of 1:10. In one embodiment, the sugar (e.g., glucose) is provided at a molar concentration ratio of methanol to sugar of 1:5. In one embodiment, the sugar (e.g., glucose) is provided at a molar concentration ratio of methanol to sugar of 1:2. In certain embodiments of the ratios provided above, the sugar is a sugar-containing biomass.

In certain embodiments, the carbon source comprises formate and a sugar (e.g., glucose). In some embodiments, the sugar (e.g., glucose) is provided at a molar concentration ratio of formate to sugar of from 200:1 to 1:200. In some embodiments, the sugar (e.g., glucose) is provided at a molar concentration ratio of formate to sugar of from 100:1 to 1:100. In some embodiments, the sugar (e.g., glucose) is provided at a molar concentration ratio of formate to sugar of from 100:1 to 5:1. In some embodiments, the sugar (e.g., glucose) is provided at a molar concentration ratio of formate to sugar of from 50:1 to 5:1. In certain embodiments, the sugar (e.g., glucose) is provided at a molar concentration ratio of formate to sugar of 100:1. In one embodiment, the sugar (e.g., glucose) is provided at a molar concentration ratio of formate to sugar of 90:1. In one embodiment, the sugar (e.g., glucose) is provided at a molar concentration ratio of formate to sugar of 80:1. In one embodiment, the sugar (e.g., glucose) is provided at a molar concentration ratio of formate to sugar of 70:1. In one embodiment, the sugar (e.g., glucose) is provided at a molar concentration ratio of formate to sugar of 60:1. In one embodiment, the sugar (e.g., glucose) is provided at a molar concentration ratio of formate to sugar of 50:1. In one embodiment, the sugar (e.g., glucose) is provided at a molar concentration ratio of formate to sugar of 40:1. In one embodiment, the sugar (e.g., glucose) is provided at a molar concentration ratio of formate to sugar of 30:1. In one embodiment, the sugar (e.g., glucose) is provided at a molar concentration ratio of formate to sugar of 20:1. In one embodiment, the sugar (e.g., glucose) is provided at a molar concentration ratio of formate to sugar of 10:1. In one embodiment, the sugar (e.g., glucose) is provided at a molar concentration ratio of formate to sugar of 5:1. In one embodiment, the sugar (e.g., glucose) is provided at a molar concentration ratio of formate to sugar of 2:1. In one embodiment, the sugar (e.g., glucose) is provided at a molar concentration ratio of formate to sugar of 1:1. In certain embodiments, the sugar (e.g., glucose) is provided at a molar concentration ratio of formate to sugar of 1:100. In one embodiment, the sugar (e.g., glucose) is provided at a molar concentration ratio of formate to sugar of 1:90. In one embodiment, the sugar (e.g., glucose) is provided at a molar concentration ratio of formate to sugar of 1:80. In one embodiment, the sugar (e.g., glucose) is provided at a molar concentration ratio of formate to sugar of 1:70. In one embodiment, the sugar (e.g., glucose) is provided at a molar concentration ratio of formate to sugar of 1:60. In one embodiment, the sugar (e.g., glucose) is provided at a molar concentration ratio of formate to sugar of 1:50. In one embodiment, the sugar (e.g., glucose) is provided at a molar concentration ratio of formate to sugar of 1:40. In one embodiment, the sugar (e.g., glucose) is provided at a molar concentration ratio of formate to sugar of 1:30. In one embodiment, the sugar (e.g., glucose) is provided at a molar concentration ratio of formate to sugar of 1:20. In one embodiment, the sugar (e.g., glucose) is provided at a molar concentration ratio of formate to sugar of 1:10. In one embodiment, the sugar (e.g., glucose) is provided at a molar concentration ratio of formate to sugar of 1:5. In one embodiment, the sugar (e.g., glucose) is provided at a molar concentration ratio of formate to sugar of 1:2. In certain embodiments of the ratios provided above, the sugar is a sugar-containing biomass.

In certain embodiments, the carbon source comprises a mixture of methanol and formate, and a sugar (e.g., glucose). In certain embodiments, sugar is provided for sufficient strain growth. In some embodiments, the sugar (e.g., glucose) is provided at a molar concentration ratio of methanol and formate to sugar of from 200:1 to 1:200. In some embodiments, the sugar (e.g., glucose) is provided at a molar concentration ratio of methanol and formate to sugar of from 100:1 to 1:100. In some embodiments, the sugar (e.g., glucose) is provided at a molar concentration ratio of methanol and formate to sugar of from 100:1 to 5:1. In some embodiments, the sugar (e.g., glucose) is provided at a molar concentration ratio of methanol and formate to sugar of from 50:1 to 5:1. In certain embodiments, the sugar (e.g., glucose) is provided at a molar concentration ratio of methanol and formate to sugar of 100:1. In one embodiment, the sugar (e.g., glucose) is provided at a molar concentration ratio of methanol and formate to sugar of 90:1. In one embodiment, the sugar (e.g., glucose) is provided at a molar concentration ratio of methanol and formate to sugar of 80:1. In one embodiment, the sugar (e.g., glucose) is provided at a molar concentration ratio of methanol and formate to sugar of 70:1. In one embodiment, the sugar (e.g., glucose) is provided at a molar concentration ratio of methanol and formate to sugar of 60:1. In one embodiment, the sugar (e.g., glucose) is provided at a molar concentration ratio of methanol and formate to sugar of 50:1. In one embodiment, the sugar (e.g., glucose) is provided at a molar concentration ratio of methanol and formate to sugar of 40:1. In one embodiment, the sugar (e.g., glucose) is provided at a molar concentration ratio of methanol and formate to sugar of 30:1. In one embodiment, the sugar (e.g., glucose) is provided at a molar concentration ratio of methanol and formate to sugar of 20:1. In one embodiment, the sugar (e.g., glucose) is provided at a molar concentration ratio of methanol and formate to sugar of 10:1. In one embodiment, the sugar (e.g., glucose) is provided at a molar concentration ratio of methanol and formate to sugar of 5:1. In one embodiment, the sugar (e.g., glucose) is provided at a molar concentration ratio of methanol and formate to sugar of 2:1. In one embodiment, the sugar (e.g., glucose) is provided at a molar concentration ratio of methanol and formate to sugar of 1:1. In certain embodiments, the sugar (e.g., glucose) is provided at a molar concentration ratio of methanol and formate to sugar of 1:100. In one embodiment, the sugar (e.g., glucose) is provided at a molar concentration ratio of methanol and formate to sugar of 1:90. In one embodiment, the sugar (e.g., glucose) is provided at a molar concentration ratio of methanol and formate to sugar of 1:80. In one embodiment, the sugar (e.g., glucose) is provided at a molar concentration ratio of methanol and formate to sugar of 1:70. In one embodiment, the sugar (e.g., glucose) is provided at a molar concentration ratio of methanol and formate to sugar of 1:60. In one embodiment, the sugar (e.g., glucose) is provided at a molar concentration ratio of methanol and formate to sugar of 1:50. In one embodiment, the sugar (e.g., glucose) is provided at a molar concentration ratio of methanol and formate to sugar of 1:40. In one embodiment, the sugar (e.g., glucose) is provided at a molar concentration ratio of methanol and formate to sugar of 1:30. In one embodiment, the sugar (e.g., glucose) is provided at a molar concentration ratio of methanol and formate to sugar of 1:20. In one embodiment, the sugar (e.g., glucose) is provided at a molar concentration ratio of methanol and formate to sugar of 1:10. In one embodiment, the sugar (e.g., glucose) is provided at a molar concentration ratio of methanol and formate to sugar of 1:5. In one embodiment, the sugar (e.g., glucose) is provided at a molar concentration ratio of methanol and formate to sugar of 1:2. In certain embodiments of the ratios provided above, the sugar is a sugar-containing biomass.

Given the teachings and guidance provided herein, those skilled in the art will understand that a NNOMO can be produced that secretes the biosynthesized compounds when grown on a carbon source such as a carbohydrate. Such compounds include, for example, succinate and any of the intermediate metabolites in the SucP. All that is required is to engineer in one or more of the required enzyme or protein activities to achieve biosynthesis of the desired compound or intermediate including, for example, inclusion of some or all of the succinate biosynthetic pathways. Accordingly, provided herein is a NNOMO that produces and/or secretes succinate when grown on a carbohydrate or other carbon source and produces and/or secretes any of the intermediate metabolites shown in the SucP when grown on a carbohydrate or other carbon source. The succinate-producing microbial organisms provided herein can initiate synthesis from an intermediate. The same holds true for intermediates in the formaldehyde assimilation and MMPs.

The NNOMOs provided herein are constructed using methods well known in the art as exemplified herein to endogenously or exogenously express at least one nucleic acid encoding a succinate biosynthetic pathway and/or exogenously express a MMPE or protein in sufficient amounts to produce succinate. It is understood that the microbial organisms are cultured under conditions sufficient to produce succinate. Following the teachings and guidance provided herein, the NNOMOs can achieve biosynthesis of succinate, resulting in intracellular concentrations between about 0.1-500 mM or more. Generally, the intracellular concentration of succinate is between about 3-150 mM, particularly between about 5-125 mM and more particularly between about 8-100 mM, including about 10 mM, 20 mM, 50 mM, 80 mM, or more. Intracellular concentrations between and above each of these exemplary ranges also can be achieved from the NNOMOs provided herein.

In some embodiments, culture conditions include anaerobic or substantially anaerobic growth or maintenance conditions. Exemplary anaerobic conditions have been described previously and are well known in the art. Exemplary anaerobic conditions for fermentation processes are described herein and are described, for example, in U.S. Publ. No. 2009/0047719. Any of these conditions can be employed with the NNOMOs as well as other anaerobic conditions well known in the art. Under such anaerobic or substantially anaerobic conditions, the succinate producers can synthesize succinate at intracellular concentrations of 5-100 mM or more as well as all other concentrations exemplified herein. It is understood that, even though the above description refers to intracellular concentrations, succinate can produce succinate intracellularly and/or secrete the product into the culture medium.

Exemplary fermentation processes include, but are not limited to, fed-batch fermentation and batch separation; fed-batch fermentation and continuous separation; and continuous fermentation and continuous separation. In an exemplary batch fermentation protocol, the production organism is grown in a suitably sized bioreactor sparged with an appropriate gas. Under anaerobic conditions, the culture is sparged with an inert gas or combination of gases, for example, nitrogen, N2/CO2 mixture, argon, helium, and the like. As the cells grow and utilize the carbon source, additional carbon source(s) and/or other nutrients are fed into the bioreactor at a rate approximately balancing consumption of the carbon source and/or nutrients. The temperature of the bioreactor is maintained at a desired temperature, generally in the range of 22-37 degrees C., but the temperature can be maintained at a higher or lower temperature depending on the growth characteristics of the production organism and/or desired conditions for the fermentation process. Growth continues for a desired period of time to achieve desired characteristics of the culture in the fermenter, for example, cell density, product concentration, and the like. In a batch fermentation process, the time period for the fermentation is generally in the range of several hours to several days, for example, 8 to 24 hours, or 1, 2, 3, 4 or 5 days, or up to a week, depending on the desired culture conditions. The pH can be controlled or not, as desired, in which case a culture in which pH is not controlled will typically decrease to pH 3-6 by the end of the run. Upon completion of the cultivation period, the fermenter contents can be passed through a cell separation unit, for example, a centrifuge, filtration unit, and the like, to remove cells and cell debris. In the case where the desired product is expressed intracellularly, the cells can be lysed or disrupted enzymatically or chemically prior to or after separation of cells from the fermentation broth, as desired, in order to release additional product. The fermentation broth can be transferred to a product separations unit. Isolation of product occurs by standard separations procedures employed in the art to separate a desired product from dilute aqueous solutions. Such methods include, but are not limited to, liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like) to provide an organic solution of the product, if appropriate, standard distillation methods, and the like, depending on the chemical characteristics of the product of the fermenation process.

In an exemplary fully continuous fermentation protocol, the production organism is generally first grown up in batch mode in order to achieve a desired cell density. When the carbon source and/or other nutrients are exhausted, feed medium of the same composition is supplied continuously at a desired rate, and fermentation liquid is withdrawn at the same rate. Under such conditions, the product concentration in the bioreactor generally remains constant, as well as the cell density. The temperature of the fermenter is maintained at a desired temperature, as discussed above. During the continuous fermentation phase, it is generally desirable to maintain a suitable pH range for optimized production. The pH can be monitored and maintained using routine methods, including the addition of suitable acids or bases to maintain a desired pH range. The bioreactor is operated continuously for extended periods of time, generally at least one week to several weeks and up to one month, or longer, as appropriate and desired. The fermentation liquid and/or culture is monitored periodically, including sampling up to every day, as desired, to assure consistency of product concentration and/or cell density. In continuous mode, fermenter contents are constantly removed as new feed medium is supplied. The exit stream, containing cells, medium, and product, are generally subjected to a continuous product separations procedure, with or without removing cells and cell debris, as desired. Continuous separations methods employed in the art can be used to separate the product from dilute aqueous solutions, including but not limited to continuous liquid-liquid extraction using a water immiscible organic solvent (e.g., toluene or other suitable solvents, including but not limited to diethyl ether, ethyl acetate, tetrahydrofuran (THF), methylene chloride, chloroform, benzene, pentane, hexane, heptane, petroleum ether, methyl tertiary butyl ether (MTBE), dioxane, dimethylformamide (DMF), dimethyl sulfoxide (DMSO), and the like), standard continuous distillation methods, and the like, or other methods well known in the art.

In addition to the culturing and fermentation conditions disclosed herein, growth condition for achieving biosynthesis of succinate can include the addition of an osmoprotectant to the culturing conditions. In certain embodiments, the NNOMOs provided herein can be sustained, cultured or fermented as described herein in the presence of an osmoprotectant. Briefly, an osmoprotectant refers to a compound that acts as an osmolyte and helps a microbial organism as described herein survive osmotic stress. Osmoprotectants include, but are not limited to, betaines, amino acids, and the sugar trehalose. Non-limiting examples of such are glycine betaine, praline betaine, dimethylthetin, dimethylslfonioproprionate, 3-dimethylsulfonio-2-methylproprionate, pipecolic acid, dimethylsulfonioacetate, choline, L-carnitine and ectoine. In one aspect, the osmoprotectant is glycine betaine. It is understood to one of ordinary skill in the art that the amount and type of osmoprotectant suitable for protecting a microbial organism described herein from osmotic stress will depend on the microbial organism used. The amount of osmoprotectant in the culturing conditions can be, for example, no more than about 0.1 mM, no more than about 0.5 mM, no more than about 1.0 mM, no more than about 1.5 mM, no more than about 2.0 mM, no more than about 2.5 mM, no more than about 3.0 mM, no more than about 5.0 mM, no more than about 7.0 mM, no more than about 10 mM, no more than about 50 mM, no more than about 100 mM or no more than about 500 mM.

The culture conditions can include, for example, liquid culture procedures as well as fermentation and other large scale culture procedures. As described herein, particularly useful yields of the biosynthetic products provided herein can be obtained under anaerobic or substantially anaerobic culture conditions.

As described herein, one exemplary growth condition for achieving biosynthesis of succinate, as well as other pathway intermediates, includes anaerobic culture or fermentation conditions. In certain embodiments, the NNOMOs provided can be sustained, cultured or fermented under anaerobic or substantially anaerobic conditions. Briefly, anaerobic conditions refer to an environment devoid of oxygen. Substantially anaerobic conditions include, for example, a culture, batch fermentation or continuous fermentation such that the dissolved oxygen concentration in the medium remains between 0 and 10% of saturation. Substantially anaerobic conditions also includes growing or resting cells in liquid medium or on solid agar inside a sealed chamber maintained with an atmosphere of less than 1% oxygen. The percent of oxygen can be maintained by, for example, sparging the culture with an $N_2/CO_2$ mixture or other suitable non-oxygen gas or gases.

The culture conditions described herein can be scaled up and grown continuously for manufacturing of succinate. Exemplary growth procedures include, for example, fed-batch fermentation and batch separation; fed-batch fermentation and continuous separation, or continuous fermentation and continuous separation. All of these processes are well known in the art. Fermentation procedures are particularly useful for the biosynthetic production of commercial quantities of succinate. Generally, and as with non-continuous culture procedures, the continuous and/or near-continuous production of succinate will include culturing a non-naturally occurring succinate producing organism provided herein in sufficient nutrients and medium to sustain and/or nearly sustain growth in an exponential phase. Continuous culture under such conditions can be included, for example, growth or culturing for 1 day, 2, 3, 4, 5, 6 or 7 days or more. Additionally, continuous culture can include longer time periods of 1 week, 2, 3, 4 or 5 or more weeks and up to several months. Alternatively, organisms provided can be cultured for hours, if suitable for a particular application. It is to be understood that the continuous and/or near-continuous culture conditions also can include all time intervals in between these exemplary periods. It is further understood that the time of culturing the microbial organism provided herein is for a sufficient period of time to produce a sufficient amount of product for a desired purpose.

Fermentation procedures are well known in the art. Briefly, fermentation for the biosynthetic production of succinate can be utilized in, for example, fed-batch fermentation and batch separation; fed-batch fermentation and continuous separation, or continuous fermentation and continuous separation. Examples of batch and continuous fermentation procedures are well known in the art.

In addition to the above fermentation procedures using the succinate producers for continuous production of substantial quantities of succinate, the succinate producers also can be, for example, simultaneously subjected to chemical synthesis procedures to convert the product to other compounds or the product can be separated from the fermentation culture and sequentially subjected to chemical and/or enzymatic conversion to convert the product to other compounds, if desired.

To generate better producers, metabolic modeling can be utilized to optimize growth conditions. Modeling can also be used to design gene knockouts that additionally optimize utilization of the pathway (see, for example, U.S. Publ. Nos. 2002/0012939, 2003/0224363, 2004/0029149, 2004/0072723, 2003/0059792, 2002/0168654 and 2004/0009466, and U.S. Pat. No. 7,127,379). Modeling analysis allows reliable predictions of the effects on cell growth of shifting the metabolism towards more efficient production of succinate.

One computational method for identifying and designing metabolic alterations favoring biosynthesis of a desired product is the OptKnock computational framework (Burgard et al., *Biotechnol. Bioeng.* 84:647-657 (2003)). Opt-Knock is a metabolic modeling and simulation program that suggests gene deletion or disruption strategies that result in genetically stable microorganisms which overproduce the target product. Specifically, the framework examines the complete metabolic and/or biochemical network of a microorganism in order to suggest genetic manipulations that force the desired biochemical to become an obligatory byproduct of cell growth. By coupling biochemical production with cell growth through strategically placed gene deletions or other functional gene disruption, the growth selection pressures imposed on the engineered strains after long periods of time in a bioreactor lead to improvements in performance as a result of the compulsory growth-coupled biochemical production. Lastly, when gene deletions are constructed there is a negligible possibility of the designed strains reverting to their wild-type states because the genes selected by OptKnock are to be completely removed from the genome. Therefore, this computational methodology can be used to either identify alternative pathways that lead to biosynthesis of a desired product or used in connection with the NNOMOs for further optimization of biosynthesis of a desired product.

Briefly, OptKnock is a term used herein to refer to a computational method and system for modeling cellular metabolism. The OptKnock program relates to a framework of models and methods that incorporate particular constraints into flux balance analysis (FBA) models. These constraints include, for example, qualitative kinetic information, qualitative regulatory information, and/or DNA microarray experimental data. OptKnock also computes solutions to various metabolic problems by, for example, tightening the flux boundaries derived through flux balance models and subsequently probing the performance limits of metabolic networks in the presence of gene additions or deletions. OptKnock computational framework allows the construction of model formulations that allow an effective query of the performance limits of metabolic networks and provides methods for solving the resulting mixed-integer linear programming problems. The metabolic modeling and simulation methods referred to herein as OptKnock are described in, for example, U.S. Publ. No. 2002/0168654, International Patent Application No. PCT/US02/00660, and U.S. Publ. No. 2009/0047719.

Another computational method for identifying and designing metabolic alterations favoring biosynthetic production of a product is a metabolic modeling and simulation system termed SimPheny®. This computational method and system is described in, for example, U.S. Publ. No. 2003/0233218, and International Patent Application No. PCT/US03/18838. SimPheny® is a computational system that can be used to produce a network model in silico and to simulate the flux of mass, energy or charge through the chemical reactions of a biological system to define a solution space that contains any and all possible functionalities of the chemical reactions in the system, thereby determining a range of allowed activities for the biological system. This approach is referred to as constraints-based modeling because the solution space is defined by constraints such as the known stoichiometry of the included reactions as well as reaction thermodynamic and capacity constraints associated with maximum fluxes through reactions. The space defined by these constraints can be interrogated to determine the phenotypic capabilities and behavior of the biological system or of its biochemical components.

These computational approaches are consistent with biological realities because biological systems are flexible and can reach the same result in many different ways. Biological systems are designed through evolutionary mechanisms that have been restricted by fundamental constraints that all living systems must face. Therefore, constraints-based modeling strategy embraces these general realities. Further, the ability to continuously impose further restrictions on a network model via the tightening of constraints results in a reduction in the size of the solution space, thereby enhancing the precision with which physiological performance or phenotype can be predicted.

Given the teachings and guidance provided herein, those skilled in the art will be able to apply various computational frameworks for metabolic modeling and simulation to design and implement biosynthesis of a desired compound in host microbial organisms. Such metabolic modeling and simulation methods include, for example, the computational systems exemplified above as SimPheny® and OptKnock. For illustration, some methods are described herein with reference to the OptKnock computation framework for modeling and simulation. Those skilled in the art will know how to apply the identification, design and implementation of the metabolic alterations using OptKnock to any of such other metabolic modeling and simulation computational frameworks and methods well known in the art.

The methods described above will provide one set of metabolic reactions to disrupt. Elimination of each reaction within the set or metabolic modification can result in a desired product as an obligatory product during the growth phase of the organism. Because the reactions are known, a solution to the bilevel OptKnock problem also will provide the associated gene or genes encoding one or more enzymes that catalyze each reaction within the set of reactions. Identification of a set of reactions and their corresponding genes encoding the enzymes participating in each reaction is generally an automated process, accomplished through correlation of the reactions with a reaction database having a relationship between enzymes and encoding genes.

Once identified, the set of reactions that are to be disrupted in order to achieve production of a desired product are implemented in the target cell or organism by functional disruption of at least one gene encoding each metabolic reaction within the set. One particularly useful means to achieve functional disruption of the reaction set is by deletion of each encoding gene. However, in some instances, it can be beneficial to disrupt the reaction by other genetic aberrations including, for example, mutation, deletion of regulatory regions such as promoters or cis binding sites for regulatory factors, or by truncation of the coding sequence at any of a number of locations. These latter aberrations, resulting in less than total deletion of the gene set can be useful, for example, when rapid assessments of the coupling of a product are desired or when genetic reversion is less likely to occur.

To identify additional productive solutions to the above described bilevel OptKnock problem which lead to further sets of reactions to disrupt or metabolic modifications that can result in the biosynthesis, including growth-coupled biosynthesis of a desired product, an optimization method, termed integer cuts, can be implemented. This method proceeds by iteratively solving the OptKnock problem exemplified above with the incorporation of an additional constraint referred to as an integer cut at each iteration. Integer cut constraints effectively prevent the solution procedure from choosing the exact same set of reactions identified in any previous iteration that obligatorily couples product biosynthesis to growth. For example, if a previously identified growth-coupled metabolic modification specifies reactions 1, 2, and 3 for disruption, then the following constraint prevents the same reactions from being simultaneously considered in subsequent solutions. The integer cut method is well known in the art and can be found described in, for example, Burgard et al., *Biotechnol. Prog.* 17:791-797 (2001). As with all methods described herein with reference to their use in combination with the OptKnock computational framework for metabolic modeling and simulation, the integer cut method of reducing redundancy in iterative computational analysis also can be applied with other computational frameworks well known in the art including, for example, SimPheny®.

The methods exemplified herein allow the construction of cells and organisms that biosynthetically produce a desired product, including the obligatory coupling of production of a target biochemical product to growth of the cell or organism engineered to harbor the identified genetic alterations. Therefore, the computational methods described herein allow the identification and implementation of metabolic modifications that are identified by an in silico method selected from OptKnock or SimPheny®. The set of metabolic modifications can include, for example, addition of one or more biosynthetic pathway enzymes and/or functional disruption of one or more metabolic reactions including, for example, disruption by gene deletion.

As discussed above, the OptKnock methodology was developed on the premise that mutant microbial networks can be evolved towards their computationally predicted maximum-growth phenotypes when subjected to long periods of growth selection. In other words, the approach leverages an organism's ability to self-optimize under selective pressures. The OptKnock framework allows for the exhaustive enumeration of gene deletion combinations that force a coupling between biochemical production and cell growth based on network stoichiometry. The identification of optimal gene/reaction knockouts requires the solution of a bilevel optimization problem that chooses the set of active reactions such that an optimal growth solution for the resulting network overproduces the biochemical of interest (Burgard et al., *Biotechnol. Bioeng.* 84:647-657 (2003)).

An in silico stoichiometric model of *E. coli* metabolism can be employed to identify essential genes for metabolic pathways as exemplified previously and described in, for example, U.S. Publ. Nos. 2002/0012939, 2003/0224363, 2004/0029149, 2004/0072723, 2003/0059792, 2002/0168654 and 2004/0009466, and in U.S. Pat. No. 7,127,379. As disclosed herein, the OptKnock mathematical framework can be applied to pinpoint gene deletions leading to the growth-coupled production of a desired product. Further, the solution of the bilevel OptKnock problem provides only one set of deletions. To enumerate all meaningful solutions, that is, all sets of knockouts leading to growth-coupled production formation, an optimization technique, termed integer cuts, can be implemented. This entails iteratively solving the OptKnock problem with the incorporation of an additional constraint referred to as an integer cut at each iteration, as discussed above.

As disclosed herein, a nucleic acid encoding a desired activity of a SucP, FAP, and/or MMP can be introduced into a host organism. In some cases, it can be desirable to modify an activity of a SucP or MMPE or protein to increase production of succinate; formaldehyde; and/or reducing equivalents. For example, known mutations that increase the activity of a protein or enzyme can be introduced into an encoding nucleic acid molecule. Additionally, optimization methods can be applied to increase the activity of an enzyme or protein and/or decrease an inhibitory activity, for example, decrease the activity of a negative regulator.

One such optimization method is directed evolution. Directed evolution is a powerful approach that involves the introduction of mutations targeted to a specific gene in order to improve and/or alter the properties of an enzyme. Improved and/or altered enzymes can be identified through the development and implementation of sensitive high-throughput screening assays that allow the automated screening of many enzyme variants (for example, >$10^4$). Iterative rounds of mutagenesis and screening typically are performed to afford an enzyme with optimized properties. Computational algorithms that can help to identify areas of the gene for mutagenesis also have been developed and can significantly reduce the number of enzyme variants that need to be generated and screened. Numerous directed evolution technologies have been developed (for reviews, see Hibbert et al., *Biomol. Eng.* 22:11-19 (2005); Huisman and Lalonde, In Biocatalysis in the pharmaceutical and biotechnology industries pgs. 717-742 (2007), Patel (ed.), CRC Press; Otten and Quax. *Biomol. Eng.* 22:1-9 (2005).; and Sen et al., *Appl Biochem. Biotechnol* 143:212-223 (2007)) to be effective at creating diverse variant libraries, and these methods have been successfully applied to the improvement of a wide range of properties across many enzyme classes. Enzyme characteristics that have been improved and/or altered by directed evolution technologies include, for example: selectivity/specificity, for conversion of non-natural substrates; temperature stability, for robust high temperature processing; pH stability, for bioprocessing under lower or higher pH conditions; substrate or product tolerance, so that high product titers can be achieved; binding ($K_m$), including broadening substrate binding to include non-natural substrates; inhibition ($K_i$), to remove inhibition by products, substrates, or key intermediates; activity (kcat), to increases enzymatic reaction rates to achieve desired flux; expression levels, to increase protein yields and overall pathway flux; oxygen stability, for operation of air sensitive enzymes under aerobic conditions; and anaerobic activity, for operation of an aerobic enzyme in the absence of oxygen.

A number of exemplary methods have been developed for the mutagenesis and diversification of genes to target desired properties of specific enzymes. Such methods are well known to those skilled in the art. Any of these can be used to alter and/or optimize the activity of a SucP and/or a MMPE or protein. Such methods include, but are not limited to EpPCR, which introduces random point mutations by reducing the fidelity of DNA polymerase in PCR reactions (Pritchard et al., *J. Theor. Biol.* 234:497-509 (2005)); Error-prone Rolling Circle Amplification (epRCA), which is similar to epPCR except a whole circular plasmid is used as the template and random 6-mers with exonuclease resistant thiophosphate linkages on the last 2 nucleotides are used to amplify the plasmid followed by transformation into cells in which the plasmid is re-circularized at tandem repeats (Fujii et al., *Nucleic Acids Res.* 32:e145 (2004); and Fujii et al., *Nat. Protocols* 1:2493-2497 (2006)); DNA or Family Shuffling, which typically involves digestion of two or more variant genes with nucleases such as Dnase I or EndoV to generate a pool of random fragments that are reassembled by cycles of annealing and extension in the presence of DNA polymerase to create a library of chimeric genes (Stemmer, *Proc. Natl. Acad. Sci. U.S.A.* 91:10747-10751 (1994); and Stemmer, *Nature* 370:389-391 (1994)); Staggered Extension (StEP), which entails template priming followed by repeated cycles of 2 step PCR with denaturation and very short duration of annealing/extension (as short as 5 sec) (Zhao et al., *Nat. Biotechnol.* 16:258-261 (1998)); Random Priming Recombination (RPR), in which random sequence primers are used to generate many short DNA fragments complementary to different segments of the template (Shao et al., *Nucleic Acids Res.* 26:681-683 (1998)).

Additional methods include Heteroduplex Recombination, in which linearized plasmid DNA is used to form heteroduplexes that are repaired by mismatch repair (Volkov et al, *Nucleic Acids Res.* 27:e18 (1999); and Volkov et al., *Methods Enzymol.* 328:456-463 (2000)); Random Chimeragenesis on Transient Templates (RACHITT), which employs Dnase I fragmentation and size fractionation of single stranded DNA (ssDNA) (Coco et al., *Nat. Biotechnol.* 19:354-359 (2001)); Recombined Extension on Truncated templates (RETT), which entails template switching of unidirectionally growing strands from primers in the presence of unidirectional ssDNA fragments used as a pool of templates (Lee et al., *J. Molec. Catalysis* 26:119-129 (2003)); Degenerate Oligonucleotide Gene Shuffling (DOGS), in which degenerate primers are used to control recombination between molecules; (Bergquist and Gibbs, *Methods Mol. Biol.* 352:191-204 (2007); Bergquist et al., *Biomol. Eng.* 22:63-72 (2005); Gibbs et al., *Gene* 271:13-20 (2001)); Incremental Truncation for the Creation of Hybrid Enzymes (ITCHY), which creates a combinatorial library with 1 base pair deletions of a gene or gene fragment of interest (Ostermeier et al., *Proc. Natl. Acad. Sci. U.S.A.* 96:3562-3567 (1999); and Ostermeier et al., *Nat. Biotechnol.* 17:1205-1209 (1999)); Thio-Incremental Truncation for the Creation of Hybrid Enzymes (THIO-ITCHY), which is similar to ITCHY except that phosphothioate dNTPs are used to generate truncations (Lutz et al., *Nucleic Acids Res.* 29:E16 (2001)); SCRATCHY, which combines two methods for recombining genes, ITCHY and DNA shuffling (Lutz et al., *Proc. Natl. Acad. Sci. U.S.A.* 98:11248-11253 (2001)); Random Drift Mutagenesis (RNDM), in which mutations made via epPCR are followed by screening/selection for those retaining usable activity (Bergquist et al., *Biomol. Eng.* 22:63-72 (2005)); Sequence Saturation Mutagenesis (SeSaM), a random mutagenesis method that generates a pool of random length fragments using random incorporation of a phosphothioate nucleotide and cleavage, which is used as a template to extend in the presence of "universal" bases such as inosine, and replication of an inosine-containing complement gives random base incorporation and, consequently, mutagenesis (Wong et al., *Biotechnol. J.* 3:74-82 (2008); Wong et al., *Nucleic Acids Res.* 32:e26 (2004); and Wong et al., *Anal. Biochem.* 341:187-189 (2005)); Synthetic Shuffling, which uses overlapping oligonucleotides designed to encode "all genetic diversity in targets" and allows a very high diversity for the shuffled progeny (Ness et al., *Nat. Biotechnol.* 20:1251-1255 (2002)); Nucleotide Exchange and Excision Technology NexT, which exploits a combination of dUTP incorporation followed by treatment with uracil DNA glycosylase and then piperidine to perform endpoint DNA fragmentation (Muller et al., *Nucleic Acids Res.* 33:e117 (2005)).

Further methods include Sequence Homology-Independent Protein Recombination (SHIPREC), in which a linker is used to facilitate fusion between two distantly related or unrelated genes, and a range of chimeras is generated between the two genes, resulting in libraries of single-crossover hybrids (Sieber et al., *Nat. Biotechnol.* 19:456-460 (2001)); Gene Site Saturation Mutagenesis™ (GSSM™), in which the starting materials include a supercoiled double stranded DNA (dsDNA) plasmid containing an insert and two primers which are degenerate at the desired site of mutations (Kretz et al., *Methods Enzymol.* 388:3-11 (2004)); Combinatorial Cassette Mutagenesis (CCM), which involves the use of short oligonucleotide cassettes to replace limited regions with a large number of possible amino acid sequence alterations (Reidhaar-Olson et al. *Methods Enzymol.* 208:564-586 (1991); and Reidhaar-Olson et al. *Science* 241:53-57 (1988)); Combinatorial Multiple Cassette Mutagenesis (CMCM), which is essentially similar to CCM and uses epPCR at high mutation rate to identify hot spots and hot regions and then extension by CMCM to cover a defined region of protein sequence space (Reetz et al., *Angew. Chem. Int. Ed Engl.* 40:3589-3591 (2001)); the Mutator Strains technique, in which conditional ts mutator plasmids, utilizing the mutD5 gene, which encodes a mutant subunit of DNA polymerase III, to allow increases of 20 to 4000-X in random and natural mutation frequency during selection and block accumulation of deleterious mutations when selection is not required (Selifonova et al., *Appl. Environ. Microbiol.* 67:3645-3649 (2001)); Low et al., *J. Mol. Biol.* 260:359-3680 (1996)).

Additional exemplary methods include Look-Through Mutagenesis (LTM), which is a multidimensional mutagenesis method that assesses and optimizes combinatorial mutations of selected amino acids (Rajpal et al., *Proc. Natl. Acad. Sci. U.S.A.* 102:8466-8471 (2005)); Gene Reassembly, which is a DNA shuffling method that can be applied to multiple genes at one time or to create a large library of chimeras (multiple mutations) of a single gene (Tunable GeneReassembly™ (TGR™) Technology supplied by Verenium Corporation), in Silico Protein Design Automation (PDA), which is an optimization algorithm that anchors the structurally defined protein backbone possessing a particular fold, and searches sequence space for amino acid substitutions that can stabilize the fold and overall protein energetics, and generally works most effectively on proteins with known three-dimensional structures (Hayes et al., *Proc. Natl. Acad. Sci. U.S.A.* 99:15926-15931 (2002)); and Iterative Saturation Mutagenesis (ISM), which involves using knowledge of structure/function to choose a likely site for enzyme improvement, performing saturation mutagenesis at chosen site using a mutagenesis method such as Stratagene QuikChange® (Stratagene; San Diego Calif.), screening/selecting for desired properties, and, using improved clone(s), starting over at another site and continue repeating until a desired activity is achieved (Reetz et al., *Nat. Protocols* 2:891-903 (2007); and Reetz et al., *Angew. Chem. Int. Ed Engl.* 45:7745-7751 (2006)).

Any of the aforementioned methods for mutagenesis can be used alone or in any combination. Additionally, any one or combination of the directed evolution methods can be used in conjunction with adaptive evolution techniques, as described herein.

Succinate can be harvested or isolated at any time point during the culturing of the microbial organism, for example, in a continuous and/or near-continuous culture period, as disclosed herein. Generally, the longer the microorganisms are maintained in a continuous and/or near-continuous growth phase, the proportionally greater amount of succinate can be produced.

Therefore, additionally provided is a method for producing succinate that includes culturing a non-naturally occurring microbial organism having one or more gene disruptions, as disclosed herein. The disruptions can occur in one or more genes encoding an enzyme that increases production of succinate, including optionally coupling succinate production to growth of the microorganism when the gene disruption reduces or eliminates an activity of the enzyme. For example, the disruptions can confer stable growth-coupled production of succinate onto the non-naturally microbial organism.

In some embodiments, the gene disruption can include a complete gene deletion. In some embodiments other methods to disrupt a gene include, for example, frameshifting by omission or addition of oligonucleotides or by mutations that render the gene inoperable. One skilled in the art will recognize the advantages of gene deletions, however, because of the stability it confers to the non-naturally occurring organism from reverting to a parental phenotype in which the gene disruption has not occurred. In particular, the gene disruptions are selected from the gene sets as disclosed herein.

Once computational predictions are made of gene sets for disruption to increase production of succinate, the strains can be constructed, evolved, and tested. Gene disruptions, including gene deletions, are introduced into host organism by methods well known in the art. A particularly useful method for gene disruption is by homologous recombination, as disclosed herein.

The engineered strains can be characterized by measuring the growth rate, the substrate uptake rate, and/or the product/byproduct secretion rate. Cultures can be grown and used as inoculum for a fresh batch culture for which measurements are taken during exponential growth. The growth rate can be determined by measuring optical density using a spectrophotometer (A600). Concentrations of glucose and other organic acid byproducts in the culture supernatant can be determined by well known methods such as HPLC, GC-MS or other well known analytical methods suitable for the analysis of the desired product, as disclosed herein, and used to calculate uptake and secretion rates.

Strains containing gene disruptions can exhibit suboptimal growth rates until their metabolic networks have adjusted to their missing functionalities. To assist in this adjustment, the strains can be adaptively evolved. By subjecting the strains to adaptive evolution, cellular growth rate becomes the primary selection pressure and the mutant cells are compelled to reallocate their metabolic fluxes in order to enhance their rates of growth. This reprogramming of metabolism has been recently demonstrated for several *E. coli* mutants that had been adaptively evolved on various substrates to reach the growth rates predicted a priori by an in silico model (Fong and Palsson, *Nat. Genet.* 36:1056-1058 (2004)). The growth improvements brought about by adaptive evolution can be accompanied by enhanced rates of succinate production. The strains are generally adaptively evolved in replicate, running in parallel, to account for differences in the evolutionary patterns that can be exhibited by a host organism (Fong and Palsson, *Nat. Genet.* 36:1056-1058 (2004); Fong et al., *J. Bacteriol.* 185:6400-6408 (2003); Ibarra et al., *Nature* 420:186-189 (2002)) that could potentially result in one strain having superior production qualities over the others. Evolutions can be run for a period of time, typically 2-6 weeks, depending upon the rate of growth improvement attained. In general, evolutions are stopped once a stable phenotype is obtained.

Following the adaptive evolution process, the new strains are characterized again by measuring the growth rate, the substrate uptake rate, and the product/byproduct secretion rate. These results are compared to the theoretical predictions by plotting actual growth and production yields alongside the production envelopes from metabolic modeling. The most successful design/evolution combinations are chosen to pursue further, and are characterized in lab-scale batch and continuous fermentations. The growth-coupled biochemical production concept behind the methods disclosed herein such as OptKnock approach should also result in the generation of genetically stable overproducers. Thus, the cultures are maintained in continuous mode for an extended period of time, for example, one month or more, to evaluate long-term stability. Periodic samples can be taken to ensure that yield and productivity are maintained.

Adaptive evolution is a powerful technique that can be used to increase growth rates of mutant or engineered microbial strains, or of wild-type strains growing under unnatural environmental conditions. It is especially useful for strains designed via methods such as OptKnock, which results in growth-coupled product formation. Therefore, evolution toward optimal growing strains will indirectly optimize production as well. Unique strains of *E. coli* K-12 MG1655 were created through gene knockouts and adaptive evolution. (Fong and Palsson, *Nat. Genet.* 36:1056-1058 (2004)). In this work, all adaptive evolutionary cultures were maintained in prolonged exponential growth by serial passage of batch cultures into fresh medium before the stationary phase was reached, thus rendering growth rate as the primary selection pressure. Knockout strains were constructed and evolved on minimal medium supplemented with different carbon substrates (four for each knockout strain). Evolution cultures were carried out in duplicate or triplicate, giving a total of 50 evolution knockout strains. The evolution cultures were maintained in exponential growth until a stable growth rate was reached. The computational predictions were accurate (within 10%) at predicting the post-evolution growth rate of the knockout strains in 38 out of the 50 cases examined. Furthermore, a combination of OptKnock design with adaptive evolution has led to improved lactic acid production strains. (Fong et al., *Biotechnol. Bioeng.* 91:643-648 (2005)). Similar methods can be applied to the strains disclosed herein and applied to various host strains.

There are a number of developed technologies for carrying out adaptive evolution. Exemplary methods are disclosed herein. In some embodiments, optimization of a NNOMOs provided herein includes utilizing adaptive evolution techniques to increase succinate production and/or stability of the producing strain.

Serial culture involves repetitive transfer of a small volume of grown culture to a much larger vessel containing fresh growth medium. When the cultured organisms have grown to saturation in the new vessel, the process is repeated. This method has been used to achieve the longest demonstrations of sustained culture in the literature (Lenski and Travisano, *Proc. Natl. Acad. Sci. USA* 91:6808-6814 (1994)) in experiments which clearly demonstrated consistent improvement in reproductive rate over a period of years. Typically, transfer of cultures is usually performed during exponential phase, so each day the transfer volume is precisely calculated to maintain exponential growth through the next 24 hour period. Manual serial dilution is inexpensive and easy to parallelize.

In continuous culture the growth of cells in a chemostat represents an extreme case of dilution in which a very high fraction of the cell population remains. As a culture grows and becomes saturated, a small proportion of the grown culture is replaced with fresh media, allowing the culture to continually grow at close to its maximum population size. Chemostats have been used to demonstrate short periods of rapid improvement in reproductive rate (Dykhuizen, *Methods Enzymol.* 613-631 (1993)). The potential usefulness of these devices was recognized, but traditional chemostats were unable to sustain long periods of selection for increased reproduction rate, due to the unintended selection of dilution-resistant (static) variants. These variants are able to resist dilution by adhering to the surface of the chemostat, and by doing so, outcompete less adherent individuals, including those that have higher reproductive rates, thus obviating the intended purpose of the device (Chao and Ramsdell, *J. Gen. Microbiol* 20:132-138 (1985)). One possible way to overcome this drawback is the implementation of a device with two growth chambers, which periodically undergo transient phases of sterilization, as described previously (Marliere and Mutzel, U.S. Pat. No. 6,686,194).

Evolugator™ is a continuous culture device developed by Evolugate, LLC (Gainesville, Fla.) and exhibits significant time and effort savings over traditional evolution techniques (de Crecy et al., *Appl. Microbiol. Biotechnol.* 77:489-496 (2007)). The cells are maintained in prolonged exponential growth by the serial passage of batch cultures into fresh medium before the stationary phase is attained. By automating optical density measurement and liquid handling, the Evolugator™ can perform serial transfer at high rates using large culture volumes, thus approaching the efficiency of a chemostat in evolution of cell fitness. For example, a mutant of *Acinetobacter* sp ADP1 deficient in a component of the translation apparatus, and having severely hampered growth, was evolved in 200 generations to 80% of the wild-type growth rate. However, in contrast to the chemostat which maintains cells in a single vessel, the machine operates by moving from one "reactor" to the next in subdivided regions of a spool of tubing, thus eliminating any selection for wall-growth. The transfer volume is adjustable, and normally set to about 50%. A drawback to this device is that it is large and costly, thus running large numbers of evolutions in parallel is not practical. Furthermore, gas addition is not well regulated, and strict anaerobic conditions are not maintained with the current device configuration. Nevertheless, this is an alternative method to adaptively evolve a production strain.

In one aspect, provided herein is a NNOMO comprising: (A) a MMP, wherein said organism comprises at least one exogenous nucleic acid encoding a MMPE expressed in a sufficient amount to enhance the availability of reducing equivalents in the presence of methanol, wherein said MMP comprises: (i) a methanol dehydrogenase (EM9); (ii) an EM9 and a formaldehyde activating enzyme (EM10); or (iii) a methanol methyltransferase (EM1) and a methylenetetrahydrofolate reductase (EM2); and (B) a succinate pathway (SucP). In certain embodiments, the organism comprises at least one nucleic acid encoding a SucP enzyme (SucPE) expressed in a sufficient amount to produce succinate, wherein said SucP comprises: (1) (i) a phosphoenolpyruvate (PEP) carboxylase (ES1A) or a PEP carboxykinase (ES1B); (ii) a malate dehydrogenase (ES3); (iii) a fumarase (ES5); and (iv) a fumarate reductase (ES6); (2) (i) a pyruvate carboxylase (ES2); (ii) a ES3; (iii) a ES5; and (iv) a ES6; or (3) (i) a malic enzyme (ES4); (ii) a ES5; and (iii) a ES6. In some embodiments, the SucP comprises (i) a ES1A or a ES1B; (ii) a ES3; (iii) a ES5; and (iv) a ES6. In other embodiments, the SucP comprises a ES1A. In another embodiments, the SucP comprises ES1B. In one embodiment, the SucP comprises (i) a ES2; (ii) a ES3; (iii) a ES5; and (iv) a ES6. In another embodiment, the SucP comprises (i) a ES4; (ii) a ES5; and (iii) a ES6. In other embodiments, the organism comprises one, two, three, or four nucleic acids, each encoding a SucPE. In some embodiments, said at least one nucleic acid encoding a succinate enzyme is an exogenous nucleic acid. In certain embodiments, the at least one exogenous nucleic acid encoding a succinate enzyme is a heterologous nucleic acid. In other embodiments, the MMP comprises an EM1 and an EM2. In one embodiment, the MMP comprises an EM9. In other embodiments, the MMP comprises an EM9 and an EM10. In yet other embodiments, the MMP comprises an EM1, an EM2, a methylenetetrahydrofolate dehydrogenase (EM3), a methenyltetrahydrofolate cyclohydrolase (EM4), and a formyltetrahydrofolate deformylase (EM5). In certain embodiments, the MMP comprises an EM1, an EM2, an EM3, an EM4 and a formyltetrahydrofolate synthetase (EM6). In one embodiment, the MMP comprises an EM9, an EM3, an EM4 and an EM5. In another embodiment, the MMP comprises an EM9, an EM3, an EM4 and an EM6. In an embodiment, the MMP comprises an EM9 and a formaldehyde dehydrogenase (EM11). In another embodiment, the MMP comprises an EM9, a S-(hydroxymethyl)glutathione synthase (EM12), a glutathione-dependent formaldehyde dehydrogenase (EM13) and a S-formylglutathione hydrolase (EM14). In another embodiment, the MMP comprises an EM9, an EM13 and an EM14. In one embodiment, the MMP comprises an EM9, an EM10, an EM3, an EM4 and an EM5. In another embodiment, the MMP comprises an EM9, an EM10, an EM3, an EM4 and an EM6. In certain embodiments, the MMP further comprises a formate dehydrogenase (EM8). In other embodiments, the MMP further comprises a formate hydrogen lyase (EM15). In certain embodiments, the MMP further comprises a hydrogenase (EM16). In some embodiments, the organism comprises two, three, four, five, six or seven exogenous nucleic acids, each encoding a MMPE. In other embodiments, the at least one exogenous nucleic acid encoding a MMPE is a heterologous nucleic acid.

In certain embodiments, the NNOMO further comprises one or more gene disruptions, wherein said one or more gene disruptions occur in one or more endogenous genes encoding protein(s) or enzyme(s) involved in: native production of ethanol, glycerol, acetate, lactate, formate, $CO_2$, and/or amino acids, by said microbial organism, and wherein said one or more gene disruptions confer increased production of succinate in said microbial organism. In some embodiments, the protein(s) or enzyme(s) is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof. In some embodiments, one or more endogenous enzymes are involved in: native production of ethanol, glycerol, acetate, lactate, formate, $CO_2$ and/or amino acids by said microbial organism, has attenuated enzyme activity or expression levels. In some embodiments, the enzyme is a pyruvate decarboxylase, an ethanol dehydrogenase, a glycerol dehydrogenase, a glycerol-3-phosphatase, a glycerol-3-phosphate dehydrogenase, a lactate dehydrogenase, an acetate kinase, a phosphotransacetylase, a pyruvate oxidase, a pyruvate:quinone oxidoreductase, a pyruvate formate lyase, an alcohol dehydrogenase, a lactate dehydrogenase, a pyruvate dehydrogenase, a pyruvate formate-lyase-2-ketobutyrate formate-lyase, a pyruvate transporter, a monocarboxylate transporter, a NADH dehydrogenase, a cytochrome oxidase, a pyruvate kinase, or any combination thereof.

In some embodiments, the NNOMO further comprises a formaldehyde assimilation pathway (FAP), wherein said organism comprises at least one exogenous nucleic acid encoding a FAPE expressed in a sufficient amount to produce an intermediate of glycolysis and/or a metabolic pathway that can be used in the formation of biomass. In certain embodiments, the FAP comprises a hexulose-6-phosphate (H6P) synthase (EF1) and a 6-phospho-3-hexuloisomerase (EF2). In some embodiments, the intermediate is a H6P, a fructose-6-phosphate (F6P), or a combination thereof. In other embodiments, the organism further comprises a FAP, wherein said organism comprises at least one exogenous nucleic acid encoding a FAP enzyme (FAPE) expressed in a sufficient amount to produce an intermediate of glycolysis and/or a metabolic pathway that can be used in the formation of biomass, and wherein said FAP comprises a DHA synthase (EF3) and a DHA kinase (EF4). In some embodiments, the intermediate is a DHA, a DHA phosphate (DHAP), or a combination thereof. In one embodiment, the organism comprises two exogenous nucleic acids, each encoding a FAPE. In certain embodiments, the at least one exogenous nucleic acid is a heterologous nucleic acid.

In certain embodiments, the organism is in a substantially anaerobic culture medium. In other embodiments, the organism is a species of bacteria, yeast, or fungus.

In another aspect, provided herein is a method for producing succinate, comprising culturing the organism comprising a MMP and SucP provided herein under conditions and for a sufficient period of time to produce succinate. In certain embodiments, the organism is a Crabtree positive, eukaryotic organism, and wherein the organism is cultured in a culture medium comprising glucose. In certain embodiments, provided herein is a bioderived or biobased product comprising succinate, or an intermediate thereof, produced according to this method. In one embodiment, the bioderived or biobased product is selected from the group consisting of a butanediol, tetrahydrofuran, pyrrolidone, solvent, paint, deicer, plastic, fuel additive, fabric, carpet, pigment, detergent, metal plating, polymer, polybutylene succinate polymer, biodegradable plastic, flexible packaging, agricultural film, compostable bag; a combination of polybutylene succinate with polymers such as polypropylene (PP), polystyrene (PS) and polycarbonate (PC), and with plastics such as polylactic acid, polyhydroxyalkanoate, and poly-3-hydroxy butyrateco-valerate; and a combination of polybutylene succinate with fibers or fillers, automotive interiors, nonwovens, construction materials, and consumer goods. Also provided herein is a bioderived succinate produced according to this method. Also provided is a culture medium comprising the bioderived succinate. In certain embodiments, the bioderived succinate has a carbon-12, carbon-13 and carbon-14 isotope ratio that reflects an atmospheric carbon dioxide uptake source. In one embodiment, the culture medium comprises the bioderived succinate has a carbon-12, carbon-13 and carbon-14 isotope ratio that reflects an atmospheric carbon dioxide uptake source. In some embodiments, the culture medium is separated from the NNOMO having the SucP. In some embodiments, the bioderived succinate of claim 44 or 48, wherein said bioderived succinate has an Fm value of at least 80%, at least 85%, at least 90%, at least 95% or at least 98%. Also provided herein is a composition comprising a bioderived succinate provided herein, and a compound other than said bioderived succinate. In one embodiment, the compound other than said bioderived succinate is a trace amount of a cellular portion of a NNOMO having a SucP. Also provided herein is a biobased product comprising a bioderived succinate provided herein, wherein said biobased product is butanediol, tetrahydrofuran, pyrrolidone, solvent, paint, deicer, plastic, fuel additive, fabric, carpet, pigment, detergent, metal plating, polymer, polybutylene succinate polymer, biodegradable plastic, flexible packaging, agricultural film, compostable bag; a combination of polybutylene succinate with polymers such as polypropylene (PP), polystyrene (PS) and polycarbonate (PC), and with plastics such as polylactic acid, polyhydroxyalkanoate, and poly-3-hydroxy butyrateco-valerate; and a combination of polybutylene succinate with fibers or fillers, automotive interiors, nonwovens, construction materials, or consumer goods. In some embodiments, the biobased product comprises at least 5%, at least 10%, at least 20%, at least 30%, at least 40% or at least 50% bioderived succinate. In certain embodiments, the biobased product comprises a portion of said bioderived succinate as a repeating unit. Also provided herein is a molded product obtained by molding the biobased product provided herein. Also provided is a process for producing the biobased product provided herein, comprising chemically reacting said bioderived succinate with itself or another compound in a reaction that produces said biobased product. A polymer comprising or obtained by converting the bioderived succinate of claims 44, 48 or 49. Also provided is a method for producing a polymer, comprising chemically of enzymatically converting the bioderived succinate provided herein to the polymer. Also provided is a composition comprising the bioderived succinate provided herein, or a cell lysate or culture supernatant thereof.

Also provided herein is a method of producing formaldehyde, comprising culturing an organism provided herein comprising a MMP under conditions and for a sufficient period of time to produce formaldehyde, and optionally wherein the formaldehyde is consumed to provide a reducing equivalent or to incorporate into succinate or target product. In certain embodiments, the organism further comprises a SucP. In some embodiments, the organism comprises EM9.

Also provided herein is a method of producing an intermediate of glycolysis and/or an intermediate of a metabolic pathway that can be used in the formation of biomass, comprising culturing an organism provided herein comprising a FAP under conditions and for a sufficient period of time to produce the intermediate, and optionally wherein the intermediate is consumed to provide a reducing equivalent or to incorporate into succinate or target product. In certain embodiments, the organism further comprises a MMP and/ or SucP. In some embodiments, the organism comprises EM9.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples provided above, it should be understood that various modifications can be made without departing from the spirit of the invention.

It is understood that modifications which do not substantially affect the activity of the various embodiments of this invention are also included within the definition of the invention provided herein. Accordingly, the following examples are intended to illustrate but not limit the present invention.

4. EXAMPLES 4.1 Example I—Production of Reducing Equivalents Via a MMP

Exemplary MMPs are provided in FIG. 1.
FIG. 1, Step A—Methanol Methyltransferase (EM1)
A complex of 3-methyltransferase proteins, denoted MtaA, MtaB, and MtaC, perform the desired EM1 activity (Sauer et al., *Eur. J. Biochem.* 243:670-677 (1997); Naidu and Ragsdale, *J. Bacteriol.* 183:3276-3281 (2001); Tallant and Krzycki, *J. Biol. Chem.* 276:4485-4493 (2001); Tallant and Krzycki, *J. Bacteriol.* 179:6902-6911 (1997); Tallant and Krzycki, *J. Bacteriol.* 178:1295-1301 (1996); Ragsdale, S. W., *Crit. Rev. Biochem. Mol. Biol.* 39:165-195 (2004)).

MtaB is a zinc protein that can catalyze the transfer of a methyl group from methanol to MtaC, a corrinoid protein. Exemplary genes encoding MtaB and MtaC can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* (Das et al., *Proteins* 67:167-176 (2007). In general, the MtaB and MtaC genes are adjacent to one another on the chromosome as their activities are tightly interdependent. The protein sequences of various MtaB and MtaC encoding genes in *M. barkeri*, *M. acetivorans*, and *M. thermoaceticum* can be identified by their following GenBank accession numbers.

| Protein | GenBank ID | GI number | Organism |
|---|---|---|---|
| MtaB1 | YP_304299 | 73668284 | *Methanosarcina barkeri* |
| MtaC1 | YP_304298 | 73668283 | *Methanosarcina barkeri* |
| MtaB2 | YP_307082 | 73671067 | *Methanosarcina barkeri* |

-continued

| Protein | GenBank ID | GI number | Organism |
|---|---|---|---|
| MtaC2 | YP_307081 | 73671066 | Methanosarcina barkeri |
| MtaB3 | YP_304612 | 73668597 | Methanosarcina barkeri |
| MtaC3 | YP_304611 | 73668596 | Methanosarcina barkeri |
| MtaB1 | NP_615421 | 20089346 | Methanosarcina acetivorans |
| MtaB1 | NP_615422 | 20089347 | Methanosarcina acetivorans |
| MtaB2 | NP_619254 | 20093179 | Methanosarcina acetivorans |
| MtaC2 | NP_619253 | 20093178 | Methanosarcina acetivorans |
| MtaB3 | NP_616549 | 20090474 | Methanosarcina acetivorans |
| MtaC3 | NP_616550 | 20090475 | Methanosarcina acetivorans |
| MtaB | YP_430066 | 83590057 | Moorella thermoacetica |
| MtaC | YP_430065 | 83590056 | Moorella thermoacetica |
| MtaA | YP_430064 | 83590056 | Moorella thermoacetica |

The MtaB1 and MtaC1 genes, YP_304299 and YP_304298, from *M. barkeri* were cloned into *E. coli* and sequenced (Sauer et al., *Eur. J. Biochem.* 243:670-677 (1997)). The crystal structure of this methanol-cobalamin methyltransferase complex is also available (Hagemeier et al., *Proc. Natl. Acad. Sci. U.S.A.* 103:18917-18922 (2006)). The MtaB genes, YP_307082 and YP_304612, in *M. barkeri* were identified by sequence homology to YP_304299. In general, homology searches are an effective means of identifying EM1s because MtaB encoding genes show little or no similarity to methyltransferases that act on alternative substrates such as trimethylamine, dimethylamine, monomethylamine, or dimethylsulfide. The MtaC genes, YP_307081 and YP_304611 were identified based on their proximity to the MtaB genes and also their homology to YP_304298. The three sets of MtaB and MtaC genes from *M. acetivorans* have been genetically, physiologically, and biochemically characterized (Pritchett and Metcalf, *Mol. Microbiol.* 56:1183-1194 (2005)). Mutant strains lacking two of the sets were able to grow on methanol, whereas a strain lacking all three sets of MtaB and MtaC genes sets could not grow on methanol. This suggests that each set of genes plays a role in methanol utilization. The *M. thermoacetica* MtaB gene was identified based on homology to the methanogenic MtaB genes and also by its adjacent chromosomal proximity to the methanol-induced corrinoid protein, MtaC, which has been crystallized (Zhou et al., *Acta Crystallogr. Sect. F. Struct. Biol. Cyrst. Commun.* 61:537-540 (2005) and further characterized by Northern hybridization and Western Blotting ((Das et al., *Proteins* 67:167-176 (2007)).

MtaA is zinc protein that catalyzes the transfer of the methyl group from MtaC to either Coenzyme M in methanogens or methyltetrahydrofolate in acetogens. MtaA can also utilize methylcobalamin as the methyl donor. Exemplary genes encoding MtaA can be found in methanogenic archaea such as *Methanosarcina barkeri* (Maeder et al., *J. Bacteriol.* 188:7922-7931 (2006) and *Methanosarcina acetivorans* (Galagan et al., *Genome Res.* 12:532-542 (2002), as well as the acetogen, *Moorella thermoacetica* ((Das et al., *Proteins* 67:167-176 (2007)). In general, MtaA proteins that catalyze the transfer of the methyl group from CH_3-MtaC are difficult to identify bioinformatically as they share similarity to other corrinoid protein methyltransferases and are not oriented adjacent to the MtaB and MtaC genes on the chromosomes. Nevertheless, a number of MtaA encoding genes have been characterized. The protein sequences of these genes in *M. barkeri* and *M. acetivorans* can be identified by the following GenBank accession numbers.

| Protein | GenBank ID | GI number | Organism |
|---|---|---|---|
| MtaA | YP_304602 | 73668587 | Methanosarcina barkeri |
| MtaA1 | NP_619241 | 20093166 | Methanosarcina acetivorans |
| MtaA2 | NP_616548 | 20090473 | Methanosarcina acetivorans |

The MtaA gene, YP_304602, from *M. barkeri* was cloned, sequenced, and functionally overexpressed in *E. coli* (Harms and Thauer, *Eur. J. Biochem.* 235:653-659 (1996)). In *M. acetivorans*, MtaA1 is required for growth on methanol, whereas MtaA2 is dispensable even though methane production from methanol is reduced in MtaA2 mutants (Bose et al., *J. Bacteriol.* 190:4017-4026 (2008)). There are multiple additional MtaA homologs in *M. barkeri* and *M. acetivorans* that are as yet uncharacterized, but may also catalyze corrinoid protein methyltransferase activity.

Putative MtaA encoding genes in *M. thermoacetica* were identified by their sequence similarity to the characterized methanogenic MtaA genes. Specifically, three *M. thermoacetica* genes show high homology (>30% sequence identity) to YP_304602 from *M. barkeri*. Unlike methanogenic MtaA proteins that naturally catalyze the transfer of the methyl group from CH_3-MtaC to Coenzyme M, an *M. thermoacetica* MtaA is likely to transfer the methyl group to methyltetrahydrofolate given the similar roles of methyltetrahydrofolate and Coenzyme M in methanogens and acetogens, respectively. The protein sequences of putative MtaA encoding genes from *M. thermoacetica* can be identified by the following GenBank accession numbers.

| Protein | GenBank ID | GI number | Organism |
|---|---|---|---|
| MtaA | YP_430937 | 83590928 | Moorella thermoacetica |
| MtaA | YP_431175 | 83591166 | Moorella thermoacetica |
| MtaA | YP_430935 | 83590926 | Moorella thermoacetica |
| MtaA | YP_430064 | 83590056 | Moorella thermoacetica |

FIG. 1, Step B—Methylenetetrahydrofolate Reductase (EM2)

The conversion of methyl-THF to methylenetetrahydrofolate is catalyzed by EM2. In *M. thermoacetica*, this enzyme is oxygen-sensitive and contains an iron-sulfur cluster (Clark and Ljungdahl, *J. Biol. Chem.* 259:10845-10849 (1984). This enzyme is encoded by metF in *E. coli* (Sheppard et al., *J. Bacteriol.* 181:718-725 (1999) and CHY_1233 in *C. hydrogenoformans* (Wu et al., *PLoS Genet.* 1:e65 (2005). The *M. thermoacetica* genes, and its *C. hydrogenoformans* counterpart, are located near the CODH/ACS gene cluster, separated by putative EM16 and heterodisulfide reductase genes. Some additional gene candidates found bioinformatically are listed below. In *Acetobacterium woodii* metF is coupled to the Rnf complex through RnfC2 (Poehlein et al, *PLoS One.* 7:e33439). Homologs of RnfC are found in other organisms by blast search. The Rnf complex is known to be a reversible complex (Fuchs (2011) *Annu. Rev. Microbiol.* 65:631-658).

| Protein | GenBank ID | GI number | Organism |
| --- | --- | --- | --- |
| Moth_1191 | YP_430048.1 | 83590039 | Moorella thermoacetica |
| Moth_1192 | YP_430049.1 | 83590040 | Moorella thermoacetica |
| metF | NP_418376.1 | 16131779 | Escherichia coli |
| CHY_1233 | YP_360071.1 | 78044792 | Carboxydothermus hydrogenoformans |
| CLJU_c37610 | YP_003781889.1 | 300856905 | Clostridium ljungdahlii DSM 13528 |
| DesfrDRAFT_3717 | ZP_07335241.1 | 303248996 | Desulfovibrio fructosovorans JJ |
| CcarbDRAFT_2950 | ZP_05392950.1 | 255526026 | Clostridium carboxidivorans P7 |
| Ccel74_010100023124 | ZP_07633513.1 | 307691067 | Clostridium cellulovorans 743B |
| Cphy_3110 | YP_001560205.1 | 160881237 | Clostridium phytofermentans ISDg |

FIG. 1, Steps C and D—Methylenetetrahydrofolate Dehydrogenase (EM3), Methenyltetrahydrofolate Cyclohydrolase (EM4)

In *M. thermoacetica, E. coli*, and *C. hydrogenoformans*, EM4 and EM3 are carried out by the bi-functional gene products of Moth_1516, folD, and CHY_1878, respectively (Pierce et al., *Environ. Microbiol.* 10:2550-2573 (2008); Wu et al., *PLoS Genet.* 1:e65 (2005); D'Ari and Rabinowitz, *J. Biol. Chem.* 266:23953-23958 (1991)). A homolog exists in *C. carboxidivorans* P7. Several other organisms also encode for this bifunctional protein as tabulated below.

| Protein | GenBank ID | GI number | Organism |
| --- | --- | --- | --- |
| Moth_1516 | YP_430368.1 | 83590359 | Moorella thermoacetica |
| folD | NP_415062.1 | 16128513 | Escherichia coli |
| CHY_1878 | YP_360698.1 | 78044829 | Carboxydothermus hydrogenoformans |
| CcarbDRAFT_2948 | ZP_05392948.1 | 255526024 | Clostridium carboxidivorans P7 |
| folD | ADK16789.1 | 300437022 | Clostridium ljungdahlii DSM 13528 |
| folD-2 | NP_951919.1 | 39995968 | Geobacter sulfurreducens PCA |
| folD | YP_725874.1 | 113867385 | Ralstonia eutropha H16 |
| folD | NP_348702.1 | 15895353 | Clostridium acetobutylicum ATCC 824 |
| folD | YP_696506.1 | 110800457 | Clostridium perfringens |
| MGA3_09460 | EIJ83438.1 | 387591119 | Bacillus methanolicus MGA3 |
| PB1_14689 | ZP_10132349.1 | 387929672 | Bacillus methanolicus PB1 |

FIG. 1, Step E—Formyltetrahydrofolate Deformylase (EM5)

This enzyme catalyzes the hydrolysis of 10-formyltetrahydrofolate (formyl-THF) to THF and formate. In *E. coli*, this enzyme is encoded by purU and has been overproduced, purified, and characterized (Nagy, et al., *J. Bacteriol.* 3:1292-1298 (1995)). Homologs exist in *Corynebacterium* sp. U-96 (Suzuki, et al., Biosci. Biotechnol. Biochem. 69(5): 952-956 (2005)), *Corynebacterium glutamicum* ATCC 14067, *Salmonella enterica*, and several additional organisms.

| Protein | GenBank ID | GI number | Organism |
| --- | --- | --- | --- |
| purU | AAC74314.1 | 1787483 | Escherichia coli K-12 MG1655 |
| purU | BAD97821.1 | 63002616 | Corynebacterium sp. U-96 |
| purU | EHE84645.1 | 35451740 | Corynebacterium glutamicum ATCC 14067 |
| purU | NP_460715.1 | 16765100 | Salmonella enterica subsp. enterica serovar Typhimurium sir. LT2 |

FIG. 1, Step F—Formyltetrahydrofolate Synthetase (EM6)

EM6 ligates formate to tetrahydrofolate at the expense of one ATP. This reaction is catalyzed by the gene product of Moth_0109 in *M. thermoacetica* (O'brien et al., *Experientia Suppl.* 26:249-262 (1976); Lovell et al., *Arch. Microbiol.* 149:280-285 (1988); Lovell et al., *Biochemistry* 29:5687-5694 (1990)), FHS in *Clostridium acidurici* (Whitehead and Rabinowitz, *J. Bacteriol.* 167:203-209 (1986); Whitehead and Rabinowitz, *J. Bacteriol.* 170:3255-3261 (1988), and CHY_2385 in *C. hydrogenoformans* (Wu et al., *PLoS Genet.* 1:e65 (2005). Homologs exist in *C. carboxidivorans* P7. This enzyme is found in several other organisms as listed below.

| Protein | GenBank ID | GI number | Organism |
| --- | --- | --- | --- |
| Moth_0109 | YP_42899.1 | 83588982 | Moorella thermoacetica |
| CHY_2385 | YP_361182.1 | 78045024 | Carboxydothermus hydrogenoformans |
| FHS | P13419.1 | 120562 | Clostridium acidurici |
| CcarbDRAFT_1913 | ZP_05391913.1 | 755524966 | Clostridium carboxidivorans P7 |
| CcarbDRAFT_2946 | ZP_05392946.1 | 255526022 | Clostridium carboxidivorans P7 |
| Dhaf_0555 | ACL18622.1 | 219536883 | Desulfitobacterium hafniense |
| Fhs | YP_001393842.1 | 153953077 | Clostridium kluyveri DSM 555 |
| Fhs | YP_003781893.1 | 300856909 | Clostridium ljungdahlii DSM 13528 |
| MGA3_08300 | EIJ83208.1 | 387590889 | Bacillus methanolicus MGA3 |
| PB1_13509 | ZP_10132113.1 | 387929436 | Bacillus methanolicus PB1 |

FIG. 1, Step G—Formate Hydrogen Lyase (EM15)

A EM15 enzyme can be employed to convert formate to carbon dioxide and hydrogen. An exemplary EM15 enzyme can be found in *Escherichia coli*. The *E. coli* EM15 consists of hydrogenase 3 and formate dehydrogenase-H (Maeda et al., *Appl Microbiol Biotechnol* 77:879-890 (2007)). It is activated by the gene product of fhlA. (Maeda et al., *Appl Microbiol Biotechnol* 77:879-890 (2007)). The addition of the trace elements, selenium, nickel and molybdenum, to a fermentation broth has been shown to enhance EM15 activity (Soini et al., *Microb. Cell Fact.* 7:26 (2008)). Various hydrogenase 3, EM8 and transcriptional activator genes are shown below.

| Protein | GenBank ID | GI number | Organism |
| --- | --- | --- | --- |
| hycA | NP_417205 | 16130632 | Escherichia coli K-12 MG1655 |
| hycB | NP_417204 | 16130631 | Escherichia coli K-12 MG1655 |
| hycC | NP_417203 | 16130630 | Escherichia coli K-12 MG1655 |
| hycD | NP_417202 | 16130629 | Escherichia coli K-12 MG1655 |
| hycE | NP_417201 | 16130628 | Escherichia coli K-12 MG1655 |
| hycF | NP_417200 | 16130627 | Escherichia coli K-12 MG1655 |
| hycG | NP_417199 | 16130626 | Escherichia coli K-12 MG1655 |
| hycH | NP_417198 | 16130625 | Escherichia coli K-12 MG1655 |
| hycI | NP_417197 | 16130624 | Escherichia coli K-12 MG1655 |
| fdhF | NP_418503 | 16131905 | Escherichia coli K-12 MG1655 |
| fhlA | NP_417211 | 16130638 | Escherichia coli K-12 MG1655 |

A EM15 enzyme also exists in the hyperthermophilic archaeon, *Thermococcus litoralis* (Takacs et al., *BMC. Microbiol* 8:88 (2008)).

| Protein | GenBank ID | GI number | Organism |
| --- | --- | --- | --- |
| mhyC | ABW05543 | 157954626 | Thermococcus litoralis |
| mhyD | ABW05544 | 157954627 | Thermococcus litoralis |
| mhyE | ABW05545 | 157954628 | Thermococcus litoralis |
| myhF | ABW05546 | 157954629 | Thermococcus litoralis |
| myhG | ABW05547 | 157954630 | Thermococcus litoralis |
| myhH | ABW05548 | 157954631 | Thermococcus litoralis |
| fdhA | AAB94932 | 2746736 | Thermococcus litoralis |
| fdhB | AAB94931 | 157954625 | Thermococcus litoralis |

Additional EM15 systems have been found in *Salmonella typhimurium, Klebsiella pneumoniae, Rhodospirillum rubrum, Methanobacterium formicicum* (Vardar-Schara et al., Microbial Biotechnology 1:107-125 (2008)).

FIG. 1, Step H—Hydrogenase (EM16)

Hydrogenase enzymes can convert hydrogen gas to protons and transfer electrons to acceptors such as ferredoxins, NAD+, or NADP+. *Ralsionia eutropha* H16 uses hydrogen as an energy source with oxygen as a terminal electron acceptor. Its membrane-bound uptake [NiFe]-hydrogenase is an "O2-tolerant" EM16 (Cracknell, et al. Proc Nat Acad Sci, 106(49) 20681-20686 (2009)) that is periplasmically-oriented and connected to the respiratory chain via a b-type cytochrome (Schink and Schlegel, *Biochim. Biophys. Acta*, 567, 315-324 (1979); Bernhard et al., *Eur. J. Biochem.* 248, 179-186 (1997)). *R. eutropha* also contains an $O_2$-tolerant soluble EM16 encoded by the Hox operon which is cytoplasmic and directly reduces NAD+ at the expense of hydrogen (Schneider and Schlegel, *Biochim. Biophys. Acta* 452, 66-80 (1976); Burgdorf, *J. Bact.* 187(9) 3122-3132 (2005)). Soluble EM16 enzymes are additionally present in several other organisms including *Geobacter sulfurreducens* (Coppi, *Microbiology* 151, 1239-1254 (2005)), *Synechocystis* str. PCC 6803 (Germer, *J. Biol. Chem.*, 284(52), 36462-36472 (2009)), and *Thiocapsa roseopersicina* (Rakhely, *Appl. Environ. Microbiol.* 70(2) 722-728 (2004)). The *Synechocystis* enzyme is capable of generating NADPH from hydrogen. Overexpression of both the Hox operon from *Synechocystis* str. PCC 6803 and the accessory genes encoded by the Hyp operon from *Nostoc* sp. PCC 7120 led to increased EM16 activity compared to expression of the Hox genes alone (Germer, *J. Biol. Chem.* 284(52), 36462-36472 (2009)).

| Protein | GenBank ID | GI Number | Organism |
| --- | --- | --- | --- |
| HoxF | NP_942727.1 | 38637753 | Ralstonia eutropha H16 |
| HoxU | NP_942728.1 | 38637754 | Ralstonia eutropha H16 |
| HoxY | NP_942729.1 | 38637755 | Ralstonia eutropha H16 |
| HoxH | NP_942730.1 | 38637756 | Ralstonia eutropha H16 |
| HoxW | NP_942731.1 | 38637757 | Ralstonia eutropha H16 |
| HoxI | NP_942732.1 | 38637758 | Ralstonia eutropha H16 |
| HoxE | NP_953767.1 | 39997816 | Geobacter sulfurreducens |
| HoxF | NP_953766.1 | 39997815 | Geobacter sulfurreducens |
| HoxU | NP_953765.1 | 39997814 | Geobacter sulfurreducens |
| HoxY | NP_953764.1 | 39997813 | Geobacter sulfurreducens |
| HoxH | NP_953763.1 | 39997812 | Geobacter sulfurreducens |
| GSU2717 | NP_953762.1 | 39997811 | Geobacter sulfurreducens |
| HoxE | NP_441418.1 | 16330690 | Synechocystis str. PCC 6803 |
| HoxF | NP_441417.1 | 16330689 | Synechocystis str. PCC 6803 |
| Unknown function | NP_441416.1 | 16330688 | Synechocystis str. PCC 6803 |
| HoxU | NP_441415.1 | 16330687 | Synechocystis str. PCC 6803 |
| HoxY | NP_441414.1 | 16330686 | Synechocystis str. PCC 6803 |
| Unknown function | NP_441413.1 | 16330685 | Synechocystis str. PCC 6803 |
| Unknown function | NP_441412.1 | 16330684 | Synechocystis str. PCC 6803 |
| HoxH | NP_441411.1 | 16330683 | Synechocystis str. PCC 6803 |
| HypF | NP_484737.1 | 17228189 | Nostoc sp. PCC 7120 |
| HypC | NP_484738.1 | 17228190 | Nostoc sp. PCC 7120 |
| HypD | NP_484739.1 | 17228191 | Nostoc sp. PCC 7120 |
| Unknown function | NP_484740.1 | 17228192 | Nostoc sp. PCC 7120 |
| HypE | NP_484741.1 | 17228193 | Nostoc sp. PCC 7120 |
| HypA | NP_484742.1 | 17228194 | Nostoc sp. PCC 7120 |
| HypB | NP_484743.1 | 17228195 | Nostoc sp. PCC 7120 |
| Hox1E | AAP50519.1 | 37787351 | Thiocapsa roseopersicina |

| Protein | GenBank ID | GI Number | Organism |
| --- | --- | --- | --- |
| Hox1F | AAP50520.1 | 37787352 | Thiocapsa roseopersicina |
| Hox1U | AAP50521.1 | 37787353 | Thiocapsa roseopersicina |
| Hox1Y | AAP50522.1 | 37787354 | Thiocapsa roseopersicina |
| Hox1H | AAP50523.1 | 37787355 | Thiocapsa roseopersicina |

The genomes of E. coli and other enteric bacteria encode up to four EM16 enzymes (Sawers, G., Antonie Van Leeuwenhoek 66:57-88 (1994); Sawers et al., J Bacteriol. 164: 1324-1331 (1985); Sawers and Boxer, Eur. J Biochem. 156:265-275 (1986); Sawers et al., J Bacteriol. 168:398-404 (1986)). Given the multiplicity of enzyme activities E. coli or another host organism can provide sufficient EM16 activity to split incoming molecular hydrogen and reduce the corresponding acceptor. Endogenous hydrogen-lyase enzymes of E. coli include hydrogenase 3, a membrane-bound enzyme complex using ferredoxin as an acceptor, and hydrogenase 4 that also uses a ferredoxin acceptor. Hydrogenase 3 and 4 are encoded by the hyc and hyf gene clusters, respectively. EM16 activity in E. coli is also dependent upon the expression of the hyp genes whose corresponding proteins are involved in the assembly of the EM16 complexes (Jacobi et al., Arch. Microbiol 158:444-451 (1992); Rangarajan et al., J Bacteriol. 190:1447-1458 (2008)). The M. thermoacetica and Clostridium ljungdahli EM16s are suitable for a host that lacks sufficient endogenous EM16 activity. M. thermoacetica and C. ljungdahli can grow with $CO_2$ as the exclusive carbon source indicating that reducing equivalents are extracted from $H_2$ to enable acetyl-CoA synthesis via the Wood-Ljungdahl pathway (Drake, H. L., J Bacteriol. 150:702-709 (1982); Drake and Daniel, Res Microbiol 155:869-883 (2004); Kellum and Drake, J Bacteriol. 160:466-469 (1984)). M. thermoacetica has homologs to several hyp, hyc, and hyf genes from E. coli. These protein sequences encoded for by these genes are identified by the following GenBank accession numbers. In addition, several gene clusters encoding EM16 functionality are present in M. thermoacetica and C. ljungdahli (see for example US 2012/0003652).

| Protein | GenBank ID | GI Number | Organism |
| --- | --- | --- | --- |
| HypA | NP_417206 | 16130633 | Escherichia coli |
| HypB | NP_417207 | 16130634 | Escherichia coli |
| HypC | NP_417208 | 16130635 | Escherichia coli |
| HypD | NP_417209 | 16130636 | Escherichia coli |
| HypE | NP_417210 | 226524740 | Escherichia coli |
| HypF | NP_417192 | 16130619 | Escherichia coli |
| HycA | NP_417205 | 16130632 | Escherichia coli |
| HycB | NP_417204 | 16130631 | Escherichia coli |
| HycC | NP_417203 | 16130630 | Escherichia coli |
| HycD | NP_417202 | 16130629 | Escherichia coli |
| HycE | NP_417201 | 16130628 | Escherichia coli |
| HycF | NP_417200 | 16130627 | Escherichia coli |
| HycG | NP_417199 | 16130626 | Escherichia coli |
| HycH | NP_417198 | 16130625 | Escherichia coli |
| HycI | NP_417197 | 16130624 | Escherichia coli |
| HyfA | NP_416976 | 90111444 | Escherichia coli |
| HyfB | NP_416977 | 16130407 | Escherichia coli |
| HyfC | NP_416978 | 90111445 | Escherichia coli |
| HyfD | NP_416979 | 16130409 | Escherichia coli |
| HyfE | NP_416980 | 16130410 | Escherichia coli |
| HyfF | NP_416981 | 16130411 | Escherichia coli |
| HyfG | NP_416982 | 16130412 | Escherichia coli |
| HyfH | NP_416983 | 16130413 | Escherichia coli |
| HyfI | NP_416984 | 16130414 | Escherichia coli |
| HyfJ | NP_416985 | 90111446 | Escherichia coli |
| HyfR | NP_416986 | 90111447 | Escherichia coli |

Proteins in M. thermoacetica whose genes are homologous to the E. coli EM16 genes are shown below.

| Protein | GenBank ID | GI Number | Organism |
| --- | --- | --- | --- |
| Moth_2175 | YP_431007 | 83590998 | Moorella thermoacetica |
| Moth_2176 | YP_431008 | 83590999 | Moorella thermoacetica |
| Moth_2177 | YP_431009 | 83591000 | Moorella thermoacetica |
| Moth_2178 | YP_431010 | 83591001 | Moorella thermoacetica |
| Moth_2179 | YP_431011 | 83591002 | Moorella thermoacetica |
| Moth_2180 | YP_431012 | 83591003 | Moorella thermoacetica |
| Moth_2181 | YP_431013 | 83591004 | Moorella thermoacetica |
| Moth_2182 | YP_431014 | 83591005 | Moorella thermoacetica |
| Moth_2183 | YP_431015 | 83591006 | Moorella thermoacetica |
| Moth_2184 | YP_431016 | 83591007 | Moorella thermoacetica |
| Moth_2185 | YP_431017 | 83591008 | Moorella thermoacetica |
| Moth_2186 | YP_431018 | 83591009 | Moorella thermoacetica |
| Moth_2187 | YP_431019 | 83591010 | Moorella thermoacetica |
| Moth_2188 | YP_431020 | 83591011 | Moorella thermoacetica |
| Moth_2189 | YP_431021 | 83591012 | Moorella thermoacetica |
| Moth_2190 | YP_431022 | 83591013 | Moorella thermoacetica |
| Moth_2191 | YP_431023 | 83591014 | Moorella thermoacetica |
| Moth_2192 | YP_431024 | 83591015 | Moorella thermoacetica |
| Moth_0439 | YP_429313 | 83589304 | Moorella thermoacetica |
| Moth_0440 | YP_429314 | 83589305 | Moorella thermoacetica |
| Moth_0441 | YP_429315 | 83589306 | Moorella thermoacetica |
| Moth_0442 | YP_429316 | 83589307 | Moorella thermoacetica |
| Moth_0809 | YP_429670 | 83589661 | Moorella thermoacetica |
| Moth_0810 | YP_429671 | 83589662 | Moorella thermoacetica |
| Moth_0811 | YP_429672 | 83589663 | Moorella thermoacetica |
| Moth_0812 | YP_429673 | 83589664 | Moorella thermoacetica |
| Moth_0814 | YP_429674 | 83589665 | Moorella thermoacetica |
| Moth_0815 | YP_429675 | 83589666 | Moorella thermoacetica |
| Moth_0816 | YP_429676 | 83589667 | Moorella thermoacetica |
| Moth_1193 | YP_430050 | 83590041 | Moorella thermoacetica |
| Moth_1194 | YP_430051 | 83590042 | Moorella thermoacetica |
| Moth_1195 | YP_430052 | 83590043 | Moorella thermoacetica |
| Moth_1196 | YP_430053 | 83590044 | Moorella thermoacetica |
| Moth_1717 | YP_430562 | 83590553 | Moorella thermoacetica |
| Moth_1718 | YP_430563 | 83590554 | Moorella thermoacetica |
| Moth_1719 | YP_430564 | 83590555 | Moorella thermoacetica |
| Moth_1883 | YP_430726 | 83590717 | Moorella thermoacetica |
| Moth_1884 | YP_430727 | 83590718 | Moorella thermoacetica |
| Moth_1885 | YP_430728 | 83590719 | Moorella thermoacetica |
| Moth_1886 | YP_430729 | 83590720 | Moorella thermoacetica |
| Moth_1887 | YP_430730 | 83590721 | Moorella thermoacetica |
| Moth_1888 | YP_430731 | 83590722 | Moorella thermoacetica |
| Moth_1452 | YP_430305 | 83590296 | Moorella thermoacetica |
| Moth_1453 | YP_430306 | 83590297 | Moorella thermoacetica |
| Moth_1454 | YP_430307 | 83590298 | Moorella thermoacetica |

Genes encoding EM16 enzymes from C. ljungdahli are shown below.

| Protein | GenBank ID | GI Number | Organism |
| --- | --- | --- | --- |
| CLJU_c20290 | ADK15091.1 | 300435324 | Clostridium ljungdahli |
| CLJU_c07030 | ADK13773.1 | 300434006 | Clostridium ljungdahli |
| CLJU_c07040 | ADK13774.1 | 300434007 | Clostridium ljungdahli |
| CLJU_c07050 | ADK13775.1 | 300434008 | Clostridium ljungdahli |
| CLJU_c07060 | ADK13776.1 | 300434009 | Clostridium ljungdahli |
| CLJU_c07070 | ADK13777.1 | 300434010 | Clostridium ljungdahli |
| CLJU_c07080 | ADK13778.1 | 300434011 | Clostridium ljungdahli |
| CLJU_c14730 | ADK14541.1 | 300434774 | Clostridium ljungdahli |
| CLJU_c14720 | ADK14540.1 | 300434773 | Clostridium ljungdahli |
| CLJU_c14710 | ADK14539.1 | 300434772 | Clostridium ljungdahli |
| CLJU_c14700 | ADK14538.1 | 300434771 | Clostridium ljungdahli |
| CLJU_c28670 | ADK15915.1 | 300436148 | Clostridium ljungdahli |

| Protein | GenBank ID | GI Number | Organism |
|---|---|---|---|
| CLJU_c28660 | ADK15914.1 | 300436147 | Clostridium ljungdahli |
| CLJU_c28650 | ADK15913.1 | 300436146 | Clostridium ljungdahli |
| CLJU_c28640 | ADK15912.1 | 300436145 | Clostridium ljungdahli |

In some cases, EM16 encoding genes are located adjacent to a CODH. In *Rhodospirillum rubrum*, the encoded CODH/hydrogenase proteins form a membrane-bound enzyme complex that has been indicated to be a site where energy, in the form of a proton gradient, is generated from the conversion of CO and $H_2O$ to $CO_2$ and $H_2$ (Fox et al., *J Bacteriol.* 178:6200-6208 (1996)). The CODH-I of *C. hydrogenoformans* and its adjacent genes have been proposed to catalyze a similar functional role based on their similarity to the *R. rubrum* CODH/hydrogenase gene cluster (Wu et al., *PLoS Genet.* 1:e65 (2005)). The *C. hydrogenoformans* CODH-1 was also shown to exhibit intense CO oxidation and $CO_2$ reduction activities when linked to an electrode (Parkin et al., *J Am. Chem. Soc.* 129:10328-10329 (2007)).

| Protein | GenBank ID | GI Number | Organism |
|---|---|---|---|
| CooL | AAC45118 | 1515468 | Rhodospirillum rubrum |
| CooX | AAC45119 | 1515469 | Rhodospirillum rubrum |
| CooU | AAC45120 | 1515470 | Rhodospirillum rubrum |
| CooH | AAC45121 | 1498746 | Rhodospirillum rubrum |
| CooF | AAC45122 | 1498747 | Rhodospirillum rubrum |
| CODH (CooS) | AAC45123 | 1498748 | Rhodospirillum rubrum |
| CooC | AAC45124 | 1498749 | Rhodospirillum rubrum |
| CooT | AAC45125 | 1498750 | Rhodospirillum rubrum |
| CooJ | AAC45126 | 1498751 | Rhodospirillum rubrum |
| CODH-I (CooS-I) | YP_360644 | 78043418 | Carboxydothermus hydrogenoformans |
| CooF | YP_360645 | 78044791 | Carboxydothermus hydrogenoformans |
| HypA | YP_360646 | 78044340 | Carboxydothermus hydrogenoformans |
| CooH | YP_360647 | 78043871 | Carboxydothermus hydrogenoformans |
| CooU | YP_360648 | 78044023 | Carboxydothermus hydrogenoformans |
| CooX | YP_360649 | 78043124 | Carboxydothermus hydrogenoformans |
| CooL | YP_360650 | 78043938 | Carboxydothermus hydrogenoformans |
| CooK | YP_360651 | 78044700 | Carboxydothermus hydrogenoformans |
| CooM | YP_360652 | 78043942 | Carboxydothermus hydrogenoformans |
| CooC | YP_360654.1 | 78043296 | Carboxydothermus hydrogenoformans |
| CooA-1 | YP_360655.1 | 78044021 | Carboxydothermus hydrogenoformans |

Some EM16 and CODH enzymes transfer electrons to ferredoxins. Ferredoxins are small acidic proteins containing one or more iron-sulfur clusters that function as intracellular electron carriers with a low reduction potential. Reduced ferredoxins donate electrons to Fe-dependent enzymes such as ferredoxin-$NADP^+$ oxidoreductase, pyruvate:ferredoxin oxidoreductase (PFOR) and 2-oxoglutarate:ferredoxin oxidoreductase (OFOR). The *H. thermophilus* gene fdx1 encodes a [4Fe-4S]-type ferredoxin that is required for the reversible carboxylation of 2-oxoglutarate and pyruvate by OFOR and PFOR, respectively (Yamamoto et al., *Extremophiles* 14:79-85 (2010)). The ferredoxin associated with the *Sulfolobus solfataricus* 2-oxoacid:ferredoxin reductase is a monomeric dicluster [3Fe-4S][4Fe-4S] type ferredoxin (Park et al. 2006). While the gene associated with this protein has not been fully sequenced, the N-terminal domain shares 93% homology with the zfx ferredoxin from *S. acidocaldarius*. The *E. coli* genome encodes a soluble ferredoxin of unknown physiological function, fdx. Some evidence indicates that this protein can function in iron-sulfur cluster assembly (Takahashi and Nakamura, 1999). Additional ferredoxin proteins have been characterized in *Helicobacter pylori* (Mukhopadhyay et al. 2003) and *Campylobacter jejuni* (van Vliet et al. 2001). A 2Fe-2S ferredoxin from *Clostridium pasteurianum* has been cloned and expressed in *E. coli* (Fujinaga and Meyer, Biochemical and Biophysical Research Communications, 192(3): (1993)). Acetogenic bacteria such as *Moorella thermoacetica*, *Clostridium carboxidivorans P7*, *Clostridium ljungdahli* and *Rhodospirillum rubrum* are predicted to encode several ferredoxins, listed below.

| Protein | GenBank ID | GI Number | Organism |
|---|---|---|---|
| fdx1 | BAE02673.1 | 68163284 | Hydrogenobacter thermophilus |
| M11214.1 | AAA83524.1 | 144806 | Clostridium pasteurianum |
| Zfx | AAY79867.1 | 68566938 | Sulfolobus acidocalarius |
| Fdx | AAC75578.1 | 1788874 | Escherichia coli |
| hp_0277 | AAD07340.1 | 2313367 | Helicobacter pylori |
| fdxA | CAL34484.1 | 112359698 | Campylobacter jejuni |
| Moth_0061 | ABC18400.1 | 83571848 | Moorella thermoacetica |
| Moth_1200 | ABC19514.1 | 83572962 | Moorella thermoacetica |
| Moth_1888 | ABC20188.1 | 83573636 | Moorella thermoacetica |
| Moth_2112 | ABC20404.1 | 83573852 | Moorella thermoacetica |
| Moth_1037 | ABC19351.1 | 83572799 | Moorella thermoacetica |
| CcarbDRAFT_4383 | ZP_05394383.1 | 255527515 | Clostridium carboxidivorans P7 |
| CcarbDRAFT_2958 | ZP_05392958.1 | 255526034 | Clostridium carboxidivorans P7 |
| CcarbDRAFT_2281 | ZP_05392281.1 | 255525342 | Clostridium carboxidivorans P7 |
| CcarbDRAFT_5296 | ZP_05395295.1 | 255528511 | Clostridium carboxidivorans P7 |
| CcarbDRAFT_1615 | ZP_05391615.1 | 255524662 | Clostridium carboxidivorans P7 |
| CcarbDRAFT_1304 | ZP_05391304.1 | 255524347 | Clostridium carboxidivorans P7 |
| cooF | AAG29808.1 | 11095245 | Carboxydothermus hydrogenoformans |
| fdxN | CAA35699.1 | 46143 | Rhodobacter capsulatus |
| Rru_A2264 | ABC23064.1 | 83576513 | Rhodospirillum rubrum |
| Rru_A1916 | ABC22716.1 | 83576165 | Rhodospirillum rubrum |
| Rru_A2026 | ABC22826.1 | 83576275 | Rhodospirillum rubrum |
| cooF | AAC45122.1 | 1498747 | Rhodospirillum rubrum |

| Protein | GenBank ID | GI Number | Organism |
| --- | --- | --- | --- |
| fdxN | AAA26460.1 | 152605 | Rhodospirillum rubrum |
| Alvin_2884 | ADC63789.1 | 288897953 | Allochromatium vinosum DSM 180 |
| Fdx | YP_002801146.1 | 226946073 | Azotobacter vinelandii DJ |
| CKL_3790 | YP_001397146.1 | 153956381 | Clostridium kluyveri DSM 555 |
| fer1 | NP_949965.1 | 39937689 | Rhodopseudomonas palustris CGA009 |
| Fdx | CAA12251.1 | 3724172 | Thauera aromatica |
| CHY_2405 | YP_361202.1 | 78044690 | Carboxydothermus hydrogenoformans |
| Fer | YP_359966.1 | 78045103 | Carboxydothermus hydrogenoformans |
| Fer | AAC83945.1 | 1146198 | Bacillus subtilis |
| fdx1 | NP_249053.1 | 15595559 | Pseudomonas aeruginosa PA01 |
| yfhL | AP_003148.1 | 89109368 | Escherichia coli K-12 |
| CLJU_c00930 | ADK13195.1 | 300433428 | Clostridium ljungdahli |
| CLJU_c00010 | ADK13115.1 | 300433348 | Clostridium ljungdahli |
| CLJU_c01820 | ADK13272.1 | 300433505 | Clostridium ljungdahli |
| CLJU_c17980 | ADK14861.1 | 300435094 | Clostridium ljungdahli |
| CLJU_c17970 | ADK14860.1 | 300435093 | Clostridium ljungdahli |
| CLJU_c22510 | ADK15311.1 | 300435544 | Clostridium ljungdahli |
| CLJU_c26680 | ADK15726.1 | 300435959 | Clostridium ljungdahli |
| CLJU_c29400 | ADK15988.1 | 300436221 | Clostridium ljungdahli |

Ferredoxin oxidoreductase enzymes transfer electrons from ferredoxins or flavodoxins to NAD(P)H. Two enzymes catalyzing the reversible transfer of electrons from reduced ferredoxins to NAD(P)+ are ferredoxin:NAD+ oxidoreductase (EC 1.18.1.3) and ferredoxin:NADP+ oxidoreductase (FNR, EC 1.18.1.2). Ferredoxin:NADP+ oxidoreductase (FNR, EC 1.18.1.2) has a noncovalently bound FAD cofactor that facilitates the reversible transfer of electrons from NADPH to low-potential acceptors such as ferredoxins or flavodoxins (Blaschkowski et al., Eur. J. Biochem. 123:563-569 (1982); Fujii et al., 1977). The Helicobacter pylori FNR, encoded by HP1164 (fqrB), is coupled to the activity of pyruvate:ferredoxin oxidoreductase (PFOR) resulting in the pyruvate-dependent production of NADPH (St et al. 2007). An analogous enzyme is found in Campylobacter jejuni (St Maurice et al., J. Bacteriol. 189: 4764-4773 (2007)). A ferredoxin:NADP+ oxidoreductase enzyme is encoded in the E. coli genome by fpr (Bianchi et al. 1993). Ferredoxin:NAD+ oxidoreductase utilizes reduced ferredoxin to generate NADH from NAD+. In several organisms, including E. coli, this enzyme is a component of multifunctional dioxygenase enzyme complexes. The ferredoxin:NAD+ oxidoreductase of E. coli, encoded by hcaD, is a component of the 3-phenylpropionate dioxygenase system involved in involved in aromatic acid utilization (Diaz et al. 1998). NADH:ferredoxin reductase activity was detected in cell extracts of Hydrogenobacter thermophilus, although a gene with this activity has not yet been indicated (Yoon et al. 2006). Additional ferredoxin: NAD(P)+ oxidoreductases have been annotated in Clostridium carboxydivorans P7. The NADH-dependent reduced ferredoxin: NADP oxidoreductase of C. kluyveri, encoded by nfnAB, catalyzes the concomitant reduction of ferredoxin and NAD+ with two equivalents of NADPH (Wang et al, J Bacteriol 192: 5115-5123 (2010)). Finally, the energy-conserving membrane-associated Rnf-type proteins (Seedorf et al, PNAS 105:2128-2133 (2008); and Herrmann, J. Bacteriol 190:784-791 (2008)) provide a means to generate NADH or NADPH from reduced ferredoxin.

| Protein | GenBank ID | GI Number | Organism |
| --- | --- | --- | --- |
| fqrB | NP_207955.1 | 15645778 | Helicobacter pylori |
| fqrB | YP_001482096.1 | 157414840 | Campylobacter jejuni |
| RPA3954 | CAE29395.1 | 39650872 | Rhodopseudomonas palustris |
| Fpr | BAH29712.1 | 225320633 | Hydrogenobacter thermophilus |
| yumC | NP_391091.2 | 255767736 | Bacillus subtilis |
| Fpr | P28861.4 | 399486 | Escherichia coli |
| hcaD | AAC75595.1 | 1788892 | Escherichia coli |
| LOC100282643 | NP_001149023.1 | 226497434 | Zea mays |
| NfnA | YP_001393861.1 | 153953096 | Clostridium kluyveri |
| NfnB | YP_001393862.1 | 153953097 | Clostridium kluyveri |
| CcarbDRAFT_2639 | ZP_05392639.1 | 255525707 | Clostridium carboxidivorans P7 |
| CcarbDRAFT_2638 | ZP_05392638.1 | 255525706 | Clostridium carboxidivorans P7 |
| CcarbDRAFT_2636 | ZP_05392636.1 | 255525704 | Clostridium carboxidivorans P7 |
| CcarbDRAFT_5060 | ZP_05395060.1 | 255528241 | Clostridium carboxidivorans P7 |
| CcarbDRAFT_2450 | ZP_05392450.1 | 255525514 | Clostridium carboxidivorans P7 |
| CcarbDRAFT_1084 | ZP_05391084.1 | 255524124 | Clostridium carboxidivorans P7 |
| RnfC | EDK33306.1 | 146346770 | Clostridium kluyveri |
| RnfD | EDK33307.1 | 146346771 | Clostridium kluyveri |
| RnfG | EDK33308.1 | 146346772 | Clostridium kluyveri |
| RnfE | EDK33309.1 | 146346773 | Clostridium kluyveri |
| RnfA | EDK33310.1 | 146346774 | Clostridium kluyveri |
| RnfB | EDK33311.1 | 146346775 | Clostridium kluyveri |
| CLJU_c11410 (RnfB) | ADK14209.1 | 300434442 | Clostridium ljungdahlii |
| CLJU_c11400 (RnfA) | ADK14208.1 | 300434441 | Clostridium ljungdahlii |
| CLJU_c11390 (RnfE) | ADK14207.1 | 300434440 | Clostridium ljungdahlii |
| CLJU_c11380 (RnfG) | ADK14206.1 | 300434439 | Clostridium ljungdahlii |

| Protein | GenBank ID | GI Number | Organism |
|---|---|---|---|
| CLJU_c11370 (RnfD) | ADK14205.1 | 300434438 | Clostridium ljungdahlii |
| CLJU_c11360 (RnfC) | ADK14204.1 | 300434437 | Clostridium ljungdahlii |
| MOTH_1518 (NfnA) | YP_430370.1 | 83590361 | Moorella thermoacetica |
| MOTH_1517 (NfnB) | YP_430369.1 | 83590360 | Moorella thermoacetica |
| CHY_1992 (NfnA) | YP_360811.1 | 78045020 | Carboxydothermus hydrogenoformans |
| CHY_1993 (NfnB) | YP_360812.1 | 78044266 | Carboxydothermus hydrogenoformans |
| CLJU_c37220 (NfnAB) | YP_003781850.1 | 300856866 | Clostridium ljungdahlii |

FIG. 1, Step I—Formate Dehydrogenase (EM8)

Formate dehydrogenase (FDH; EM8) catalyzes the reversible transfer of electrons from formate to an acceptor. Enzymes with FDH activity utilize various electron carriers such as, for example, NADH (EC 1.2.1.2), NADPH (EC 1.2.1.43), quinols (EC 1.1.5.6), cytochromes (EC 1.2.2.3) and EM16s (EC 1.1.99.33). FDH enzymes have been characterized from Moorella thermoacetica (Andreesen and Ljungdahl, J Bacteriol 116:867-873 (1973); Li et al., J Bacteriol 92:405-412 (1966); Yamamoto et al., J Biol Chem. 258:1826-1832 (1983). The loci, Moth_2312 is responsible for encoding the alpha subunit of EM8 while the beta subunit is encoded by Moth_2314 (Pierce et al., Environ Microbiol (2008)). Another set of genes encoding EM8 activity with a propensity for $CO_2$ reduction is encoded by Sfum_2703 through Sfum_2706 in Syntrophobacter fumaroxidans (de Bok et al., Eur J Biochem. 270:2476-2485 (2003)); Reda et al., PNAS 105:10654-10658 (2008)). A similar set of genes presumed to carry out the same function are encoded by CHY_0731, CHY_0732, and CHY_0733 in C. hydrogenoformans (Wu et al., PLoS Genet 1:e65 (2005)). EM8s are also found many additional organisms including C. carboxidivorans P7, Bacillus methanolicus, Burkholderia stabilis, Moorella thermoacetica ATCC 39073, Candida boidinii, Candida methylica, and Saccharomyces cerevisiae S288c. The soluble EM8 from Ralstonia eutropha reduces $NAD^+$ (fdsG, -B, -A, -C, -D) (Oh and Bowien, 1998).

Several EM8 enzymes have been identified that have higher specificity for NADP as the cofactor as compared to NAD. This enzyme has been deemed as the NADP-dependent formate dehydrogenase and has been reported from 5 species of the Burkholderia cepacia complex. It was tested and verified in multiple strains of Burkholderia multivorans, Burkholderia stabilis, Burkholderia pyrrocinia, and Burkholderia cenocepacia (Hatrongjit et al., Enzyme and Microbial Tech., 46: 557-561 (2010)). The enzyme from Burkholderia stabilis has been characterized and the apparent $K_m$ of the enzyme were reported to be 55.5 mM, 0.16 mM and 1.43 mM for formate, NADP, and NAD respectively. More gene candidates can be identified using sequence homology of proteins deposited in Public databases such as NCBI, JGI and the metagenomic databases.

| Protein | GenBank ID | GI Number | Organism |
|---|---|---|---|
| Moth_2312 | YP_431142 | 148283121 | Moorella thermoacetica |
| Moth_2314 | YP_431144 | 83591135 | Moorella thermoacetica |
| Sfum_2703 | YP_846816.1 | 116750129 | Syntrophobacter fumaroxidans |
| Sfum_2704 | YP_846817.1 | 116750130 | Syntrophobacter fumaroxidans |
| Sfum_2705 | YP_846818.1 | 116750131 | Syntrophobacter fumaroxidans |
| Sfum_2706 | YP_846819.1 | 116750132 | Syntrophobacter fumaroxidans |
| CHY_0731 | YP_359585.1 | 78044572 | Carboxydothermus hydrogenoformans |
| CHY_0732 | YP_359586.1 | 78044500 | Carboxydothermus hydrogenoformans |
| CHY_0733 | YP_359587.1 | 78044647 | Carboxydothermus hydrogenoformans |
| CcarbDRAFT_0901 | ZP_05390901.1 | 255523938 | Clostridium carboxidivorans P7 |
| CcarbDRAFT_4380 | ZP_05394380.1 | 255527512 | Clostridium carboxidivorans P7 |
| fdhA, MGA3_06625 | EIJ82879.1 | 387590560 | Bacillus methanolicus MGA3 |
| fdhA, PB1_11719 | ZP_10131761.1 | 387929084 | Bacillus methanolicus PB1 |
| fdhD, MGA3_06630 | EIJ82880.1 | 387590561 | Bacillus methanolicus MGA3 |
| fdhD, PB1_11724 | ZP_10131762.1 | 387929085 | Bacillus methanolicus PB1 |
| fdh | ACF35003.1 | 194220249 | Burkholderia stabilis |
| fdh | ACF35004.1 | 194220251 | Burkholderia pyrrocinia |
| fdh | ACF35002.1 | 194220247 | Burkholderia cenocepacia |
| fdh | ACF35001.1 | 194220245 | Burkholderia multivorans |
| fdh | ACF35000.1 | 194220243 | Burkholderia cepacia |
| FDH1 | AAC49766.1 | 2276465 | Candida boidinii |
| fdh | CAA57036.1 | 1181204 | Candida methylica |
| FDH2 | P0CF35.1 | 294956522 | Saccharomyces cerevisiae S288c |
| FDH1 | NP_015033.1 | 6324964 | Saccharomyces cerevisiae S288c |
| fdsG | YP_725156.1 | 113866667 | Ralstonia eutropha |
| fdsB | YP_725157.1 | 113866668 | Ralstonia eutropha |
| fdsA | YP_725158.1 | 113866669 | Ralstonia eutropha |
| fdsC | YP_725159.1 | 113866670 | Ralstonia eutropha |
| fdsD | YP_725160.1 | 113866671 | Ralstonia eutropha |

FIG. 1, Step J—Methanol Dehydrogenase (EM9)

NAD+ dependent EM9 enzymes (EC 1.1.1.244) catalyze the conversion of methanol and NAD+ to formaldehyde and NADH. An enzyme with this activity was first characterized in *Bacillus methanolicus* (Heggeset, et al., *Applied and Environmental Microbiology*, 78(15):5170-5181 (2012)). This enzyme is zinc and magnesium dependent, and activity of the enzyme is enhanced by the activating enzyme encoded by act (Kloosterman et al, *J Biol Chem* 277:34785-92 (2002)). The act is a Nudix hydrolase. Several of these candidates have been identified and shown to have activity on methanol. Additional NAD(P)+ dependent enzymes can be identified by sequence homology. EM9 enzymes utilizing different electron acceptors are also known in the art. Examples include cytochrome dependent enzymes such as mxaIF of the methylotroph *Methylobacterium extorquens* (Nunn et al, Nucl Acid Res 16:7722 (1988)). EM9 enzymes of methanotrophs such as *Methylococcus capsulatis* function in a complex with methane monooxygenase (MMO) (Myronova et al., *Biochem* 45:11905-14 (2006)). Methanol can also be oxidized to formaldehyde by alcohol oxidase enzymes such as methanol oxidase (EC 1.1.3.13) of *Candida boidinii* (Sakai et al., *Gene* 114: 67-73 (1992)).

Table X: Exemplary Methanol Dehydrogenase Enzymes

| Protein | GenBank ID | GI Number | Organism |
|---|---|---|---|
| mdh, MGA3_17392 | EIJ77596.1 | 387585261 | *Bacillus methanolicus* MGA3 |
| mdh2, MGA3_07340 | EIJ83020.1 | 387590701 | *Bacillus methanolicus* MGA3 |
| mdh3, MGA3_10725 | EIJ80770.1 | 387588449 | *Bacillus methanolicus* MGA3 |
| act, MGA3_09170 | EIJ83380.1 | 387591061 | *Bacillus methanolicus* MGA3 |
| mdh, PB1_17533 | ZP_10132907.1 | 387930234 | *Bacillus methanolicus* PB1 |
| mdh1, PB1_14569 | ZP_10132325.1 | 387929648 | *Bacillus methanolicus* PB1 |
| mdh2, PB1_12584 | ZP_10131932.1 | 387929255 | *Bacillus methanolicus* PB1 |
| act, PB1_14394 | ZP_10132290.1 | 387929613 | *Bacillus methanolicus* PB1 |
| BFZC1_05383 | ZP_07048751.1 | 299535429 | *Lysinibacillus fusiformis* |
| BFZC1_20163 | ZP_07051637.1 | 299538354 | *Lysinibacillus fusiformis* |
| Bsph_4187 | YP_001699778.1 | 169829620 | *Lysinibacillus sphaericus* |
| Bsph_1706 | YP_001697432.1 | 169827274 | *Lysinibacillus sphaericus* |
| mdh2 | YP_004681552.1 | 339322658 | *Cupriavidus necator* N-1 |
| nudF1 | YP_004684845.1 | 339325152 | *Cupriavidus necator* N-1 |
| BthaA_010200007655 | ZP_5587334.1 | 257139072 | *Burkholderia thailandensis* E264 |
| BTH_I1076 (MutT/NUDIX NTP pyrophosphatase) | YP_441629.1 | 83721454 | *Burkholderia thailandensis* E264 |
| BalcAV_11743 | ZP_10819291.1 | 402299711 | *Bacillus alcalophilus* ATCC 27647 |
| BalcAV_05251 | ZP_10818002.1 | 402298299 | *Bacillus alcalophilus* ATCC 27647 |
| alcohol dehydrogenase | YP_725376.1 | 113866887 | *Ralstonia eutropha* H16 |
| alcohol dehydrogenase | YP_001447544 | 156976638 | *Vibrio harveyi* ATCC BAA-1116 |
| P3TCK_27679 | ZP_01220157.1 | 90412151 | *Photobacterium profundum* 3TCK |
| alcohol dehydrogenase | YP_694908 | 110799824 | *Clostridium perfringens* ATCC 13124 |
| adhB | NP_717107 | 24373064 | *Shewanella oneidensis* MR-1 |
| alcohol dehydrogenase | YP_237055 | 66047214 | *Pseudomonas syringae* pv. *syringae* B728a |
| alcohol dehydrogenase | YP_359772 | 78043360 | *Carboxydothermus hydrogenoformans* Z-2901 |
| alcohol dehydrogenase | YP_003990729 | 312112413 | *Geobacillus* sp. Y4.1MC1 |
| PpeoK3_010100018471 | ZP_10241531.1 | 390456003 | *Paenibacillus peoriae* KCTC 3763 |
| OBE_12016 | EKC54576 | 406526935 | human gut metagenome |
| alcohol dehydrogenase | YP_003310546 | 269122369 | *Sebaldella termitidis* ATCC 33386 |
| alcohol dehydrogenase | YP_001343716 | 152978087 | *Actinobacillus succinogenes* 130Z |
| dhaT | AAC45651 | 2393887 | *Clostridium pasteurianum* DSM 525 |
| alcohol dehydrogenase | NP_561852 | 18309918 | *Clostridium perfringens* str. 13 |
| BAZO_10081 | ZP_11313277.1 | 410459529 | *Bacillus azotoformans* LMG 9581 |
| alcohol dehydrogenase | YP_007491369 | 452211255 | *Methanosarcina mazei* Tuc01 |
| alcohol dehydrogenase | YP_004860127 | 347752562 | *Bacillus coagulans* 36D1 |
| alcohol dehydrogenase | YP_002138168 | 197117741 | *Geobacter bemidjiensis* Bem |
| DesmeDRAFT_1354 | ZP_08977641.1 | 354558386 | *Desulfitobacterium metallireducens* DSM 15288 |
| alcohol dehydrogenase | YP_001337153 | 152972007 | *Klebsiella pneumoniae* subsp. *pneumoniae* MGH 78578 |
| alcohol dehydrogenase | YP_001113612 | 134300116 | *Desulfotomaculum reducens* MI-1 |
| alcohol dehydrogenase | YP_001663549 | 167040564 | *Thermoanaerobacter* sp. X514 |
| ACINNAV82_2382 | ZP_16224338.1 | 421788018 | *Acinetobacter baumannii* Naval-82 |

| Protein | GenBank ID | GI Number | Organism |
| --- | --- | --- | --- |
| DVU2405 | YP_011618 | 46580810 | Desulfovibrio vulgaris str. Hildenborough |
| alcohol dehydrogenase | YP_005052855 | 374301216 | Desulfovibrio africanus str. Walvis Bay |
| alcohol dehydrogenase | YP_002434746 | 218885425 | Desulfovibrio vulgaris str. 'Miyazaki F' |
| alcohol dehydrogenase | AGF87161 | 451936849 | uncultured organism |
| DesfrDRAFT_3929 | ZP_07335453.1 | 303249216 | Desulfovibrio fructosovorans JJ |
| alcohol dehydrogenase | NP_617528 | 20091453 | Methanosarcina acetivorans C2A |
| alcohol dehydrogenase | NP_343875.1 | 15899270 | Sulfolobus solfataricus P-2 |
| adh4 | YP_006863258 | 408405275 | Nitrososphaera gargensis Ga9.2 |
| BD31_I0957 | ZP_10117398.1 | 386875211 | Nitrosopumilus solaria BD31 |
| alcohol dehydrogenase | YP_004108045.1 | 316933063 | Rhodopseudomonas palustris DX-1 |
| Ta0841 | NP_394301.1 | 16081897 | Thermoplasma acidophilum |
| PTO1151 | YP_023929.1 | 48478223 | Picrophilus torridus DSM9790 |
| alcohol dehydrogenase | ZP_10129817.1 | 387927138 | Bacillus methanolicus PB-1 |
| cgR_2695 | YP_001139613.1 | 145296792 | Corynebacterium glutamicum R |
| alcohol dehydrogenase | YP_004758576.1 | 340793113 | Corynebacterium variabile |
| HMPREF1015_01790 | ZP_09352758.1 | 365156443 | Bacillus smithii |
| ADH1 | NP_014555.1 | 6324486 | Saccharomyces cerevisiae |
| NADH-dependent butanol dehydrogenase A | YP_001126968.1 | 138896515 | Geobacillus themodenitrificans NG80-2 |
| alcohol dehydrogenase | WP_007139094.1 | 494231392 | Flavobacterium frigoris |
| methanol dehydrogenase | WP_003897664.1 | 489994607 | Mycobacterium smegmatis |
| ADH1B | NP_000659.2 | 34577061 | Homo sapiens |
| PMI01_01199 | ZP_10750164.1 | 399072070 | Caulobacter sp. AP07 |
| BurJ1DRAFT_3901 | ZP_09753449.1 | 375107188 | Burkholderiales bacterium Joshi_001 |
| YiaY | YP_026233.1 | 49176377 | Escherichia coli |
| MCA0299 | YP_112833.1 | 53802410 | Methylococcus capsulatis |
| MCA0782 | YP_113284.1 | 53804880 | Methylococcus capsulatis |
| mxaI | YP_002965443.1 | 240140963 | Methylobacterium extorquens |
| mxaF | YP_002965446.1 | 240140966 | Methylobacterium extorquens |
| AOD1 | AAA34321.1 | 170820 | Candida boidinii |

An in vivo assay was developed to determine the activity of methanol dehydrogenases. This assay relies on the detection of formaldehyde (HCHO), thus measuring the forward activity of the enzyme (oxidation of methanol). To this end, a strain comprising a BDOP and lacking frmA, frmB, frmR was created using Lamba Red recombinase technology (Datsenko and Wanner, Proc. Natl. Acad. Sci. USA, 6 97(12): 6640-5 (2000). Plasmids expressing methanol dehydrogenases were transformed into the strain, then grown to saturation in LB medium+antibiotic at 37° C. with shaking. Transformation of the strain with an empty vector served as a negative control. Cultures were adjusted by O.D. and then diluted 1:10 into M9 medium+0.5% glucose+antibiotic and cultured at 37° C. with shaking for 6-8 hours until late log phase. Methanol was added to 2% v/v and the cultures were further incubated for 30 min. with shaking at 37° C. Cultures were spun down and the supernatant was assayed for formaldehyde produced using DETECTX Formaldehyde Detection kit (Arbor Assays; Ann Arbor, Mich.) according to manufacturer's instructions. The frmA, frmB, frmR deletions resulted in the native formaldehyde utilization pathway to be deleted, which enables the formation of formaldehyde that can be used to detect methanol dehydrogenase activity in the NNOMO.

The activity of several enzymes was measured using the assay described above. The results of four independent experiments are provided in Table 1 below.

TABLE 1

Results of in vivo assays showing formaldehyde (HCHO) production by various NNOMO comprising a plasmid expressing a methanol dehydrogenase.

| Accession number | HCHO (μM) |
| --- | --- |
| Experiment 1 | |
| EIJ77596.1 | >50 |
| EIJ83020.1 | >20 |
| EIJ80770.1 | >50 |
| ZP_10132907.1 | >20 |
| ZP_10132325.1 | >20 |
| ZP_10131932.1 | >50 |
| ZP_07048751.1 | >50 |
| YP_001699778.1 | >50 |
| YP_004681552.1 | >10 |
| ZP_10819291.1 | <1 |
| Empty vector | 2.33 |
| Experiment 2 | |
| EIJ77596.1 | >50 |
| NP_00659.2 | >50 |
| YP_004758576.1 | >20 |
| ZP_09352758.1 | >50 |
| ZP_10129817.1 | >20 |
| YP_001139613.1 | >20 |

TABLE 1-continued

Results of in vivo assays showing formaldehyde (HCHO) production by various NNOMO comprising a plasmid expressing a methanol dehydrogenase.

| Accession number | HCHO (µM) |
|---|---|
| NP_014555.1 | >10 |
| WP_007139094.1 | >10 |
| NP_343875.1 | >1 |
| YP_006863258 | >1 |
| NP_394301.1 | >1 |
| ZP_10750164.1 | >1 |
| YP_023929.1 | >1 |
| ZP_08977641.1 | <1 |
| ZP_10117398.1 | <1 |
| YP_004108045.1 | <1 |
| ZP_09753449.1 | <1 |
| Empty vector | 0.17 |
| Experiment 3 | |
| EIJ77596.1 | >50 |
| NP_561852 | >50 |

FIG. 1, Step K—Spontaneous or Formaldehyde Activating Enzyme (EM10)

The conversion of formaldehyde and THF to methylenetetrahydrofolate can occur spontaneously. It is also possible that the rate of this reaction can be enhanced by an EM10. A formaldehyde activating enzyme (Fae) has been identified in *Methylobacterium extorquens* AM1 which catalyzes the condensation of formaldehyde and tetrahydromethanopterin to methylene tetrahydromethanopterin (Vorholt, et al., J. Bacteriol., 182(23), 6645-6650 (2000)). It is possible that a similar enzyme exists or can be engineered to catalyze the condensation of formaldehyde and tetrahydrofolate to methylenetetrahydrofolate. Homologs exist in several organisms including *Xanthobacter autotrophicus* Py2 and *Hyphomicrobium denitrificans* ATCC 51888.

| Protein | GenBank ID | GI Number | Organism |
|---|---|---|---|
| MexAM1_META1p1766 | Q9FA38.3 | 17366061 | *Methylobacterium extorquens* AM1 |
| Xaut_0032 | YP_001414948.1 | 154243990 | *Xanthobacter autotrophicus* Py2 |
| Hden_1474 | YP_003755607.1 | 300022996 | *Hyphomicrobium denitrificans* ATCC 51888 |

TABLE 1-continued

Results of in vivo assays showing formaldehyde (HCHO) production by various NNOMO comprising a plasmid expressing a methanol dehydrogenase.

| Accession number | HCHO (µM) |
|---|---|
| YP_002138168 | >50 |
| YP_026233.1 | >50 |
| YP_001447544 | >50 |
| Metalibrary | >50 |
| YP_359772 | >50 |
| ZP_01220157.1 | >50 |
| ZP_07335453.1 | >20 |
| YP_001337153 | >20 |
| YP_694908 | >20 |
| NP_717107 | >20 |
| AAC45651 | >10 |
| ZP_11313277.1 | >10 |
| ZP_16224338.1 | >10 |
| YP_001113612 | >10 |
| YP_004860127 | >10 |
| YP_003310546 | >10 |
| YP_001343716 | >10 |
| NP_717107 | >10 |
| CAA80989.1 | >50 |
| YP_002434746 | >10 |
| Empty vector | 0.11 |
| Experiment 4 | |
| EIJ77596.1 | >50 |
| ZP_10241531.1 | >90 |
| YP_005052855 | >85 |
| ZP_10132907.1 | >50 |
| NP_617528 | >50 |
| NP_617528 | >50 |
| ZP_08977641.1 | >20 |
| YP_237055 | >20 |
| Empty vector | 49.36 |

FIG. 1, Step L—Formaldehyde Dehydrogenase (EM11)

Oxidation of formaldehyde to formate is catalyzed by EM11. An NAD+ dependent EM11 enzyme is encoded by fdhA of *Pseudomonas putida* (Ito et al, *J Bacteriol* 176: 2483-2491 (1994)). Additional EM11 enzymes include the NAD+ and glutathione independent EM11 from *Hyphomicrobium zavarzinii* (Jerome et al, Appl Microbiol Biotechnol 77:779-88 (2007)), the glutathione dependent EM11 of *Pichia pastoris* (Sunga et al, Gene 330:39-47 (2004)) and the NAD(P)+ dependent EM11 of *Methylobacter marinus* (Speer et al, FEMS Microbiol Lett, 121(3):349-55 (1994)).

| Protein | GenBank ID | GI Number | Organism |
|---|---|---|---|
| fdhA | P46154.3 | 1169603 | *Pseudomonas putida* |
| faoA | CAC85637.1 | 19912992 | *Hyphomicrobium zavarzinii* |
| Fld1 | CCA39112.1 | 328352714 | *Pichia pastoris* |
| Fdh | P47734.2 | 221222447 | *Methylobacter marinus* |

In addition to the EM11 enzymes listed above, alternate enzymes and pathways for converting formaldehyde to formate are known in the art. For example, many organisms employ glutathione-dependent formaldehyde oxidation pathways, in which formaldehyde is converted to formate in three steps via the intermediates S-hydroxymethylglutathione and S-formylglutathione (Vorholt et al, *J Bacteriol* 182:6645-50 (2000)). The enzymes of this pathway are S-(hydroxymethyl)glutathione synthase (EC 4.4.1.22), glutathione-dependent formaldehyde dehydrogenase (EC 1.1.1.284) and S-formylglutathione hydrolase (EC 3.1.2.12).

FIG. 1, Step M—Spontaneous or S-(Hydroxymethyl)Glutathione Synthase (EM12)

While conversion of formaldehyde to S-hydroxymethylglutathione can occur spontaneously in the presence of glutathione, it has been shown by Goenrich et al (Goenrich, et al., J Biol Chem 277(5); 3069-72 (2002)) that an enzyme from *Paracoccus denitrificans* can accelerate this spontaneous condensation reaction. The enzyme catalyzing the conversion of formaldehyde and glutathione was purified and named glutathione-dependent formaldehyde-activating enzyme (Gfa). The gene encoding it, which was named gfa, is located directly upstream of the gene for glutathione-dependent formaldehyde dehydrogenase, which catalyzes the subsequent oxidation of S-hydroxymethylglutathione. Putative proteins with sequence identity to Gfa from *P. denitrificans* are present also in *Rhodobacter sphaeroides, Sinorhizobium meliloti,* and *Mesorhizobium loti*.

| Protein | GenBank ID | GI Number | Organism |
|---|---|---|---|
| Gfa | Q51669.3 | 38257308 | *Paracoccus denitrificans* |
| Gfa | ABP71667.1 | 145557054 | *Rhodobacter sphaeroides* ATCC 17025 |
| Gfa | Q92WX6.1 | 38257348 | *Sinorhizobium meliloti* 1021 |
| Gfa | Q98LU4.2 | 38257349 | *Mesorhizohium loti* MAFF303099 |

FIG. 1, Step N—Glutathione-Dependent Formaldehyde Dehydrogenase (EM13)

Glutathione-dependent formaldehyde dehydrogenase (GS-FDH) belongs to the family of class III alcohol dehydrogenases. Glutathione and formaldehyde combine non-enzymatically to form hydroxymethylglutathione, the true substrate of the GS-FDH catalyzed reaction. The product, S-formylglutathione, is further metabolized to formic acid.

| Protein | GenBank ID | GI Number | Organism |
|---|---|---|---|
| frmA | YP_488650.1 | 388476464 | *Escherichia coli* K-12 MG1655 |
| SFA1 | NP_010113.1 | 6320033 | *Saccharomyces cerevisiae* S288c |
| flhA | AAC44551.1 | 1002865 | *Paracoccus denitrificans* |
| adhI | AAB09774.1 | 986949 | *Rhodobacter sphaeroides* |

FIG. 1, Step O—S-Formylglutathione Hydrolase (EM14)

EM14 is a glutathione thiol esterase found in bacteria, plants and animals. It catalyzes conversion of S-formylglutathione to formate and glutathione. The fghA gene of *P. denitrificans* is located in the same operon with gfa and flhA, two genes involved in the oxidation of formaldehyde to formate in this organism. In *E. coli*, FrmB is encoded in an operon with FrmR and FrmA, which are proteins involved in the oxidation of formaldehyde. YeiG of *E. coli* is a promiscuous serine hydrolase; its highest specific activity is with the substrate S-formylglutathione.

| Protein | GenBank ID | GI Number | Organism |
|---|---|---|---|
| frmB | NP_414889.1 | 16128340 | *Escherichia coli* K-12 MG1655 |
| yeiG | AAC75215.1 | 1788477 | *Escherichia coli* K-12 MG1655 |
| fghA | AAC44554.1 | 1002868 | *Paracoccus denitrificans* |

4.2 Example II—Enhanced Yield of Succinate from Carbohydrates Using Methanol

Exemplary MMPs for enhancing the availability of reducing equivalents are provided in FIG. 1.

Succinate production can be achieved in a recombinant organism by the pathway shown in FIG. 2. For example, pathways for the production of succinate from glucose, $CO_2$, and reducing equivalents (e.g., MeOH) at a theoretical yield of 2.0 mol succinate/mol glucose are provided. Exemplary enzymes for the conversion of glucose to succinate by this route include. 2A) a PEP carboxylase (ES1A) or a PEP carboxykinase (ES1B); 2B) a ES2; 2C) a ES3; 2D) a ES4; 2E) a ES5; and 2F) a ES6. Succinate production can be carried out by 2A, 2C, 2E and 2F; 2B, 2C, 2E and 2F; or 2D, 2E and 2F. Oxidative TCA cycle enzymes and enzymes for the conversion of phosphoenolpyruvate to acetyl-CoA are not required to produce succinate at the theoretical yield in this example. Note that several other carbohydrates can be converted to phosphoenolpyruvate and succinate by this simplified route including xylose, arabinose, galactose, and glycerol.

FIG. 2, Step A—PEP Carboxylase (ES1A) or PEP Carboxykinase (ES1B)

Carboxylation of phosphoenolpyruvate to oxaloacetate is catalyzed by ES1A. Exemplary ES1A enzymes are encoded by ppc in *E. coli* (Kai et al., *Arch. Biochem. Biophys.* 414:170-179 (2003), ppcA in *Methylobacterium extorquens* AM1 (Arps et al., *J. Bacteriol.* 175:3776-3783 (1993), and ppc in *Corynebacterium glutamicum* (Eikmanns et al., *Mol. Gen. Genet.* 218:330-339 (1989).

| Protein | GenBank ID | GI Number | Organism |
|---|---|---|---|
| Ppc | NP_418391 | 16131794 | *Escherichia coli* |
| ppcA | AAB58883 | 28572162 | *Methylobacterium extorquens* |
| Ppc | ABB53270 | 80973080 | *Corynebacterium glutamicum* |

An alternative enzyme for converting phosphoenolpyruvate to oxaloacetate is ES1B, which simultaneously forms an ATP while carboxylating PEP. In most organisms ES1B serves a gluconeogenic function and converts oxaloacetate to PEP at the expense of one ATP. *S. cerevisiae* is one such organism whose native ES1B, PCK1, serves a gluconeogenic role (Valdes-Hevia et al., *FEBS Lett.* 258:313-316 (1989). *E. coli* is another such organism, as the role of ES1B in producing oxaloacetate is believed to be minor when compared to ES1A, which does not form ATP, possibly due to the higher $K_m$ for bicarbonate of ES1B (Kim et al., *Appl. Environ. Microbiol.* 70:1238-1241 (2004)). Nevertheless, activity of the native *E. coli* ES1B from PEP towards oxaloacetate has been recently demonstrated in ppc mutants of *E. coli* K-12 (Kwon et al., *J. Microbiol. Biotechnol.* 16:1448-1452 (2006)). These strains exhibited no growth defects and had increased succinate production at high $NaHCO_3$ concentrations. Alternately, the activity of the *E. coli* enzyme in the oxaloacetate-consuming direction can be reduced by introducing an amino acid substitution at the oxaloacetate binding site (pck R65Q) (Cotelesage et al., *Int. J Biochem. Cell Biol.* 39:1204-1210 (2007)). Mutant strains of *E. coli* can adopt Pck as the dominant $CO_2$-fixing enzyme following adaptive evolution (Zhang et al., supra, 2009). In some organisms, particularly rumen bacteria, ES1B is quite efficient in producing oxaloacetate from PEP and generating ATP. Examples of ES1B genes that have been cloned into *E. coli* include those from *Mannheimia succiniciproducens* (Lee et al., *Biotechnol. Bioprocess Eng.* 7:95-99 (2002)), *Anaerobiospirillum succiniciproducens* (Laivenieks et al., *Appl. Environ. Microbiol.* 63:2273-2280 (1997), and *Actinobacillus succinogenes* (Kim et al. supra). The PEPCK enzyme from *Megathyrsus maximus* has a low Km for $CO_2$, a substrate thought to be rate-limiting in the *E. coli* enzyme (Chen et al., *Plant Physiol* 128:160-164 (2002); Cotelesage et al., *Int. J Biochem. Cell Biol.* 39:1204-1210 (2007)). The ES1B enzyme of *Haemophilus influenza* is effective at forming oxaloacetate from PEP.

| Protein | GenBank ID | GI Number | Organism |
| --- | --- | --- | --- |
| PCK1 | NP_013023 | 6322950 | *Saccharomyces cerevisiae* |
| Pck | NP_417862.1 | 16131280 | *Escherichia coli* |
| pckA | YP_089485.1 | 52426348 | *Mannheimia succiniciproducens* |

| Protein | GenBank ID | GI Number | Organism |
| --- | --- | --- | --- |
| pckA | O09460.1 | 3122621 | *Anaerobiospirillum succiniciproducens* |
| pckA | Q6W6X5 | 75440571 | *Actinobacillus succinogenes* |
| AF532733.1:1 . . . 1929 | AAQ10076.1 | 33329363 | *Megathyrsus maximus* |
| pckA | P43923.1 | 1172573 | *Haemophilus influenza* |

FIG. 2, Step B—Pyruvate Carboxylase (ES2)

Pyruvate carboxylase (EC 6.4.1.1) directly converts pyruvate to oxaloacetate at the cost of one ATP. Pyruvate carboxylase enzymes are encoded by PYC1 (Walker et al., *Biochem. Biophys. Res. Commun.* 176:1210-1217 (1991) and PYC2 (Walker et al., supra) in *Saccharomyces cerevisiae*, and pyc in *Mycobacterium smegmatis* (Mukhopadhyay and Purwantini, *Biochim. Biophys. Acta* 1475:191-206 (2000)).

| Protein | GenBank ID | AAGI Number | Organism |
| --- | --- | --- | --- |
| PYC1 | NP_011453 | 6321376 | *Saccharomyces cerevisiae* |
| PYC2 | NP_009777 | 6319695 | *Saccharomyces cerevisiae* |
| Pyc | YP_890857.1 | 118470447 | *Mycobacterium smegmatis* |

FIG. 2, Step C—Malate Dehydrogenase (ES3)

Oxaloacetate is converted into malate by ES3 (EC 1.1.1.37), an enzyme which functions in both the forward and reverse direction. *S. cerevisiae* possesses three copies of ES3, MDH1 (McAlister-Henn and Thompson, *J. Bacteriol.* 169:5157-5166 (1987), MDH2 (Minard and McAlister-Henn, *Mol. Cell. Biol.* 11:370-380 (1991); Gibson and McAlister-Henn, *J. Biol. Chem.* 278:25628-25636 (2003)), and MDH3 (Steffan and McAlister-Henn, *J. Biol. Chem.* 267:24708-24715 (1992)), which localize to the mitochondrion, cytosol, and peroxisome, respectively. Close homologs to the cytosolic ES3, MDH2, from *S. cerevisiae* are found in several organisms including *Kluyveromyces lactis* and *Candida tropicalis*. *E. coli* is known to have an active ES3 encoded by mdh. In some embodiments, the exogenous malate dehydrogenase genes are *Rhizopus delemar* malate dehydrogenase genes encoding the amino acid sequence disclosed in WO2013112939 as SEQ ID NO:167 or its variants.

| Protein | GenBank ID | GI Number | Organism |
| --- | --- | --- | --- |
| MDH1 | NP_012838 | 6322765 | *Saccharomyces cerevisiae* |
| MDH2 | NP_014515 | 116006499 | *Saccharomyces cerevisiae* |
| MDH3 | NP_010205 | 6320125 | *Saccharomyces cerevisiae* |
| KLLA0E07525p | XP_454288.1 | 50308571 | *Kluyveromyces lactic* NRRL Y-1140 |
| YALI0D16753g | XP_502909.1 | 50550873 | *Yarrowia lipolytica* |
| CTRG_01021 | XP_002546239.1 | 255722609 | *Candida tropicalis* MYA-3404 |
| Mdh | NP_417703.1 | 16131126 | *Escherichia coli* |

FIG. 2, Step D—Malic Enzyme (ES4)

ES4 can be applied to convert $CO_2$ and pyruvate to malate at the expense of one reducing equivalent. ES4s for this purpose can include, without limitation, ES4 (NAD-dependent) and ES4 (NADP-dependent). For example, one of the *E. coli* ES4s (Takeo, *J. Biochem.* 66:379-387 (1969)) or a similar enzyme with higher activity can be expressed to enable the conversion of pyruvate and $CO_2$ to malate. By fixing carbon to pyruvate as opposed to PEP, ES4 allows the high-energy phosphate bond from PEP to be conserved by pyruvate kinase whereby ATP is generated in the formation of pyruvate or by the phosphotransferase system for glucose transport. Although ES4 is typically assumed to operate in the direction of pyruvate formation from malate, overexpression of the NAD-dependent enzyme, encoded by maeA, has been demonstrated to increase succinate production in *E. coli* while restoring the lethal ΔpflΔldhA phenotype under anaerobic conditions by operating in the carbon-fixing direction (Stols and Donnelly, *Appl. Environ. Microbiol.* 63(7) 2695-2701 (1997)). A similar observation was made upon overexpressing the ES4 from *Ascaris suum* in *E. coli* (Stols et al., *Appl. Biochem. Biotechnol.* 63-65(1), 153-158 (1997)). The second *E. coli* ES4, encoded by maeB, is NADP-dependent and also decarboxylates oxaloacetate and other alpha-keto acids (Iwakura et al., *J. Biochem.* 85(5): 1355-65 (1979)).

| Protein | GenBank ID | GI Number | Organism |
| --- | --- | --- | --- |
| maeA | NP_415996 | 90111281 | *Escherichia coli* |
| maeB | NP_416958 | 16130388 | *Escherichia coli* |
| NAD-ME | P27443 | 126732 | *Ascaris suum* |
| MAE1 | NP_012896.1 | 6322823 | *Saccharomyces cerevisiae* |
| MAE1 | XP_716669.1 | 68478574 | *Candida albicans* |

FIG. 2, Step E—Fumarase (ES5)

Fumarate hydratase (EC 4.2.1.2) catalyzes the reversible hydration of fumarate to malate. The three ES5s of *E. coli*, encoded by fumA, fumB and fumC, are regulated under different conditions of oxygen availability. FumB is oxygen sensitive and is active under anaerobic conditions. FumA is active under microanaerobic conditions, and FumC is active under aerobic growth conditions (Tseng et al., *J. Bacteriol.* 183:461-467 (2001); Woods et al., *Biochim. Biophys. Acta* 954:14-26 (1988); Guest et al., *J. Gen. Microbiol.* 131:2971-2984 (1985)). *S. cerevisiae* contains one copy of a ES5-encoding gene, FUM1, whose product localizes to both the cytosol and mitochondrion (Sass et al., *J. Biol. Chem.* 278:45109-45116 (2003)). Additional ES5 enzymes are found in *Campylobacter jejuni* (Smith et al., *Int. J. Biochem. Cell. Biol.* 31:961-975 (1999)), *Thermus thermophilus* (Mizobata et al., *Arch. Biochem. Biophys.* 355:49-55 (1998)) and *Rattus norvegicus* (Kobayashi et al., *J. Biochem.* 89:1923-1931 (1981)). Similar enzymes with high sequence homology include fum1 from *Arabidopsis thaliana* and fumC from *Corynebacterium glutamicum*. The MmcBC ES5 from *Pelotomaculum thermopropionicum* is another class of ES5 with two subunits (Shimoyama et al., *FEMS Microbiol. Lett.* 270:207-213 (2007)).

| Protein | GenBank ID | GI Number | Organism |
|---------|------------|-----------|----------|
| fumA | NP_416129.1 | 16129570 | *Escherichia coli* |
| fumB | NP_418546.1 | 16131948 | *Escherichia coli* |
| fumC | NP_416128.1 | 16129569 | *Escherichia coli* |
| FUM1 | NP_015061 | 6324993 | *Saccharomyces cerevisiae* |
| fumC | Q8NRN8.1 | 39931596 | *Corynebacterium glutamicum* |
| fumC | O69294.1 | 9789756 | *Campylobacter jejuni* |
| fumC | P84127 | 75427690 | *Thermus thermophilus* |
| fumH | P14408.1 | 120605 | *Rattus norvegicus* |
| MmcB | YP_001211906 | 147677691 | *Pelotomaculum thermopropionicum* |
| MmcC | YP_001211907 | 147677692 | *Pelotomaculum thermopropionicum* |

FIG. 2, Step F—Fumarate Reductase (ES6)

ES6 catalyzes the reduction of fumarate to succinate. The ES6 of *E. coli*, composed of four subunits encoded by frdABCD, is membrane-bound and active under anaerobic conditions. The electron donor for this reaction is menaquinone and the two protons produced in this reaction do not contribute to the proton gradient (Iverson et al., *Science* 284:1961-1966 (1999)). The yeast genome encodes two soluble ES6 isozymes encoded by FRDS1 (Enomoto et al., *DNA Res.* 3:263-267 (1996)) and FRDS2 (Muratsubaki et al., *Arch. Biochem. Biophys.* 352:175-181 (1998)), which localize to the cytosol and promitochondrion, respectively, and are used during anaerobic growth on glucose (Arikawa et al., *FEMS Microbiol. Lett.* 165:111-116 (1998)).

| Protein | GenBank ID | GI Number | Organism |
|---------|------------|-----------|----------|
| FRDS1 | P32614 | 418423 | *Saccharomyces cerevisiae* |
| FRDS2 | NP_012585 | 6322511 | *Saccharomyces cerevisiae* |
| frdA | NP_418578.1 | 16131979 | *Escherichia coli* |
| frdB | NP_418577.1 | 16131978 | *Escherichia coli* |
| frdC | NP_418576.1 | 16131977 | *Escherichia coli* |
| frdD | NP_418475.1 | 16131877 | *Escherichia coli* |

Succinate dehydrogenase, encoded by sdhCDAB of *E. coli*, can also catalyze the reduction of fumarate to succinate. The reversibility of both enzymes is sufficient for SDH and FRD enzymes to complement each other and support growth if the organism is genetically manipulated to express only one or the other. When SDH is expressed under anoxic conditions in the absence of FRD, the SDH complex is able to support a low rate of cell growth by operating as a menaquinol-fumarate reductase (Maklashina et al, *J Bacteriol* 180:5989-96 (1998)). In another study, Maklashina and coworkers found that the amino acid at position 50 of SdhA is a key residue for determining directionality of the reaction, and that SDH is a more efficient ES6s when Glu is present at this position (Maklashina et al, *J Biol Chem* 281:11357-65 (2006)).

| Protein | GenBank ID | GI Number | Organism |
|---------|------------|-----------|----------|
| sdhC | NP_415249.1 | 16128696 | *Escherichia coli* |
| sdhD | NP_415250.1 | 16128697 | *Escherichia coli* |
| sdhA | NP_415251.1 | 16128698 | *Escherichia coli* |
| sdhB | NP_415252.1 | 16128699 | *Escherichia coli* |

4.3 Example III—Methods of Using Formaldehyde Produced from the Oxidation of Methanol in the Formation of Intermediates of Central Metabolic Pathways for the Formation of Biomass Provided herein are exemplary pathways, which utilize formaldehyde produced from the oxidation of methanol (see, e.g., FIG. 1, step J) in the formation of intermediates of certain central metabolic pathways that can be used for the formation of biomass. Exemplary MMPs for enhancing the availability of reducing equivalents, as well as the producing formaldehyde from methanol (step J), are provided in FIG. 1.

One exemplary pathway that can utilize formaldehyde produced from the oxidation of methanol (e.g., as provided in FIG. 1) is shown in FIG. 3, which involves condensation of formaldehyde and D-ribulose-5-phosphate to form H6P by EF1 (FIG. 3, step A). The enzyme can use $Mg^{2+}$ or $Mn^{2+}$ for maximal activity, although other metal ions are useful, and even non-metal-ion-dependent mechanisms are contemplated. H6P is converted into F6P by EF2 (FIG. 3, step B).

Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and glyceraldehyde-3-phosphate (G3P), which is an intermediate in glycolysis (FIG. 4, step A). The DHA obtained from DHA synthase is then further phosphorylated to form DHAP by an EF4 (FIG. 4, step B). DHAP can be assimilated into glycolysis and several other pathways.

FIG. 3, Steps A and B—H6P Synthase (EF1) (Step A) and 6-Phospho-3-Hexuloisomerase (EF2) (Step B)

Both of the EF1 and EF2 enzymes are found in several organisms, including methanotrops and methylotrophs where they have been purified (Kato et al., 2006, BioSci Biotechnol Biochem. 70(1):10-21. In addition, these enzymes have been reported in heterotrophs such as *Bacillus subtilis* also where they are reported to be involved in formaldehyde detoxification (Mitsui et al., 2003, AEM 69(10):6128-32, Yasueda et al., 1999. J Bac 181(23):7154-60. Genes for these two enzymes from the methylotrophic bacterium *Mycobacterium gastri* MB19 have been fused and *E. coli* strains harboring the hps-phi construct showed more efficient utilization of formaldehyde (Orita et al., 2007. Appl Microbiol Biotechnol. 76:439-445). In some organisms, these two enzymes naturally exist as a fused version that is bifunctional.

Exemplary candidate genes for hexulose-6-phosphate synthase are:

| Protein | GenBank ID | GI number | Organism |
|---------|------------|-----------|----------|
| Hps | AAR39392.1 | 40074227 | *Bacillus methanolicus* MGA3 |
| Hps | EIJ81375.1 | 387589055 | *Bacillus methanolicus* PB1 |
| RmpA | BAA83096.1 | 5706381 | *Methylomonas aminofaciens* |
| RmpA | BAA90546.1 | 6899861 | *Mycobacterium gastri* |
| YckG | BAA08980.1 | 1805418 | *Bacillus subtilis* |
| Hps | YP_544362.1 | 91774606 | *Methylobacillus flagellatus* |
| Hps | YP_545763.1 | 91776007 | *Methylobacillus flagellatus* |
| Hps | AAG29505.1 | 11093955 | *Aminomonas aminovorus* |
| SgbH | YP_004038706.1 | 313200048 | *Methylovorus* sp. MP688 |
| Hps | YP_003050044.1 | 253997981 | *Methylovorus glucosetrophus* SIP3-4 |

| Protein | GenBank ID | GI number | Organism |
|---|---|---|---|
| Hps | YP_003990382.1 | 312112066 | Geobacillus sp. Y4.1MC1 |
| Hps | gb|AAR91478.1 | 40795504 | Geobacillus sp. M10EXG |
| Hps | YP_007402409.1 | 448238351 | Geobacillus sp. GHH01 |

Exemplary gene candidates for EF2 are:

| Protein | GenBank ID | GI number | Organism |
|---|---|---|---|
| Phi | AAR39393.1 | 40074228 | Bacillus methanolicus MGA3 |
| Phi | EIJ81376.1 | 387589056 | Bacillus methanolicus PB1 |
| Phi | BAA83098.1 | 5706383 | Methylomonas aminofaciens |
| RmpB | BAA90545.1 | 6899860 | Mycobacterium gastri |
| Phi | YP_545762.1 | 91776006 | Methylobacillus flagellatus KT |
| Phi | YP_003051269.1 | 253999206 | Methylovorus glucosetrophus SIP 3-4 |
| Phi | YP_003990383.1 | 312112067 | Geobacillus sp. Y4.1MC1 |
| Phi | YP_007402408.1 | 448238350 | Geobacillus sp. GHH01 |

Candidates for enzymes where both of these functions have been fused into a single open reading frame include the following:

| Protein | GenBank ID | GI number | Organism |
|---|---|---|---|
| PH1938 | NP_143767.1 | 14591680 | Pyrococcus horikoshii OT3 |
| PF0220 | NP_577949.1 | 18976592 | Pyrococcus furiosus |
| TK0475 | YP_182888.1 | 57640410 | Thermococcus kodakaraensis |
| PAB1222 | NP_127388.1 | 14521911 | Pyrococcus abyssi |
| MCA2738 | YP_115138.1 | 53803128 | Methylococcus capsulatas |
| Metal_3152 | EIC30826.1 | 380884949 | Methylomicrobium album BG8 |

An experimental system was designed to test the ability of a methanol dehydrogenase (MeDH) in conjunction with the enzymes H6P synthase (HPS) and 6-phospho-3-hexuloisomerase (PHI) of the Ribulose Monophosphate (RuMP) pathway to assimilate methanol carbon into the glycolytic pathway and the TCA cycle. Escherichia coli strain ECh-7150 (ΔlacIA, ΔpflB, ΔptsI, ΔPpckA(pckA), ΔPglk(glk), glk::glfB, ΔhycE, ΔfrmR, ΔfrmA, ΔfrmB) was constructed to remove the glutathione-dependent formaldehyde detoxification capability encoded by the FrmA and FrmB enzyme. This strain was then transformed with plasmid pZA23S variants that either contained or lacked gene 2616A encoding a fusion of the HPS and PHI enzymes. These two transformed strains were then each transformed with pZS*13S variants that contained gene 2315L (encoding an active MeDH), or gene 2315 RIP2 (encoding a catalytically inactive MeDH), or no gene insertion. Genes 2315 and 2616 are internal nomenclatures for NAD-dependent methanol dehydrogenase from Bacillus methanolicus MGA3 and 2616 is a fused phs-hpi constructs as described in Orita et al. (2007) Appl Microbiol Biotechnol 76:439-45.

The six resulting strains were aerobically cultured in quadruplicate, in 5 ml minimal medium containing 1% arabinose and 0.6 M 13C-methanol as well as 100 ug/ml carbenicillin and 25 μg/ml kanamycin to maintain selection of the plasmids, and 1 mM IPTG to induce expression of the methanol dehydrogenase and HPS-PHI fusion enzymes. After 18 hours incubation at 37° C., the cell density was measured spectrophotometrically at 600 nM wavelength and a clarified sample of each culture medium was submitted for analysis to detect evidence of incorporation of the labeled methanol carbon into TCA-cycle derived metabolites. The label can be further enriched by deleting the gene araD that competes with ribulose-5-phosphate.

$^{13}C$ carbon derived from labeled methanol provided in the experiment was found to be significantly enriched in the TCA-cycle derived amino acid glutamate, but only in the strain expressing both catalytically active MeDH 2315L and the HPS-PHI fusion 2616A together (data not shown). Moreover, this strain grew significantly better than the strain expressing catalytically active MeDH but lacking expression of the HPS-PHI fusion (data not shown), suggesting that the HPS-PHI enzyme is capable of reducing growth inhibitory levels of formaldehyde that cannot be detoxified by other means in this strain background. These results show that co-expression of an active MeDH and the enzymes of the RuMP pathway can effectively assimilate methanol derived carbon and channel it into TCA-cycle derived products.

FIG. 4, Step A—DHA Synthase (EF3)

Another exemplary pathway that involves the detoxification and assimilation of formaldehyde produced from the oxidation of methanol (e.g., as provided in FIG. 1) is shown in FIG. 4 and proceeds through DHA. EF3 is a special transketolase that first transfers a glycoaldehyde group from xylulose-5-phosphate to formaldehyde, resulting in the formation of DHA and glyceraldehyde-3-phosphate (G3P), which is an intermediate in glycolysis (FIG. 4, step A). The DHA obtained from DHA synthase is then further phosphorylated to form DHAP by an EF4 (FIG. 4, step B). DHAP can be assimilated into glycolysis and several other pathways.

The EF3 enzyme in Candida boidinii uses thiamine pyrophosphate and $Mg^{2+}$ as cofactors and is localized in the peroxisome. The enzyme from the methanol-growing carboxydobacterium, Mycobacter sp. strain JC1 DSM 3803, was also found to have DHA synthase and kinase activities (Ro et al., 1997, JBac 179(19):6041-7). DHA synthase from this organism also has similar cofactor requirements as the enzyme from C. boidinii. The $K_m$s for formaldehyde and xylulose 5-phosphate were reported to be 1.86 mM and 33.3 microM, respectively. Several other mycobacteria, excluding only Mycobacterium tuberculosis, can use methanol as the sole source of carbon and energy and are reported to use EF3 (Part et al., 2003, JBac 185(1):142-7.

| Protein | GenBank ID | GI number | Organism |
|---|---|---|---|
| DAS1 | AAC83349.1 | 3978466 | Candida boidinii |
| HPODL_2613 | EFW95760.1 | 320581540 | Ogataea parapolymorpha DL-1 (Hansenula polymorpha DL-1) |
| | AAG12171.2 | 18497328 | Mycobacter sp. strain JC1 DSM 3803 |

FIG. 4, Step B—DHA Kinase (EF4)

DHA obtained from DHA synthase is further phosphorylated to form DHAP by an EF4. DHAP can be assimilated into glycolysis and several other pathways. EF4 has been purified from Ogataea angusta to homogeneity (Bystrkh, 1983, Biokhimiia, 48(10): 1611-6). The enzyme, which phosphorylates DHA and, to a lesser degree, glyceraldehyde, is a homodimeric protein of 139 kDa. ATP is the preferred phosphate group donor for the enzyme. When ITP, GTP, CTP and UTP are used, the activity drops to about 30%. In several organisms such as Klebsiella pneumoniae and Citrobacter fruendii (Daniel et al., 1995, JBac 177(15):

4392-40), DHA is formed as a result of oxidation of glycerol and is converted into DHAP by the kinase EF4 of *K. pneumoniae* has been characterized (Jonathan et al, 1984, JBac 160(1):55-60). It is very specific for DHA, with a $K_m$ of 4 µM, and has two apparent $K_m$ values for ATP, one at 25 to 35 µM, and the other at 200 to 300 µM. DHA can also be phosphorylated by glycerol kinases but the EF4 from *K. puemoniae* is different from glycerol kinase in several respects. While both enzymes can phosphorylate DHA, EF4 does not phosphorylate glycerol, neither is it inhibited by fructose-1,6-diphosphate. In *Saccharomyces cerevisiae*, EF4s (I and II) are involved in rescuing the cells from toxic effects of DHA (Molin et al., 2003, J Biol Chem. 17; 278(3): 1415-23).

In *Escherichia coli*, EF4 is composed of the three subunits DhaK, DhaL, and DhaM and it functions similarly to a phosphotransferase system (PTS) in that it utilizes phosphoenolpyruvate as a phosphoryl donor (Gutknecht et al., 2001, EMBO J. 20(10):2480-6). It differs in not being involved in transport. The phosphorylation reaction requires the presence of the EI and HPr proteins of the PTS system. The DhaM subunit is phosphorylated at multiple sites. DhaK contains the substrate binding site (Garcia-Alles et al., 2004, 43(41):13037-45; Siebold et al., 2003, PNAS. 100(14): 8188-92). The $K_M$ for DHA for the *E. coli* enzyme has been reported to be 6 µM. The K subunit is similar to the N-terminal half of ATP-dependent EF4 of *Citrobacter freundii* and eukaryotes.

Exemplary EF4 gene candidates for this step are:

| Protein | GenBank ID | GI number | Organism |
| --- | --- | --- | --- |
| DAK1 | P54838.1 | 1706391 | *Saccharomyces cerevisiae* S288c |
| DAK2 | P43550.1 | 1169289 | *Saccharomyces cerevisiae* S288c |
| D186_20916 | ZP_16280678.1 | 421847542 | *Citrobacter freundii* |
| DAK2 | ZP_18488498.1 | 425085405 | *Klebsiella pneumoniae* |
| DAK | AAC27705.1 | 3171001 | *Ogataea angusta* |
| DhaK | NP_415718.6 | 162135900 | *Escherichia coli* |
| DhaL | NP_415717.1 | 16129162 | *Escherichia coli* |
| DhaM | NP_415716.4 | 226524708 | *Escherichia coli* |

4.4 Example IV—Methods for Handling Anaerobic Cultures

This example describes methods used in handling anaerobic cultures.

A. Anaerobic Chamber and Conditions.

Exemplary anaerobic chambers are available commercially (see, for example, Vacuum Atmospheres Company, Hawthorne Calif.; MBraun, Newburyport Mass.). Conditions included an $O_2$ concentration of 1 ppm or less and 1 atm pure $N_2$. In one example, 3 oxygen scrubbers/catalyst regenerators were used, and the chamber included an $O_2$ electrode (such as Teledyne; City of Industry Calif.). Nearly all items and reagents were cycled four times in the airlock of the chamber prior to opening the inner chamber door. Reagents with a volume >5 mL were sparged with pure $N_2$ prior to introduction into the chamber. Gloves are changed twice/yr and the catalyst containers were regenerated periodically when the chamber displays increasingly sluggish response to changes in oxygen levels. The chamber's pressure was controlled through one-way valves activated by solenoids. This feature allowed setting the chamber pressure at a level higher than the surroundings to allow transfer of very small tubes through the purge valve.

The anaerobic chambers achieved levels of $O_2$ that were consistently very low and were needed for highly oxygen sensitive anaerobic conditions. However, growth and handling of cells does not usually require such precautions. In an alternative anaerobic chamber configuration, platinum or palladium can be used as a catalyst that requires some hydrogen gas in the mix. Instead of using solenoid valves, pressure release can be controlled by a bubbler. Instead of using instrument-based $O_2$ monitoring, test strips can be used instead.

B. Anaerobic Microbiology.

In particular, serum or media bottles are fitted with thick rubber stoppers and aluminum crimps are employed to seal the bottle. Medium, such as Terrific Broth, is made in a conventional manner and dispensed to an appropriately sized serum bottle. The bottles are sparged with nitrogen for ~30 min of moderate bubbling. This removes most of the oxygen from the medium and, after this step, each bottle is capped with a rubber stopper (such as Bellco 20 mm septum stoppers; Bellco, Vineland, N.J.) and crimp-sealed (Bellco 20 mm). Then the bottles of medium are autoclaved using a slow (liquid) exhaust cycle. At least sometimes a needle can be poked through the stopper to provide exhaust during autoclaving; the needle needs to be removed immediately upon removal from the autoclave. The sterile medium has the remaining medium components, for example buffer or antibiotics, added via syringe and needle. Prior to addition of reducing agents, the bottles are equilibrated for 30-60 minutes with nitrogen (or CO depending upon use). A reducing agent such as a 100×150 mM sodium sulfide, 200 mM cysteine-HCl is added. This is made by weighing the sodium sulfide into a dry beaker and the cysteine into a serum bottle, bringing both into the anaerobic chamber, dissolving the sodium sulfide into anaerobic water, then adding this to the cysteine in the serum bottle. The bottle is stoppered immediately as the sodium sulfide solution generates hydrogen sulfide gas upon contact with the cysteine. When injecting into the culture, a syringe filter is used to sterilize the solution. Other components are added through syringe needles, such as B12 (10 µM cyanocobalamin), nickel chloride ($NiCl_2$, 20 microM final concentration from a 40 mM stock made in anaerobic water in the chamber and sterilized by autoclaving or by using a syringe filter upon injection into the culture), and ferrous ammonium sulfate (final concentration needed is 100 µM—made as 100-1000× stock solution in anaerobic water in the chamber and sterilized by autoclaving or by using a syringe filter upon injection into the culture). To facilitate faster growth under anaerobic conditions, the 1 liter bottles were inoculated with 50 mL of a preculture grown anaerobically. Induction of the pA1-lacO1 promoter in the vectors was performed by addition of isopropyl β-D-1-thiogalactopyranoside (IPTG) to a final concentration of 0.2 mM and was carried out for about 3 hrs.

Large cultures can be grown in larger bottles using continuous gas addition while bubbling. A rubber stopper with a metal bubbler is placed in the bottle after medium addition and sparged with nitrogen for 30 minutes or more prior to setting up the rest of the bottle. Each bottle is put together such that a sterile filter will sterilize the gas bubbled in and the hoses on the bottles are compressible with small C clamps. Medium and cells are stirred with magnetic stir bars. Once all medium components and cells are added, the bottles are incubated in an incubator in room air but with continuous nitrogen sparging into the bottles.

4.5 Example V—Strategies for Increased Production of Succinate

This example describes exemplary strategies to increase production of succinate.

Several strain engineering strategies can be implemented to increase the production of succinate in an organism and to couple it to growth.

Overexpression of carbon-fixing enzymes such as ES1A or ES1B (PEPCK), ES4, and ES2 can be used to redirect carbon flux into succinate formation. Catabolite repression can be removed or reduced by truncating the gene responsible for forming cAMP, adenylate cyclase, cyaA (Crasnier et al, *Mol. Gen. Genet* 243:409-416 (1994)), and by mutating the catabolite repressor protein, crp (Eppler and Boos, *Mol. Microbiol.* 33:1221-1231 (1999); Karimova et al, *Res. Microbiol.* 155:76-79 (2004); Zhu and Lin, *J. Bacteriol.* 170:2352-2358 (1988)). Decreasing or eliminating byproducts such as ethanol, glycerol, acetate, lactate and formate can be used to improve yields of succinate. In *E. coli* and other prokaryotes, decreasing or eliminating such byproducts can be effected by deletions in alcohol dehydrogenase (adhE), lactate dehydrogenase (ldhA), acetate kinase (ackA), pyruvate oxidase (poxB), and pyruvate formate lyase (pflB). The homologue of pflB, pyruvate formate-lyase 2-ketobutyrate formate-lyase (tdcE), can also be deleted in *E. coli*. Further, deletion of transporters such as the phosphotransferase system (PTS) of glucose uptake increases the PEP pool in the organism and this has been demonstrated to improve succinate production in the literature. This can be accomplished by deletion, mutation or truncation of ptsG, ptsH, ptsI or crr or their combinations (Zhang et al, *Proc. Natl. Acad. Sci. USA* 106(48):20180-20185 (2009), Flores et al, *Mol. Microbiol. Biotechnol.* 13:105-116 (2007); Sanchez et al., *Biotechnol. Prog.* 21(2):358-365 (2005)). This deletion can optionally be accompanied by overexpression of glucokinase encoded by glk and galactose permease encoded by galP. Similarly, deletion in pyruvate kinase (pykA, pykF) prevents the conversion of PEP to pyruvate and improves succinate production. Further, high concentrations of $CO_2$ in the fermenters allow the function of PEPCK and ES2 in the anaplerotic direction, as needed for succinate production. While exemplified above with specific genes, it is understood by those skilled in the art that genes performing the same or similar functions can be genetically modified in the appropriate host organism to achieve a similar improvement in succinate production.

Similar strategies to those proposed above can be used for production of succinate in yeasts such as *Saccharomyces cerevisiae* and *Candida*. Carbon flux towards succinate can be improved by deleting or tuning down competing pathways. Typical fermentation products of yeast include ethanol, glycerol and $CO_2$. The elimination of these byproducts can be accomplished by approaches delineated herein. Other potential byproducts include lactate, acetate, formate and amino acids.

Ethanol can be formed from pyruvate in two enzymatic steps catalyzed by pyruvate decarboxylase and ethanol dehydrogenase. *Saccharomyces cerevisiae* has three pyruvate decarboxylases (PDC1, PDC5 and PDC6). PDC1 is the major isozyme and is strongly expressed in actively fermenting cells. PDC5 also functions during glycolytic fermentation, but is expressed only in the absence of PDC1 or under thiamine limiting conditions. PDC6 functions during growth on nonfermentable carbon sources. Deleting PDC1 and PDC5 can reduce ethanol production significantly; however these deletions can lead to mutants with increased PDC6 expression. Deletion of all three eliminates ethanol formation completely but also can cause a growth defect because of inability of the cells to form sufficient acetyl-CoA for biomass formation. This, however, can be overcome by evolving cells in the presence of reducing amounts of C2 carbon source (ethanol or acetate) (van Maris et al, AEM69: 2094-9 (2003)). It has also been reported that deletion of the positive regulator PDC2 of pyruvate decarboxylases PDC1 and PDC5, reduced ethanol formation to ~10% of that made by wild-type (Hohmann et al, *Mol Gen Genet* 241:657-66 (1993)). Pyruvate decarboxylase (PDC) is a key enzyme in alcoholic fermentation, catalyzing the decarboxylation of pyruvate to acetaldehyde. The PDC1 enzyme from *Saccharomyces cerevisiae* has been extensively studied (Killenberg-Jabs et al., *Eur. J. Biochem.* 268:1698-1704 (2001); Li et al., *Biochemistry.* 38:10004-10012 (1999); ter Schure et al., *Appl. Environ. Microbiol.* 64:1303-1307 (1998)). Other well-characterized PDC enzymes are found in *Zymomonas mobilus* (Siegert et al., *Protein Eng Des Sel* 18:345-357 (2005)), *Acetobacter pasteurians* (Chandra et al., 176:443-451 (2001)) and *Kluyveromyces lactis* (Krieger et al., 269: 3256-3263 (2002)). The PDC1 and PDC5 enzymes of *Saccharomyces cerevisiae* are subject to positive transcriptional regulation by PDC2 (Hohmann et al, *Mol Gen Genet* 241: 657-66 (1993)). Pyruvate decarboxylase activity is also possessed by a protein encoded by CTRG_03826 (GI: 255729208) in *Candida tropicalis*, PDC1 (GI number: 1226007) in *Kluyveromyces lactis*, YAL10D10131g (GI: 50550349) in *Yarrowia lipolytica*, PAS_chr3_0188 (GI: 254570575) in *Pichia pastoris*, pyruvate decarboxylase (GI: GI: 159883897) in *Schizosaccharomyces pombe*, ANI_1_1024084 (GI: 145241548), ANI_1_796114 (GI: 317034487), ANI_1_936024 (GI: 317026934) and ANI_1_2276014 (GI: 317025935) in *Aspergillus niger*.

| Protein | GenBank ID | GI Number | Organism |
|---|---|---|---|
| Pdc | P06672.1 | 118391 | *Zymomonas mobilis* |
| pdc1 | P06169 | 30923172 | *Saccharomyces cerevisiae* |
| Pdc2 | NP_010366.1 | 6320286 | *Saccharomyces cerevisiae* |
| Pdc5 | NP_013235.1 | 6323163 | *Saccharomyces cerevisiae* |
| CTRG_03826 | XP_002549529 | 255729208 | *Candida tropicalis,* |
| CU329670.1:585597.587312 | CAA90807 | 159883897 | *Schizosaccharomyces pombe* |
| YALI0D10131g | XP_502647 | 50550349 | *Yarrowia lipolytica* |
| PAS_chr3_0188 | XP_002492397 | 254570575 | *Pichia pastoris* |
| Pdc | Q8L388 | 20385191 | *Acetobacter pasteurians* |
| pdc1 | Q12629 | 52788279 | *Kluyveromyces lactis* |
| ANI_1_1024084 | XP_001393420 | 145241548 | *Aspergillus niger* |
| ANI_1_796114 | XP_001399817 | 317026934 | *Aspergillus niger* |

| Protein | GenBank ID | GI Number | Organism |
|---|---|---|---|
| ANI_1_936024 | XP_001396467 | 317034487 | Aspergillus niger |
| ANI_1_2276014 | XP_001388598 | 317025935 | Aspergillus niger |

Ethanol dehydrogenases that convert acetaldehyde into ethanol and/or other short chain alcohol dehydrogenases can be deleted or attenuated to provide carbon and reducing equivalents for the SucP. To date, seven alcohol dehydrogenases, ADHI-ADHVII, have been reported in S. cerevisiae (de Smidt et al, FEMS Yeast Res 8:967-78 (2008)). ADH1 (GI: 1419926) is the key enzyme responsible for reducing acetaldehyde to ethanol in the cytosol under anaerobic conditions. It has been reported that a yeast strain deficient in ADH1 cannot grow anaerobically because an active respiratory chain is the only alternative path to regenerate NADH and lead to a net gain of ATP (Drewke et al, J Bacteriol 172:3909-17 (1990)). This enzyme is an ideal candidate for downregulation to limit ethanol production. ADH2 is severely repressed in the presence of glucose. In K. lactis, two NAD-dependent cytosolic alcohol dehydrogenases have been identified and characterized. These genes also show activity for other aliphatic alcohols. The genes ADH1 (GI: 113358) and ADHII (GI: 51704293) are preferentially expressed in glucose-grown cells (Bozzi et al, Biochim Biophys Acta 1339:133-142 (1997)). Cytosolic alcohol dehydrogenases are encoded by ADH1 (GI: 608690) in C. albicans, ADH1 (GI: 3810864) in S. pombe, ADH1 (GI: 5802617) in Y. lipolytica, ADH1 (GI: 2114038) and ADHII (GI: 2143328) in Pichia stipitis or Scheffersomyces stipitis (Passoth et al, Yeast 14:1311-23 (1998)). Candidate alcohol dehydrogenases are shown the table below.

| Protein | GenBank ID | GI number | Organism |
|---|---|---|---|
| SADH | BAA24528.1 | 2815409 | Candida parapsilosis |
| ADH1 | NP_014555.1 | 6324486 | Saccharomyces cerevisiae s288c |
| ADH2 | NP_014032.1 | 6323961 | Saccharomyces cerevisiae s288c |
| ADH3 | NP_013800.1 | 6323729 | Saccharomyces cerevisiae s288c |
| ADH4 | NP_011258.2 | 269970305 | Saccharomyces cerevisiae s288c |
| ADH5 (SFA1) | NP_010113.1 | 6320033 | Saccharomyces cerevisiae s288c |
| ADH6 | NP_014051.1 | 6323980 | Saccharomyces cerevisiae s288c |
| ADH7 | NP_010030.1 | 6319949 | Saccharomyces cerevisiae s288c |
| adhP | CAA44614.1 | 2810 | Kluyveromyces lactis |
| ADH1 | P20369.1 | 113358 | Kluyveromyces lactis |
| ADH2 | CAA45739.1 | 2833 | Kluyveromyces lactis |
| ADH3 | P49384.2 | 51704294 | Kluyveromyces lactis |
| ADH1 | CAA57342.1 | 608690 | Candida albicans |
| ADH2 | CAA21988.1 | 3859714 | Candida albicans |
| SAD | XP_712899.1 | 68486457 | Candida albicans |
| ADH1 | CAA21782.1 | 3810864 | Schizosaccharomyces pombe |
| ADH1 | AAD51737.1 | 5802617 | Yarrowia lipolytica |
| ADH2 | AAD51738.1 | 5802619 | Yarrowia lipolytica |
| ADH3 | AAD51739.1 | 5802621 | Yarrowia lipolytica |
| AlcB | AAX53105.1 | 61696864 | Aspergillus niger |
| ANI_1_282024 | XP_001399347.1 | 145231748 | Aspergillus niger |
| ANI_1_126164 | XP_001398574.2 | 317037131 | Aspergillus niger |
| ANI_1_1756104 | XP_001395505.2 | 317033815 | Aspergillus niger |
| ADH2 | CAA73827.1 | 2143328 | Scheffersomyces stipitis |

Attenuation or deletion of one or more glycerol-3-phosphatase or glycerol-3-phosphate (G3P) dehydrogenase enzymes can eliminate or reduce the formation of glycerol, and thereby conserve carbon and reducing equivalents for production of succinate.

G3P phosphatase catalyzes the hydrolysis of G3P to glycerol. Enzymes with this activity include the glycerol-1-phosphatase (EC 3.1.3.21) enzymes of Saccharomyces cerevisiae (GPP1 and GPP2), Candida albicans and Dunaleilla parva (Popp et al, Biotechnol Bioeng 100:497-505 (2008); Fan et al, FEMS Microbiol Lett 245:107-16 (2005)). The D. parva gene has not been identified to date. These and additional G3P phosphatase enzymes are shown in the table below.

| Protein | GenBank ID | GI Number | Organism |
|---|---|---|---|
| GPP1 | DAA08494.1 | 285812595 | Saccharomyces cerevisiae |
| GPP2 | NP_010984.1 | 6320905 | Saccharomyces cerevisiae |
| GPP1 | XP_717809.1 | 68476319 | Candida albicans |
| KLLA0C08217g | XP_452565.1 | 50305213 | Kluyveromyces lactis |
| KLLA0C11143g | XP_452697.1 | 50305475 | Kluyveromyces lactis |
| ANI_1_380074 | XP_001392369.1 | 145239445 | Aspergillus niger |
| ANI_1_444054 | XP_001390913.2 | 317029125 | Aspergillus niger |

S. cerevisiae has three G3P dehydrogenase enzymes encoded by GPD1 and GDP2 in the cytosol and GUT2 in the mitochondrion. GPD2 is known to encode the enzyme responsible for the majority of the glycerol formation and is responsible for maintaining the redox balance under anaerobic conditions. GPD1 is primarily responsible for adaptation of S. cerevisiae to osmotic stress (Bakker et al., FEMS Microbiol Rev 24:15-37 (2001)). Attenuation of GPD1, GPD2 and/or GUT2 will reduce glycerol formation. GPD1 and GUT2 encode G3P dehydrogenases in Yarrowia lipolytica (Beopoulos et al, AEM 74:7779-89 (2008)). GPD1 and GPD2 encode for G3P dehydrogenases in S. pombe. Similarly, G3P dehydrogenase is encoded by CTRG_02011 in *Candida tropicalis* and a gene represented by GI: 20522022 in *Candida albicans*.

| Protein | GenBank ID | GI number | Organism |
|---|---|---|---|
| GPD1 | CAA98582.1 | 1430995 | *Saccharomyces cerevisiae* |
| GPD2 | NP_014582.1 | 6324513 | *Saccharomyces cerevisiae* |
| GUT2 | NP_012111.1 | 6322036 | *Saccharomyces cerevisiae* |
| GPD1 | CAA22119.1 | 6066826 | *Yarrowia lipolytica* |
| GUT2 | CAG83113.1 | 49646728 | *Yarrowia lipolytica* |
| GPD1 | CAA22119.1 | 3873542 | *Schizosaccharomyces pombe* |
| GPD2 | CAA91239.1 | 1039342 | *Schizosaccharomyces pombe* |
| ANI_1_786014 | XP_001389035.2 | 317025419 | *Aspergillus niger* |
| ANI_1_1768134 | XP_001397265.1 | 145251503 | *Aspergillus niger* |
| KLLA0C04004g | XP_452375.1 | 50304839 | *Kluyveromyces lactis* |
| CTRG_02011 | XP_002547704.1 | 255725550 | *Candida tropicalis* |
| GPD1 | XP_714362.1 | 68483412 | *Candida albicans* |
| GPD2 | XP_713824.1 | 68484586 | *Candida albicans* |

Enzymes that form acid byproducts such as acetate, formate and lactate can also be tuned down or deleted. Such enzymes include acetate kinase, phosphotransacetylase and pyruvate oxidase.

An exemplary acetate kinase is the *E. coli* acetate kinase, encoded by ackA (Skarstedt and Silverstein *J. Biol. Chem.* 251:6775-6783 (1976)). Homologs exist in several other organisms including *Salmonella enterica* and *Chlamydomonas reinhardtii*. Information related to these proteins and genes is shown below:

| Protein | GenBank ID | GI number | Organism |
|---|---|---|---|
| AckA | NP_416799.1 | 16130231 | *Escherichia coli* |
| AckA | NP_461279.1 | 16765664 | *Salmonella enterica* subsp. *enterica* serovar *Typhimurium* str. LT2 |
| ACK1 | XP_001694505.1 | 159472745 | *Chlamydomonas reinhardtii* |
| ACK2 | XP_001691682.1 | 159466992 | *Chlamydomonas reinhardtii* |

An exemplary phosphate-transferring acyltransferase is phosphotransacetylase, encoded by pta. The pta gene from *E. coli* encodes an enzyme that can convert acetyl-CoA into acetyl-phosphate, and vice versa (Suzuki, T. *Biochim. Biophys. Acta* 191:559-569 (1969)). This enzyme can also utilize propionyl-CoA instead of acetyl-CoA forming propionate in the process (Hesslinger et al. *Mol. Microbiol* 27:477-492 (1998)). Homologs exist in several other organisms including *Salmonella enterica* and *Chlamydomonas reinhardtii*.

| Protein | GenBank ID | GI number | Organism |
|---|---|---|---|
| Pta | NP_416800.1 | 16130232 | *Escherichia coli* |
| Pta | NP_461280.1 | 16765665 | *Salmonella enterica* subsp. *enterica* serovar *Typhimurium* str. LT2 |
| PAT2 | XP_001694504.1 | 159472743 | *Chlamydomonas reinhardtii* |
| PAT1 | XP_001691787.1 | 159467202 | *Chlamydomonas reinhardtii* |

Pyruvate oxidase (acetate-forming) or pyruvate:quinone oxidoreductase (PQO) catalyzes the oxidative decarboxylation of pyruvate into acetate, using ubiquione (EC 1.2.5.1) or quinone (EC 1.2.2.1) as an electron acceptor. The *E. coli* enzyme, PoxB, is localized on the inner membrane (Abdel-Hamid et al., *Microbiol* 147:1483-98 (2001)). The enzyme has thiamin pyrophosphate and flavin adenine dinucleotide (FAD) cofactors (Koland and Gennis, Biochemistry 21:4438-4442 (1982)); O'Brien et al., Biochemistry 16:3105-3109 (1977); O'Brien and Gennis, J. Biol. Chem. 255:3302-3307 (1980)). PoxB has similarity to pyruvate decarboxylase of *S. cerevisiae* and *Zymomonas mobilis*. The pqo transcript of *Corynebacterium glutamicum* encodes a quinone-dependent and acetate-forming pyruvate oxidoreductase (Schreiner et al., *J Bacteriol* 188:1341-50 (2006)). Similar enzymes can be inferred by sequence homology.

| Protein | GenBank ID | GI Number | Organism |
|---|---|---|---|
| poxB | NP_415392.1 | 16128839 | *Escherichia coli* |
| Pqo | YP_226851.1 | 62391449 | *Corynebacterium glutamicum* |
| poxB | YP_309835.1 | 74311416 | *Shigella sonnei* |
| poxB | ZP_03065403.1 | 194433121 | *Shigella dysenteriae* |

Deletion or attenuation of pyruvate formate lyase could limit formation of formate. Pyruvate formate-lyase (PFL, EC 2.3.1.54), encoded by pflB in *E. coli*, can convert pyruvate into acetyl-CoA and formate. The activity of PFL can be enhanced by an activating enzyme encoded by pflA (Knappe et al., *Proc. Natl. Acad. Sci U.S.A.* 81:1332-1335 (1984); Wong et al., *Biochemistry* 32:14102-14110 (1993)). Keto-acid formate-lyase (EC 2.3.1.-), also known as 2-ketobutyrate formate-lyase (KFL) and pyruvate formate-lyase 4, is the gene product of tdcE in *E. coli*. This enzyme catalyzes the conversion of 2-ketobutyrate to propionyl-CoA and formate during anaerobic threonine degradation, and can also substitute for pyruvate formate-lyase in anaerobic catabolism (Simanshu et al., *J Biosci.* 32:1195-1206 (2007)). The enzyme is oxygen-sensitive and, like PflB, can require post-translational modification by PFL-AE to activate a glycyl radical in the active site (Hesslinger et al., *Mol. Microbiol* 27:477-492 (1998)). A pyruvate formate-lyase from *Archaeglubus fulgidus* encoded by pflD has been cloned, expressed in *E. coli* and characterized (Lehtio et al., *Protein Eng Des Sel* 17:545-552 (2004)). The crystal structures of the *A. fulgidus* and *E. coli* enzymes have been resolved (Lehtio et al., *J Mol. Biol.* 357:221-235 (2006); Leppanen et al., *Structure.* 7:733-744 (1999)). Additional PFL and PFL-AE candidates are found in *Lactococcus lactis* (Melchiorsen et al., *Appl Microbiol Biotechnol* 58:338-344 (2002)), and *Streptococcus mutans* (Takahashi-Abbe et al., *Oral. Microbiol Immunol.* 18:293-297 (2003)), *Chlamydomonas reinhardtii* (Hemschemeier et al., *Eukaryot. Cell* 7:518-526 (2008b); Atteia et al., *J. Biol. Chem.* 281:9909-9918 (2006)) and *Clostridium pasteurianum* (Weidner et al., *J Bacteriol.* 178:2440-2444 (1996)).

| Protein | GenBank ID | GI Number | Organism |
|---|---|---|---|
| pflB | NP_415423 | 16128870 | Escherichia coli |
| pflA | NP_415422.1 | 16128869 | Escherichia coli |
| tdcE | AAT48170.1 | 48994926 | Escherichia coli |
| pflD | NP_070278.1 | 11499044 | Archaeglubus fulgidus |
| Pfl | CAA03993 | 2407931 | Lactococcus lactis |
| Pfl | BAA09085 | 1129082 | Streptococcus mutans |
| PFL1 | XP_001689719.1 | 159462978 | Chlamydomonas reinhardtii |
| PflA1 | XP_001700657.1 | 159485246 | Chlamydomonas reinhardtii |
| Pfl | Q46266.1 | 2500058 | Clostridium pasteurianum |
| Act | CAA63749.1 | 1072362 | Clostridium pasteurianum |

Alcohol dehydrogenases that convert pyruvate to lactate are also candidates for deletion or attenuation. Lactate dehydrogenase enzymes include IdhA of *E. coli* and ldh from *Ralstonia eutropha* (Steinbuchel and Schlegel, *Eur. J. Biochem.* 130:329-334 (1983)). Other alcohol dehydrogenases listed above may also exhibit LDH activity.

| Protein | GenBank ID | GI number | Organism |
|---|---|---|---|
| ldhA | NP_415898.1 | 16129341 | Escherichia coli |
| Ldh | YP_725182.1 | 113866693 | Ralstonia eutropha |

Tuning down activity of the mitochondrial pyruvate dehydrogenase complex will limit flux into the mitochondrial TCA cycle. Under anaerobic conditions and in conditions where glucose concentrations are high in the medium, the capacity of this mitochondrial enzyme is very limited and there is no significant flux through it. However, in some embodiments, this enzyme can be disrupted or attenuated to increase succinate production. Exemplary pyruvate dehydrogenase genes include PDB1, PDA1, LAT1 and LPD1.

The pyruvate dehydrogenase (PDH) complex catalyzes the conversion of pyruvate to acetyl-CoA. The *E. coli* PDH complex is encoded by the genes aceEF and lpdA. Enzyme engineering efforts have improved the *E. coli* PDH enzyme activity under anaerobic conditions (Kim et al., *J. Bacteriol.* 190:3851-3858 (2008); Kim et al., *Appl. Environ. Microbiol.* 73:1766-1771 (2007); Zhou et al., *Biotechnol. Lett.* 30:335-342 (2008)). In contrast to the *E. coli* PDH, the *B. subtilis* complex is active and required for growth under anaerobic conditions (Nakano et al., 179:6749-6755 (1997)). The *Klebsiella pneumoniae* PDH, characterized during growth on glycerol, is also active under anaerobic conditions (Menzel et al., 56:135-142 (1997)). Crystal structures of the enzyme complex from bovine kidney (Zhou et al., 98:14802-14807 (2001)) and the E2 catalytic domain from *Azotobacter vinelandii* are available (Mattevi et al., *Science.* 255:1544-1550 (1992)). Some mammalian PDH enzymes complexes can react on alternate substrates such as 2-oxobutanoate. Comparative kinetics of *Rattus norvegicus* PDH and BCKAD indicate that BCKAD has higher activity on 2-oxobutanoate as a substrate (Paxton et al., *Biochem. J.* 234:295-303 (1986)). The *S. cerevisiae* PDH complex can consist of an E2 (LAT1) core that binds E1 (PDA1, PDB1), E3 (LPD1), and Protein X (PDX1) components (Pronk et al., *Yeast* 12:1607-1633 (1996)). The PDH complex of *S. cerevisiae* is regulated by phosphorylation of E1 involving PKP1 (PDH kinase I), PTC5 (PDH phosphatase I), PKP2 and PTC6. Modification of these regulators may also enhance PDH activity. Coexpression of lipoyl ligase (LplA of *E. coli* and AIM22 in *S. cerevisiae*) with PDH in the cytosol may be necessary for activating the PDH enzyme complex. Increasing the supply of cytosolic lipoate, either by modifying a metabolic pathway or media supplementation with lipoate, may also improve PDH activity.

| Gene | Accession No. | GI Number | Organism |
|---|---|---|---|
| aceE | NP_414656.1 | 16128107 | Escherichia coli |
| aceF | NP_414657.1 | 16128108 | Escherichia coli |
| Lpd | NP_414658.1 | 16128109 | Escherichia coli |
| lplA | NP_418803.1 | 16132203 | Escherichia coli |
| pdhA | P21881.1 | 3123238 | Bacillus subtilis |
| pdhB | P21882.1 | 129068 | Bacillus subtilis |
| pdhC | P21883.2 | 129054 | Bacillus subtilis |
| pdhD | P21880.1 | 118672 | Bacillus subtilis |
| aceE | YP_001333808.1 | 152968699 | Klebsiella pneumoniae |
| aceF | YP_001333809.1 | 152968700 | Klebsiella pneumoniae |
| lpdA | YP_001333810.1 | 152968701 | Klebsiella pneumoniae |
| Pdha1 | NP_001004072.2 | 124430510 | Rattus norvegicus |
| Pdha2 | NP_446446.1 | 16758900 | Rattus norvegicus |
| Dlat | NP_112287.1 | 78365255 | Rattus norvegicus |
| Dld | NP_955417.1 | 40786469 | Rattus norvegicus |
| LAT1 | NP_014328 | 6324258 | Saccharomyces cerevisiae |
| PDA1 | NP_011105 | 37362644 | Saccharomyces cerevisiae |
| PDB1 | NP_009780 | 6319698 | Saccharomyces cerevisiae |
| LPD1 | NP_116635 | 14318501 | Saccharomyces cerevisiae |
| PDX1 | NP_011709 | 6321632 | Saccharomyces cerevisiae |
| AIM22 | NP_012489.2 | 83578101 | Saccharomyces cerevisiae |

Another strategy for reducing flux into the TCA cycle is to limit transport of pyruvate into the mitochondria by tuning down or deleting the mitochondrial pyruvate carrier. Transport of pyruvate into the mitochondria in *S. cerevisiae* is catalyzed by a heterocomplex encoded by MPC1 and MPC2 (Herzig et al, Science 337:93-6 (2012); Bricker et al, *Science* 337:96-100 (2012)). *S. cerevisiae* encodes five other putative monocarboxylate transporters (MCH1-5), several of which may be localized to the mitochondrial membrane (Makuc et al, *Yeast* 18:1131-43 (2001)). NDT1 is another putative pyruvate transporter, although the role of this protein is disputed in the literature (Todisco et al, *J Biol Chem* 20:1524-31 (2006)). Exemplary pyruvate and monocarboxylate transporters are shown in the table below:

| Protein | GenBank ID | GI number | Organism |
|---|---|---|---|
| MPC1 | NP_011435.1 | 6321358 | Saccharomyces cerevisiae |
| MPC2 | NP_012032.1 | 6321956 | Saccharomyces cerevisiae |
| MPC1 | XP_504811.1 | 50554805 | Yarrowia lipolytica |
| MPC2 | XP_501390.1 | 50547841 | Yarrowia lipolytica |
| MPC1 | XP_719951.1 | 68471816 | Candida albicans |
| MPC2 | XP_71690.1 | 68479656 | Candida albicans |
| MCH1 | NP_010229.1 | 6320149 | Saccharomyces cerevisiae |
| MCH2 | NP_012701.2 | 330443640 | Saccharomyces cerevisiae |
| MCH3 | NP_014274.1 | 6324204 | Saccharomyces cerevisiae |
| MCH5 | NP_014951.2 | 330443742 | Saccharomyces cerevisiae |
| NDT1 | NP_012260.1 | 6322185 | Saccharomyces cerevisiae |
| ANI_1_1592184 | XP_001401484.2 | 317038471 | Aspergillus niger |
| CaJ7_0216 | XP_888808.1 | 77022728 | Candida albicans |
| YALI0E16478g | XP_504023.1 | 50553226 | Yarrowia lipolytica |
| KLLA0D14036g | XP_453688.1 | 50307419 | Kluyveromyces lactis |

One exemplary method to provide an increased number of reducing equivalents, such as NAD(P)H, for enabling the formation of succinate is to constrain the use of such reducing equivalents during respiration. Respiration can be limited by: reducing the availability of oxygen, attenuating NADH dehydrogenases and/or cytochrome oxidase activity, attenuating G3P dehydrogenase, and/or providing excess glucose to Crabtree positive organisms.

Restricting oxygen availability by culturing the non-naturally occurring eukaryotic organisms in a fermenter is one approach for limiting respiration and thereby increasing the ratio of NAD(P)H to NAD(P). The ratio of NAD(P)H/NAD(P) increases as culture conditions get more anaerobic, with completely anaerobic conditions providing the highest ratios of the reduced cofactors to the oxidized ones. For example, it has been reported that the ratio of NADH/NAD=0.02 in aerobic conditions and 0.75 in anaerobic conditions in *E. coli* (de Graes et al, J Bacteriol 181:2351-57 (1999)).

Respiration can also be limited by reducing expression or activity of NADH dehydrogenases and/or cytochrome oxidases in the cell under aerobic conditions. In this case, respiration will be limited by the capacity of the electron transport chain. Such an approach has been used to enable anaerobic metabolism of *E. coli* under completely aerobic conditions (Portnoy et al, *AEM* 74:7561-9 (2008)). *S. cerevisiae* can oxidize cytosolic NADH directly using external NADH dehydrogenases, encoded by NDE1 and NDE2. One such NADH dehydrogenase in *Yarrowia lipolytica* is encoded by NDH2 (Kerscher et al, *J Cell Sci* 112:2347-54 (1999)). These and other NADH dehydrogenase enzymes are listed in the table below.

| Protein | GenBank ID | GI number | Organism |
| --- | --- | --- | --- |
| NDE1 | NP_013865.1 | 6323794 | *Saccharomyces cerevisiae* s288c |
| NDE2 | NP_010198.1 | 6320118 | *Saccharomyces cerevisiae* s288c |
| NDH2 | AJ006852.1 | 3718004 | *Yarrowia lipolytica* |
| ANI_1_610074 | XP_001392541.2 | 317030427 | *Aspergillus niger* |
| ANI_1_2462094 | XP_001394893.2 | 317033119 | *Aspergillus niger* |
| KLLA0E21891g | XP_454942.1 | 50309857 | *Kluyveromyces lactis* |
| KLLA0C06336g | XP_452480.1 | 50305045 | *Kluyveromyces lactis* |
| NDE1 | XP_720034.1 | 68471982 | *Candida albicans* |
| NDE2 | XP_717986.1 | 68475826 | *Candida albicans* |

Cytochrome oxidases of *Saccharomyces cerevisiae* include the COX gene products. COX1-3 are the three core subunits encoded by the mitochondrial genome, whereas COX4-13 are encoded by nuclear genes. Attenuation or deletion of any of the cytochrome genes results in a decrease or block in respiratory growth (Hermann and Funes, Gene 354:43-52 (2005)). Cytochrome oxidase genes in other organisms can be inferred by sequence homology.

| Protein | GenBank ID | GI number | Organism |
| --- | --- | --- | --- |
| COX1 | CAA09824.1 | 4160366 | *Saccharomyces cerevisiae* s288c |
| COX2 | CAA09845.1 | 4160387 | *Saccharomyces cerevisiae* s288c |
| COX3 | CAA09846.1 | 4160389 | *Saccharomyces cerevisiae* s288c |
| COX4 | NP_011328.1 | 6321251 | *Saccharomyces cerevisiae* s288c |
| COX5A | NP_014346.1 | 6324276 | *Saccharomyces cerevisiae* s288c |
| COX5B | NP_012155.1 | 6322080 | *Saccharomyces cerevisiae* s288c |
| COX6 | NP_011918.1 | 6321842 | *Saccharomyces cerevisiae* s288c |
| COX7 | NP_013983.1 | 6323912 | *Saccharomyces cerevisiae* s288c |
| COX8 | NP_013499.1 | 6323427 | *Saccharomyces cerevisiae* s288c |
| COX9 | NP_010216.1 | 6320136 | *Saccharomyces cerevisiae* s288c |
| COX12 | NP_013139.1 | 6323067 | *Saccharomyces cerevisiae* s288c |
| COX13 | NP_011324.1 | 6321247 | *Saccharomyces cerevisiae* s288c |

Cytosolic NADH can also be oxidized by the respiratory chain via the G3P dehydrogenase shuttle, consisting of cytosolic NADH-linked G3P dehydrogenase and a membrane-bound G3P:ubiquinone oxidoreductase. The deletion or attenuation of G3P dehydrogenase enzymes will also prevent the oxidation of NADH for respiration. Enzyme candidates encoding these enzymes were described above.

Additionally, in Crabtree positive organisms, fermentative metabolism can be achieved in the presence of excess of glucose. For example, *S. cerevisiae* makes ethanol even under aerobic conditions. The formation of ethanol and glycerol can be reduced/eliminated and replaced by the production of succinate in a Crabtree positive organism by feeding excess glucose to the Crabtree positive organism. In another aspect provided herein is a method for producing succinate, comprising culturing a non-naturally occurring eukaryotic organism under conditions and for a sufficient period of time to produce succinate, wherein the eukaryotic organism is a Crabtree positive organism that comprises at least one nucleic acid encoding a SucPE and wherein eukaryotic organism is in a culture medium comprising excess glucose.

Reduced activity of pyruvate kinase encoded by pyk1 and pyk2 can also be used to increase the pool of PEP for succinate production. Pyruvate kinase, also known as phosphoenolpyruvate synthase (EC 2.7.9.2), converts pyruvate and ATP to PEP and AMP. This enzyme is encoded by the PYK1 (Burke et al., *J. Biol. Chem.* 258:2193-2201 (1983)) and PYK2 (Boles et al., *J. Bacteriol.* 179:2987-2993 (1997)) genes in *S. cerevisiae*. In *E. coli*, this activity is catalyzed by the gene products of pykF and pykA. Selected homologs of the *S. cerevisiae* enzymes are also shown in the table below.

| Protein | GenBank ID | GI Number | Organism |
| --- | --- | --- | --- |
| PYK1 | NP_009362 | 6319279 | *Saccharomyces cerevisiae* |
| PYK2 | NP_014992 | 6324923 | *Saccharomyces cerevisiae* |
| pykF | NP_416191.1 | 16129632 | *Escherichia coli* |
| pykA | NP_416368.1 | 16129807 | *Escherichia coli* |
| KLLA0F23397g | XP_456122.1 | 50312181 | *Kluyveromyces lactis* |
| CaO19.3575 | XP_714934.1 | 68482353 | *Candida albicans* |
| CaO19.11059 | XP_714997.1 | 68482226 | *Candida albicans* |
| YALI0F09185p | XP_505195 | 210075987 | *Yrowia lipolytica* |
| ANI_1_1126064 | XP_001391973 | 145238652 | *Aspergillus niger* |

4.6 Example VI—Increased Production of Succinate in Microbial Organisms

This example describes engineering of microbial organisms for increased production of succinate.

In *E. coli*, the relevant genes are expressed in a synthetic operon behind an inducible promoter on a medium- or high-copy plasmid; for example the PBAD promoter which is induced by arabinose, on a plasmid of the pBAD series (Guzman et al., *J. Bacteriol.* 177:4121-4130 (1995)). In *S. cerevisiae*, genes are integrated into the chromosome behind the PDC1 promoter, replacing the native ES2 gene. It has been reported that this results in higher expression of foreign genes than from a plasmid (Ishida et al., *Appl. Environ. Microbiol.* 71:1964-1970 (2005)), and will also ensure expression during anaerobic conditions.

Cells containing the relevant constructs are grown in suitable growth media, for example, minimal media containing glucose. The addition of arabinose can be included in the case of *E. coli* containing genes expressed under the PBAD promoter. Periodic samples are taken for both gene expression and enzyme activity analysis. Enzyme activity assays are performed on crude cell extracts using procedures well known in the art. Alternatively, assays based on the oxidation of NAD(P)H, which is produced in all dehydrogenase reaction steps and detectable by spectrophotometry can be utilized. In addition, antibodies can be used to detect the level of particular enzymes. In lieu of or in addition to enzyme activity measurements, RNA can be isolated from parallel samples and transcript of the gene of interest measured by reverse transcriptase PCR. Any constructs lacking detectable transcript expression are reanalyzed to ensure the encoding nucleic acids are harbored in an expressible form. Where transcripts are detected, this result indicates either a lack of translation or production of inactive enzyme. A variety of methods well known in the art can additionally be employed, such as codon optimization, engineering a strong ribosome binding site, use of a gene from a different species, and prevention of N-glycosylation (for expression of bacterial enzymes in yeast) by conversion of Asn residues to Asp. Once all required enzyme activities are detected, the next step is to measure the production of succinate in vivo. Triplicate shake flask cultures are grown aerobically, anaerobically or microaerobically, depending on the conditions required, and periodic samples taken. Organic acids present in the culture supernatants are analyzed by HPLC using the Aminex AH-87X column. The elution time of succinate will be determined using a standard purchased from a chemical supplier.

4.7 Example VII—In Vivo Labeling Assay for Conversion of Methanol to $CO_2$

This example describes a functional methanol pathway in a microbial organism.

Strains with functional reductive TCA branch and pyruvate formate lyase deletion were grown aerobically in LB medium overnight, followed by inoculation of M9 high-seed media containing IPTG and aerobic growth for 4 hrs. These strains had methanol dehydrogenase/ACT pairs in the presence and absence of formaldehyde dehydrogenase or formate dehydrogenase. ACT is an activator protein (a Nudix hydrolase). At this time, strains were pelleted, resuspended in fresh M9 medium high-seed media containing 2% $^{13}CH_3OH$, and sealed in anaerobic vials. Head space was replaced with nitrogen and strains grown for 40 hours at 37° C. Following growth, headspace was analyzed for $^{13}CO_2$. Media was examined for residual methanol as well as BDO and byproducts. All constructs expressing methanol dehydrogenase (MeDH) mutants and MeDH/ACT pairs grew to slightly lower ODs than strains containing empty vector controls. This is likely due to the high expression of these constructs (Data not shown). One construct (2315/2317) displayed significant accumulation of labeled $CO_2$ relative to controls in the presence of FalDH, FDH or no coexpressed protein. This shows a functional MeOH pathway in E. coli and that the endogenous glutathione-dependent formaldehyde detoxification genes (frmAB) are sufficient to carry flux generated by the current MeDH/ACT constructs.

2315 is internal laboratory designation for the MEDH from Bacillus methanolicus MGA3 (GenBank Accession number: EIJ77596.1; GI number: 387585261), and 2317 is internal laboratory designation for the activator protein from the same organism (locus tag: MGA3_09170; GenBank Accession number: EIJ83380; GI number: 387591061).

Sequence analysis of the NADH-dependent methanol dehydrogenase from Bacillus methanolicus places the enzyme in the alcohol dehydrogenase family III. It does not contain any tryptophan residues, resulting in a low extinction coefficient (18,500 $M^{-1}$, $cm^{-1}$) and should be detected on SDS gels by Coomassie staining.

The enzyme has been characterized as a multisubunit complex built from 43 kDa subunits containing one Zn and 1-2 Mg atoms per subunit. Electron microscopy and sedimentation studies determined it to be a decamer, in which two rings with five-fold symmetry are stacked on top of each other (Vonck et al., J. Biol. Chem. 266:3949-3954, 1991). It is described to contain a tightly but not covalently bound cofactor and requires exogenous $NAD^+$ as $e^-$-acceptor to measure activity in vitro. A strong increase (10-40-fold) of in vitro activity was observed in the presence of an activator protein (ACT), which is a homodimer (21 kDa subunits) and contains one Zn and one Mg atom per subunit.

The mechanism of the activation was investigated by Kloosterman et al., J. Biol. Chem. 277:34785-34792, 2002, showing that ACT is a Nudix hydrolase and Hektor et al., J. Biol. Chem. 277:46966-46973, 2002, demonstrating that mutation of residue S97 to G or T in MeDH changes activation characteristics along with the affinity for the cofactor. While mutation of residues G15 and D88 had no significant impact, a role of residue G13 for stability as well as of residues G95, D100, and K103 for the activity is suggested. Both papers together propose a hypothesis in which ACT cleaves MeDH-bound $NAD^+$. MeDH retains AMP bound and enters an activated cycle with increased turnover.

The stoichiometric ratio between ACT and MeDH is not well defined in the literature. Kloosterman et al., supra determine the ratio of dimeric Act to decameric MeDH for full in vitro activation to be 10:1. In contrast, Arfman et al. J. Biol. Chem. 266:3955-3960, 1991 determined a ratio of 3:1 in vitro for maximum and a 1:6 ratio for significant activation, but observe a high sensitivity to dilution. Based on expression of both proteins in Bacillus, the authors estimate the ratio in vivo to be around 1:17.5.

However, our in vitro experiments with purified activator protein (2317A) and methanol dehydrogenase (2315A) showed the ratio of ACT to MeDH to be 10:1. This in vitro test was done with 5 M methanol, 2 mM NAD and 10 µM methanol dehydrogenase 2315A at pH 7.4.

Throughout this application various publications have been referenced. The disclosures of these publications in their entireties, including GenBank and GI number publications, are hereby incorporated by reference in this application in order to more fully describe the state of the art to which this invention pertains. Although the invention has been described with reference to the examples and embodiments provided above, it should be understood that various modifications can be made without departing from the spirit of the invention.

What is claimed is:

1. A non-naturally occurring microbial organism comprising:
   (a) a methanol metabolic pathway (MMP), wherein said non-naturally occurring microbial organism comprises at least one exogenous nucleic acid encoding a MMP enzyme expressed in a sufficient amount for biosynthesis of succinate, and wherein said MMP comprises:
   (i) a methanol dehydrogenase (EM9) from bacteria,
   (ii) an EM9 from bacteria and a formaldehyde activating enzyme (EM10), or
   (iii) a methanol methyltransferase (EM1) and a methylenetetrahydrofolate reductase (EM2), and wherein EM9 converts methanol to formaldehyde,
wherein EM10 converts formaldehyde to methylenetetrahydrofolate (THF),
wherein EM1 converts methanol to methyl-THF, and
wherein EM2 converts methyl-THF to methylene-THF;
(b) a succinate pathway (SucP); and
(c) a formaldehyde assimilation pathway (FAP), wherein said non-naturally occurring microbial organism comprises at least one exogenous nucleic acid encoding a FAP enzyme and wherein said FAP comprises:
(i) a hexulose-6-phosphate synthase (EF1) and a 6-phospho-3-hexuloisomerase (EF2), or
(ii) a dihydroxyacetone synthase (EF3) or a dihydroxyacetone kinase (EF4);
wherein EF1 converts formaldehyde and D-ribulose-5-phosphate to hexulose-6-phosphate,
wherein EF2 converts hexulose-6-phosphate to fructose-6-phosphate,
wherein EF3 converts formaldehyde and xylulose-6-phosphate to dihydroxyacetone, and
wherein EF4 converts dihydroxyacetone to dihydroxyacetone-phosphate; and
wherein said non-naturally occurring microbial organism comprises an *Escherichia coli* or *Saccharomyces cerevisiae*.

2. The non-naturally occurring microbial organism of claim 1, wherein said non-naturally occurring microbial organism comprises at least one nucleic acid encoding a SucP enzyme (SucPE) expressed in a sufficient amount to produce succinate, wherein said SucP comprises:
(a) a phosphoenolpyruvate (PEP) carboxylase (ES1A) or a PEP carboxykinase (ES1 B), a malate dehydrogenase (ES3), a fumarase (ES5), and a fumarate reductase (ES6);
(b) a pyruvate carboxylase (ES2), an ES3, an ES5, and an ES6; or
(c) a malic enzyme (ES4), an ES5, and an ES6;
wherein ES1A and ES1B convert PEP to oxaloacetate,
wherein ES2 converts pyruvate to oxaloacetate,
wherein ES3 converts oxaloacetate to malate,
wherein ES4 converts pyruvate to malate,
wherein ES5 converts malate to fumarate, and
wherein ES6 converts fumarate to succinate.

3. The non-naturally occurring microbial organism of claim 1, wherein:
(a) said MMP comprises:
(i) an EM9 from bacteria, a methylenetetrahydrofolate dehydrogenase (EM3), a methenyltetrahydrofolate cyclohydrolase (EM4), and a formyltetrahydrofolate deformylase (EM5);
(ii) an EM9 from bacteria, an EM3, an EM4, and a formyltetrahydrofolate synthetase (EM6);
(iii) an EM9 from bacteria and a formaldehyde dehydrogenase (EM11);
(iv) an EM9 from bacteria, a S-(hydroxymethyl)glutathione synthase (EM12), a glutathione-dependent formaldehyde dehydrogenase (EM13), and a S-formylglutathione hydrolase (EM14);
(v) an EM9 from bacteria, an EM13, and an EM14;
(vi) an EM9 from bacteria, an EM10, an EM3, an EM4, and an EM5;
(vii) an EM9 from bacteria, an EM10, an EM3, an EM4, and an EM6;
(viii) an EM1, an EM2, an EM3, an EM4, and an EM5; or
(ix) an EM1, an EM2, an EM3, an EM4 and an EM6;
wherein EM3 converts methylene-THF to methenyl-THF,
wherein EM4 converts methenyl-THF to formyl-THF,
wherein EM5 and EM6 convert formyl-THF to formate,
wherein EM11 converts formaldehyde to formate,
wherein EM12 converts formaldehyde to S-hydroxymethylglutathione,
wherein EM13 converts S-hydroxymethylglutathione to S-formylglutathione, and
wherein EM14 converts S-formylglutathione to formate.

4. The non-naturally occurring microbial organism of claim 1, wherein:
said non-naturally occurring microbial organism comprises two exogenous nucleic acids, each encoding a FAP enzyme.

5. The non-naturally occurring microbial organism of claim 1, wherein:
(a) said at least one exogenous nucleic acid is a heterologous nucleic acid; and/or
(b) said non-naturally occurring microbial organism is in a substantially anaerobic culture medium.

6. A method for producing succinate, comprising:
culturing the non-naturally occurring microbial organism of claim 1 under conditions and for a sufficient period of time to produce succinate.

7. The method of claim 6, wherein said method further comprises separating said succinate from other components in said culture.

8. The method of claim 7, wherein said separating comprises extraction, continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, or ultrafiltration.

9. The method of claim 6, wherein said culturing is in a culture medium comprising glucose.

10. The non-naturally occurring microbial organism of claim 1, wherein said non-naturally occurring microbial organism is *Saccharomyces cerevisiae* and is Crabtree positive.

11. The non-naturally occurring microbial organism of claim 1, wherein said MMP comprises an EM9 from bacteria.

12. The non-naturally occurring microbial organism of claim 1, wherein said MMP comprises an EM9 from bacteria and EM10.

13. The non-naturally occurring microbial organism of claim 1, wherein said MMP comprises an EM1 and an EM2.

14. The non-naturally occurring microbial organism of claim 1, wherein said FAP comprises an EF1 and an EF2.

15. The non-naturally occurring microbial organism of claim 1, wherein said FAP comprises an EF3 or an EF4.

16. The non-naturally occurring microbial organism of claim 2, wherein said non-naturally occurring microbial organism comprises one, two, three, or four nucleic acids, each encoding a SucPE.

17. The non-naturally occurring microbial organism of claim 2, wherein said at least one nucleic acid encoding a succinate enzyme is an exogenous or heterologous nucleic acid.

18. The non-naturally occurring microbial organism of claim 3, wherein said MMP further comprises a formate dehydrogenase (EM8), a formate hydrogen lyase (EM15), or a hydrogenase (EM16);

wherein EM8 converts formate to reducing equivalents, wherein EM15 converts formate to reducing equivalents, and wherein EM16 converts hydrogen gas to reducing equivalents.

19. The non-naturally occurring microbial organism of claim 3, wherein said non-naturally occurring microbial organism comprises two, three, four, five, six, or seven exogenous nucleic acids, each encoding a MMP enzyme.

* * * * *